US008541421B2

(12) United States Patent
Tachdjian et al.

(10) Patent No.: US 8,541,421 B2
(45) Date of Patent: *Sep. 24, 2013

(54) METHODS OF ENHANCING SWEET TASTE OF COMPOSITIONS USING SUBSTITUTED THIENO{2,3-D}PYRIMIDINES

(75) Inventors: Catherine Tachdjian, San Diego, CA (US); Xiao-Qing Tang, San Diego, CA (US); Sara Werner, San Diego, CA (US); Marketa Rinnova, San Diego, CA (US); Qing Chen, San Diego, CA (US); Guy Servant, San Diego, CA (US); Xiaodong Li, San Diego, CA (US); Feng Zhang, San Diego, CA (US); Haitian Liu, San Diego, CA (US); Albert Zlotnik, San Diego, CA (US); Mark Zoller, La Jolla, CA (US); Boris Klebansky, Demarest, CA (US); Richard Fine, Ridgewood, CA (US); Xinshan Kang, Pine Brook, CA (US)

(73) Assignee: Senomyx Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/051,586

(22) Filed: Mar. 18, 2011

(65) Prior Publication Data

US 2011/0230502 A1 Sep. 22, 2011

Related U.S. Application Data

(63) Continuation of application No. 11/836,074, filed on Aug. 8, 2007, now Pat. No. 7,928,111, which is a continuation-in-part of application No. 11/760,592, filed on Jun. 8, 2007.

(51) Int. Cl.
*A61K 31/519* (2006.01)

(52) U.S. Cl.
USPC ........ 514/260.1; 424/452; 424/461; 424/479; 424/493; 544/278

(58) Field of Classification Search
USPC .............. 424/452, 461, 479, 493; 514/260.1; 544/278
See application file for complete search history.

(56) References Cited

U.S. PATENT DOCUMENTS

| 3,843,804 | A | 10/1974 | Evers et al. |
|---|---|---|---|
| 3,845,770 | A | 11/1974 | Theeuwes et al. |
| 3,857,972 | A | 12/1974 | Evers et al. |
| 3,916,899 | A | 11/1975 | Theeuwes et al. |
| 3,957,783 | A | 5/1976 | Hirohashi et al. |
| 3,960,860 | A | 6/1976 | Katz et al. |
| 4,146,716 | A | 3/1979 | Cox et al. |
| 4,196,207 | A | 4/1980 | Webber |
| 4,377,580 | A | 3/1983 | Ueda et al. |
| 4,765,539 | A | 8/1988 | Noakes et al. |
| 5,112,598 | A | 5/1992 | Biesalski |
| 5,380,541 | A | 1/1995 | Beyts et al. |
| 5,504,095 | A | 4/1996 | Nakane et al. |
| 5,556,611 | A | 9/1996 | Biesalski |
| 5,698,155 | A | 12/1997 | Grosswald et al. |
| 5,950,619 | A | 9/1999 | van der Linden et al. |
| 5,954,047 | A | 9/1999 | Armer et al. |
| 5,970,974 | A | 10/1999 | van der Linden et al. |
| 7,105,650 | B2 | 9/2006 | Adler |
| 7,928,111 | B2 | 4/2011 | Tachdjian et al. |
| 2003/0008344 | A1 | 1/2003 | Adler et al. |
| 2003/0054448 | A1 | 3/2003 | Adler et al. |
| 2003/0232407 | A1 | 12/2003 | Zoller et al. |
| 2004/0127435 | A1 | 7/2004 | Carson et al. |
| 2005/0032158 | A1 | 2/2005 | Adler et al. |
| 2006/0045953 | A1 | 3/2006 | Tachdjian et al. |
| 2006/0135552 | A1 | 6/2006 | Malherbe et al. |
| 2007/0104709 | A1 | 5/2007 | Li et al. |
| 2008/0306053 | A1 | 12/2008 | Tachdjian et al. |
| 2008/0306093 | A1 | 12/2008 | Servant et al. |
| 2011/0224155 | A1 | 9/2011 | Tachdjian et al. |

FOREIGN PATENT DOCUMENTS

| EP | 0530994 A1 | 3/1993 |
|---|---|---|
| WO | WO 03/001876 A2 | 1/2003 |
| WO | WO 03/022214 A2 | 3/2003 |
| WO | WO 2007/004709 A1 | 1/2007 |
| WO | WO 2007/047988 A2 | 4/2007 |

OTHER PUBLICATIONS

Albrecht et al., "Synthesis of 1,2,6-Thiadiazine 1,1-Dioxides via Isoxazolylsulfamides," J. Org. Chem. 44:4191-4194 (1979).
Aldermin, "A Review of Cellulose Ethers in Hydrophilic Matrices for Oral Controlled-Release Dosage Forms," Int. J. Pharm. Tech. & Prod. Mfr. 5(3):1-9 (1984).
Bamba et al., "Release mechanisms in Gelforming Sustained Release Preparations," Int. J. Pharm. 2:307-315 (1979).
Bellur, et al., "Synthesis of 4-(3-hydroxyalkyl)pyrimidines by ring transformation reactions of 2-alkylidenetetrahydrofirans with amidines," Tetrahedron 62:5426-5434 (2006).
Berge et al., "Pharmaceutical Salts," J. Pharm. Sci 66(1):1-19 (1977).
Blackburn et al., "Identification and characterization of aminopiperidinequinolones and quinazolinones as MCHr1 antagonists," Bioorg. & Med. Chem. Lett. 16:2621-2627 (2006).
Boarland et al., "Monosubsitiuted Pyrimidines, and the Action of Thiourea on Chloropyrimidines," J. Chem. Soc. 1218-1221 (1951).
Brown, et al., "Evolution of a Series of Peptisioleukotriene Antagonists' Synthesis and Structure-Activity Relationships of 1,6-Disubstituted Indoles and Indazoles," J. Med. Chem. 33:1771-1781 (1990).
Buck et al., "A Novel Multigene Family May Encode Odorant Receptors. A Molecular Basis for Odor Recognition," Cell 65(1):175-187 (1991).
Chandrashekar et al., "T2Rs Function as Bitter Taste Receptors," Cell 100:703-711 (2000).
Clauβ et al., "Cycloadditionen von Halogensulfonylirocyanaten an Acctylene," Tetrahedron Lett. 2:119-122 (1970).

(Continued)

*Primary Examiner* — Douglas M Willis
(74) *Attorney, Agent, or Firm* — Cooley LLP

(57) ABSTRACT

The present invention provides, in part, substituted thieno[2,3-d]pyrimidines and methods of contacting compositions with such compounds to enhance the sweet taste of said compositions.

15 Claims, 13 Drawing Sheets

(56) References Cited

OTHER PUBLICATIONS

Da Settimo et al., "Naphtho[1,2-d]isothiazole Acid Derivatives as a Novel Class of Selective Aldose Reductase Inhibitors," J. Med. Chem. 48:6897-6907 (2005).
Dorwald, "Side Reactions in Organic Synthesis: A Guide to Successful Synthesis Design," Weinheim: WILEY-VCH Verlag Gmbh & o KGaA, 2005, ISBN: 3-527-31021-5.
During et al., "Controlled Release of Dopamine from a Polymeric Brain Implant In Vivo Characterization," Ann. Neurol. 25:351-356 (1989).
Elmegeed et al., "Novel synthesis aminesteroidal heterocycles intervention for inhibiting iron-induced oxidative stress," Eur. J. Med. Chem. 49:1283-1294 (2005).
El-Sherbeny et al., "Novel Pyridothienopyrimidine and Pyridothienothazine Derivatives as Potential Antiviral and Antitumor Agents," Med. Chem. Res. 10:122-135 (2000).
Etter et al., "An Enolized Sulfonamide Formed by Strong Hydrogen Bonding to Triphenylphosphine Oxide," J. Org. Chem. 51:5405-5408 (1986).
Francis et al., "Anxiolytie Properties of Certain Annelated [1,2,4]Triazolo[1,5-e]pyrimidin-5(6H)-ones," J. Med. Chem. 34:2899-2906 (1991).
Goya et al., "Fused 1,2,6-Thiadiazines: Teunhydrobenzo[b]thieno[2,3-c] [1,2,6]thiadinzine 2,2-Dioxides," Arch. Pharm. (Weinheim) 317:777-781 (1984).
Goya et al., "N-Glucosyl-5-Amino-4-Carbarnoyl- and 4-Dhoxycarbonylimidazoles as Potential Precursors of 4-Oxoimidazo[4,5-c]-1,2,6-thiadiazine 2,2-Dioxides," Heterocycles 24:3451-3458 (1986).
Hauser et al., "Synthesis of 5-Phenyl-4,6-Dimethyl-2-Pyrimidol and Derivatives from the Cyclization of Urea with 3-Phenyl-2, 4-Pentanedione," J. Org. Chem. 18:588-593 (1953).
Hirayama et al., "The Discovery of YM-60828: A Potent, Selective and Orally-Bioavailable Factor Xa Inhibitor," Bioorg. & Med. Chem. 10:1509-1523 (2002).
Hirota et al., "Synthesis and Biological Evaluation of 2,8-Disubstituted 9-Benzyladenines: Discovery of 8-Mercaptoadenines as Potent Interferon-Inducers," Bioorg. Med. Chem. 11:2715-2722 (2003).
Hoon et al., Pinative Mammalian Taste Receptors: A Class of Taste-Specific GPCRs with Distinct Topographic Selectivity, Cell 96:541-551 (1991).
Howard et al., "Intracerebral drug delivery in rats with lesion-induced memory deficits," J. Neurosurg. 71:105-112 (1989).
Hu et al., "Organic Reactions in tonic Liquids: Gewald Synthesis of 2-Aminothiophenes Catalyzed by Ethytenediammorium Diacetate," Synthetic Communication 34:3801-3806 (2004).
Jordan, "Tamoxifen: A Most Unlikely Pioneering Medicine," Nature Reviews Drug Discovery 2003, vol. 2, pp. 205-213.
Jung et al., "Discovery of Novel and Potent thiazoloquanazolines as Selective Aurora A and B Kinase Inhibitors," J. Med. Chem. 49:955-970 (2006).
Kamal et al., "Cyclization of 2-(Carbamoyloxy)- and 2-(Sulfamoyloxy)benzoates Mediated by Liver Microsomes," J. Org. Chem. 53:4112-4114 (1988).
Kamal et al., "Enzymatic Cyclization of 2-(Carbamoyloxy)Benzoates, 2-(Sulfemoyloxy)-Benzoates and 2-(Carbamoylozy)benzopenones with Yeast and Lipase," Heterocycles 29:1391-1397 (1989).
Kambe et al., "Discovery of thiochroman dervatives bearing a carboxy-containing side chain as orally active pure antiestrogens," Bioorg. & Med. Chem. Lett. 16:4090-4094 (2006).
Kanuma et al., "Lead optimization of 4-(dimethylamino)quinazolines, potent and selective antagonists for the melanin-concentrating hormone receptor 1," Bioorg. & Med. Chem. Lett. 15:3853-3856 (2005).
Khabnadideh et al., "Design, synthesis and evaluation of 2,4-diaminoquinazolines as inhibitors of trypanosomal and leishmanial dihydrofolate reductase," Bioorg. Med. Chem. 13:2637-2649 (2005).

Klinger et al., "Inhibition of Carbonic Anhydrase-II Sulfamate and Sulfamide Groups. An Investigation Involving Direct Thermodynamic Binding Measurements," J. Med. Chem 49:3496-3500 (2006).
Kyte et al., "A Simple Method for Displaying the Hydropathic Character of a Protein," J. Mol. Biol. 157:105-132 (1982).
Langer et al., "Chemical and Physical Structure of Polymers as Carriers for Controlled Release of Bioactive Agents: A Reviews," J. Macromol. Sci. Rev. Macromol. Chem. 23:61-126 (1983).
Langer, "New Methods of Drug Delivery," Science 249:1527-1533 (1990).
Lee et al., "Acetonlinte-Mediated Synthesis of 2,4-Diehloroquinoline from 2-Ethynyl-aniline and 2,4-Dichloroquinazoline from Amhrinilonitrile," Synlett. 2006 No. 1:65-68 (2006).
Leistner et al., "Eine einfache Synthese von 2-Alhyliho-4-amino-thieno[2,3-d]pyrimidinen," Arch. Pharm. (Weinheim) 322:227-230 (1989).
Levy et al., "Inhibition of Calcification of Bioprosthetic Heart Valves by Local Controlled-Release Diphosphonate," Science 228:190-192 (1985).
Li et al., "Human receptors for sweet and unami taste," Proc. Natl. Acad. Sci. USA 99:4692-4696 (2002).
Linkies et al., "Ein nenes Verliahren zur Herstellung von 6-Methyl-1,2,3-oxathiazin-4(3H)-on-2,2-dioxid Kaliunsalz (Acesulian-K)," Synthesis 405-406 (1990).
Liu et al., "Discovery of a new class of 4-amilopyrimidines as potent c-Jun N-terminal kinase inhibitors: Synthesis and SAR studies," Bioorg. & Med. Chem. Lett. 17:668-672 (2007).
Naganawa et al., "Further optimization of sulfonamide analogs as EPI receptor antagonists: Synthesis and evaluation of bioisosteres for the carboxylic acid group," Bioorg. Med. Chem. 14:7121-7137 (2006).
Nie et al., "Distinct Contributions of T1R2 and T1R3 Taste Receptors Subunits to the Detection of Sweet Stimuli," Curr. Biol. 15(21):1948-1952 (2005).
Pal et al., "Synthesis and Cyclooxygenase-2 (COX-2) Inhibiting Properties of 1,5-Diarylpyrazoles Processing N-Substitution on the Sulfonamide (-SO2NH2) Moiety," Letters in Drug Design & Discovery 2:329-340 (2005).
Rad-Moghadam et al., "One-pot Three-component Synthesis of 2-Substituted 4-Aminoquinazolines," J. Heterocyclic Chem. 43:913-916 (2006).
Rasmussen et al., "The Electrophilic Addition of Chlorsulfonyl Isocyanate to Ketones. A Convenient Synthesis of Oxazines, Oxathiazines, and Dracils," J. Org. Chem. 35:2114-2115 (1978).
Reddy et al., "An Efficient Synthesis of 3,4-Dihydro-4-Imino-2(1H)-Quinazolinones," Synthetic Commun. 18:525-530 (1988).
Robinson et al., "Sulfonamide Ligands Attained through Opening of Saccharin Derivatives," Eur. J. Org. Chem. 19:4483-4489 (2006).
Rodriguez-Hahn et al., "A Study of the Thorpe-Ziegler Reaction in Very Mild Conditions," Synthetic Commun. 14:967-972 (1984).
Roy et al., "Auto-Redox Reaction: Tin(H) Chloride-Mediated One-Step Reductive Cyclization Leading to the Synthesis of Novel Biheterocyclic 5,6-Dihydro-quinazoline[4,3-b]quinazolin-8-ones with Three-Point Diversity," J. Org. Chem. 71:382-385 (2006).
Saudek et al., "A Preliminary Trial of the Programmable Implantable Medication System for Insulin Delivery," N. Engl. J Med. 321:574-579 (1989).
Seijas et al., "Microwave enhanced synthesis of 4-aminoquinazolines," Tetrahedron Lett. 41:2215-2217 (2000).
Sharma et al., "Synthesis and QSAR studies on 5-[2-(2-methylprop 1-enyl)-1H benzimidazol-1yl]-4,6-diphenyl-pyrimidin-2-(5H)-thione derivatives as antibacterial agents," Eur. J. Med. Chem. 41:833-840 (2006).
Silve et al., "Delineating a Ca2+ Binding Pocket within the Venus Plytrap Module of the Human Calcium Sensing Receptor," The Journal of Biological Chemistry, Nov. 2005, vol. 280, pp. 37917-37923.
Tripathi et al., "Reaction of Flavanones with Chlorosulphonyl Isocyanate," Indian J. Chem. Sect. B 26B:1082-1083 (1987).
Uehling et al., "Biarylaniline Phenethanolamines as Potent and Selective β3 Adrenergic Receptor Agonists" J. Med. Chem. 49:2758-2771 (2006).

Verma et al., "Osmotically Controlled Oral Drug Delivery," Drug Dev. Ind. Pharm. 26:695-708 (2000).

Verschoyle et al., "Pharmacokinetics of Isotretinoin (ISO) in Rats Following Oral Dosing or Aerosol Inhalation," British J. Cancer 80, Suppl 2:96 Abstract No. P269 (1999).

Vippagunta et al., "Crystailine solids," Adv. Drug Deliv. Rev. 48:3-26 (2001).

Wilson et al., "Synthesis of 5-denzalhavin derivatives and their activation of p53 in cells," Bioorg. & Med. Chem. 15:77-86 (2007).

Wilson. "Traceless Solid-Phase Synthesis of 2,4-Diaminoquinazolines," Org. Lett. 3:585-588 (2000).

Winkler et al., "Synthesis and microbial transformation of β-amino nitriles," Tetrahedron 61:4249-4260 (2005).

Wright, "The Reaction of Sulfamide with α- and β-Diletones. The Preparation of 1,2,5-thialiazole 1,1-Dioxides and 1,2,6-Thiadiazine 1,1-Dioxides," J. Org. Chem. 29:1905-1909 (1964).

Xu et al., "Oxidative cyclization of N-alkyl-o-methylarenesulfonamides to biologically important saccharin derivatives," Tetrahedron 62:7902-7910 (2006).

Xu et al., "Purine and Pyrididine Nucleotides Inhibit a Noninactivating K1 Current and Depolnrize Adrenal Cortieal Cells through a G Protein-coupled Receptor," Molecular Pharmacology, 1999, vol. 55, pp. 364-376.

Yamada et al., "Discovery of Novel and Potent Small-Molecule Inhibitors of NO and Cytokine Production as Antisepsis Agents: Synthesis and Biological Activity of Alkl 6-(N-Substituted sulfamoyl)cyclohex-1-ene-1-carboxylate," J. Med. Chem. 48:7457-7467 (2005).

Yoshizawa et al., "Efficient solvent-free Thrope reaction," Green Chem. 4:68-70 (2002).

Zunszam et al., "Search for the pharmacophore in prazosin for Transport-P," Bioorg. & Med. Chem. 13:3681-3689 (2005).

Young, "International Search Report," 5 pages, based on International Application No. PCT/US2008/065650 (mailed Nov. 20, 2008).

Young, "Written Opinion of the International Searching Authority," 19 pages, based on International Application No. PCT/US2008/065650 (mailed Nov. 20, 2008).

Vakili, Office Action, U.S. Appl. No. 11/760,592, 13 pages (mailed Jan. 7, 2010).

Vakili, Office Action, U.S. Appl. No. 11/760,592, 19 pages (mailed Oct. 7, 2010).

Willis, Office Action, U.S. Appl. No. 11/836,074, 7 pages (mailed Nov. 8, 2010).

Willis, Office Action, U.S. Appl. No. 11/836,074, 18 pages (mailed Jun. 10, 2009).

Willis, Office Action, U.S. Appl. No. 11/836,074, 18 pages (mailed Jun. 23, 2008).

Willis, Office Action, U.S. Appl. No. 11/836,074, 11 pages (mailed Sep. 29, 2009).

Willis, Office Action, U.S. Appl. No. 11/836,074, 13 pages (mailed Oct. 30, 2008).

Cheng et al., "Potential Purine Antagonists. XII. Synthesis of 1-Alkyl(aryl)-4,6-disubstituted Pyrazolo[3,4-d]pyrimidines." Journal of Organic Chemistry, Jun. 1, 1958 23(1):852-861.

Supplementary European Search Report based on EP Application No. 08770047, mailed on Sep. 14, 2009.

European Search Opinion based on EP Application No. 08770047, mailed on Sep. 14, 2009.

Campillo et al., "A study of peculiar tautomerism of pyrido[2,3-c][1,2,6]thiadiazine 2,2-dioxide system," J. Mol. Struct. 678:83-89 (2004).

Chien et al., "Nucleosides XI. Synthesis and Antiviral Evaluation of 5'-Alkylthio-5'-deoxy Quinazolinone Nucleoside Derivatives as S-Adenosyl-L-homocysteine Analogs," Chem. Pharm. Bull. 52(12):1422-1426 (2004).

Corbett et al., "Novel 2,2-Dioxide-4,4-disubstituted-1,3-H-2,1,3-benzothiadiazines as Non-Nucleside Reverse Transcriptase Inhibitors," Bioorg. Med. Chem. Lett. 10:193-195 (2000).

Dominguez et al., "Efficient synthesis of 4,4-disubstituted-3,4-dihydro-1H-2,1,3-benzothiadiazine 2,2-dioxides," Tetrahedron Lett. 41:9825-9828 (2000).

Garcia-Munoz et al., "Synthesis of Purine-Like Ring Systems Derived From 1,2,6-Thiadiazine 1,1-Dioxide," J. Heterocyclic Chem. 13:793-796 (1976).

Goya and Martinez, "Synthesis and Cytostatic Screening of an $SO_2$ Analogue of Doridosine," Arch. Pharm. (Weinheim) 321:99-101 (1988).

Goya et al., "Fused 1,2,6-Thiadiazines: Tetrahydrobenzo[b]thieno[2,3-c][1,2,6]thisdiazine 2,2-Dioxides," Arch. Pharm. (Weinheim) 317:777-781 (1984).

Goya et al., CAPLUS Accession No. 1987:18628, 2 pages, abstract of ES 531159 A1 (1985).

Meyer, Jr. and Skibo, "Synthesis of Fused [1,2,6]Thiadiazine 1,1-Dioxides as Potential Transition-State Analogue Inhibitors of Xanthine Oxidase and Guanase," J. Med. Chem. 22(8):944-948 (1979).

Reddy et al., "An Efficient Synthesis of 3,4-Dihydro-4-Imino-2(1H)-Quinazolinones," Synth. Commun. 18(5):525-530 (1988).

Rosowsky and Modest, "Quinazolines. III. Synthesis of 1,3-Diaminobenzo[f]quinazoline and Related Compounds," J. Org. Chem. 31:2607-2613 (1966).

Srivastava et al., "Solid Phase Synthesis of Structurally Diverse Pyrimido[4,5-d] Pyrimidines for the Potential Use in Combinatorial Chemistry," Bioorg. Med. Chem. Lett. 9:965-966 (1999).

| | | | | | | | | |
|---|---|---|---|---|---|---|---|---|
| exon_4 | 2000188 | 1457 | rs28374389 | N.D. | | nonsynonymous | G | Val [V] | 1 | 486 |
| | 2000300 | 1345 | | N.D. | | contig reference | A | Ile [I] | 1 | 486 |
| | | | rs9439751 | N.D. | | synonymous | A | Leu [L] | 3 | 448 |
| | 2000315 | 1330 | | N.D. | | contig reference | G | Leu [L] | 3 | 448 |
| | | | rs35775756 | N.D. | | synonymous | T | Asp [D] | 3 | 443 |
| | | | | N.D. | | contig reference | C | Asp [D] | 3 | 443 |
| exon_3 | 2005063 | 1244 | rs35605435 | N.D. | | nonsynonymous | A | Ile [I] | 1 | 415 |
| | 2005356 | 951 | rs34545913 | N.D. | | contig reference | G | Val [V] | 1 | 415 |
| | | | | N.D. | | nonsynonymous | C | Pro [P] | 2 | 317 |
| | 2005357 | 950 | rs34447754 | N.D. | | contig reference | G | Arg [R] | 2 | 317 |
| | | | | N.D. | | nonsynonymous | G | Gly [G] | 1 | 317 |
| | | | | N.D. | | contig reference | C | Arg [R] | 1 | 317 |
| | 2005424 | 883 | rs28470550 | N.D. | Yes | synonymous | G | Thr [T] | 3 | 294 |
| | | | | N.D. | Yes | contig reference | T | Thr [T] | 3 | 294 |
| | 2005735 | 572 | rs35874116 | N.D. | | nonsynonymous | G | Val [V] | 1 | 191 |
| | | | | N.D. | | contig reference | A | Ile [I] | 1 | 191 |
| exon_1 | 2010471 | 27 | rs9701796 | N.D. | No | nonsynonymous | G | Cys [C] | 2 | 9 |
| | | | | N.D. | No | contig reference | C | Ser [S] | 2 | 9 |
| exon_1 | 2010496 | 2 | | | | start codon | | | | 1 |

FIG. 2B

METHODS OF ENHANCING SWEET TASTE OF COMPOSITIONS USING SUBSTITUTED THIENO{2,3-D}PYRIMIDINES

CROSS-REFERENCE TO RELATED APPLICATIONS

This application is a continuation of U.S. patent application Ser. No. 11/836,074, filed Aug. 8, 2007, which is a continuation-in-part of U.S. patent application Ser. No. 11/760,592, filed Jun. 8, 2007. This application is also related to U.S. application Ser. No. 12/663,634, filed Dec. 8, 2009, which is a U.S. National Stage application of International Application No. PCT/US2008/065650, filed on Jun. 3, 2008 and published as WO 2008/154221, which claims priority to U.S. patent application Ser. No. 11/760,592, filed Jun. 8, 2007; U.S. patent application Ser. No. 11/836,074, filed Aug. 8, 2007; and U.S. Patent Provisional Application Ser. No. 61/027,410, filed Feb. 8, 2008. The contents of the above applications are hereby incorporated by reference in their entireties for all purposes.

BACKGROUND OF THE INVENTION

The taste system provides sensory information about the chemical composition of the external world. Taste transduction is one of the most sophisticated forms of chemical-triggered sensation in animals. Signaling of taste is found throughout the animal kingdom, from simple metazoans to the most complex of vertebrates. Sensations associated with taste are thought to involve distinct signaling pathways mediated by receptors, i.e., metabotropic or ionotropic receptors. Cells which express taste receptors, when exposed to certain chemical stimuli, elicit taste sensation by depolarizing to generate an action potential, which is believed to trigger the sensation. This event is believed to trigger the release of neurotransmitters at gustatory afferent neuron synapses, thereby initiating signaling along neuronal pathways that mediate taste perception.

As such, taste receptors specifically recognize molecules that elicit specific taste sensation. These molecules are also referred to herein as "tastants." Many taste receptors belong to the 7-transmembrane receptor superfamily, which are also known as G protein-coupled receptors (GPCRs). Other tastes are believed to be mediated by channel proteins. G protein-coupled receptors control many physiological functions, such as endocrine function, exocrine function, heart rate, lipolysis, carbohydrate metabolism, and transmembrane signaling.

For example, family C of G-protein coupled receptors (GPCRs) from humans comprises eight metabotropic glutamate (mGlu(1-8)) receptors, two heterodimeric gamma-aminobutyric acid(B) (GABA(B)) receptors, a calcium-sensing receptor (CaR), three taste (T1R) receptors, a promiscuous L-alpha-amino acid receptor (GPRC6A), and five orphan receptors. The family C GPCRs are characterized by a large amino-terminal domain, which binds the endogenous orthosteric agonists. Additionally, allosteric modulators which bind to the seven transmembrane domains of the receptors have also been reported.

In general, upon ligand binding to a GPCR, the receptor presumably undergoes a conformational change leading to activation of a G protein. G proteins are comprised of three subunits: a guanyl nucleotide binding α-subunit, a β-subunit, and a γ-subunit. G proteins cycle between two forms, depending on whether GDP or GTP is bound to the α-subunit. When GDP is bound, the G protein exists as a heterotrimer: the $G_{\alpha\beta\gamma}$ complex. When GTP is bound, the α-subunit dissociates from the heterotrimer, leaving a $G_{\beta\gamma}$ complex. When a $G_{\alpha\beta\gamma}$ complex operatively associates with an activated G protein-coupled receptor in a cell membrane, the rate of exchange of GTP for bound GDP is increased and the rate of dissociation of the bound $G_\alpha$ subunit from the $G_{\alpha\beta\gamma}$ complex increases. The free $G_\alpha$ subunit and $G_{\beta\gamma}$ complex are thus capable of transmitting a signal to downstream elements of a variety of signal transduction pathways. These events form the basis for a multiplicity of different cell signaling phenomena, including for example the signaling phenomena that are identified as neurological sensory perceptions such as taste and/or smell.

Mammals are believed to have five basic taste modalities: sweet, bitter, sour, salty, and umami (the taste of monosodium glutamate). Numerous physiological studies in animals have shown that taste receptor cells may selectively respond to different chemical stimuli. In mammals, taste receptor cells are assembled into taste buds that are distributed into different papillae in the tongue epithelium. Circumvallate papillae, found at the very back of the tongue, contain hundreds to thousands of taste buds. By contrast, foliate papillae, localized to the posterior lateral edge of the tongue, contain dozens to hundreds of taste buds. Further, fungiform papillae, located at the front of the tongue, contain only a single or a few taste buds.

Each taste bud, depending on the species, contains 50-150 cells, including precursor cells, support cells, and taste receptor cells. Receptor cells are innervated at their base by afferent nerve endings that transmit information to the taste centers of the cortex through synapses in the brain stem and thalamus. Elucidating the mechanisms of taste cell signaling and information processing is important to understanding the function, regulation, and perception of the sense of taste.

The gustatory system has been selected during evolution to detect nutritive and beneficial compounds as well as harmful or toxic substances. Outside the tongue, expression of $G\alpha_{gust}$ has also been localized to gastric and pancreatic cells, suggesting that a taste-sensing mechanism may also exist in the gastrointestinal (GI) tract. Expression of taste receptors has also been found in the lining of stomach and intestine, suggesting that taste receptors may play a role in molecular sensing of therapeutic entities and toxins.

Complete or partial sequences of numerous human and other eukaryotic chemosensory receptors are currently known. Within the last several years, a number of groups including the present assignee Senomyx, Inc. have reported the identification and cloning of genes from two GPCR families that are involved in taste modulation and have obtained experimental results related to the understanding of taste biology. These results indicate that bitter, sweet and amino acid taste, also referred as umami taste, are triggered by activation of two types of specific receptors located at the surface of taste receptor cells (TRCs) on the tongue i.e., T2Rs and T1Rs. It is currently believed that at least 26 to 33 genes encode functional receptors (T2Rs) for bitter tasting substances in human and rodent respectively.

By contrast there are only 3 T1Rs, T1R1, T1R2 and T1R3, which are involved in umami and sweet taste. Structurally, the T1R and T2R receptors possess the hallmark of G protein-coupled receptors (GPCRs), i.e., 7 transmembrane domains flanked by small extracellular and intracellular amino- and carboxyl-termini respectively.

T2Rs have been cloned from different mammals including rats, mice and humans. T2Rs comprise a novel family of human and rodent G protein-coupled receptors that are expressed in subsets of taste receptor cells of the tongue and palate epithelia. These taste receptors are organized in clusters in taste cells and are genetically linked to loci that influence bitter taste. The fact that T2Rs modulate bitter taste has been demonstrated in cell-based assays. For example, mT2R-5, hT2R-4 and mT2R-8 have been shown to be activated by bitter molecules in in vitro gustducin assays, providing experimental proof that T2Rs function as bitter taste receptors. See also T2Rs disclosed in U.S. Pat. No. 7,105,650.

T1R family members in general include T1R1, T1R2, and T1R3, e.g., rT1R3, mT1R3, hT1R3, rT1R2, mT1R2, hT1R2, and rT1R1, mT1R1 and hT1R1. It is known that the three T1R gene members T1R1, T1R2 and T1R3 form functional heterodimers that specifically recognize sweeteners and amino acids. It is generally believed that T1R2/T1R3 combination recognizes natural and artificial sweeteners while the T1R1/T1R3 combination recognizes several L-amino acids and monosodium glutamate (MSG), respectively. For example, co-expression of T1R1 and T1R3 in recombinant host cells results in a hetero-oligomeric taste receptor that responds to umami taste stimuli. Umami taste stimuli include by way of example monosodium glutamate and other molecules that elicit a "savory" taste sensation. By contrast, co-expression of T1R2 and T1R3 in recombinant host cells results in a hetero-oligomeric sweet taste receptor that responds to both naturally occurring and artificial sweeteners.

There is a need in the art to develop various ways of identifying compounds or other entities suitable for modifying receptors and their ligands associated with chemosensory or chemosensory related sensation or reaction. In addition, there is a need in the art for compounds or other entities with such characteristics.

BRIEF SUMMARY OF THE INVENTION

The present invention is based, at least in part, on the discovery that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Accordingly, the present invention provides screening methods for identifying modifiers of chemosensory receptors and their ligands as well as modifiers capable of modulating chemosensory receptors and their ligands.

In one embodiment, the present invention provides a method of screening for a candidate of a chemosensory receptor ligand modifier. The method comprises determining whether a test entity is suitable to interact with a chemosensory receptor via an interacting site within the Venus flytrap domain of the chemosensory receptor.

In another embodiment, the present invention provides a method of screening for a candidate of a chemosensory receptor ligand modifier. The method comprises determining whether a test entity is suitable to interact with a chemosensory receptor via a first interacting site within the Venus flytrap domain of the chemosensory receptor, wherein the first interacting site is identified in light of a second interacting site identified based on the interaction between a chemosensory receptor ligand and the chemosensory receptor.

In yet another embodiment, the present invention provides a method of screening for a candidate of a chemosensory receptor modifier. The method comprises determining whether a test entity is suitable to interact with a chemosensory receptor via an interacting site within the Venus flytrap domain of the chemosensory receptor, wherein the interacting site includes an interacting residue selected from the group consisting of N143, S144, I167, S40, S144, S165, Y103, D142, P277, K65, R383, D307, E302, D278, P185, T184, T326, E302, V384, A305, I325, I306, D307, E382, I279, I67, V66, V309, S303, T242, F103, Q328, and S168 of T1R2 and a combination thereof, wherein a test entity suitable to interact with the interacting site of the chemosensory receptor is indicative of a candidate of a chemosensory receptor modifier.

In yet another embodiment, the present invention provides a method of modulating the activity of a chemosensory receptor ligand. The method comprises contacting a chemosensory receptor ligand modifier with a cell containing T1R2 Venus flytrap domain in the presence of a chemosensory receptor ligand, wherein the chemosensory receptor ligand modifier interacts with an interacting site of the chemosensory receptor.

In still another embodiment, the present invention provides a chemosensory receptor ligand modifier, wherein in the presence of a chemosensory receptor ligand it interacts with T1R2 Venus flytrap domain via at least three interacting residues selected from the group consisting of N143, S144, I167, S40, S144, S165, Y103, D142, P277, K65, R383, D307, E302, D278, P185, T184, T326, E302, V384, A305, I325, I306, E382, I279, I67, V66, V309, S303, T242, F103, Q328, and S168 of T1R2.

In still another embodiment, the present invention provides a chemosensory receptor ligand enhancer having structural Formula (I)

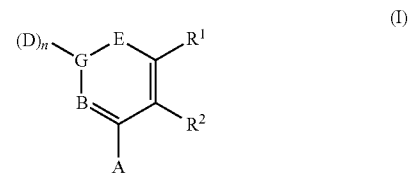

or a salt, hydrate, solvate or N-oxide thereof wherein:
G forms a single bond with either D or E and a double bond with the other of D or E;
$R^1$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —$NO_2$, —$OR^3$, —$S(O)_aR^3$, —$NR^3R^4$, —$CONR^3R^4$, —$CO_2R^3$, —$NR^3CO_2R^4$, —$NR^3CONR^4R^5$, —$NR^3CSNR^4R^5$ or —$NR^3C(=NH)NR^4R^5$, —$SO_2NR^2R^3$, —$NR^2SO_2R^3$, —$NR^2SO_2NR^3R^4$, —$B(OR^2)(OR^3)$, —$P(O)(OR^2)(OR^3)$ or —$P(O)(R^2)(OR^3)$;
$R^2$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —$NO_2$, —$OR^6$, —$S(O)_bR^6$, —$NR^6R^7$, —$CONR^6R^7$, —$CO_2R^6$, —$NR^6CO_2R^7$, —$NR^6CONR^7R^8$, —$NR^6CSNR^7R^8$ or —$NR^6C(=NH)NR^7R^8$, —$SO_2NR^5R^6$, —$NR^5SO_2R^6$, —$NR^5SO_2NR^6R^7$, —$B(OR^5)(OR^6)$, —$P(O)(OR^5)(OR^6)$, —$P(O)(R^5)(OR^6)$ or alternatively, $R^1$ and $R^2$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

with the proviso that $R^1$ and $R^2$ are not both hydrogen;

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^9$, —S(O)$_c$R$^9$, —NR$^9$R$^{10}$, —NOR$^9$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$;

B is —N— or —C(R$^{12}$)—;

$R^{12}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{13}$R$^{14}$, —CN, —OR$^{13}$, —S(O)$_d$R$^{13}$, —CO$_2$R$^{13}$ or —CONR$^{13}$R$^{14}$;

G is —C— or —S(O)$_2$—;

provided that when G is —S(O)$_2$—, G forms a single bond with E;

D is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl, substituted heteroarylalkyl, —OR$^{15}$, —NOR$^{15}$, —S(O)$_e$R$^{15}$, —NR$^{15}$R$^{16}$, —NCN, —CO$_2$R$^{15}$, —CONR$^{15}$R$^{16}$ when the bond between D and G is a single bond;

D is =O, =S, =N—OR$^{15}$, =NHNHR$^{15}$ when G form a double bond with D;

n is 0 when G is —S(O)$_2$— and n is 1 when G is —C—;

E is —NR$^{17}$—, —N— or —C(R$^{18}$)—;

provided that E is —NR$^{17}$— only when G forms a single bond with E;

$R^{17}$ is alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl or —CO$_2$R$^{19}$;

$R^{18}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{20}$R$^{21}$; —CN, —OR$^{20}$, —S(O)$_f$R$^{20}$, —CO$_2$R$^{20}$ or —CONR$^{20}$R$^{21}$;

a, b, c, d, e and f are independently 0, 1 or 2; and $R^3$-$R^{11}$, $R^{13}$-$R^{16}$, $R^{18}$, $R^{20}$ and $R^{21}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^3$ and $R^4$, $R^4$ and $R^5$, $R^6$ and $R^7$, $R^7$ and $R^8$, $R^9$ and $R^{10}$, $R^{10}$ and $R^{11}$, $R^{13}$ and $R^{14}$, $R^{15}$ and $R^{16}$ and $R^{20}$ and $R^{21}$ together with the atoms to which they are bonded form a cycloheteroalkyl or substituted cycloheteroalkyl ring.

In still another embodiment, the present invention provides chemosensory receptor ligand enhancer having structural Formula (XVI):

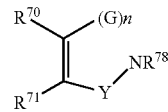

or a salt, solvate, hydrate or N-oxide thereof wherein:

each G is independently —C(R$^{77}$)(R$^{78}$)—, —C(O)—, —NR$^{77}$— or —S(O)$_2$—;

n is 1, 2 or 3;

provided that when n is greater than one then only one G is —C(O)—, —C(S), —S(O)$_2$— or —NR$^{77}$—;

Y is —C(O)—, —C(S) or —S(O)$_2$—;

$R^{70}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{72}$, —S(O)$_a$R$^{72}$, —NR$^{72}$R$^{73}$, —CONR$^{72}$R$^{73}$, —CO$_2$R$^{72}$, —NR$^{72}$CO$_2$R$^{73}$, —NR$^{72}$CONR$^{73}$R$^{74}$, —NR$^{72}$CSNR$^{73}$R$^{74}$ or —NR$^{72}$C(=NH)NR$^{73}$R$^{74}$, —SO$_2$NR$^{72}$R$^{73}$, —NR$^{72}$SO$_2$R$^{73}$, —NR$^{72}$SO$_2$NR$^{73}$R$^{74}$, —B(OR$^{72}$)(OR$^{73}$), —P(O)(OR$^{72}$)(OR$^{73}$) or —P(O)(R$^{72}$)(OR$^{73}$);

$R^{71}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{74}$, —S(O)$_b$R$^{74}$, —NR$^{74}$R$^{75}$, —CONR$^{74}$R$^{75}$, —CO$_2$R$^{74}$, —NR$^{74}$CO$_2$R$^{75}$, —NR$^{74}$CONR$^{75}$R$^{76}$, —NR$^{74}$CSNR$^{75}$R$^{76}$ or —NR$^{74}$C(=NH)NR$^{75}$R$^{76}$, —SO$_2$NR$^{74}$R$^{75}$, —NR$^{74}$SO$_2$R$^{75}$, —NR$^{74}$SO$_2$NR$^{75}$R$^{76}$, —B(OR$^{74}$)(OR$^{75}$), —P(O)(OR$^{74}$)(OR$^{75}$), —P(O)(R$^{74}$)(OR$^{75}$) or alternatively, $R^{71}$ and $R^{72}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

a and b are independently 0, 1 or 2;

$R^{72}$-$R^{76}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{72}$ and $R^{73}$, $R^{73}$ and $R^{74}$, $R^{74}$ and $R^{75}$ and $R^{75}$ and $R^{76}$ together with the atoms to which they are bonded form a cycloheteroalkyl or substituted cycloheteroalkyl ring; and $R^{77}$-$R^{78}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{77}$ and $R^{78}$, together with the atoms to which they are bonded form a cycloalkyl, substituted cycloalkyl, cycloheteroalkyl or substituted cycloheteroalkyl ring.

In still another embodiment, the present invention provides chemosensory receptor ligand enhancer and having structural Formula (XXII):

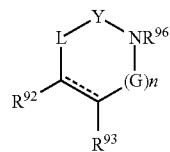
(XXII)

or a salt, solvate, hydrate or N-oxide thereof wherein:
each G is independently —C($R^{94}$)($R^{95}$)—, —C(O)—, —$NR^{94}$— or —S(O)$_2$—;
n is 1, 2 or 3;
provided that when n is greater than one then only one G is —C(O)—, —S(O)$_2$— or —$NR^{94}$—;
Y is —C(O)—, —C(S)— or —S(O)$_2$—;
L is —C($R^{104}$)($R^{105}$)—, —O—, or —$NR^{104}$—;
$R^{92}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —$OR^{98}$, —S(O)$_y R^{98}$, —$NR^{98}R^{99}$, —$CONR^{98}R^{99}$, —$CO_2 R^{98}$, —$NR^{98}CO_2 R^{99}$, —$NR^{98}CONR^{99}R^{100}$, —$NR^{98}CSNR^{99}R^{100}$ or —$NR^{98}C(=NH)NR^{99}R^{100}$, —$SO_2 NR^{98}R^{99}$, —$NR^{98}SO_2 R^{99}$, —$NR^{98}SO_2 NR^{99}R^{100}$, —B($OR^{98}$)($OR^{99}$), —P(O)($OR^{98}$)($OR^{99}$) or —P(O)($R^{98}$)($OR^{99}$);
$R^{93}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —$OR^{100}$, —S(O)$_z R^{101}$, —$NR^{101}R^{102}$, —$CONR^{101}R^{102}$, —$CO_2 R^{101}$, —$NR^{101}CO_2 R^{102}$, —$NR^{101}CONR^{102}R^{103}$, —$NR^{101}CSNR^{102}R^{103}$, or —$NR^{101}C(=NH)NR^{102}R^{103}$, —$SO_2 NR^{101}R^{102}$, —$NR^{101}SO_2 R^{102}$, —$NR^{101}SO_2 NR^{102}R^{103}$, —B($OR^{101}$)($OR^{102}$), —P(O)($OR^{101}$)($OR^{102}$), —P(O)($R^{101}$)($OR^{102}$) or alternatively, $R^{92}$ and $R^{93}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;
x and y are independently, 0, 1 or 2;
$R^{98}$-$R^{103}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{98}$ and $R^{99}$, $R^{99}$ and $R^{100}$, $R^{101}$ and $R^{102}$ and $R^{101}$ and $R^{102}$ together with the atoms to which they are bonded form a cycloalkyl, substituted cycloalkyl, cycloheteroalkyl or substituted cycloheteroalkyl ring;
$R^{94}$-$R^{95}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{94}$ and $R^{95}$, together with the atoms to which they are bonded form a cycloalkyl, substituted cycloalkyl, cycloheteroalkyl or substituted cycloheteroalkyl ring;
$R^{96}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; and
$R^{104}$-$R^{105}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, $R^{104}$ and $R^{105}$, together with the atoms to which they are bonded form a cycloalkyl, substituted cycloalkyl, cycloheteroalkyl or substituted cycloheteroalkyl ring.

DETAILED DESCRIPTION OF THE INVENTION

Figure 1:
FIG. 1 contains exemplary human T1R1 polymorphic variations.
Figure 2A:
FIG. 2 contains exemplary human T1R2 polymorphic variations.
Figure 3:
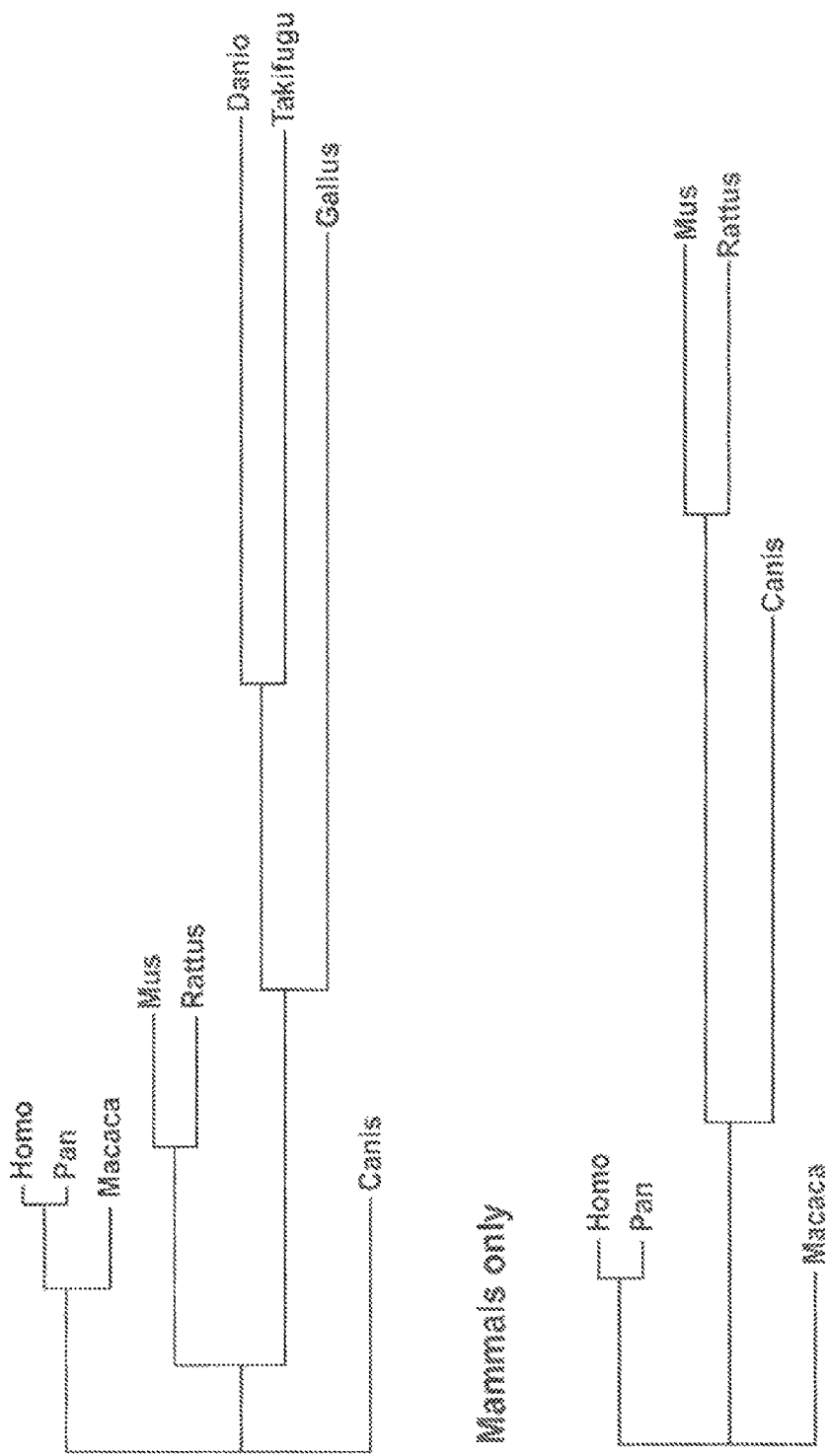
FIG. 3 shows the dendograms for the sequence alignments of T1R1.
Figure 4:
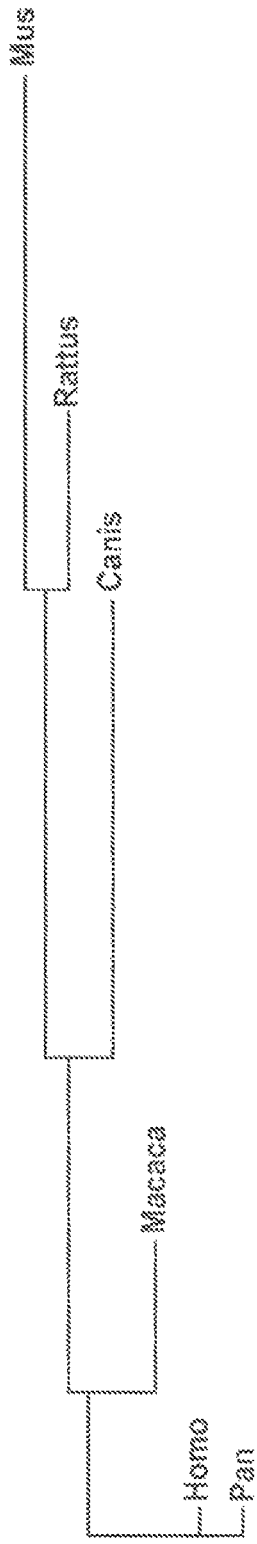
FIG. 4 shows the dendograms for the sequence alignments of T1R2.
Figure 5:
FIG. 5 shows exemplary interacting spaces for sucralose and one of the compound of the present invention. Protein is represented as a ribbon diagram.
Figure 6:
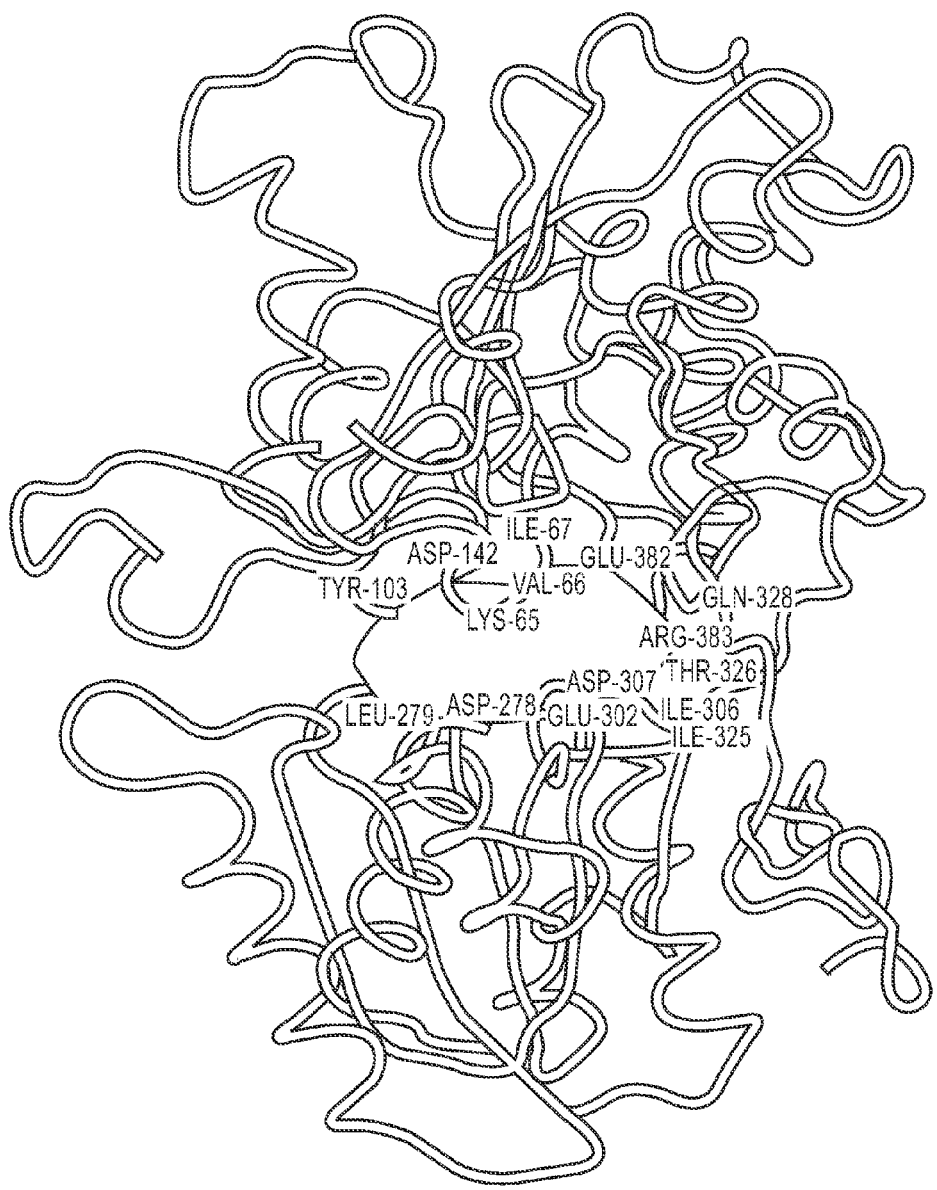
FIG. 6 shows exemplary interacting spaces and residues for sucralose and one of the compounds of the present invention. Protein is represented as a ribbon diagram.
Figure 7A:
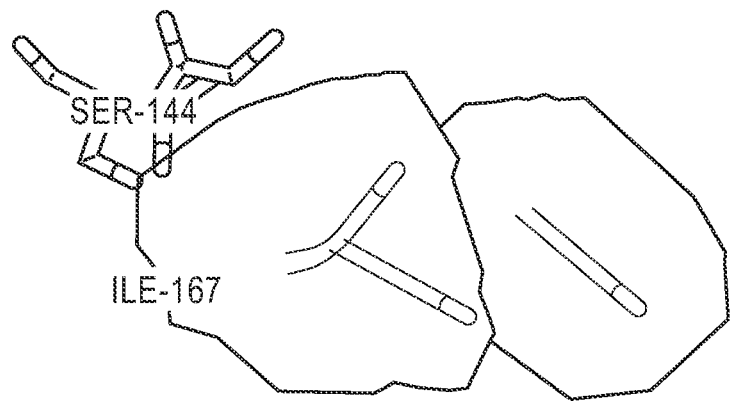
FIG. 7 shows exemplary interacting spaces and residues associated with the hinge region for sucralose and one of the compounds of the present invention.
Figure 7B:
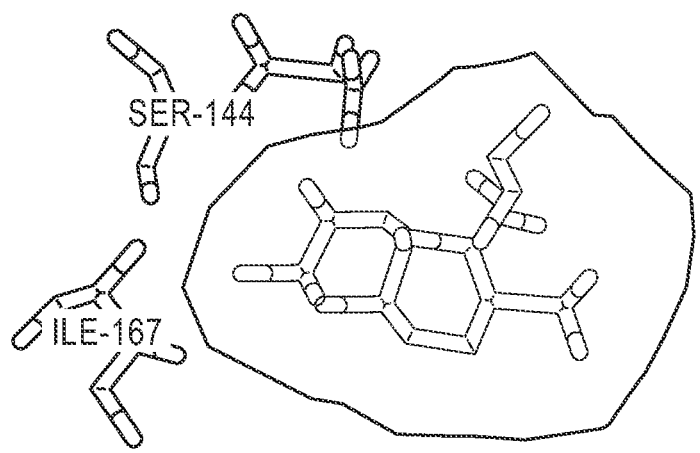
Figure 8A:
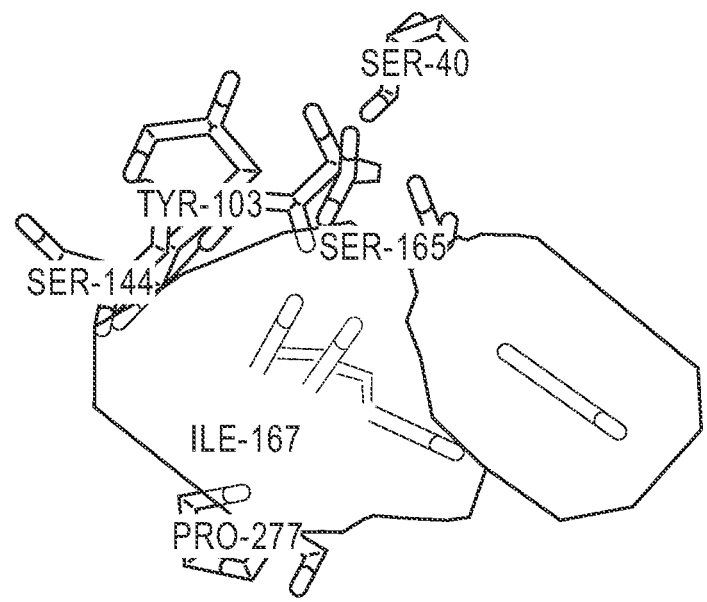
FIG. 8 shows exemplary partial interacting surfaces and interacting residues proximal to the hinge region for sucrose and sucralose.
Figure 8B:
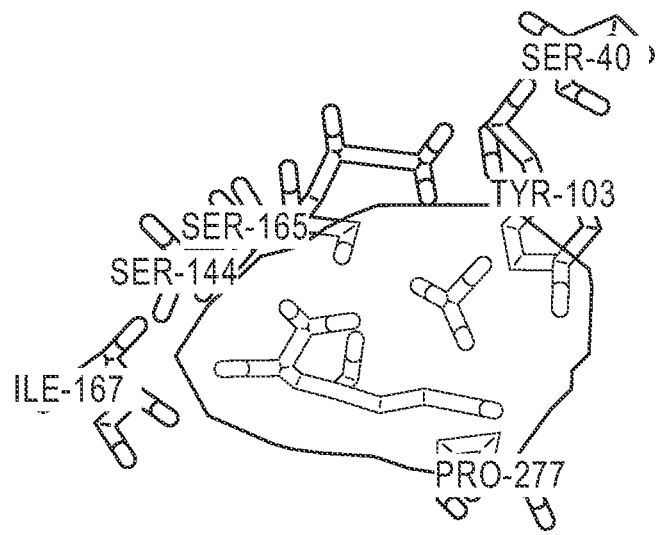
Figure 9B:
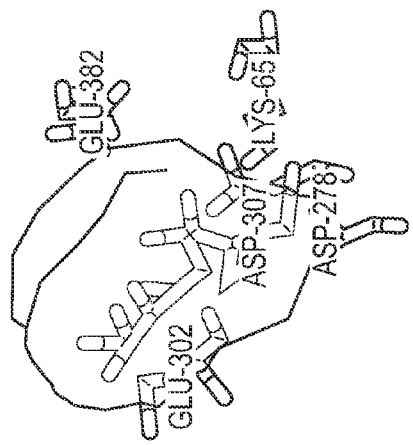
FIG. 9 shows exemplary interacting spaces and residues associated with the lobes for sucralose and one of the compounds of the present invention.
Figure 9C:
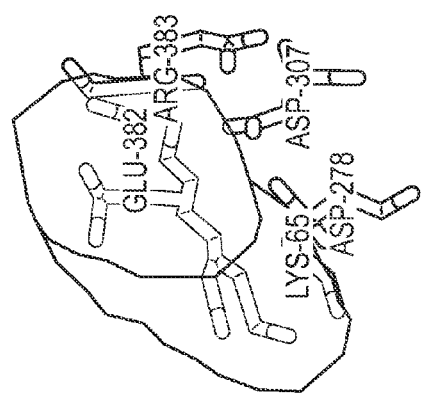
Figure 9A:
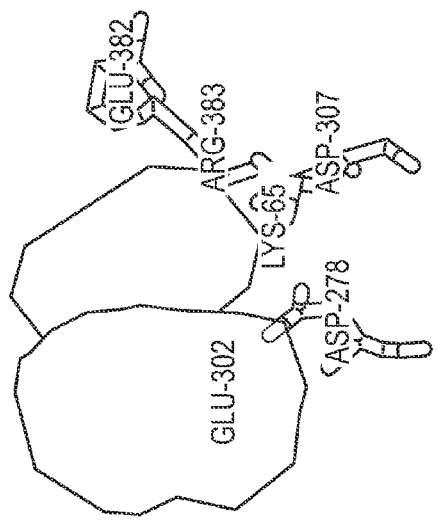
Figure 10A:
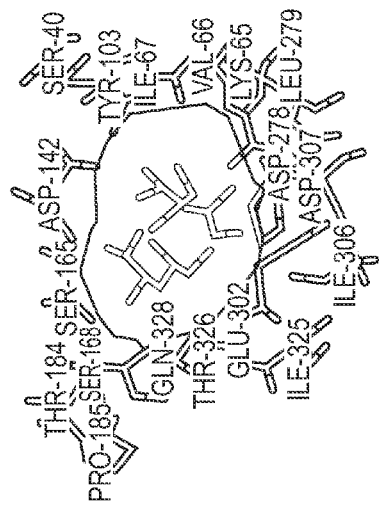
FIG. 10 shows exemplary interacting spaces and residues associated with an interacting site for sucralose and one of the compounds of the present invention.
Figure 10B:
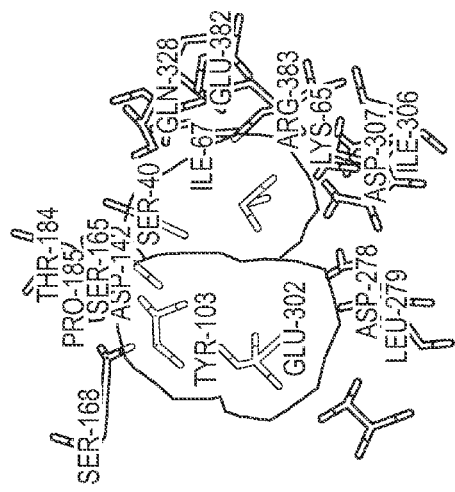
Figure 10C:
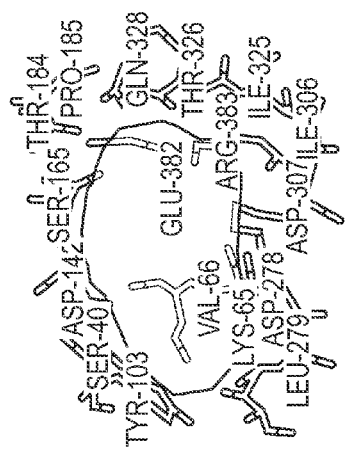

Prior to specifically describing the invention, the following definitions are provided.
The term "T1R" family includes polymorphic variants, alleles, mutants, and
homologs that: (1) have about 30-40% amino acid sequence identity, more specifically about 40, 50, 60, 70, 75, 80, 85, 90, 95, 96, 97, 98, or 99% amino acid sequence identity to the T1Rs known or disclosed, e.g., in patent application U.S. Ser. No. 10/179,373 filed on Jun. 26, 2002, Ser. No. 09/799,629 filed on Apr. 5, 2001 and U.S. Ser. No. 10/035,045 filed on Jan. 3, 2002, over a window of about 25 amino acids, optimally 50-100 amino acids; (2) specifically bind to antibodies raised against an immunogen comprising an amino acid sequence selected from the group consisting of the T1R sequences disclosed infra, and conservatively modified variants thereof; (3) specifically hybridize (with a size of at least about 100, optionally at least about 500-1000 nucleotides) under stringent hybridization conditions to a sequence selected from the group consisting of the T1R DNA sequences disclosed infra, and conservatively modified variants thereof; (4) comprise a sequence at least about 40% identical to an amino acid sequence selected from the group consisting of the T1R amino acid sequences disclosed infra or (5) are amplified by primers that specifically hybridize under stringent hybridization conditions to the described T1R sequences.

In particular, these "T1Rs" include taste receptor GPCRs referred to as hT1R1, hT1R2, hT1R3, rT1R1, rT1R2, rT1R3, mT1R1, mT1R2, and mT1R3 having the nucleic acid sequences and amino acid sequences known or disclosed, e.g., in U.S. Ser. No. 10/179,373 filed on Jun. 26, 2002, U.S. Ser. No. 09/799,629 filed on Apr. 5, 2001 and U.S. Ser. No. 10/035,045 filed on Jan. 3, 2002, and variants, alleles, mutants, orthologs and chimeras thereof which specifically bind and/or respond to sweet, umami, or any other chemosensory related ligands including activators, inhibitors and enhancers. Also T1Rs include taste receptor GPCRs expressed in humans or other mammals, e.g., cells associated with taste and/or part of gastrointestinal system including without any limitation, esophagus, stomach, intestine (small and large), colon, liver, biliary tract, pancreas, gallbladder, etc. Also, T1R polypeptides include chimeric sequences derived from portions of a particular T1R polypeptide such as T1R1, T1R2 or T1R3 of different species or by combining portions of different T1Rs wherein such chimeric T1R sequences are combined to produce a functional sweet or umami taste receptor. For example chimeric T1Rs may comprise the extracellular region of one T1R, i.e., T1R1 or T1R2 and the transmembrane region of another T1R, either T1R1 or T1R2.

Topologically, certain chemosensory GPCRs have an "N-terminal domain;" "extracellular domains," a "transmembrane domain" comprising seven transmembrane regions, and corresponding cytoplasmic and extracellular loops, "cytoplasmic regions," and a "C-terminal region" (see, e.g., Hoon et al., *Cell* 96:541-51 (1999); Buck et al., *Cell* 65:175-87 (1991)). These regions can be structurally identified using methods known to those of skill in the art, such as sequence analysis programs that identify hydrophobic and hydrophilic domains (see, e.g., Stryer, Biochemistry, (3rd ed. 1988); see also any of a number of Internet based sequence analysis programs, such as those found at dot.imgen.bcm.tmc.edu). These regions are useful for making chimeric proteins and for in vitro assays of the invention, e.g., ligand binding assays.

"Extracellular domains" therefore refers to the domains of chemosensory receptors, e.g., T1R polypeptides that protrude from the cellular membrane and are exposed to the extracellular face of the cell. Such regions would include the "N-terminal domain" that is exposed to the extracellular face of the cell, as well as the extracellular loops of the transmembrane domain that are exposed to the extracellular face of the cell, i.e., the extracellular loops between transmembrane regions 2 and 3, transmembrane regions 4 and 5, and transmembrane regions 6 and 7. The "N-terminal domain" starts at the N-terminus and extends to a region close to the start of the transmembrane region. These extracellular regions are useful for in vitro ligand binding assays, both soluble and solid phase. In addition, transmembrane regions, described below, can also be involved in ligand binding, either in combination with the extracellular region or alone, and are therefore also useful for in vitro ligand binding assays.

"Transmembrane domain," which comprises the seven transmembrane "regions," refers to the domains of chemosensory receptors, e.g., T1R polypeptides that lie within the plasma membrane, and may also include the corresponding cytoplasmic (intracellular) and extracellular loops, also referred to as transmembrane "regions." The seven transmembrane regions and extracellular and cytoplasmic loops can be identified using standard methods, as described in Kyte et al., *J. Mol. Biol.* 157:105-32 (1982)), or in Stryer, supra.

"Cytoplasmic domains" refers to the domains of chemosensory receptors, e.g., T1R proteins that face the inside of the cell, e.g., the "C-terminal domain" and the intracellular loops of the transmembrane domain, e.g., the intracellular loops between transmembrane regions 1 and 2, transmembrane regions 3 and 4, and transmembrane regions 5 and 6. "C-terminal domain" refers to the region that spans from the end of the last transmembrane region to the C-terminus of the protein, and which is normally located within the cytoplasm.

The term "7-transmembrane receptor" means a polypeptide belonging to a superfamily of transmembrane proteins that have seven regions that span the plasma membrane seven times (thus, the seven regions are called "transmembrane" or "TM" domains TM I to TM VII).

The phrase "functional effects" or "activity" in the context of the disclosed assays for testing compounds that modulate a chemosensory receptor, e.g., enhance T1R family member mediated signal transduction such as sweet or umami receptor functional effects or activity includes the determination of any parameter that is indirectly or directly under the influence of the particular chemosensory receptor, e.g., functional, physical and chemical effects. It includes, without any limitation, ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

The term "determining the functional effect" or receptor "activity" means assays for a compound that increases or decreases a parameter that is indirectly or directly under the influence of a chemosensory receptor, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte chemosensory receptor, e.g., T1R gene expression; tissue culture cell chemosensory receptor, e.g., T1R expression; transcriptional activation of chemosensory receptor, e.g., T1R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modifiers" of chemosensory receptor, e.g., T1R proteins are used interchangeably to refer to inhibitory, activating, or modulating molecules identified using in vitro and in vivo assays for chemosensory signal transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize, or up regulate chemosensory signal transduction, e.g., agonists. Modifiers include compounds that, e.g., alter, directly or indirectly, the activity of a receptor or the interaction of a receptor with its ligands, e.g., receptor ligands and optionally bind to or interact with activators or inhibitors; G Proteins; kinases (e.g., homologs of rhodopsin kinase and beta adrenergic receptor kinases that are involved in deactivation and desensitization of a receptor); and arrestins, which also deactivate and desensitize receptors. Modifiers include genetically modified versions of chemosensory receptors, e.g., T1R family members, e.g., with altered activity, as well as naturally occurring and synthetic ligands, antagonists, agonists, small chemical molecules and the like. In the present invention this includes, without any limitation, sweet ligands (agonists or antagonists), umami ligands (agonists and antagonists), sweet enhancers and umami enhancers and sweet taste or umami taste inhibitors.

"Enhancer" herein refers to a compound that modulates (increases) the activation of a particular receptor, preferably the chemosensory, e.g., T1R2/T1R3 receptor or T1R1/T1R3 receptor but which by itself does not result in substantial activation of the particular receptor. Herein such enhancers will enhance the activation of a chemosensory receptor by its ligand. Typically the "enhancer" will be specific to a particular ligand, i.e., it will not enhance the activation of a chemosensory receptor by chemosensory ligands other than the particular chemosensory ligand or ligands closely related thereto.

"Putative enhancer" herein refers to a compound identified, e.g., in silico or not, as a potential enhancer using assays which are described herein but which enhancer activity has not yet been confirmed in vivo, e.g., in suitable taste tests.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The "extra-cellular domain" and chemosensory receptor, e.g., T1R receptor regions or compositions described herein also include "analogs," or "conservative variants" and "mimetics" ("peptidomimetics") with structures and activity that substantially correspond to the exemplary sequences. Thus, the terms "conservative variant" or "analog" or "mimetic" refer to a polypeptide which has a modified amino acid sequence, such that the change(s) do not substantially alter the polypeptide's (the conservative variant's) structure and/or activity, as defined herein. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or nonpolar, etc.) such that the substitutions of even critical amino acids does not substantially alter structure and/or activity.

More particularly, "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein.

For instance, the codons GCA, GCC, GCG and GCU all encode the amino acid alanine Thus, at every position where an alanine is specified by a codon, the codon can be altered to any of the corresponding codons described without altering the encoded polypeptide.

Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gln or glu; met/leu or tyr or ile; phe/met or leu or tyr; ser/thr; thr/ser; trp/tyr; tyr/trp or phe; val/ile or leu. An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (I); 5) Isoleucine (I), Leucine (L), Methionine (M), Valine (V); and 6) Phenylalanine (F), Tyrosine (Y), Tryptophan (W); (see also, e.g., Creighton, Proteins, W. H. Freeman and Company (1984); Schultz and Schimer, Principles of Protein Structure, Springer-Verlag (1979)). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations."

The terms "mimetic" and "peptidomimetic" refer to a synthetic chemical compound that has substantially the same structural and/or functional characteristics of the polypeptides, e.g., extra-cellular domain or any region therewith of T1R2 or T1R1. The mimetic can be either entirely composed of synthetic, non-natural analogs of amino acids, or may be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

As with polypeptides of the invention which are conservative variants, routine experimentation will determine whether a mimetic is within the scope of the invention, i.e., that its structure and/or function is not substantially altered. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(O)—CH$_2$— for —C(O)—NH—), aminomethylene —CH$_2$(NH)—, ethylene, olefin —CH=CH—, ether —CH$_2$O—, thioether —CH$_2$S—, tetrazole (CN$_4$), thiazole, retroamide, thioamide or ester (see, e.g., Spatola, Chemistry and Biochemistry of Amino Acids, Peptides and Proteins, Vol. 7, 267-357, Marcell Dekker, Peptide Backbone Modifications, NY (1983)). A polypeptide can also be characterized as a mimetic by containing all or some non-natural residues in place of naturally occurring amino acid residues; non-natural residues are well described in the scientific and patent literature.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms (C$_1$-C$_{20}$ alkyl). In other embodiments, an alkyl group comprises from 1 to 10 carbon atoms (C$_1$-C$_{10}$ alkyl). In still other embodiments, an alkyl group comprises from 1 to 6 carbon atoms (C$_1$-C$_6$ alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —O—R$^{199}$, where R$^{199}$ is alkyl or substituted alkyl as defined herein.

"Acyl" by itself or as part of another substituent refers to a radical —C(O)R$^{200}$, where R$^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms (C$_6$-C$_{20}$ aryl). In other embodiments, an aryl group comprises from 6 to 15 carbon atoms (C$_6$-C$_{15}$ aryl). In still other embodiments, an aryl group comprises from 6 to 15 carbon atoms (C$_6$-C$_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is (C$_6$-C$_{30}$) arylalkyl, e.g., the alkanyl, alkenyl or alkynyl moiety of the arylalkyl group is (C$_1$-C$_{10}$) alkyl and the aryl moiety is (C$_6$-C$_{20}$) aryl. In other embodiments, an arylalkyl group is (C$_6$-C$_{20}$) arylalkyl, e.g., the alkanyl, alkenyl or alkynyl moiety of the arylalkyl group is (C$_1$-C$_8$) alkyl and the aryl moiety is (C$_6$-C$_{12}$) aryl. In still other embodiments, an arylalkyl group is (C$_6$-C$_{15}$) arylalkyl, e.g., the alkanyl, alkenyl or alkynyl moiety of the arylalkyl group is (C$_1$-C$_5$) alkyl and the aryl moiety is (C$_6$-C$_{10}$) aryl.

"Cycloalkyl," by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms (C$_3$-C$_{10}$ cycloalkyl). In other embodiments, the cycloalkyl group comprises from 3 to 7 ring atoms (C$_3$-C$_7$ cycloalkyl).

"Cycloheteroalkyl," by itself or as part of another substituent, refers to a saturated or unsaturated cyclic alkyl radical in which one or more carbon atoms (and optionally any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl) In other embodiments, the cycloalkyl group comprise from 5 to 7 ring atoms (5-7 membered cycloheteroalkyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroalkyl," "Heteroalkanyl," "Heteroalkenyl" and "Heteroalkynyl," "by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$, —POR$^{206}$, —O—P(O)$_2$, —SO—, —SO$_2$—, —SnR$^{207}$R$^{208}$— and the like, where R$^{201}$, R$^{202}$, R$^{203}$, R$^{204}$, R$^{205}$, R$^{206}$, R$^{207}$ and R$^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2$$NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$ where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^-$, —$SR^-$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$ where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Vehicle" refers to a diluent, adjuvant, excipient or carrier with which a compound is administered.

The present invention is based, at least in part, on the discovery that an extra-cellular domain, e.g., the Venus flytrap domain of a chemosensory receptor, especially one or more interacting sites within the Venus flytrap domain, is a suitable target for compounds or other entities to modulate the chemosensory receptor and/or its ligands. Accordingly, the present invention provides screening methods for identifying chemosensory receptor modifiers as well as chemosensory receptor ligand modifiers. In addition, the present invention provides compounds and compositions capable of modulating chemosensory receptors as well as chemosensory receptor ligands.

According to one aspect of the present invention, it provides methods of screening for chemosensory receptor modifiers by determining whether a test entity is suitable to interact with a chemosensory receptor via one or more interacting sites within the extra-cellular domain of the chemosensory receptor, e.g., the Venus flytrap domain of the chemosensory receptor. According to another aspect of the present invention, it provides methods of screening for chemosensory receptor ligand modifiers by determining whether a test entity is suitable to interact with a chemosensory receptor, and optionally its ligand via one or more interacting sites within the extra-cellular domain, e.g., the Venus flytrap domain of the chemosensory receptor, optionally in the presence of a chemosensory receptor ligand.

In general, the extra-cellular domain of a chemosensory receptor refers to the extra-cellular amino-terminus of a chemosensory receptor and usually includes a ligand-binding domain and a cysteine-rich linker domain, which connects the ligand-binding domain and the rest of the protein. In Class C GPCRs, the ligand binding domain is generally referred to as a Venus flytrap domain, the structure of which has been elucidated, e.g., using X-ray crystallography.

A Venus flytrap domain typically consists of two relatively rigid lobes connected by three strands forming a flexible "hinge" region. In the absence of a ligand, the Venus flytrap domain tends to adopt open conformations with well-separated lobes as well as closed conformations with lobes closer together. In one example, the Venus flytrap domain includes a region from amino acid 36 to amino acid 509 of human T1R1, amino acid 31 to amino acid 507 of human T1R2, and/or amino acid 35 to amino acid 511 of human T1R3.

The Venus flytrap domain of the present invention includes any ligand binding domain or ligand interacting domain within the extra-cellular domain of a chemosensory receptor. In one embodiment, the Venus flytrap domain of the present invention includes any ligand binding domain of a member of the T1R family. In another embodiment, the Venus flytrap domain of the present invention includes any extra-cellular domain of a chemosensory receptor with a structure comprising two lobes connected by a hinge region. In yet another embodiment, the Venus flytrap domain of the present invention includes any domain corresponding to the structure and/or function of a region including amino acid 36 to amino acid 509 of human T1R1, amino acid 31 to amino acid 507 of human T1R2, and/or amino acid 35 to amino acid 511 of human T1R3. In still another embodiment, the Venus flytrap domain of the present invention includes any ligand binding domain of T1R1, T1R2, and/or T1R3 as well as any polymorphic variation, allele, or mutation thereof. Exemplary illustrations of polymorphic variations for T1R1 and T1R2 are shown in FIGS. 1-4.

According to the present invention, a chemosensory receptor can be any receptor associated with chemosensory sensation or chemosensory ligand triggered signal transduction, e.g., via taste receptors or taste related receptors expressed in taste bud, gastrointestinal tract, etc. In one embodiment, a chemosensory receptor is a receptor that belongs to the 7-transmembrane receptor superfamily or G protein-coupled receptors (GPCRs). In another embodiment, a chemosensory receptor is a receptor carrying out signal transduction via one or more G proteins. In yet another embodiment, a chemosensory receptor is a receptor that belongs to family C or class C of GPCRs. In yet another embodiment, a chemosensory receptor is a receptor that belongs to the T1R family. In yet another embodiment, a chemosensory receptor is a receptor of T1R1, T1R2, T1R3, or their equivalences or variances or a combination thereof. In still another embodiment, a chemosensory receptor is a hetero-dimer of T1R2 and T1R3, or their equivalences or variances.

According to the present invention, an interacting site within the Venus flytrap domain of a chemosensory receptor can be one or more interacting residues or a three dimensional interacting space or a combination thereof. In one embodiment, the interacting site of the present invention is within the Venus flytrap domain of T1R2. In another embodiment, the interacting site of the present invention is within the Venus flytrap domain of T1R3. In yet another embodiment, the interacting site of the present invention is within the Venus flytrap domain of both T1R2 and T1R3.

Usually such an interacting site can be determined by any suitable means known or later discovered in the art. For example, such interacting site can be determined based on computer modeling, e.g., using software such as Homology or Modeller (by Accelrys Corporation) to construct three dimensional homology models of a chemosensory receptor Venus flytrap domain, e.g., the T1R2 and/or T1R3 Venus flytrap domains based on crystal structures of homologous Venus flytrap domains.

Such an interacting site can also be determined, e.g., based on X-ray crystallography and the three dimensional structure of a chemosensory receptor determined therefrom, e.g., the T1R2, T1R3, or T1R2/T1R3 heterodimer. Alternatively, for example, such an interacting site can be determined based on molecular mechanical techniques, e.g., normal mode analysis, loop generation techniques, Monte Carlo and/or molecular dynamics simulations to explore motions and alternative conformations of the Venus flytrap domains, docking simulations to dock candidate receptor ligands and candidate receptor ligand modifiers into these models or into experimentally determined structures of chemosensory receptors, e.g., T1R1 and T1R2.

In addition, for example, such an interacting site can be determined based on mutagenesis, e.g., site-directed mutagenesis or a combination of two or more suitable methods known or later discovered, e.g., methods described herein.

In one example, such an interacting site is located in part of a chemosensory receptor, e.g., T1R2 and can be determined in the presence or absence of the other part of the chemosensory receptor, e.g., T1R3. In another example, such an interacting site can be determined in the presence or absence of a chemosensory receptor modifier and/or chemosensory receptor ligand modifier.

In one embodiment, the interacting site within the Venus flytrap domain of a chemosensory receptor includes one or more interacting residues of the Venus flytrap domain of a chemosensory receptor. According to the present invention, the interacting residue of the Venus flytrap domain of a chemosensory receptor is a residue associated with any direct or indirect interaction between a chemosensory receptor and a chemosensory receptor modifier or a chemosensory receptor ligand modifier or both.

In one example, the interacting residue of the present invention includes any residue of a chemosensory receptor associated with an interaction between a chemosensory receptor modifier and a chemosensory receptor. In another example, the interacting residue of the present invention includes any residue of a chemosensory receptor associated with an interaction between a chemosensory receptor ligand modifier and a chemosensory receptor. In yet another example, the interacting residue of the present invention includes any residue of a chemosensory receptor associated with an interaction between a chemosensory receptor, a chemosensory receptor modifier and a chemosensory receptor ligand modifier.

In still another example, the interacting residue of the present invention includes any residue of a chemosensory receptor associated with an interaction between a chemosensory receptor and a sweet flavor entity, e.g. any natural or synthesized sweet flavor compound including, without any limitation, non-caloric sweet flavor compounds, reduced caloric sweet flavor compounds, non-target caloric sweet flavor compounds, etc. Exemplary sweet flavor compounds include, without any limitation, cyclamic acid, mogroside, tagatose, maltose, galactose, mannose, sucrose, fructose, lactose, aspartame, neotame and other aspartame derivatives, saccharin, sucralose, acesulfame K, glucose, erythritol, D-tryptophan, glycine, mannitol, sorbitol, maltitol, lactitol, isomalt, hydroganeted glucose syrup (HGS), hydrogenated starch hydrolyzate (HSH), stevioside, rebaudioside A and other sweet Stevia-based glycosides, alitame, carrelame and other guanidine-based sweeteners, tagatose, xylitol, high fructose corn syrup, etc.

In still another example, the interacting residue of the present invention includes any residue of a chemosensory receptor associated with an interaction between a chemosensory receptor and a sweet flavor entity enhancer. In still another example, the interacting residue of the present invention includes any residue of a chemosensory receptor associated with an interaction between a chemosensory receptor, a sweet flavor entity, and a sweet flavor entity enhancer.

In another instance, the interacting residue of the present invention is a residue within the Venus flytrap domain of a chemosensory receptor, wherein any mutation of which could result in a change of the activity of the chemosensory receptor or the impact of a chemosensory receptor ligand to the chemosensory receptor or both. For example, the interacting residue of the present invention can include any residue within the Venus flytrap domain of a chemosensory receptor, wherein the mutation of which results in a detectable change, e.g., qualitative or quantitative change of the activity of the chemosensory receptor in response to a chemosensory receptor modifier and/or chemosensory receptor ligand modifier.

In yet another instance, the interacting residue of the present invention is a residue within the Venus flytrap domain of a chemosensory receptor that interacts or forms productive interaction(s), e.g., van der Waals, burial of hydrophobic atoms or atomic groups, hydrogen bonds, ring stacking interactions, or salt-bridging electrostatic interactions with a chemosensory receptor modifier or chemosensory receptor ligand modifier, or both.

In still another instance, the interacting residue of the Venus flytrap domain of a chemosensory receptor can be any residue constituting one or more interacting structural components of the Venus flytrap domain, which are associated, directly or indirectly, with the interaction between a chemosensory receptor and a chemosensory receptor modifier or a chemosensory receptor ligand modifier or both. For example, the Venus flytrap domain structure of a chemosensory receptor generally includes two lobes joint by a hinge region. Residues constituting an interacting structural component of the Venus flytrap domain can be, e.g., residues constituting the hinge region, the inner side of each lobe, or residues on each lobe that are brought into close proximity during activation or conformational change of the Venus flytrap domain, including without any limitation, residues on the inner surfaces of the lobes pointing towards each other or on the tips of the lobes where the residues are partially exposed to solvent but still close to residues on the opposite lobe, etc.

Exemplary interacting residues of the Venus flytrap domain of a chemosensory receptor include any one or more residues of 1) N143, S144, and I167 of a human T1R2, 2) S40, S144, S165, Y103, D142, and P277 of a human T1R2, 3) K65, R383, D307, E302, and D278 of a human T1R2, 4) I167, P185, T184, T326, E302, V384, A305, I325, I306, R383, D307, E382, D278, I279, I67, V66, V309, D142, S165, S40, S303, T242, F103, Q328, and S168 of a human T1R2, 5) N143, S144, I167, K65, R383, D307, E302, D278, P185, T184, T326, E302, V384, A305, I325, I306, D307, E382, I279, I67, V66, V309, D142, S165, S40, S303, T242, F103, Q328, and S168 of a human T1R2, and 6) N143, I167, K65, R383, D307, E302, D278, P185, T184, T326, V384, A305, I325, I306, D307, E382, I279, I67, V66, V309, D142, S165, S40, S303, T242, F103, Q328, and S168 of a human T1R2.

Exemplary interacting residues of the Venus flytrap domain of a chemosensory receptor with respect to a chemosensory receptor modifier include one or more residues of 1) N143, S144, and I167 of a human T1R2, 2) S40, S144, S165, Y103, D142, and P277 of a human T1R2, 3) I167, P185, T184, T326, E302, V384, A305, I325, I306, R383, D307, E382, D278, I279, I67, V66, V309, D142, S165, S40, S303, T242, F103, Q328, and S168 of a human T1R2, 4) N143 and I167 of a human T1R2, 5) S40, S165, Y103, D142, and P277 of a human T1R2, and 6) I167, P185, T184, T326, V384, A305, I325, I306, R383, D307, E382, D278, I279, I67, V66, V309, D142, S165, S40, S303, T242, F103, Q328, and S168 of a human T1R2.

Exemplary interacting residues of the Venus flytrap domain of a chemosensory receptor with respect to a sweet flavor entity such as sucrose and sucralose include one or more residues of S40, S144, Y103, D142, P277 of a human T1R2. Exemplary interacting residues of the Venus flytrap domain of a chemosensory receptor with respect to a sweet flavor entity such as saccharin or acesulfame K include one or more residues of K65, R383, D307, E302, and D278 of a human T1R2.

Exemplary interacting residues of the Venus flytrap domain of a chemosensory receptor with respect to a chemosensory receptor ligand modifier, e.g., chemosensory receptor ligand enhancer include one or more residues of 1) K65, R383, D307, E302, and D278 of a human T1R2, 2) S40, S144, S165, Y103, D142, and P277 of a human T1R2, and 3) I167, P185, T184, T326, E302, V384, A305, I325, I306, R383, D307, E382, D278, I279, I67, V66, V309, D142, S165, S40, S303, T242, F103, Q328, and S168 of a human T1R2.

In the context of the present invention, any reference to a particular interacting residue, e.g., N143 of a human T1R2 receptor, includes all of its corresponding residues, e.g., 1) any residue of a human or non-human T1R2 that corresponds to the same position in any method of sequence alignment, 2) any residue of a human or non-human T1R2 that corresponds to the same position in any method of computer modeling in the presence or absence of a ligand or ligand modifier, 3) any residue of a human or non-human T1R2 that corresponds to the structural or functional role of the particular interacting residue, 4) any residue of a human or non-human T1R2 that is a polymorphic variation, alleles, mutation, etc. of the particular residue, 5) any residue of a human or non-human T1R2 that is a conservative substitution or conservatively modified variant of the particular residue, and 6) any corresponding residue of a human or non-human T1R2 in its modified form, e.g., artificial chemical mimetic of the particular interacting residue or un-modified form, e.g., naturally occurring form.

In another embodiment, the interacting site within the Venus flytrap domain of a chemosensory receptor is a three dimensional interacting space within the Venus flytrap domain outlined or defined, partially or entirely, by interacting residues or one or more interfaces, e.g., interacting points, lines or surfaces between a chemosensory receptor and one or more chemosensory receptor modifiers or chemosensory receptor ligand modifiers or a combination thereof. According to the present invention, a residue outlining or lining a space includes any residue having one or more backbones and/or side-chain atoms that are positioned so that they can potentially interact with atoms of a chemosensory receptor ligand or chemosensory receptor ligand modifier or both.

For example, the interacting space of the present invention can be any partial or whole space within the Venus flytrap domain that is usually occupied by one or more chemosensory receptor modifiers or chemosensory receptor ligand modifiers when they interact with a chemosensory receptor individually or together. In one example, the interacting space of the present invention is a space within the Venus flytrap domain usually occupied by a chemosensory receptor modifier, e.g., sweet flavor entity. In another example, the interacting space of the present invention is a space within the Venus flytrap domain usually occupied by a chemosensory receptor ligand modifier, e.g., sweet flavor enhancer in the presence of a chemosensory receptor ligand. In yet another example, the interacting space of the present invention is a space within the Venus flytrap domain usually occupied by a chemosensory receptor modifier, e.g., sweet flavor entity and a chemosensory receptor ligand modifier, e.g., sweet flavor entity enhancer. In still another example, the interacting space of the present invention is a space within the Venus flytrap domain that is defined, shaped, or transformed into based on an interaction between a chemosensory receptor and its ligand or its ligand modifier occurred partially or entirely outside of the space.

According to the present invention, the Venus flytrap domain of a chemosensory receptor can be generally viewed as two lobes joined by a hinge region. Exemplary interacting space within the Venus flytrap domain of a chemosensory receptor includes any space associated with the hinge region, the inner side of one or two lobes, the tip of one or two lobes or a combination thereof of a chemosensory receptor.

Exemplary interacting space within the Venus flytrap domain of a chemosensory receptor with respect to a chemosensory receptor modifier includes any space within the Venus flytrap domain outlined or at least partially defined by the hinge region. According to the present invention, the hinge region usually comprises residues that are close to the three strands connecting the two lobes. In one example, the hinge region comprises residues that are homologous to residues observed coordinating agonists and antagonists in crystal structures of one or more Venus flytrap domains such as that of the mGluR receptor. In another example, the hinge region of T1R2 includes residues N143, S144, and I167 of T1R2.

Exemplary interacting sites within the Venus flytrap domain of a chemosensory receptor with respect to a chemosensory receptor ligand modifier include any space outlined or at least partially defined by the inner side of one or two lobes away from the hinge region, as well as residues on the tips of the lobes that are brought into close proximity to residues on the other lobe.

In yet another embodiment, the interacting site within the Venus flytrap domain of a chemosensory receptor is a combination of one or more interacting residues with an interacting space of the chemosensory receptor. For example, the interacting site of a chemosensory receptor can be interacting residues associated with one interacting structural component of a chemosensory receptor in combination with a three dimensional space adjacent, e.g., not less than 1 Angstrom and not more than 30 Angstroms, to that interacting structural component. Another example of the interacting site of a chemosensory receptor includes interacting residues associated with one interacting structural component of a chemosensory receptor in combination with a three dimensional space apart from the interacting structural component.

In general, the screening methods provided by the present invention can be carried out by any suitable means known or later discovered. In one embodiment, the screening methods provided by the present invention are carried out in silico, e.g., via "virtue screening" using any suitable computer modeling system or via specific or rational design of a compound using any suitable computer design system.

In another embodiment, the screening methods provided by the present invention are carried out via biological assays, e.g., high throughput screening of interactions between compounds and a chemosensory receptor or its fragments, e.g., genetically modified chemosensory receptors or fragments thereof such as mutated Venus flytrap domains of chemosensory receptors. In yet another embodiment, the screening methods provided by the present invention are carried out via a combination of biological assay(s) and computer modeling and/or design. For example, the screening methods provided by the present invention can be a combination of high-throughput screening of interactions between computer designed or pre-screened compounds and mutated Venus flytrap domains of chemosensory receptors.

In one example, the screening method provided by the present invention for chemosensory receptor modifiers includes determining an interacting site using a known chemosensory receptor modifier, e.g., structurally similar to a chemosensory receptor modifier of interest and then determining whether a test entity is suitable to interact with the chemosensory receptor via the interacting site so determined.

In another example, the screening method provided by the present invention for chemosensory receptor modifiers includes determining whether a test entity is suitable to interact with a chemosensory receptor via a predetermined interacting site, e.g., an interacting site selected or determined prior to screening, including without any limitation, selected or determined based on known chemosensory receptor modifiers or desired characteristics of a chemosensory receptor modifiers.

In yet another example, the screening method provided by the present invention for chemosensory receptor ligand modifiers includes determining a docking site for a chemosensory receptor ligand and subsequently determining whether a test entity is suitable to interact with the chemosensory receptor ligand via an interacting site selected in light of the docking of the chemosensory receptor ligand. According to the present invention, docking process can include any known or later discovered methods. For instance, docking can be a process in which the center of mass, orientations, and internal degrees of freedom of a molecule are modified to fit them into a predetermined space in a structural model. In one example, docking can be a process which includes translating and rotating a chemosensory receptor ligand relative to the chemosensory receptor structural model, e.g., the Venus flytrap domain of a chemosensory receptor model while simultaneously adjusting internal torsional angles of the chemosensory receptor ligand to fit it into the interacting site of the chemosensory receptor. An example of a widely used docking program is GLIDE from Schroedinger, Inc.

In yet another example, the screening method provided by the present invention for chemosensory receptor ligand modifiers includes determining a docking site for a chemosensory receptor ligand and subsequently determining an interacting site using a known modifier of the chemosensory receptor ligand and then determining whether a test entity is suitable to interact with the chemosensory receptor ligand via the interacting site so determined.

In yet another example, the screening method provided by the present invention for chemosensory receptor ligand modifiers includes determining whether a test entity is suitable to interact with a chemosensory receptor via a predetermined interacting site for chemosensory receptor ligand modifiers.

In still another example, the screening method provided by the present invention for chemosensory receptor ligand modifiers includes determining whether a test entity is suitable to interact with a chemosensory receptor by determining, e.g., concurrently whether a chemosensory receptor ligand and the test entity are suitable to interact with the chemosensory receptor in a predetermined interacting site of the chemosensory receptor or an interacting site determined using known chemosensory receptor ligand and its modifier of interest.

In still another example, the screening method provided by the present invention for chemosensory receptor ligand modifiers includes determining whether a test entity is suitable to interact with a chemosensory receptor via an interacting site, either pre-determined or not, as well as whether a test entity is suitable to interact with a chemosensory receptor ligand.

In still another example, the screening method provided by the present invention for chemosensory receptor ligand modifiers includes determining whether a test entity is suitable to interact with a chemosensory receptor via an interacting site, either pre-determined or not, as well as whether such interaction can stabilize a conformation, e.g., a semi-closed or closed conformation within the Venus flytrap domain formed by the interaction between a chemosensory receptor ligand and a chemosensory receptor, e.g., by forming productive additional interactions within the hinge region, lobes of the Venus flytrap domain, or tips of the flytrap domain via van der Waals, burial of hydrophobic atoms or atomic groups, hydrogen bonds, ring stacking interactions, or salt-bridging electrostatic interactions, etc.

In general, any suitable means known or later discovered can be used to determine whether a test entity is suitable to interact with an interacting site of the present invention. For example, one could determine the suitability of a test entity based on whether part or all of a test entity fits into a particular space entailed by an interacting site, e.g., whether a test entity fits into a particular space entailed by an interacting site substantially the same way a known chemosensory receptor modifier or chemosensory receptor ligand modifier does.

Alternatively one could determine the suitability of a test entity with respect to an interacting site based on whether it forms interactions with a chemosensory receptor similar to the interactions formed by a known chemosensory receptor modifier or chemosensory receptor ligand modifier when they interact with the interacting site.

In addition, one could determine the suitability of a test entity based on whether it forms productive interactions with an interacting site, e.g., van der Waals, burial of hydrophobic atoms or atomic groups, hydrogen bonds, ring stacking interactions, or salt-bridging electrostatic interactions, etc. In one embodiment, one could determine the suitability of a test entity being a chemosensory receptor ligand modifier based on whether it forms productive interactions with an interacting site without forming van der Waals overlapping with one or more atoms of a chemosensory receptor or the chemosensory receptor ligand, e.g., in the context of one or more conformations of the Venus flytrap domain in light of the possible flexibility of the Venus flytrap domain.

According to the present invention, a test entity suitable to interact with one or more interacting sites within the Venus flytrap domain of a chemosensory receptor is indicative of a candidate for a chemosensory receptor modifier or chemosensory receptor ligand modifier. In one embodiment, a test entity suitable to interact with one or more interacting sites within the Venus flytrap domain of T1R2 is indicative of a candidate for a T1R2 receptor modifier or T1R2 receptor ligand modifier. In another embodiment, a test entity suitable to interact with one or more interacting sites within the Venus flytrap domain of T1R2 is indicative of a candidate for a T1R receptor modifier or T1R receptor ligand modifier. In yet another embodiment, a test entity suitable to interact with one or more interacting sites within the Venus flytrap domain of T1R2 is indicative of a candidate for a receptor modifier or receptor ligand modifier for a receptor of GPCR superfamily. In still another embodiment, a test entity suitable to interact with one or more interaction sites within the Venus flytrap domain of a chemosensory receptor is indicative of a candidate for a receptor modifier or receptor ligand modifier of a receptor that corresponds to the chemosensory receptor or belongs to the same family or class as of the chemosensory receptor.

According to the present invention, a test entity suitable to interact with one or more interacting sites within the Venus flytrap domain of a chemosensory receptor is indicative of a candidate for a chemosensory receptor modifier or chemosensory receptor ligand modifier. In one embodiment, a test entity suitable to interact with one or more interacting sites within the Venus flytrap domain of T1R2 is indicative of a candidate for a T1R2 receptor modifier or T1R2 receptor ligand modifier.

In one example, a test entity suitable to interact with one or more interacting sites containing one or more interacting residues of K65, D278, L279, D307, R383, and V384 of human T1R2 is indicative of a candidate for a T1R2 receptor ligand enhancer.

In another example, a test entity suitable to interact with one or more interacting sites containing one or more interacting residues of S40, S144, Y103, D142, and P277 of human T1R2 is indicative of a candidate for a T1R2 receptor ligand enhancer with respect to sucrose or sucralose or any ligand with a structure similar to sucrose or sucralose or any ligand interacting with T1R2 in a way similar to that of sucrose or sucralose, e.g., via one or more interacting spaces and/or residues used by sucrose or sucralose.

In the context of the present application, any reference to a modifier, e.g. enhancer or inhibitor of a T1R2 receptor or T1R2 receptor ligand includes a modifier for any T1R receptor, any receptor of GPCR super-family, or any receptor corresponding to T1R2 receptor, e.g., any receptor with a structure, function, or expression pattern overlapping or similar to that of T1R2. In the present invention, a test entity can be any compound or molecule, e.g., any compound or entity that potentially could be a source for a desired chemosensory receptor modifier or chemosensory receptor ligand modifier. For example, a test entity can be a member of a combinatorial library, a member of a natural compound library, a "specifically designed" compound that is designed based on various desirable features or rationales, etc.

In general, a chemosensory receptor modifier or ligand includes any compound or entity capable of interacting with, e.g., binding to a chemosensory receptor or modulating the structure or function of a chemosensory receptor, e.g., activate, deactivate, increase, or decrease the signal transduction activity of a chemosensory receptor, especially via G-protein signal transduction pathway.

In one embodiment, a chemosensory receptor modifier or ligand is a compound or entity with sweet flavor including without any limitation any natural or synthesized sweet flavor compound, e.g., non-caloric sweet flavor compounds, reduced caloric sweet flavor compounds, non-target caloric sweet flavor compounds, etc. Exemplary sweet flavor compounds include, without any limitation, cyclamic acid, mogroside, tagatose, maltose, galactose, mannose, sucrose, fructose, lactose, aspartame, neotame and other aspartame derivatives, saccharin, sucralose, acesulfame K, glucose, erythritol, D-tryptophan, glycine, mannitol, sorbitol, maltitol, lactitol, isomalt, hydroganeted glucose syrup (HGS), hydrogenated starch hydrolyzate (HSH), stevioside, rebaudioside A and other sweet Stevia-based glycosides, alitame, carrelame and other guanidine-based sweeteners, tagatose, xylitol, high fructose corn syrup, etc.

In another embodiment, a chemosensory receptor modifier or ligand (used interchangeably in the present invention) is a compound or entity capable of activating a chemosensory receptor, e.g., activating the G-protein signal transduction pathway associated with the chemosensory receptor. In yet another embodiment, a chemosensory receptor modifier or ligand is a compound or entity capable of blocking or decreasing the activation of a chemosensory receptor. In still another embodiment, a chemosensory receptor modifier or ligand is a compound or entity capable of modulating the activity of a chemosensory receptor and inducing a therapeutically desirable reaction or signal transduction. In still another embodiment, a chemosensory receptor modifier or ligand is a chemosensory receptor ligand modifier.

According to the present invention, a chemosensory receptor ligand modifier includes any compound or entity capable of interacting or modulating the activity of a chemosensory receptor modifier or the activity of a chemosensory receptor in the presence of a chemosensory receptor modifier. In one embodiment, a chemosensory receptor ligand modifier is an enhancer of a chemosensory receptor modifier. In another embodiment, a chemosensory receptor ligand modifier is an antagonist of a chemosensory receptor modifier. In yet another embodiment, a chemosensory receptor ligand modifier is an enhancer of a chemosensory receptor modifier without having substantial activity of the chemosensory receptor modifier. In still another embodiment, a chemosensory receptor ligand modifier is an enhancer of a sweet flavored compound without having substantial sweet flavor by itself, e.g., as judged by animals or humans such as majority of a panel of at least eight human taste testers, via procedures commonly known in the field. In still yet another embodiment, a chemosensory receptor ligand modifier is an enhancer or inhibitor of a chemosensory receptor modifier and capable of inducing a desirable therapeutic reaction or signal transduction.

According to another aspect of the present invention, it provides chemosensory receptor ligand modifiers. In one embodiment, it provides chemosensory receptor ligand modifiers identified by the screen methods of the present invention. In another embodiment, it provides chemosensory receptor ligand modifiers capable of interacting with a chemosensory receptor via an interacting site of the present invention. In yet another embodiment, it provides chemosensory receptor ligand modifiers capable of interacting with a chemosensory receptor via one or more interacting residues of the chemosensory receptor. In still another embodiment, it provides chemosensory receptor ligand modifiers capable of interacting with a chemosensory receptor via an interacting space within the Venus flytrap domain that is outlined, defined, or shaped, partially or entirely, by interacting residues of the chemosensory receptor. In still yet another embodiment, it provides chemosensory receptor ligand modifiers excluding, e.g., natural or synthesized sweet enhancers known prior to the present invention.

In the context of the present invention, "capable of interacting with" or "interacting with" means that a compound or molecule binds to or forms one or more molecular interactions, e.g., productive interactions with another molecule, e.g., a chemosensory receptor. Exemplary molecular interactions, e.g., productive interactions include van der Waals, burial of hydrophobic atoms or atomic groups, hydrogen bonds, ring stacking interactions, salt-bridging electrostatic interactions, or a combination thereof.

In one embodiment, the present invention provides chemosensory receptor ligand modifiers capable of interacting with a chemosensory receptor via a group of interacting residues or a space within the Venus flytrap domain that is outlined, shaped, or defined, partially or entirely by the group or any subgroup of interacting residues, optionally in the presence of a chemosensory receptor ligand, e.g., 1) S40, S144, S165, Y103, D142, P277 of a human T1R2, 2) K65, R383, D307, E302, and D278 of a human T1R2, 3) I167, P185, T184, T326, E302, V384, A305, I325, I306, R383, D307, E382, D278, I279, I67, V66, V309, D142, S165, S40, S303, T242, F103, Q328, and S168 of a human T1R2, 4) S40, S144, S165, Y103, D142, P277, K65, R383, D307, E302, and D278 of a human T1R2, 5) S40, S144, S165, Y103, D142, P277, I167, P185, T184, T326, E302, V384, A305, I325, I306, R383, D307, E382, D278, I279, I67, V66, V309, S303, T242, F103, Q328, and S168 of a human T1R2, 6) K65, R383, D307, E302, D278, I167, P185, T184, T326, E302, V384, A305, I325, I306, E382, I279, I67, V66, V309, D142, S165, S40, S303, T242, F103, Q328, and S168 of a human T1R2, 7) S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2, 8) N143, S144, and I167 of a human T1R2, or 9) N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In another embodiment, the present invention provides chemosensory receptor ligand enhancers capable of interacting with a chemosensory receptor in the presence of a chemosensory receptor ligand via one or more interacting residues of K65, D278, L279, D307, R383, V384 of a human T1R2.

In yet another embodiment, the present invention provides sucrose or sucralose enhancers capable of interacting with a chemosensory receptor in the presence of sucrose or sucralose via one or more interacting residues of S40, S144, Y103, D142, P277 of a human T1R2.

In still another embodiment, the present invention provides chemosensory receptor ligand modifiers capable of interacting with a chemosensory receptor, optionally in the presence of a chemosensory receptor ligand via at least 1, 2, 3, 4, 5, 6, 7, 8, 9, or 10 interacting residues selected from the group of N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In still another embodiment, the present invention provides chemosensory receptor ligand modifiers capable of interacting with a chemosensory receptor to stabilize a conformation, e.g., semi-closed or closed conformation formed by the interaction between a chemosensory receptor and a chemosensory receptor ligand.

In still yet another embodiment, the present invention provides chemosensory receptor ligand modifiers, e.g., saccharin, saccharin analogues, acesulfame K, acesulfame K analogues, or any compound capable of interacting with a chemosensory receptor via an interacting site that is similar to or overlaps with an interacting site used by saccharin or acesulfame K. In one example, the present invention provides chemosensory receptor ligand enhancers, e.g., saccharin, saccharin analogues, acesulfame K, or acesulfame K analogues that interact with a chemosensory receptor via an interacting site including one or more interacting residues of K65, R383, D307, E302 and D278 of a human T1R2.

According to yet another aspect of the present invention, it provides chemosensory receptor modifiers. In one embodiment, it provides chemosensory receptor modifiers identified by the screen methods of the present invention. In another embodiment, it provides chemosensory receptor modifiers capable of interacting with a chemosensory receptor via an interacting site of the present invention. In yet another embodiment, it provides chemosensory receptor modifiers capable of interacting with a chemosensory receptor via one or more interacting residues of the chemosensory receptor. In still another embodiment, it provides chemosensory receptor modifiers capable of interacting with a chemosensory receptor via an interacting space within the Venus flytrap domain that is outlined, defined, or shaped, partially or entirely, by interacting residues of the chemosensory receptor. In still yet another embodiment, it provides chemosensory receptor modifiers excluding, e.g., natural or synthesized sweet flavor entities known prior to the present invention.

In one embodiment, the present invention provides chemosensory receptor modifiers capable of interacting with a chemosensory receptor via a group of interacting residues or a space within the Venus flytrap domain that is outlined, shaped, or defined, partially or entirely by the group or any subgroup of interacting residues, e.g., 1) S40, S144, S165, Y103, D142, P277 of a human T1R2, 2) K65, R383, D307, E302, and D278 of a human T1R2, 3) I167, P185, T184, T326, E302, V384, A305, I325, I306, R383, D307, E382, D278, I279, I67, V66, V309, D142, S165, S40, S303, T242, F103, Q328, and S168 of a human T1R2, 4) S40, S144, S165, Y103, D142, P277, K65, R383, D307, E302, and D278 of a human T1R2, 5) S40, S144, S165, Y103, D142, P277, I167, P185, T184, T326, E302, V384, A305, I325, I306, R383, D307, E382, D278, I279, I67, V66, V309, S303, T242, F103, Q328, and S168 of a human T1R2, 6) K65, R383, D307, E302, D278, I167, P185, T184, T326, E302, V384, A305, I325, I306, E382, I279, I67, V66, V309, D142, S165, S40, S303, T242, F103, Q328, and S168 of a human T1R2, 7) S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2, 8) N143, S144, and I167 of a human T1R2, or 9) N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In still another embodiment, the present invention provides chemosensory receptor modifiers capable of interacting with a chemosensory receptor via at least 1, 2, 3, 4, 5, 6, 7, 8, 9, or 10 interacting residues selected from the group of N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

According to still another aspect of the present invention, it provides methods for modulating a chemosensory receptor and/or its ligand by modulating one or more interacting sites of the chemosensory receptor. For example, one can modulate a chemosensory receptor by contacting, in vivo or in vitro, a chemosensory receptor modifier or chemosensory receptor ligand modifier or both, (e.g., optionally excluding natural sweet flavor entity or sweet enhancers known prior to the present invention) with cells containing the chemosensory receptor, wherein the chemosensory receptor modifier or chemosensory receptor ligand is capable of interacting with or targeting one or more interacting sites of the chemosensory receptor.

In one embodiment, the method of modulating a chemosensory receptor and/or its ligand is by modulating one or more interacting residues or interacting spaces or a combination thereof. In another embodiment, the method of modulating a chemosensory receptor and/or its ligand is by interacting with one or more interacting residues in the presence of a chemosensory receptor ligand. In yet another embodiment, the method of modulating a chemosensory receptor or its ligand includes modulating the impact of a chemosensory receptor ligand on the chemosensory receptor by interacting with the chemosensory receptor via one or more interacting residues in the presence of the chemosensory receptor ligand.

In yet another embodiment, the method of modulating a chemosensory receptor and/or its ligand is by interacting with the chemosensory receptor via a group of interacting residues or a space outlined, shaped, or defined, partially or entirely, by the group or subgroup of interacting residues, optionally in the presence of a chemosensory receptor ligand, e.g., 1) S40, S144, S165, Y103, D142, P277 of a human T1R2, 2) K65, R383, D307, E302, and D278 of a human T1R2, 3) I167, P185, T184, T326, E302, V384, A305, I325, I306, R383, D307, E382, D278, I279, I67, V66, V309, D142, S165, S40, S303, T242, F103, Q328, and S168 of a human T1R2, 4) S40, S144, S165, Y103, D142, P277, K65, R383, D307, E302, and D278 of a human T1R2, 5) S40, S144, S165, Y103, D142, P277, I167, P185, T184, T326, E302, V384, A305, I325, I306, R383, D307, E382, D278, I279, I67, V66, V309, S303, T242, F103, Q328, and S168 of a human T1R2, 6) K65, R383, D307, E302, D278, I167, P185, T184, T326, E302, V384, A305, I325, I306, E382, I279, I67, V66, V309, D142, S165, S40, S303, T242, F103, Q328, and S168 of a human T1R2, 7) S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2, 8) N143, S144, and I167 of a human T1R2, or 9) N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In yet another embodiment, the method of modulating a chemosensory receptor and/or its ligand is by interacting with the chemosensory receptor via one or more interacting residues of N143, S144, and I167 of a human T1R2.

In yet another embodiment, the method of modulating a chemosensory receptor and/or its ligand is by interacting with the chemosensory receptor, optionally in the presence of a chemosensory receptor ligand via one or more interacting residues of K65, D278, L279, D307, R383, V384 of a human T1R2.

In still another embodiment, the method of modulating a chemosensory receptor and/or its ligand is by interacting with the chemosensory receptor, optionally in the presence of sucrose or sucralose via one or more interacting residues of S40, S144, Y103, D142, P277 of a human T1R2.

In still another embodiment, the method of enhancing a chemosensory receptor and/or its ligand is by interacting with the chemosensory receptor, optionally in the presence of a chemosensory receptor ligand via one or more interacting residues of K65, D278, L279, D307, R383, V384, S40, S144, Y103, D142, P277 of a human T1R2.

In still another embodiment, the method of modulating a chemosensory receptor and/or its ligand is by interacting with the chemosensory receptor, optionally in the presence of a chemosensory receptor ligand via at least 1, 2, 3, 4, 5, 6, 7, 8, 9, or 10 interacting residues selected from the group of N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

In still another embodiment, the method of modulating a chemosensory receptor and/or its ligand is by interacting with the chemosensory receptor, optionally in the presence of a chemosensory receptor ligand via at least 1, 2, 3, 4, 5, 6, 7, 8, 9, or 10 interacting residues selected from the group of N143, S40, S144, S165, Y103, D142, P277, K65, R383, D307, E302, D278, I167, P185, T184, T326, E302, V384, A305, I325, I306, E382, I279, I67, V66, V309, S303, T242, F103, Q328, and S168 of a human T1R2.

According to the present invention, a method of modulating a chemosensory receptor and/or its ligand includes modulating the activity, structure, function, expression, and/or modification of a chemosensory receptor as well as modulating, treating, or taking prophylactic measure of a condition, e.g., physiological or pathological condition, associated with a chemosensory receptor.

In general, a physiological or pathological condition associated with a chemosensory receptor includes a condition associated with a taste, e.g., sweet, umami, bitter, sour, salty, or a combination thereof or a condition associated with, e.g., gastrointestinal system, metabolic disorders, functional gastrointestinal disorders, etc.

In one embodiment, the method of the present invention, e.g., modulating a chemosensory receptor and/or its ligand includes modulating, increasing or decreasing a sweet or umami taste or a subject's reaction, physiological or otherwise, to a sweet or umami taste. In another embodiment, the method of the present invention, e.g., modulating a chemosensory receptor and/or its ligand includes enhancing a sweet or umami taste or a subject's reaction, physiological or otherwise, to a sweet or umami taste.

In yet another embodiment, the method of the present invention, e.g., modulating a chemosensory receptor and/or its ligand includes modulation, treatment, and/or prophylactic measure of a condition associated with gastrointestinal system including without any limitation conditions associated with esophageal motility (e.g., cricopharyngeal achalasia, globus hystericus, achalasia, diffuse esophageal spasm and related motor disorders, scleroderma involving the esophagus, etc.), inflammatory disorders (e.g., gastroesophageal reflux and esophagitis, infectious esophagitis, etc.), peptic ulcer, duodenal ulcer, gastric ulcer, gastrinoma, stress ulcers and erosions, drug-associated ulcers and erosions, gastritis, esophageal cancer, tumors of the stomach, disorders of absorption (e.g., absorption of specific nutrients such as carbohydrate, protein, amino acid, fat, cholesterol and fat-soluble vitamins, water and sodium, calcium, iron, water-soluble vitamins, etc.), disorders of malabsorption, defects in mucosal function (e.g., inflammatory or infiltrative disorders, biochemical or genetic abnormalities, endocrine and metabolic disorders, protein-losing enteropathy, etc.), autoimmune diseases of the digestive tract (e.g., celiac disease, Crohn's disease, ulcerative colitis, etc.), irritable bowel syndrome, inflammatory bowel disease, complications of inflammatory bowel disease, extraintestinal manifestations of inflammatory bowel disease, disorders of intestinal motility, vascular disorders of the intestine, anorectial disorders (e.g., hemorrhoids, anal inflammation, etc.), colorectal cancer, tumors of the small intestine, cancers of the anus, derangements of hepatic metabolism, hyperbilirubinemia, hepatitis, alcoholic liver disease and cirrhosis, biliary cirrhosis, neoplasms of the liver, infiltrative and metabolic diseases affecting the liver (e.g., fatty liver, reye's syndrome, diabetic glycogenosis, glycogen storage disease, Wilson's disease, hemochromatosis), diseases of the gallbladder and bile ducts, disorders of the pancreas (e.g., pancreatitis, pancreatic exocrine insufficiency, pancreatic cancer, etc.), endocrine tumors of the gastrointestinal tract and pancreas, etc.

In still another embodiment, the method of the present invention, e.g., modulating a chemosensory receptor and/or its ligand includes modulation, treatment, and/or prophylactic measure of a condition associated with metabolic disorders, e.g., appetite, body weight, food or liquid intake or a subject's reaction to food or liquid intake, or state of satiety or a subject's perception of a state of satiety, nutrition intake and regulation, (e.g., protein-energy malnutrition, physiologic impairments associated with protein-energy malnutrition, etc.), obesity, secondary obesity (e.g., hypothyroidism, Cushing's disease, insulinoma, hypothalamic disorders, etc.), eating disorders (e.g., anorexia nervosa, bulimia, etc.), vitamin deficiency and excess, insulin metabolism, diabetes (type I and type II) and complications thereof (e.g., circulatory abnormalities, retinopathy, diabetic nephropathy, diabetic neuropathy, diabetic foot ulcers, etc.), glucose metabolism, fat metabolism, hypoglycemia, hyperglycemia, hyperlipoproteinemias, etc.

In still yet another embodiment, the method of the present invention, e.g., modulating a chemosensory receptor and/or its ligand includes modulation, treatment, and/or prophylactic measure of a condition associated with functional gastrointestinal disorders, e.g., in the absence of any particular pathological condition such as peptic ulcer and cancer, a subject has abdominal dyspepsia, e.g., feeling of abdominal distention, nausea, vomiting, abdominal pain, anorexia, reflux of gastric acid, or abnormal bowel movement (constipation, diarrhea and the like), optionally based on the retention of contents in gastrointestinal tract, especially in stomach. In one example, functional gastrointestinal disorders include a condition without any organic disease of the gastrointestinal tract, but with one or more reproducible gastrointestinal symptoms that affect the quality of life of a subject, e.g., human.

Exemplary functional gastrointestinal disorders include, without any limitation, functional dyspepsia, gastroesophageal reflux condition, diabetic gastroparesis, reflux esophagitis, postoperative gastrointestinal dysfunction and the like, nausea, vomiting, sickly feeling, heartburn, feeling of abdominal distention, heavy stomach, belching, chest writhing, chest pain, gastric discomfort, anorexia, dysphagia, reflux of gastric acid, abdominal pain, constipation, diarrhea, breathlessness, feeling of smothering, low incentive or energy level, pharyngeal obstruction, feeling of foreign substance, easy fatigability, stiff neck, myotonia, mouth dryness (dry mouth, thirst, etc.) tachypnea, burning sensation in the gastricintestinal tract, cold sensation of extremities, difficulty in concentration, impatience, sleep disorder, headache, general malaise, palpitation, night sweat, anxiety, dizziness, vertigo, hot flash, excess sweating, depression, etc.

In still yet another embodiment, the method of the present invention, e.g., modulating a chemosensory receptor and/or its ligand includes increasing or promoting digestion, absorption, blood nutrient level, and/or motility of gastrointestinal tract in a subject, e.g., promotion of gastric emptying (e.g., clearance of stomach contents), reduction of abdominal distention in the early postprandial period, improvement of anorexia, etc. In general, such promotion can be achieved either directly or via increasing the secretion of a regulatory entity, e.g., hormones, etc.

In still yet another embodiment, the method of the present invention, e.g., modulating a chemosensory receptor and/or its ligand includes increasing one or more gastrointestinal functions of a subject, e.g., to improve the quality of life or healthy state of a subject.

In still yet another embodiment, the method of the present invention, e.g., modulating a chemosensory receptor and/or its ligand includes modulating the activity of T1R (e.g., T1R1, T1R2, or T1R3) expressing cells, e.g., liver cells (e.g., hepatocytes, endothelial cells, Kupffer cells, Stellate cells, epithelial cells of bile duct, etc.), heart cells (e.g., endothelial, cardiac, and smooth muscle cells, etc.), pancreatic cells (e.g., alpha cell, beta cell, delta cell, neurosecretory PP cell, D1 cell, etc.), cells in the nipple (e.g., ductal epithelial cells, etc.), stomach cells (e.g., mucous cells, parietal cells, chief cells, G cells, P/D1 cells), intestinal cells (e.g., enteroendocrine cells, brush cells, etc.), salivary gland cells (e.g., Seromucous cells, mucous cells, myoepithelial cells, intercalated duct cell, striated duct cell, etc.), L cells (e.g., expressing GLP-1, etc.), enterochromaffin cells (e.g., expressing serotonin), enterochromaffin-like cells, G cells (e.g., expressing gastrin), D cells (delta cells, e.g., expressing somatostatin), I cells (e.g., expressing cholescystokinin (CCK), K cells (e.g., expressing gastric inhibitory polypeptide), P/D1 cells (e.g., expressing ghrelin), chief cells (e.g., expressing pepsin), and S cells (e.g., expressing secretin). In one example, the method of the present invention includes increasing the expression level of T1R in T1R expressing cells. In another example, the method of the present invention includes increasing the secretion level of T1R expressing cells.

In still yet another embodiment, the method of the present invention, e.g., modulating a chemosensory receptor and/or its ligand includes modulating the expression, secretion, and/ or functional level of T1R expressing cells associated with hormone, peptide, enzyme producing. In one example, the method of the present invention includes modulating the level of glucose, e.g., inhibitors of a chemosensory receptor such as T1R2 can be used to decrease glucose level (e.g., glucose absorption) in a subject. In another example, the method of the present invention includes modulating the level of incretins, e.g., agonist of a chemosensory receptor such as T1R2 can be used to increase glucagons-like peotide 1 (GLP-1) and thus increase the production of insulin. In yet another example, the method of the present invention includes modulating the expression, secretion, and/or activity level of hormones or peptides produced by T1R expressing cells or gastrointestinal hormone producing cells, e.g., ligands for 5HT receptors (e.g., serotonin), incretins (e.g., GLP-1 and glucose-dependent insulinotropic polypeptide (GIP)), gastrin, secretin, pepsin, cholecystokinin, amylase, ghrelin, leptin, somatostatin, etc. In still another example, the method of the present invention includes modulating the pathways associated with hormones, peptides, and/or enzymes secreted by T1R expressing cells.

Exemplary chemosensory receptor ligand modifiers provided by the present invention and/or suitable to be used for methods of the present invention include compounds of the following formulae.

In a first aspect, a compound of structural Formula (I) is provided:

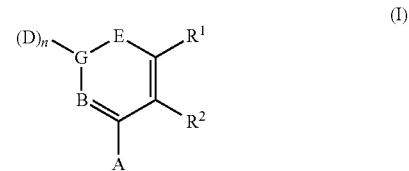

(I)

or a salt, hydrate, solvate or N-oxide thereof wherein:

G forms a single bond with either D or E and a double bond with the other of D or E;

$R^1$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^3$, —S(O)$_a$R$^3$, —NR$^3$R$^4$, —CONR$^3$R$^4$, —CO$_2$R$^3$, —NR$^3$CO$_2$R$^4$, —NR$^3$CONR$^4$R$^5$, —NR$^3$CSNR$^4$R$^5$ or —NR$^3$C(=NH)NR$^4$R$^5$, —SO$_2$NR$^2$R$^3$, —NR$^2$SO$_2$R$^3$, —NR$^2$SO$_2$NR$^3$R$^4$, —B(OR$^2$)(OR$^3$), —P(O)(OR$^2$)(OR$^3$) or —P(O)(R$^2$)(OR$^3$);

$R^2$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^6$, —S(O)$_b$R$^6$, —NR$^6$R$^7$, —CONR$^6$R$^7$, —CO$_2$R$^6$, —NR$^6$CO$_2$R$^7$, —NR$^6$CONR$^7$R$^8$, —NR$^6$CSNR$^7$R$^8$ or —NR$^6$C(=NH)NR$^7$R$^8$, —SO$_2$NR$^5$R$^6$, —NR$^5$SO$_2$R$^6$, —NR$^5$SO$_2$NR$^6$R$^7$, —B(OR$^5$)(OR$^6$), —P(O)(OR$^5$)(OR$^6$), —P(O)(R$^5$)(OR$^6$) or alternatively, R$^1$ and R$^2$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

with the proviso that R$^1$ and R$^2$ are not both hydrogen;

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —NO$_2$, —OR$^9$, —S(O)$_c$R$^9$, —NR$^9$COR$^{10}$, —NHOR$^9$, —NR$^9$R$^{10}$, —NOR$^9$, —CONR$^9$R$^{10}$, —CO$_2$R$^9$R$^{10}$, —NR$^9$CONR$^{10}$R$^{11}$, —NR$^9$CSNR$^{10}$R$^{11}$, —NR$^9$C(=NH)NR$^{10}$R$^{11}$, —B(OR$^{10}$)(OR$^{11}$), —P(O)(OR$^{10}$)(OR$^{11}$) or —P(O)(R$^{10}$)(OR$^{11}$);

B is —N— or —C(R$^{12}$)—;

R$^{12}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{13}$R$^{14}$, —CN, —OR$^{13}$, —S(O)$_d$R$^{13}$, —CO$_2$R$^{13}$ or —CONR$^{13}$R$^{14}$;

G is —C— or —S(O)$_2$—;

provided that when G is —S(O)$_2$, G forms a single bond with E;

D is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl, substituted heteroarylalkyl, —OR$^5$, —NOR$^{15}$, —S(O)$_e$R$^{15}$, —NR$^{15}$R$^{16}$, —NCN, —CO$_2$R$^{15}$, —CONR$^{15}$R$^{16}$ when the bond between D and G is a single bond;

D is =O, =S, =N—OR$^{15}$, =NHNHR$^{15}$ when G form a double bond with D;

n is 0 when G is —S(O)$_2$— and n is 1 when G is —C—;

E is —NR$^{17}$, —N— or —C(R$^{18}$)—;

provided that E is —NR$^{17}$— only when G forms a single bond with E;

R$^{17}$ is alkyl, substituted alkyl, aryl, substituted aryl, arylalkyl, substituted arylalkyl, acyl, substituted acyl, heteroalkyl, substituted heteroalkyl, heteroaryl, heteroarylalkyl, substituted heteroarylalkyl or —CO$_2$R$^{19}$;

R$^{18}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{20}$R$^{21}$, —CN, OR$^{20}$, —S(O)$_f$R$^{20}$, —CO$_2$R$^{20}$ or —CONR$^{20}$R$^{21}$;

a, b, c, d, e and f are independently 0, 1 or 2; and

R$^3$-R$^{11}$, R$^{13}$-R$^{16}$, R$^{18}$, R$^{20}$ and R$^{21}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively, R$^3$ and R$^4$, R$^4$ and R$^5$, R$^6$ and R$^7$, R$^7$ and R$^8$, R$^9$ and R$^{10}$, R$^{10}$ and R$^{11}$, R$^{13}$ and R$^{14}$, R$^{15}$ and R$^{16}$ and R$^{20}$ and R$^{21}$ together with the atoms to which they are bonded form a cycloheteroalkyl or substituted cycloheteroalkyl ring.

In some embodiments, R$^1$ is hydrogen, alkyl, substituted alkyl, —CN, —NO$_2$, —OR$^2$, —S(O)$_a$R$^3$, —NR$^3$R$^4$, —CONR$^3$R$^4$, —CO$_2$R$^3$ and R$^2$ is hydrogen, alkyl, substituted alkyl, —CN, —NO$_2$, —OR$^6$, —S(O)$_b$R$^6$, —NR$^6$R$^7$, —CONR$^6$R$^7$ or —CO$_2$R$^6$. In other embodiments, R$^1$ is hydrogen, —CH$_3$, —OH, —NH$_2$, —OR$^3$ or —CO$_2$R$^3$ and R$^2$ is —CH$_3$, —OH, —NH$_2$, —OR$^6$ or —CO$_2$R$^6$ and R$^3$ and R$^6$ are independently hydrogen or —CH$_3$. In still other embodiments, R$^1$ and R$^2$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring.

In some embodiments, a compound of structural Formula (II) is provided:

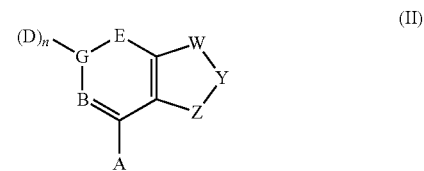

wherein:

Y forms a single bond with either W or Z and a double bond with the other of W or Z;

W is —C(R$^{24}$)—, —S—, —N—, —N(R$^{25}$)— or —O—;

Y is —C(R$^{26}$)— or —N—;

Z is —C(R$^{27}$)—, —S—, —N—, —N(R$^{28}$)—, or —O—;

R$^{24}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl —CN, —NO$_2$, —OR$^{29}$, —S(O)$_g$R$^{29}$, —OCOR$^{29}$, —NR$^{29}$R$^{30}$, —CONR$^{29}$R$^{30}$, —CO$_2$R$^{29}$, —NR$^{29}$COR$^{30}$, —SO$_2$NR$^{29}$R$^{30}$, —NR$^{29}$SO$_2$R$^{30}$, —B(OR$^{29}$)(OR$^{30}$), —P(O)(OR$^{29}$)(OR$^{30}$) or —P(O)(R$^{29}$)(OR$^{30}$);

R$^{26}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl —CN, —NO$_2$, —OR$^{31}$, —S(O)$_h$R$^{31}$, —OCOR$^{31}$, —NR$^{31}$R$^{32}$, —CONR$^{31}$R$^{32}$, —CO$_2$R$^{31}$, —NR$^{31}$COR$^{32}$, —SO$_2$NR$^{31}$R$^{32}$, —NR$^{31}$SO$_2$R$^{32}$, —B(OR$^{31}$)(OR$^{32}$), —P(O)(OR$^{31}$)(OR$^{32}$) or —P(O)(R$^{31}$)(OR$^{32}$);

R$^{27}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl —CN, —NO$_2$, —OR$^{33}$, —S(O)$_i$R$^{33}$, —OCOR$^{33}$, —NR$^{33}$R$^{34}$, —CONR$^{33}$R$^{34}$, —CO$_2$R$^{33}$, —NR$^{33}$COR$^{34}$, —SO$_2$NR$^{33}$R$^{34}$, —NR$^{33}$SO$_2$R$^{34}$, —B(OR$^{33}$)(OR$^{34}$), —P(O)(OR$^{33}$)(OR$^{34}$) or —P(O)(R$^{33}$)(OR$^{34}$) or alternatively R$^{24}$ and R$^{26}$ or R$^{26}$ and R$^{27}$ together with the atoms to which they are bonded form a cycloalkyl, substituted cycloalkyl, cycloheteroalkyl or substituted cycloheteroalkyl ring;

g, h and i are independently 0, 1 or 2;

$R^{25}$ and $R^{28}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; and $R^{29}$-$R^{34}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively $R^{29}$ and $R^{30}$, $R^{31}$ and $R^{32}$ and $R^{33}$ and $R^{34}$ together with the atoms to which they are bonded form a cycloheteroalkyl or substituted cycloheteroalkyl ring; with the provisos that with the provisos that when W is —O— or —S— or —NR$^{25}$ then Z is —C(R$^{27}$) or —N—; Z is —O— or —S— or —NR$^{25}$ then W is —C(R$^{27}$) or —N—; and when B is —N— then A is not halo.

In some embodiments, W is —S—, NR$^{25}$, —N— —O— or —C(R$^{24}$)—, Y is —CR$^{26}$— and Z is —S—, —NR$^{28}$—, —N—, —O— or —C(R$^{27}$)—. In other embodiments, A is hydrogen, alkyl, substituted alkyl, aryl, substituted aryl, —OR$^1$, —SR$^1$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$, D is —OR$^{15}$, —S(O)$_e$R$^{15}$, Cl, —NR$^{15}$NR$^{16}$, —CO$_2$R$^{15}$ or —CONR$^{15}$R$^{16}$ or D is =O, =S, =N—OR$^{15}$ or =NHNHR$^{15}$ B is —N—, W is —S—, NR$^{25}$, —N—, —O— or —C(R$^{24}$)—, Y is —CR$^{26}$— and Z is —S—, —NR$^{28}$—, —N—, —O— or —C(R$^{27}$)—. In still other embodiments, A is hydrogen, alkyl, substituted alkyl, aryl, substituted aryl, —OR$^1$, —SR$^1$, —CN, —NR$^8$R$^9$, —CONR$^8$R$^9$, —CO$_2$R$^8$, —NR$^8$CO$_2$R$^9$, —NR$^8$CONR$^9$R$^{10}$, —NR$^8$CSNR$^9$R$^{10}$ or —NR$^8$C(=NH)NR$^9$R$^{10}$, D is —OR$^{15}$, —Cl, —S(O)$_e$R$^{15}$, —NR$^{15}$NR$^{16}$, —CO$_2$R$^{15}$ or —CONR$^{15}$R$^{16}$, or D is =O, =S, =N—OR$^{15}$ or =NHNHR$^{15}$, B is —N—, W is —C(R$^{24}$)—, —NR$^{25}$ or —N—, Y is —N— and Z is —C(R$^{27}$)—, —NR$^{28}$— or —N—. In still other embodiments, W is —C(R$^{24}$)—, —NR$^{25}$ or —N—, Y is —N— and Z is —C(R$^{27}$)—, —NR$^{28}$— or —N—.

In some embodiments, a compound of structural Formula (IIa) is provided:

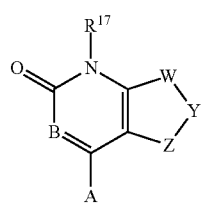

(IIa)

wherein:

A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —NO$_2$, —OR$^9$, —S(O)$_c$R$^9$, —NR$^9$COR$^{10}$, —NHOR$^9$, —NR$^9$R$^{10}$, —NOR$^9$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$, —NR$^9$C(=NH)NR$^{10}$R$^{11}$, —B(OR$^{10}$)(OR$^{11}$), —P(O)(OR$^{10}$)(OR$^{11}$) or —P(O)(R$^{10}$)(OR$^{11}$);

$R^{17}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl or —CO$_2$R$^{19}$;

B is —N— or —C(R$^{12}$)—;

$R^{12}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{13}$R$^{14}$, —CN, —OR$^{13}$, —S(O)$_d$R$^{13}$, —CO$_2$R$^{13}$ or —CONR$^{13}$R$^{14}$;

Y forms a single bond with either W or Z and a double bond with the other of W or Z;

W is —C(R$^{24}$)—, —S—, —N—, —N(R$^{25}$)— or —O—;

Y is —C(R$^{26}$)— or —N—;

Z is —C(R$^{27}$)—, —S—, —N—, —N(R$^{28}$)— or —O—;

$R^{24}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl —CN, —NO$_2$, —OR$^{29}$, —S(O)$_g$R$^{29}$, —OCOR$^{29}$, —NR$^{29}$R$^{30}$, —CONR$^{29}$R$^{30}$, —CO$_2$R$^{29}$, —NR$^{29}$COR$^{30}$, —SO$_2$NR$^{29}$R$^{30}$, —NR$^{29}$SO$_2$R$^{30}$, —B(OR$^{29}$)(OR$^{30}$), —P(O)(OR$^{29}$)(OR$^{30}$) or —P(O)(R$^{29}$)(OR$^{30}$);

$R^{26}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl —CN, —NO$_2$, —OR$^{31}$, —S(O)$_h$R$^{31}$, —OCOR$^{31}$, —NR$^{31}$R$^{32}$, —CONR$^{31}$R$^{32}$, —CO$_2$R$^{31}$, —NR$^{31}$COR$^{32}$, —SO$_2$NR$^{31}$R$^{32}$, —NR$^{31}$SO$_2$R$^{32}$, —B(OR$^{31}$)(OR$^{32}$), —P(O)(OR$^{31}$)(OR$^{32}$) or —P(O)(R$^{31}$)(OR$^{32}$);

$R^{27}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl —CN, —NO$_2$, —OR$^{33}$, —S(O)$_i$R$^{33}$, —OCOR$^{33}$, —NR$^{33}$R$^{34}$, —CONR$^{33}$R$^{34}$, —CO$_2$R$^{33}$, —NR$^{33}$COR$^{34}$, —SO$_2$NR$^{33}$R$^{34}$, —NR$^{33}$SO$_2$R$^{34}$, —B(OR$^{33}$)(OR$^{34}$), —P(O)(OR$^{33}$)(OR$^{34}$) or —P(O)(R$^{33}$)(OR$^{34}$) or alternatively $R^{24}$ and $R^{26}$ or $R^{26}$ and $R^{27}$ together with the atoms to which they are bonded form a cycloalkyl, substituted cycloalkyl, cycloheteroalkyl or substituted cycloheteroalkyl ring;

c, d, g, h and i are independently 0 or 1 or 2;

$R^{25}$ and $R^{28}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; and $R^9$-$R^{11}$, $R^{13}$, $R^{14}$, $R^{19}$ and $R^{29}$-$R^{34}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl alternatively $R^9$ and $R^{10}$, $R^{10}$ and $R^{11}$, $R^{13}$ and $R^{14}$, $R^{29}$ and $R^{30}$, $R^{31}$ and $R^{32}$ and $R^{33}$ and $R^{34}$ together with the atoms to which they are bonded form a cycloheteroalkyl or substituted cycloheteroalkyl ring;

with the provisos that: when W is —O— or —S— or —NR$^{25}$ then Z is —C(R$^{27}$) or —N—; when Z is —O— or —S— or —NR$^{28}$ then W is —C(R$^{24}$) or —N—; and when B is —N— then A is not halo.

In some embodiments, A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —S(O)$_c$R$^9$, —NR$^9$R$^{10}$, —CONR$^9$R$^{10}$, —CO$_2$R$^9$ or —NR$^9$CO$_2$R$^{10}$. In other embodiments, A is hydrogen, alkyl, substituted alkyl, aryl, substituted aryl, —CN, —NO$_2$, —S(O)$_c$R$^9$, —NR$^9$R$^{10}$, —CONR$^9$R$^{10}$, —CO$_2$R$^9$ or —NR$^9$CO$_2$R$^{10}$. In still other embodiments, A is —OR$^9$, —NR$^9$CONR$^{10}$R$^{11}$, —NR$^9$CSNR$^{10}$R$^{11}$ or —NR$^9$C(=NH)NR$^{10}$R$^{11}$. In still other embodiments, A is —OH, —NH$_2$, —NHCH$_3$, —N(CH$_3$)$_2$, —NHC(O)CH$_3$, —NOCH$_3$, —NHOCH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$.

In some embodiments, R$^{17}$ is hydrogen, alkyl, substituted alkyl, arylalkyl, or substituted arylalkyl. In other embodiments, R$^{17}$ is hydrogen, methyl, ethyl, propyl, iso-propyl, n-butyl, iso-butyl, sec-butyl, t-butyl, phenyl or benzyl.

In some embodiments, A is hydrogen, alkyl, substituted alkyl, aryl, substituted aryl, —CN, —NO$_2$, —S(O)$_c$R$^9$, —NR$^9$COR$^{10}$, —NR$^9$R$^{10}$, —CONR$^9$R$^{10}$, —CO$_2$R$^9$ or —NR$^9$CO$_2$R$^{10}$ and R$^{17}$ is hydrogen, alkyl, substituted alkyl, arylalkyl, or substituted arylalkyl. In other embodiments, A is —OR$^9$, —NR$^9$CONR$^{10}$R$^{11}$, —NR$^9$CSNR$^{10}$R$^{11}$ or —NR$^9$C(=NH)NR$^{10}$R$^{11}$ and R$^{17}$ is hydrogen, alkyl, substituted alkyl, arylalkyl, or substituted arylalkyl. In still other embodiments, A is —OH, —NH$_2$, —NHCH$_3$, —N(CH$_3$)$_2$, —NHC(O)CH$_3$, —NOCH$_3$, —NHOCH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$ and R$^{17}$ is hydrogen, methyl, ethyl, propyl, iso-propyl, n-butyl, iso-butyl, sec-butyl, t-butyl, phenyl or benzyl.

In some embodiments, a compound of structural Formula (IIb) is provided:

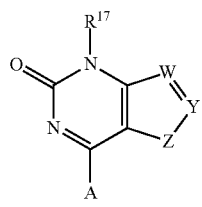

(IIb)

wherein:
W is —C(R$^{24}$)— or —N—;
Y is —C(R$^{26}$)— or —N—; and
Z is —S—, —N(R$^{28}$)— or —O—. In some embodiments, W is —C(R$^{24}$)—, Y is —C(R$^{26}$)— and Z is —S—, —N(R$^{28}$)— or —O—.

In some embodiments, R$^{24}$ is hydrogen, alkyl, substituted alkyl, acyl, substituted acyl, heteroalkyl, substituted heteroalkyl, —CN, —NO$_2$, —OR$^{29}$, —S(O)$_g$R$^{29}$, —OCOR$^{29}$, —NR$^{29}$R$^{30}$, —CONR$^{29}$R$^{30}$ or —CO$_2$R$^{29}$ and R$^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OCOR$^{31}$, —NR$^{31}$R$^{32}$, —CONR$^{31}$R$^{32}$ or —CO$_2$R$^{31}$. In other embodiments, R$^{24}$ is hydrogen, —CF$_3$, alkyl or substituted alkyl and R$^{26}$ is hydrogen, —CF$_3$, alkyl or substituted alkyl.

In some embodiments, A is hydrogen, alkyl, substituted alkyl, aryl, substituted aryl, —CN, —NO$_2$, —S(O)$_c$R$^9$, —NR$^9$R$^{10}$, —CONR$^9$R$^{10}$, —CO$_2$R$^9$ or —NR$^9$CO$_2$R$^{10}$, R$^{17}$ is hydrogen, alkyl, substituted alkyl, arylalkyl, or substituted arylalkyl, R$^{24}$ is hydrogen, alkyl, substituted alkyl, acyl, substituted acyl, heteroalkyl, substituted heteroalkyl, —CN, —NO$_2$, —OR$^{29}$, —S(O)$_g$R$^{29}$, —OCOR$^{29}$, —NR$^{29}$R$^{30}$, —CONR$^{29}$R$^{30}$ or —CO$_2$R$^{29}$ and R$^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OCOR$^{31}$, —NR$^{31}$R$^{32}$, —CONR$^{31}$R$^{32}$ or —CO$_2$R$^{31}$. In other embodiments, A is —OR$^9$, —NR$^9$CONR$^{10}$R$^{11}$, —NR$^9$CSNR$^{10}$R$^{11}$ or —NR$^9$C(=NH)NR$^{10}$R$^{11}$ and R$^{17}$ is hydrogen, alkyl, substituted alkyl, arylalkyl, or substituted arylalkyl, R$^{24}$ is hydrogen, alkyl, substituted alkyl, acyl, substituted acyl, heteroalkyl, substituted heteroalkyl, —CN, —NO$_2$, —OR$^{29}$, —S(O)$_g$R$^{29}$, —OCOR$^{29}$, —NR$^{29}$R$^{30}$, —CONR$^{29}$R$^{30}$ or —CO$_2$R$^{29}$ and R$^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OCOR$^{31}$, —NR$^{31}$R$^{32}$, —CONR$^{31}$R$^{32}$ or —CO$_2$R$^{31}$. In still other embodiments, A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$, R$^{17}$ is hydrogen, methyl, ethyl, propyl, iso-propyl, n-butyl, iso-butyl, sec-butyl, t-butyl, phenyl or benzyl, R$^{24}$ is hydrogen, —CF$_3$, methyl, ethyl, propyl, iso-propyl, n-butyl, iso-butyl, sec-butyl or t-butyl and R$^{26}$ is hydrogen, —CF$_3$, methyl, ethyl, propyl, iso-propyl, n-butyl, iso-butyl, sec-butyl or t-butyl.

In some embodiments, A is —NH$_2$, R$^{17}$ is hydrogen or methyl, R$^{24}$ is hydrogen, —CF$_3$, methyl or ethyl and R$^{26}$ is hydrogen, —CF$_3$, methyl or ethyl. In other embodiments, A is —NH$_2$, R$^{17}$ is hydrogen or methyl, R$^{24}$ is hydrogen, —CF$_3$, methyl or ethyl and R$^{26}$ is hydrogen, —CF$_3$, methyl or ethyl.

In many of the above embodiments, R$^{28}$ is hydrogen, alkyl or arylalkyl. In many of the above embodiments, R$^{28}$ is hydrogen, methyl or benzyl. In some of the above embodiments, Z is S.

In some embodiments, a compound of structural Formula (IIc) is provided:

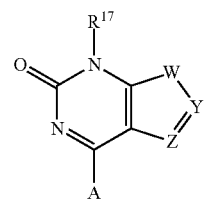

(IIc)

wherein W is —S—, —N(R$^{25}$)— or —O—, Y is —C(R$^{26}$)— or —N— and Z is —C(R$^{27}$)— or —N—. In some embodiments, W is —S—, —N(R$^{25}$)— or —O—, Y is —C(R$^{26}$)— and Z is —C(R$^{27}$)—.

In some embodiments, R$^{27}$ is hydrogen, alkyl, substituted alkyl, acyl, substituted acyl, heteroalkyl, substituted heteroalkyl, —CN, —NO$_2$, —OR$^{33}$, —S(O)$_i$R$^{33}$, —OCOR$^{33}$, —NR$^{33}$R$^{34}$, —CONR$^{33}$R$^{34}$ or —CO$_2$R$^{33}$ and R$^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OCOR$^{31}$, —NR$^{31}$R$^{32}$, —CONR$^{31}$R$^{32}$ or —CO$_2$R$^{31}$. In other embodiments, R$^{27}$ is hydrogen, —CF$_3$, alkyl or substituted alkyl and R$^{26}$ is hydrogen, —CF$_3$, alkyl or substituted alkyl.

In some embodiments, A is hydrogen, alkyl, substituted alkyl, aryl, substituted aryl, —CN, —NO$_2$, —S(O)$_c$R$^9$, —NR$^9$R$^{10}$, —CONR$^9$R$^{10}$, —CO$_2$R$^9$ or —NR$^9$CO$_2$R$^{10}$, R$^{17}$ is hydrogen, alkyl, substituted alkyl, arylalkyl, or substituted arylalkyl, $R^{27}$ is hydrogen, alkyl, substituted alkyl, acyl, substituted acyl, heteroalkyl, substituted heteroalkyl, —CN, —NO$_2$, —OR$^{33}$, —S(O)$_i$R$^{33}$, —OCOR$^{33}$, —NR$^{33}$R$^{34}$, —CONR$^{33}$R$^{34}$ or —CO$_2$R$^{33}$ and $R^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OCOR$^{31}$, —NR$^{31}$R$^{32}$, —CONR$^{31}$R$^{32}$ or —CO$_2$R$^{31}$. In other embodiments, A —OR$^9$, —NR$^9$CONR$^{10}$R$^{11}$, —NR$^9$CSNR$^{10}$R$^{11}$ or —NR$^9$C(=NH)NR$^{10}$R$^{11}$ and $R^{17}$ is hydrogen, alkyl, substituted alkyl, arylalkyl, or substituted arylalkyl, $R^{27}$ is hydrogen, alkyl, substituted alkyl, acyl, substituted acyl, heteroalkyl, substituted heteroalkyl, —CN, —NO$_2$, —OR$^{33}$, —S(O)$_i$R$^{33}$, —OCOR$^{33}$, —NR$^{33}$R$^{34}$, —CONR$^{33}$R$^{34}$ or —CO$_2$R$^{33}$ and $R^{26}$ is hydrogen, alkyl, substituted alkyl, acyl, substituted acyl, heteroalkyl, substituted heteroalkyl, —CN, —NO$_2$, —OR$^{31}$, —S(O)$_h$R$^{31}$, —OCOR$^{31}$, —NR$^{31}$R$^{32}$, —CONR$^{31}$R$^{32}$ or —CO$_2$R$^{31}$. In still other embodiments, A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$, $R^{17}$ is hydrogen, methyl, ethyl, propyl, iso-propyl, n-butyl, iso-butyl, sec-butyl, t-butyl, phenyl or benzyl, $R^{27}$ is hydrogen, —CF$_3$, methyl, ethyl, propyl, iso-propyl, n-butyl, iso-butyl, sec-butyl or t-butyl and $R^{26}$ is hydrogen, —CF$_3$, methyl, ethyl, propyl, iso-propyl, n-butyl, iso-butyl, sec-butyl or t-butyl.

In some embodiments, A is —NH$_2$, $R^{17}$ is hydrogen or methyl, $R^{27}$ is hydrogen, —CF$_3$, methyl or ethyl and $R^{26}$ is hydrogen, —CF$_3$, methyl or ethyl. In other embodiments, $R^{17}$ is hydrogen or methyl, $R^{27}$ is hydrogen, —CF$_3$, methyl or ethyl and $R^{26}$ is hydrogen, —CF$_3$, methyl or ethyl.

In some embodiments, $R^{25}$ is hydrogen, alkyl or arylalkyl. In other embodiments, $R^{25}$ is hydrogen, methyl or benzyl. In still other embodiments, Z is S.

In some embodiments, a compound of structural Formula (III) is provided:

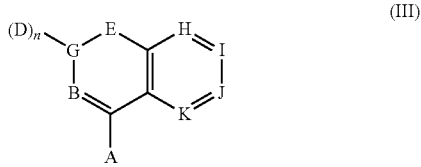

(III)

wherein:
H is —C(R$^{35}$)— or —N—;
I is —C(R$^{36}$) or —N—;
J is —C(R$^{37}$)— or —N—;
K is —C(R$^{38}$)— or —N—;
$R^{35}$ is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl or substituted heteroarylalkyl, —CN, —NO$_2$, —OR$^{39}$, —S(O)$_j$R$^{39}$, —OCOR$^{39}$, —NR$^{39}$R$^{40}$, —CONR$^{39}$R$^{40}$, —CO$_2$R$^{39}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$);
$R^{36}$ is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl or substituted heteroarylalkyl, —CN, —NO$_2$, —OR$^{41}$, —S(O)$_k$R$^{41}$, —OCOR$^{41}$, —NR$^{41}$COR$^{42}$, —NR$^{41}$R$^{42}$, —CONR$^{41}$R$^{42}$, —CO$_2$R$^{41}$, —SO$_2$NR$^{41}$R$^{42}$, —NR$^{41}$SO$_2$R$^{42}$, —B(OR$^{41}$)(OR$^{42}$), —P(O)(OR$^{41}$)(OR$^{42}$) or —P(O)(R$^{41}$)(OR$^{42}$);
$R^{37}$ is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl or substituted heteroarylalkyl, —CN, —NO$_2$, —OR$^{43}$, —S(O)$_l$R$^{43}$, —OCOR$^{43}$, —NR$^{43}$COR$^{44}$, —NR$^{43}$R$^{44}$, —CONR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$);
$R^{38}$ is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl or substituted heteroarylalkyl, —CN, —NO$_2$, —OR$^{45}$, —S(O)$_m$R$^{45}$, —OCOR$^{45}$, —NR$^{45}$COR$^{46}$, —NR$^{45}$R$^{46}$, —CONR$^{45}$R$^{46}$, —CO$_2$R$^{45}$, —SO$_2$NR$^{45}$R$^{46}$, —NR$^{45}$SO$_2$R$^{46}$, —B(OR$^{45}$)(OR$^{46}$), —P(O)(OR$^{45}$)(OR$^{46}$) or —P(O)(R$^{45}$)(OR$^{46}$);
j, k, l and m are independently 0, 1 or 2; and
$R^{39}$-$R^{46}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively $R^{39}$ and $R^{40}$, $R^{41}$ and $R^{42}$, $R^{43}$ and $R^{44}$ and $R^{45}$ and $R^{46}$ together with the atoms to which they are bonded form a cycloheteroalkyl or substituted cycloheteroalkyl ring;
with the proviso that at most, three of H, I, J and K are —N—.

In some embodiments, H is —C(R$^{35}$)— or —N—; I is —C(R$^{36}$)—; J is —C(R$^{37}$)—; and K is —C(R$^{38}$)— or —N—. In other embodiments, A is hydrogen, alkyl, substituted alkyl, aryl, substituted aryl, —OR$^1$, —SR$^1$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$, D is —OR$^{15}$, —NOR$^{15}$, —S(O)$_e$R$^{15}$, —NR$^{15}$NR$^{16}$, —CO$_2$R$^{15}$ or —CONR$^{15}$R$^{16}$ or D is =O, =S, =N—OR$^{15}$, B is —N—, H is —C(R$^{35}$)— or —N—, I is —C(R$^{36}$)—, J is —C(R$^{37}$)— and K is —C(R$^{38}$)— or —N—.

In some embodiments, a compound of structural Formula (IIIa) is provided:

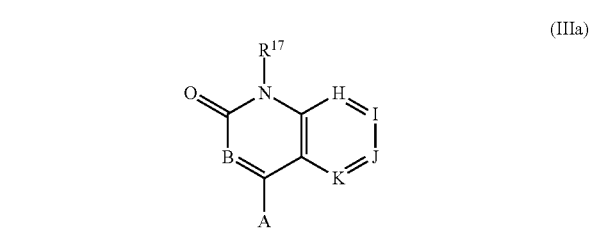

(IIIa)

or a salt, hydrate or solvate thereof wherein:
A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, halo, —CN, —NO$_2$, —OR$^9$, —S(O)$_c$R$^9$, —NR$^9$R$^{10}$, —NOR$^9$, —NHOR$^9$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$, —NR$^9$C(=NH)NR$^{10}$R$^{11}$, —B(OR$^{10}$)(OR$^{11}$), —P(O)(OR$^{10}$)(OR$^{11}$) or —P(O)(R$^{10}$)(OR$^{11}$);

R$^{17}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl or —CO$_2$R$^{19}$;

B is —N— or —C(R$^{12}$)—;

R$^{12}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —NR$^{13}$R$^{14}$, —CN, —OR$^{13}$, —S(O)$_d$R$^{13}$, —CO$_2$R$^{13}$ or —CONR$^{13}$R$^{14}$;

H is —C(R$^{35}$)— or —N—;
I is —C(R$^{36}$) or —N—;
J is —C(R$^{37}$)— or —N—;
K is —C(R$^{38}$)— or —N—;

R$^{35}$ is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl or substituted heteroarylalkyl, —CN, —NO$_2$, —OR$^{39}$, —S(O)$_j$R$^{39}$, —OCOR$^{39}$, —NR$^{39}$COR$^{40}$, —CONR$^{39}$R$^{40}$, CO$_2$R$^{39}$, SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$);

R$^{36}$ is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl or substituted heteroarylalkyl, —CN, —NO$_2$, —OR$^{41}$, —S(O)$_k$R$^{41}$, —OCOR$^{41}$, —NR$^{41}$COR$^{42}$, —NR$^{41}$R$^{42}$, —CONR$^{41}$R$^{42}$, —CO$_2$R$^{41}$, —SO$_2$NR$^{41}$R$^{42}$, —NR$^{41}$SO$_2$R$^{42}$, —B(OR$^{41}$)(OR$^{42}$), —P(O)(OR$^{41}$)(OR$^{42}$) or —P(O)(R$^{41}$)(OR$^{42}$);

R$^{37}$ is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl or substituted heteroarylalkyl, —CN, —NO$_2$, —OR$^{43}$, —S(O)$_l$R$^{43}$, —OCOR$^{43}$, —NR$^{43}$R$^{44}$, —CONR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$);

R$^{38}$ is hydrogen, alkyl, substituted alkyl, aryl, substituted aryl, arylalkyl, substituted arylalkyl, acyl, substituted acyl, halo, chloro, fluoro, heteroalkyl, substituted heteroalkyl, heteroaryl, substituted heteroaryl, heteroarylalkyl or substituted heteroarylalkyl, —CN, —NO$_2$, —OR$^{45}$, —S(O)$_m$R$^{45}$, —OCOR$^{45}$, —NR$^{45}$COR$^{46}$, —NR$^{45}$R$^{46}$, —CONR$^{45}$R$^{46}$, —CO$_2$R$^{45}$, —SO$_2$NR$^{45}$R$^{46}$, —NR$^{45}$SO$_2$R$^{46}$, —B(OR$^{45}$)(OR$^{46}$), —P(O)(OR$^{45}$)(OR$^{46}$) or —P(O)(R$^{45}$)(OR$^{46}$);

c, d, j, k, l and m are independently 0, 1 or 2; and

R$^9$, R$^{13}$, R$^{14}$, R$^{19}$ and R$^{39}$-R$^{46}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively R$^{13}$ and R$^{14}$, R$^{39}$ and R$^{40}$, R$^{41}$ and R$^{42}$, R$^{43}$ and R$^{44}$ and R$^{45}$ and R$^{46}$ together with the atoms to which they are bonded form a cycloheteroalkyl or substituted cycloheteroalkyl ring;

with the proviso that at most, three of H, I, J and K are —N—. In some embodiments, none of H, I, J, K are —N—.

In other embodiments, A is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —S(O)$_c$R$^9$, —NR$^9$COR$^{10}$, —NR$^9$R$^{10}$, —CONR$^9$R$^{10}$, —CO$_2$R$^9$ or —NR$^9$CO$_2$R$^{10}$. In other embodiments, A is hydrogen, alkyl, substituted alkyl, aryl, substituted aryl, —CN, —NO$_2$, —S(O)$_c$R$^9$, —NR$^9$R$^{10}$, —CONR$^9$R$^{10}$, —CO$_2$R$^9$ or —NR$^9$CO$_2$R$^{10}$. In still other embodiments, A is —OR$^9$, —NR$^9$CONR$^{10}$R$^{11}$, —NR$^9$CSNR$^{10}$R$^{11}$ or —NR$^9$C(=NH)NR$^{10}$R$^{11}$. In still other embodiments, A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$.

In some embodiments, R$^{17}$ is hydrogen, alkyl, substituted alkyl, arylalkyl, or substituted arylalkyl. In other embodiments, R$^{17}$ is hydrogen, methyl, ethyl, propyl, iso-propyl, n-butyl, iso-butyl, sec-butyl, t-butyl, phenyl or benzyl.

In some embodiments, A is hydrogen, alkyl, substituted alkyl, aryl, substituted aryl, —CN, —NO$_2$, —S(O)$_c$R$^9$, —NR$^9$R$^{10}$, —CONR$^9$R$^{10}$, —CO$_2$R$^9$, —NR$^9$COR$^{10}$ or —NR$^9$CO$_2$R$^{10}$ and R$^{17}$ is hydrogen, alkyl, substituted alkyl, arylalkyl, or substituted arylalkyl. In other embodiments, A is —OR$^9$, —NR$^9$CONR$^{10}$R$^{11}$, —NR$^9$CSNR$^{10}$R$^{11}$ or —NR$^9$C(=NH)NR$^{10}$R$^{11}$ and R$^{17}$ is hydrogen, alkyl, substituted alkyl, arylalkyl, or substituted arylalkyl. In still other embodiments, A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$ and R$^{17}$ is hydrogen, methyl, ethyl, propyl, iso-propyl, n-butyl, iso-butyl, sec-butyl, t-butyl, phenyl or benzyl.

In some embodiments, R$^{35}$ is hydrogen, —OH, —NR$^{39}$R$^{40}$, —NR$^{39}$COR$^{40}$, —OCOR$^{39}$, —CF$_3$, —OCF$_3$, —OCH$_3$, —OC$_2$H$_5$, —OC$_3$H$_7$, —CH$_3$, —C$_2$H$_5$, —CH(CH$_3$)$_2$, chloro, fluoro, —CH$_2$OH, —CH$_2$OCH$_3$, —CN, —C(O)NR$^{39}$R$^{40}$, —CO$_2$R$^{40}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$); R$^{36}$ is hydrogen, —OH, —NR$^{41}$R$^{42}$, —NR$^{41}$COR$^{42}$, —OCOR$^{41}$, —CF$_3$, —OCF$_3$, —OH, —OCH$_3$, —OC$_2$H$_5$, —OC$_3$H$_7$, —CH$_3$, —C$_2$H$_5$, —CH(CH$_3$)$_2$, chloro, fluoro, —CH$_2$OH, —CH$_2$OCH$_3$, —CN, —C(O)NR$^{41}$R$^{42}$, —CO$_2$R$^{41}$, —SO$_2$NR$^{41}$R$^{42}$, —NR$^{41}$SO$_2$R$^{42}$, —B(OR$^{41}$)(OR$^{42}$), —P(O)(OR$^{41}$)(OR$^{42}$) or —P(O)(R$^{41}$)(OR$^{42}$); R$^{37}$ is hydrogen, —OH, —NR$^{43}$R$^{44}$, —NR$^{43}$COR$^{44}$, —OCOR$^{43}$, —CF$_3$, —OCF$_3$, OH, —OCH$_3$, —OC$_2$H$_5$, —OC$_3$H$_7$, chloro, fluoro, —CH$_3$, —C$_2$H$_5$, —CH(CH$_3$)$_2$, —CH$_2$OH, —CH$_2$OCH$_3$, —CN, —C(O)NR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$); and R$^{38}$ is hydrogen, —OH, —NR$^{45}$R$^{46}$, —NR$^{45}$COR$^{46}$, —OCOR$^{45}$, —CF$_3$, —OCF$_3$, —OH, —OCH$_3$, —OC$_2$H$_5$, —OC$_3$H$_7$, —CH$_3$, —C$_2$H$_5$, —CH(CH$_3$)$_2$, chloro, fluoro, —CH$_2$OH, —CH$_2$OCH$_3$, —CN, —C(O)NR$^{45}$R$^{46}$, —CO$_2$R$^{45}$, —SO$_2$NR$^{45}$R$^{46}$, —NR$^{45}$SO$_2$R$^{46}$, —B(OR$^{45}$)(OR$^{46}$), —P(O)(OR$^{45}$)(OR$^{46}$) or —P(O)(R$^{45}$)(OR$^{46}$). In other embodiments, R$^{35}$ is hydrogen, —OH, —OCH$_3$, —OC$_2$H$_5$, —OC$_3$H$_7$, —CH$_3$, —C$_2$H$_5$, —CH(CH$_3$)$_2$, chloro, fluoro, —CH$_2$OH, —CH$_2$OCH$_3$, —CN, —C(O)NR$^{39}$R$^{40}$ or —CO$_2$R$^{40}$; R$^{36}$ is hydrogen, —OH, —OCH$_3$, —OC$_2$H$_5$, —OC$_3$H$_7$, —CH$_3$, —C$_2$H$_5$, —CH(CH$_3$)$_2$, chloro, fluoro, —CH$_2$OH, —CH$_2$OCH$_3$, —CN, —C(O)NR$^{41}$R$^{42}$ or —CO$_2$R$^{41}$; R$^{37}$ is hydrogen, —OH, —OCH$_3$, —OC$_2$H$_5$, —OC$_3$H$_7$, chloro, fluoro, —CH$_3$, —C$_2$H$_5$, —CH(CH$_3$)$_2$, —CH$_2$OH, —CH$_2$OCH$_3$, —CN, —C(O)NR$^{43}$R$^{44}$ or —CO$_2$R$^{43}$; and R$^{38}$ is hydrogen, —OH, —OCH$_3$, —OC$_2$H$_5$, —OC$_3$H$_7$, —CH$_3$, —C$_2$H$_5$, —CH(CH$_3$)$_2$, chloro, fluoro, —CH$_2$OH, —CH$_2$OCH$_3$, —CN, —C(O)NR$^{45}$R$^{46}$ or —CO$_2$R$^{45}$.

In some embodiments, A is —NH$_2$, R$^{17}$ is hydrogen, methyl, ethyl or benzyl R$^{35}$, R$^{36}$, R$^{37}$ and R$^{38}$ independently hydrogen, methyl, —OH or OCH$_3$. In other embodiments, A is —NH$_2$, R$^{17}$ is hydrogen, methyl, ethyl or benzyl and R$^{35}$, R$^{36}$, R$^{37}$ and R$^{38}$ are independently hydrogen, methyl, —OH or OCH$_3$. In still other embodiments, A is —NH$_2$, R$^{17}$ is hydrogen or methyl, and R$^{35}$, R$^{36}$, R$^{37}$ and R$^{38}$ are independently hydrogen or methyl. In still other embodiments, A is —NH$_2$, R$^{17}$ is hydrogen or methyl, and R$^{35}$, R$^{36}$, R$^{37}$ and R$^{38}$ are independently hydrogen or methyl. In still other embodiments, B is —N—.

In some embodiments, a compound of structural Formula (IV) is provided:

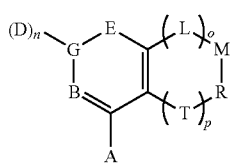

(IV)

wherein:
L is —CHR$^{60}$—, —NR$^{47}$, —O— or —S—;
M is —CHR$^{61}$—, —NR$^{48}$, —O— or —S—;
R is —CHR$^{62}$—, —NR$^{49}$, —O— or —S—;
T is —CHR$^{63}$—, —NR$^{50}$, —O— or —S—;
o and p are independently 0 or 1;
R$^{60}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, —CN, —NO$_2$, —OR$^{64}$, —S(O)$_t$R$^{64}$, —OCOR$^{64}$, —NR$^{64}$COR$^{65}$, —NR$^{64}$R$^{65}$, —CONR$^{64}$R$^{65}$, —CO$_2$R$^{64}$, —SO$_2$NR$^{64}$R$^{65}$, —NR$^{64}$SO$_2$R$^{65}$, —B(OR$^{64}$)(OR$^{65}$), —P(O)(OR$^{64}$)(OR$^{65}$) or —P(O)(R$^{64}$)(OR$^{65}$);
R$^{61}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, —CN, —NO$_2$, —OR$^{66}$, —S(O)$_u$R$^{66}$, —OCOR$^{66}$, —NR$^{66}$COR$^{67}$, —NR$^{66}$R$^{67}$, —CONR$^{66}$R$^{67}$, —CO$_2$R$^{66}$, —SO$_2$NR$^{66}$R$^{67}$, —NR$^{66}$SO$_2$R$^{67}$, —B(OR$^{66}$)(OR$^{67}$), —P(O)(OR$^{66}$)(OR$^{67}$) or —P(O)(R$^{66}$)(OR$^{67}$);
R$^{62}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, —CN, —NO$_2$, —OR$^{68}$, —S(O)$_v$R$^{68}$, —OCOR$^{68}$, —NR$^{68}$COR$^{69}$, —NR$^{68}$R$^{69}$, —CONR$^{68}$R$^{69}$, —CO$_2$R$^{68}$, —SO$_2$NR$^{68}$R$^{69}$, —NR$^{68}$SO$_2$R$^{69}$, —B(OR$^{68}$)(OR$^{69}$), —P(O)(OR$^{68}$)(OR$^{69}$) or —P(O)(R$^{68}$)(OR$^{69}$);

R$^{63}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl, —CN, —NO$_2$, —OR$^{70}$, —S(O)$_x$R$^{70}$, —OCOR$^{70}$, —NR$^{70}$COR$^{71}$, —NR$^{70}$R$^{71}$, —CONR$^{70}$R$^{71}$, —CO$_2$R$^{70}$, —SO$_2$NR$^{70}$R$^{71}$, —NR$^{70}$SO$_2$R$^{71}$, —B(OR$^{70}$)(OR$^{71}$), —P(O)(OR$^{70}$)(OR$^{71}$) or —P(O)(R$^{70}$)(OR$^{71}$);

t, u, v and x are independently 0, 1 or 2;
R$^{64}$-R$^{71}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively R$^{64}$ and R$^{65}$, R$^{66}$ and R$^{67}$, R$^{68}$ and R$^{69}$ and R$^{70}$ and R$^{71}$ together with the atoms to which they are bonded form a cycloheteroalkyl or substituted cycloheteroalkyl ring; and
R$^{47}$-R$^{50}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl;
with the provisos that that at most only one of L, M, R and T is a heteroatom.

In some embodiments, L, R and T are —CH$_2$, o and p are 1 and M is —N(R$^{48}$)—, —S— or —O— and R$^{48}$ is hydrogen, —CH$_3$ or —COCH$_3$. In other embodiments, A is hydrogen, alkyl, substituted alkyl, aryl, substituted aryl, —OR$^9$, —SR$^9$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$, D is —OR$^{15}$, —NOR$^{15}$, —S(O)$_e$R$^{15}$, —NR$^{15}$NR$^{16}$, —CO$_2$R$^{15}$ or —CONR$^{15}$R$^{16}$ or D is =O, =S, =N—OR$^{15}$, B is —N—, L, R and T are —CH$_2$, o and p are 1 and M is —N(R$^{48}$)—, —S— or —O— and R$^{48}$ is hydrogen, —CH$_3$ or —COCH$_3$.

In some of the above embodiments, A is hydrogen, alkyl, substituted alkyl, aryl, substituted aryl, —OR$^9$, —SR$^9$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$. In other of the above embodiments, A is —OH, —NH$_2$, —NHCH$_3$, —N(CH$_3$)$_2$, —NHC(O)CH$_3$, —NHC(O)OCH$_3$, —NHOCH$_3$, —NOCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$.

In some of the above embodiments, D is —OR$^{15}$, —S(O)$_e$R$^{15}$, —NR$^{15}$NR$^{16}$, —CO$_2$R$^{15}$, —CONR$^{15}$R$^{16}$, Cl, =N—OR$^{15}$ or =NHNHR$^{15}$. In other of the above embodiments, D is —OH, —SH or —NH$_2$.

In some of the above embodiments, R$^{17}$ is hydrogen, alkyl, substituted alkyl, arylalkyl, or substituted arylalkyl. In some of the above embodiments, R$^{17}$ is hydrogen, —CH$_3$, —CH$_2$CH$_3$ or —CH$_2$Ph.

In some of the above embodiments, R$^{12}$ is hydrogen, alkyl, substituted alkyl, aryl, substituted aryl, —OR$^{13}$, —SR$^{13}$, —CN, —CONR$^{13}$R$^{14}$ or —CO$_2$R$^{12}$. In other of the above embodiments, R$^{12}$ is hydrogen, —OH, —SH, —CN, —CH$_2$OH or —CO$_2$H.

In some of the above embodiments, A is hydrogen, alkyl, substituted alkyl, aryl, substituted aryl, —OR$^1$, —SR$^1$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$, D is —OR$^{15}$, Cl, —S(O)$_e$R$^{15}$, —NR$^{15}$NR$^{16}$, —CO$_2$R$^{15}$ or —CONR$^{15}$R$^{16}$ or D is =O, =S, =N—OR$^{15}$, =NHNHR$^{15}$ and R$^{12}$ is hydrogen, alkyl, substituted alkyl, aryl, substituted aryl, —OR$^{13}$, —SR$^{13}$, —CN, —CONR$^{13}$R$^{14}$ or —CO$_2$R$^{13}$. In other of the above embodiments, A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$, D is OH, SH or NH$_2$ or D is =O, =S, =N—OR$^{15}$ or =NHNHR$^{15}$ and R$^{12}$ is hydrogen, —OH, —SH, —CN, —CH$_2$OH or —CO$_2$H.

In some of the above embodiments, A is hydrogen, alkyl, substituted alkyl, aryl, substituted aryl, —OR$^1$, —SR$^1$, —CN, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$ or —NR$^9$C(=NH)NR$^{10}$R$^{11}$ and R$^{17}$ is hydrogen, alkyl, substituted alkyl, arylalkyl or substituted arylalkyl. In other of the above embodiments, A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$ and R$^{17}$ is hydrogen, —CH$_3$, —CH$_2$CH$_3$ or —CH$_2$Ph.

In some of the above embodiments, A is hydrogen, alkyl, substituted alkyl, aryl, substituted aryl, —OR$^1$, —SR$^1$, —CN, —NR$^8$R$^9$, —CONR$^8$R$^9$, —CO$_2$R$^8$, —NR$^8$CO$_2$R$^9$, —NR$^8$CONR$^9$R$^{10}$, —NR$^8$CSNR$^9$R$^{10}$ or —NR$^8$C(=NH)NR$^9$R$^{10}$, G is —S(O)$_2$— and R$^{12}$ is hydrogen, alkyl, substituted alkyl, aryl, substituted aryl, —OR$^{13}$, —SR$^{13}$, —CN, —CONR$^{13}$R$^{14}$ or —CO$_2$R$^{14}$. In other of the above embodiments, A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$, G is —S(O)$_2$— and R$^{12}$ is hydrogen, —OH, —SH, —CN, —CH$_2$OH or —CO$_2$H.

In some of the above embodiments, A is hydrogen, alkyl, substituted alkyl, aryl, substituted aryl, —OR$^1$, —SR$^1$, —CN, —NR$^8$R$^9$, —CONR$^8$R$^9$, —CO$_2$R$^8$, —NR$^8$CO$_2$R$^9$, —NR$^8$CONR$^9$R$^{10}$, —NR$^8$CSNR$^9$R$^{10}$ or —NR$^8$C(=NH)NR$^9$R$^{10}$, G is —S(O)$_2$— and R$^{17}$ is hydrogen, alkyl, substituted alkyl, arylalkyl or substituted arylalkyl. In other of the above embodiments, A is —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$, G is —S(O)$_2$— and R$^{17}$ is hydrogen, —CH$_3$, —CH$_2$CH$_3$ or —CH$_2$Ph.

In some embodiments, a compound of structural Formula (V) is provided:

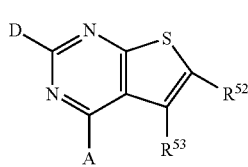

(V)

wherein:
D is hydrogen, alkyl, aryl, halo, chloro, fluoro, —OH, —NH$_2$, —SR$^{51}$, —CH$_3$, phenyl, —CO$_2$H or —CONH$_2$;
R$^{51}$ is hydrogen, alkyl, substituted alkyl, aryl alkyl, —CH$_3$, —CH$_2$CH$_3$, benzyl or —CH$_2$CO$_2$C$_2$H$_5$;

A is —NH$_2$, —NHCH$_3$, —N(CH$_3$)$_2$, —NHC(O)CH$_3$, —NHC(O)OCH$_3$, —NHC(O)NH$_2$, —NHOCH$_3$, —NOCH$_3$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$;
R$^{52}$ is hydrogen, methyl, ethyl, alkyl, chloro, fluoro, —CO$_2$R$^{54}$, —CONR$^{54}$R$^{55}$, —SO$_2$NR$^{54}$R$^{55}$, —NR$^{54}$SO$_2$R$^{55}$, —B(OR$^{54}$)(OR$^{55}$), —P(O)(OR$^{54}$)(OR$^{55}$) or —P(O)(R$^{54}$)(OR$^{55}$);
R$^{53}$ is hydrogen, alkoxy, alkyl, substituted alkyl, chloro, fluoro, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —C(O)NR$^{56}$R$^{57}$, —CO$_2$R$^{56}$, —SO$_2$NR$^{56}$R$^{57}$, —NR$^{56}$SO$_2$R$^{57}$, —B(OR$^{56}$)(OR$^{57}$), —P(O)(OR$^{56}$)(OR$^{57}$) or —P(O)(R$^{56}$)(OR$^{57}$); and
R$^{54}$-R$^{57}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively R$^{54}$ and R$^{55}$ and R$^{56}$ and R$^{57}$ together with the atoms to which they are bonded form a cycloheteroalkyl or substituted cycloheteroalkyl ring;
provided that when R$^{52}$ and R$^{53}$ are hydrogen then D is —SH and A is —NH$_2$.

In some embodiments, R$^{51}$ is alkyl, substituted alkyl, aryl alkyl, —CH$_3$, —CH$_2$CH$_3$, benzyl or —CH$_2$CO$_2$C$_2$H$_5$, R$^{52}$ is hydrogen, methyl, ethyl, alkyl, —CO$_2$R$^{54}$, —CONR$^{54}$R$^{55}$, —SO$_2$NR$^{54}$R$^{55}$, —NR$^{54}$SO$_2$R$^{55}$, —B(OR$^{54}$)(OR$^{55}$), —P(O)(OR$^{54}$)(OR$^{55}$) or —P(O)(R$^{54}$)(OR$^{55}$) and R$^{53}$ is hydrogen, alkoxy, alkyl, substituted alkyl, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —C(O)NR$^{56}$R$^{57}$, —CO$_2$R$^{56}$, —SO$_2$NR$^{56}$R$^{57}$, —NR$^{56}$SO$_2$R$^{57}$, —B(OR$^{56}$)(OR$^{57}$), —P(O)(OR$^{56}$)(OR$^{57}$) or —P(O)(R$^{56}$)(OR$^{57}$).

In some embodiments, when D is methyl, A is dimethylamino and R$^{53}$ is hydrogen then R$^{52}$ is not methyl, ethyl or carboxyl; when D is methyl, A is dimethylamino and R$^{53}$ is methyl then R$^{52}$ is not methyl; when D is —SCH$_3$, A is dimethylamino and R$^{53}$ is hydrogen then R$^{52}$ is not carboethoxy; when D is hydrogen, A is dimethylamino and R$^{53}$ is hydrogen then R$^{52}$ is not carboxyl or carboethoxy; when D is hydrogen, A is dimethylamino and R$^{53}$ is methyl then R$^{52}$ is not methyl; when D is hydrogen, A is methylamino and R$^{53}$ is hydrogen then R$^{52}$ is not methyl, ethyl or carboethoxy; when D is hydrogen, A is methylamino and R$^{53}$ is methyl then R$^{52}$ is not methyl or carboethoxy; when D is hydrogen, A is methylamino and R$^{53}$ is —CH$_2$NMe then R$^{52}$ is not methyl or carboethoxy; when D is phenyl, A is methylamino and R$^{53}$ is hydrogen then R$^{52}$ is not methyl; when D is phenyl, A is —NH(CO)CH$_3$ and R$^{53}$ is methyl then R$^{52}$ is not carbomethoxy.

In some embodiments, a compound of structural formula (VI) is provided:

(VI)

where R$^{58}$ is hydrogen, —CH$_3$, —C$_2$H$_5$, phenyl or benzyl.

In other embodiments, a compound of structural formula (VII) is provided:

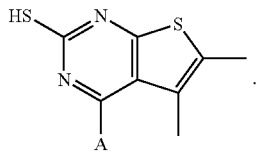
(VII)

where A is hydrogen, —CH$_3$, —C$_2$H$_5$, phenyl or benzyl.

In still other embodiments, a compound of structural formula (VIII) is provided:

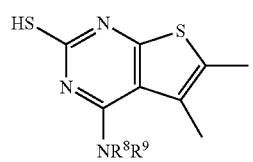
(VIII)

where R$^8$, R$^9$ are independently hydrogen, —CH$_3$, —C$_2$H$_5$, phenyl or benzyl provided that both R$^8$ and R$^9$ are not hydrogen.

In still other embodiments, a compound of structural formula (IX) is provided:

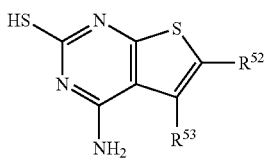
(IX)

wherein R$^{52}$ is —OCH$_3$, —OC$_2$H$_5$, —OC$_3$H$_7$, —C$_2$H$_5$, —CH(CH$_3$)$_2$, —CH$_2$OH, —CH$_2$OCH$_3$, —CN, —C(O)NR$^{54}$R$^{55}$, —CO$_2$R$^{54}$, —SO$_2$NR$^{54}$R$^{55}$, —NR$^{54}$SO$_2$R$^{55}$, —B(OR$^{54}$)(OR$^{55}$), —P(O)(OR$^{54}$)(OR$^{55}$), —P(O)(R$^{54}$)(OR$^{55}$) or substituted alkyl;

R$^{53}$ is methyl, alkyl, CO$_2$R$^{56}$ or —CONR$^{56}$R$^{57}$, —SO$_2$NR$^{56}$R$^{57}$, —NR$^{56}$SO$_2$R$^{57}$, —B(OR$^{56}$)(OR$^{57}$), —P(O)(OR$^{56}$)(OR$^{57}$) or —P(O)(R$^{56}$)(OR$^{57}$); and R$^{54}$-R$^{57}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, R$^{54}$ and R$^{55}$ and R$^{56}$ and R$^{57}$ together with the atoms to which they are bonded form a cycloheteroalkyl or substituted cycloheteroalkyl ring.

In still other embodiments, a compound of structural formula (X) is provided:

(X)

where D is —OH, —SH or —NH$_2$, R$^{52}$ is —OCH$_3$, —OC$_2$H$_5$, —OC$_3$H$_7$, —C$_2$H$_5$, —CH(CH$_3$)$_2$, —CH$_2$OH, —CH$_2$OCH$_3$, —CN, —C(O)NR$^{54}$R$^{55}$, —CO$_2$R$^{54}$ or substituted alkyl, R$^{52}$ is —OCH$_3$, —OC$_2$H$_5$, —OC$_3$H$_7$, —C$_2$H$_5$, —CH(CH$_3$)$_2$, —CH$_2$OH, —CH$_2$OCH$_3$, —CN, —C(O)NR$^{54}$R$^{55}$, —CO$_2$R$^{54}$, —SO$_2$NR$^{54}$R$^{55}$, —NR$^{54}$SO$_2$R$^{55}$, —B(OR$^{54}$)(OR$^{55}$), —P(O)(OR$^{54}$)(OR$^{55}$), —P(O)(R$^{54}$)(OR$^{55}$) or substituted alkyl and R$^{54}$ and R$^{55}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively R$^{54}$ and R$^{55}$ together with the atoms to which they are bonded form a cycloheteroalkyl or substituted cycloheteroalkyl ring.

In some embodiments, compounds having the structure below are provided:

1

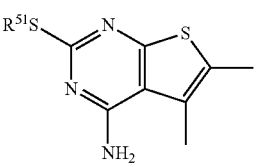
2

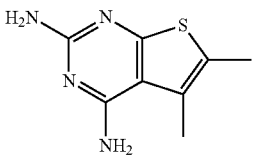
3

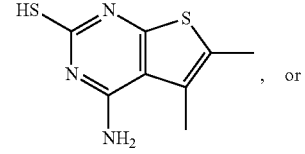
4

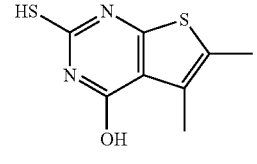
5 where R$^{51}$ is —CH$_3$, —CH$_2$CH$_3$, benzyl or —CH$_2$CO$_2$CH$_2$CH$_3$.

In other embodiments, a compound having the structure below is provided:

7

In still other embodiments, a compound having the structure below is provided:

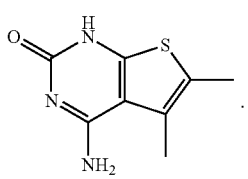
1
In still other embodiments, compounds having the structure below are provided:
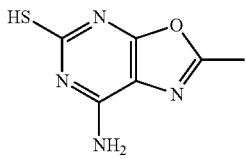
11
13
15
17
19
21
23
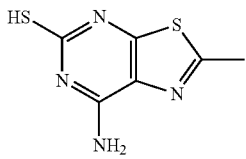
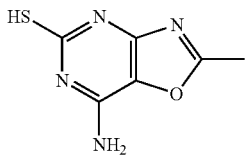
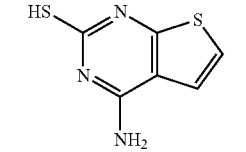
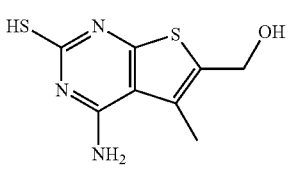
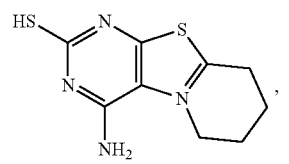
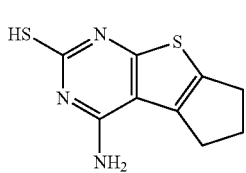
25
27
29
31
33
35
37
39
41

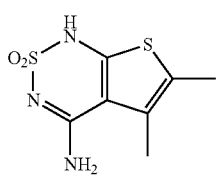
In still other embodiments, compounds having the structures below are provided:
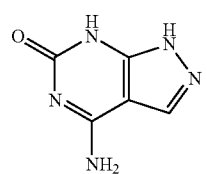
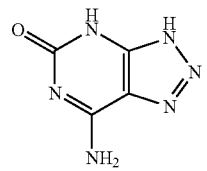
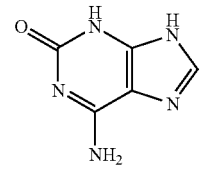
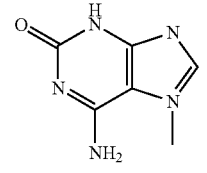
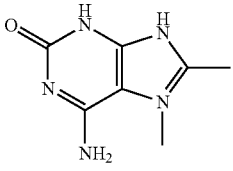
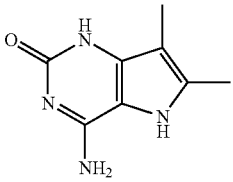
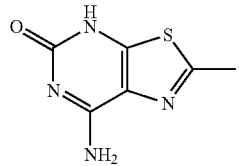
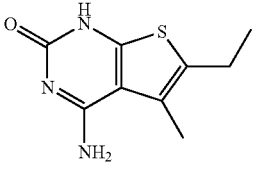
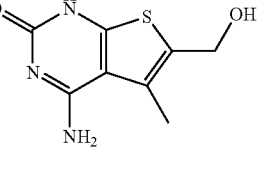
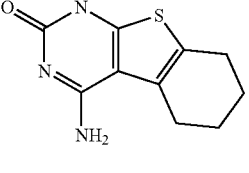
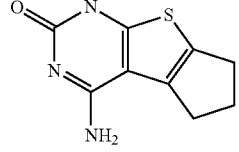

-continued
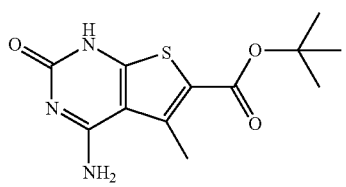
82
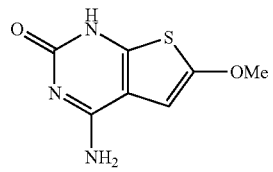
79
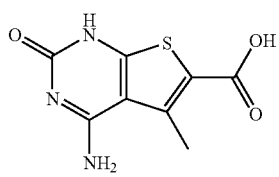
84
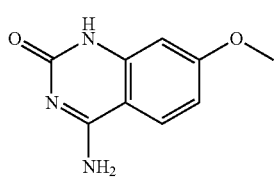
204
In still other embodiments, compounds having the structures below are provided:
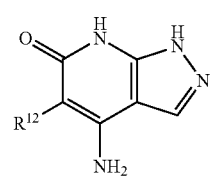
83
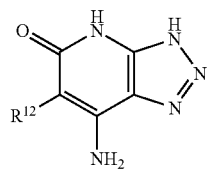
85
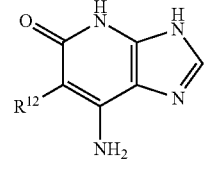
87
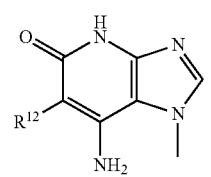
89
-continued
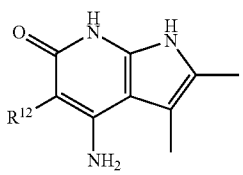
91
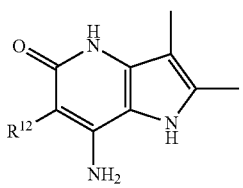
93
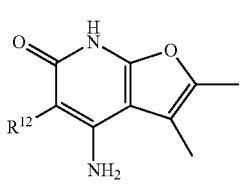
95
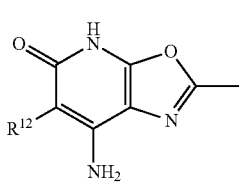
97
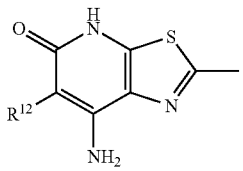
99
101
103
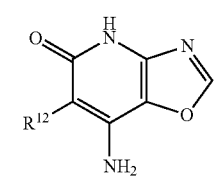
105

107

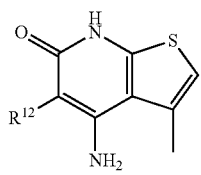

wherein R[12] is —OH, —SH, —CN, —CH$_2$OH, —CO$_2$R[13] or —CONR[13]R[14].

In some embodiments, compounds having the structure below are provided:

129

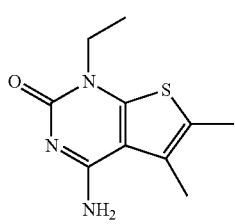

135

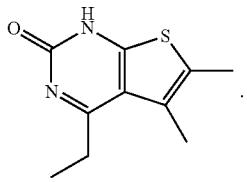

In some embodiments, a compound having the structure below is provided:

69

In some embodiments, a compound having the structure below is provided:

77

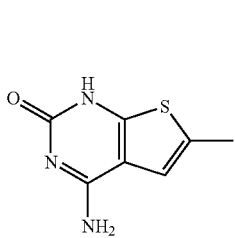

In still other embodiments, compounds having the structures below are provided:

109

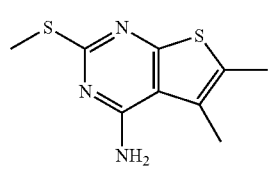

111

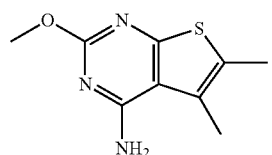

113

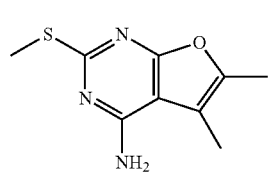

115

117

119

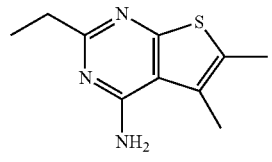

121

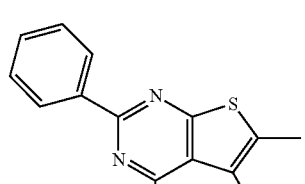

123

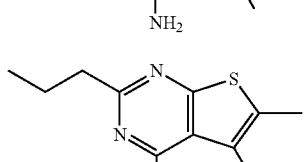

125

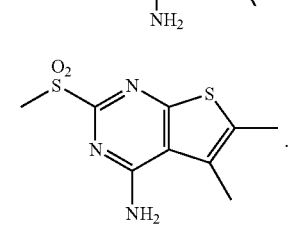

In still other embodiments, compounds having the structure below are provided:

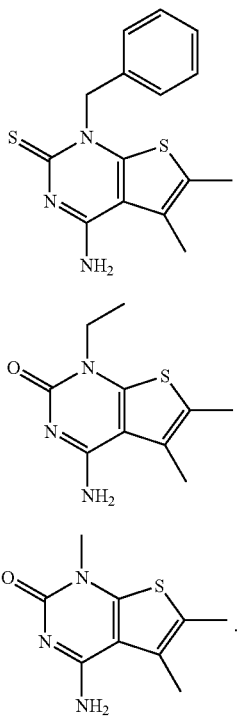

In still other embodiments, compounds having the structure below are provided:

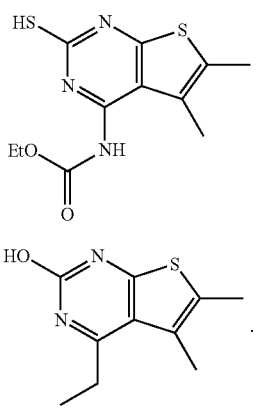

In some embodiments, a compound of structural Formula (XI) is provided:

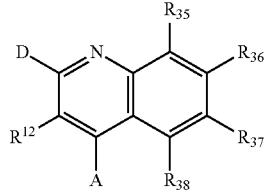

wherein:
$R^{12}$ is —OH, —SH, —CN, —CH$_2$OH, —CO$_2$R$^{13}$ or —CONR$^{13}$R$^{14}$;
D is —OH or —SH;
A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$;

$R^{35}$ is hydrogen, —OH, —OCH$_3$, —OC$_2$H$_5$, —OC$_3$H$_7$, alkyl, —CH$_3$, —C$_2$H$_5$, —CH(CH$_3$)$_2$, chloro, fluoro, —CH$_2$OH, —CH$_2$OCH$_3$, —CN, —C(O)NR$^{39}$R$^{40}$, —CO$_2$R$^{40}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$);

$R^{36}$ is hydrogen, —OH, —OCH$_3$, —OC$_2$H$_5$, —OC$_3$H$_7$, —CH$_3$, —C$_2$H$_5$, —CH(CH$_3$)$_2$, chloro, fluoro, —CH$_2$OH, —CH$_2$OCH$_3$, —CN, —C(O)NR$^{41}$R$^{42}$, —CO$_2$R$^{41}$, —SO$_2$NR$^{41}$R$^{42}$, —NR$^{41}$SO$_2$R$^{42}$, —B(OR$^{41}$)(OR$^{42}$), —P(O)(OR$^{41}$)(OR$^{42}$) or —P(O)(R$^{41}$)(OR$^{42}$);

$R^{37}$ is hydrogen, —OH, —OCH$_3$, —OC$_2$H$_5$, —OC$_3$H$_7$, chloro, fluoro, —CH$_3$, —C$_2$H$_5$, —CH(CH$_3$)$_2$, —CH$_2$OH, —CH$_2$OCH$_3$, —CN, —C(O)NR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$);

$R^{38}$ is hydrogen, —OH, —OCH$_3$, —OC$_2$H$_5$, —OC$_3$H$_7$, —CH$_3$, —C$_2$H$_5$, —CH(CH$_3$)$_2$, chloro, fluoro, —CH$_2$OH, —CH$_2$OCH$_3$, —CN, —C(O)NR$^{45}$R$^{46}$, —CO$_2$R$^{45}$, —SO$_2$NR$^{45}$R$^{46}$, —NR$^{45}$SO$_2$R$^{46}$, —B(OR$^{45}$)(OR$^{46}$), —P(O)(OR$^{45}$)(OR$^{46}$) or —P(O)(R$^{45}$)(OR$^{46}$); and $R^{39}$-$R^{46}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively $R^{39}$ and $R^{40}$, $R^{41}$ and $R^{42}$, $R^{43}$ and $R^{44}$ and $R^{45}$ and $R^{46}$ together with the atoms to which they are bonded form a cycloheteroalkyl or substituted cycloheteroalkyl ring;

provided that when $R^{12}$ is hydrogen then $R^{36}$, $R^{37}$, $R^{38}$ and $R^{39}$ are not hydrogen. In some embodiments, $R^{12}$ is —OH, —SH, —CN, —CH$_2$OH or —CO$_2$H.

In some embodiments, $R^{35}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —C(O)NR$^{39}$R$^{40}$, —CO$_2$R$^{40}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$), $R^{36}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —C(O)NR$^{41}$R$^{42}$, —CO$_2$R$^{41}$, —SO$_2$NR$^{41}$R$^{42}$, —NR$^{41}$SO$_2$R$^{42}$, —B(OR$^{41}$)(OR$^{42}$), —P(O)(OR$^{41}$)(OR$^{42}$) or —P(O)(R$^{41}$)(OR$^{42}$), $R^{37}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —C(O)NR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$) and $R^{38}$ is hydrogen, —OCH$_3$, —OC$_2$H$_5$, —OC$_3$H$_7$, alkyl, —CH$_3$, —C$_2$H$_5$, —CH(CH$_3$)$_2$, —CH$_2$OH, —CH$_2$OCH$_3$, —CN, —C(O)NR$^{45}$R$^{46}$, —CO$_2$R$^{45}$, —SO$_2$NR$^{45}$R$^{46}$, —NR$^{45}$SO$_2$R$^{46}$, —B(OR$^{45}$)(OR$^{46}$), —P(O)(OR$^{45}$)(OR$^{46}$) or —P(O)(R$^{45}$)(OR$^{46}$).

In some embodiments, when $R^{36}$, $R^{37}$, $R^{38}$ and $R^{39}$ are hydrogen, D is —OH and A is —CO$_2$H then $R^{12}$ is not —CO$_2$H or —OH; when $R^{36}$, $R^{37}$, $R^{38}$ and $R^{39}$ are hydrogen, D is —OH and A is —NH$_2$ then $R^{12}$ is not —CO$_2$H or CN; when $R^{36}$, $R^{38}$ and $R^{39}$ are hydrogen, $R^{37}$ is —OMe, D is —OH and A is —CH$_2$OH then $R^{12}$ is not —CH$_2$OH; when $R^{36}$, $R^{38}$ and $R^{39}$ are hydrogen, $R^{37}$ is hydrogen or methyl, D is —OH and A is —CO$_2$H then $R^{12}$ is not —SH.

In some embodiments, a compound of Formula (XII) is provided:

(XII)

wherein:
R$^{12}$ is —OH, —SH, —CN, —CH$_2$OH, —CO$_2$R$^{13}$ or —CONR$^{13}$R$^{14}$;
D is —SH or —OH;
A is —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$;
R$^{36}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —C(O)NR$^{41}$R$^{42}$, —CO$_2$R$^{41}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$);
R$^{37}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —C(O)NR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$); and
R$^{41}$-R$^{44}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively R$^{41}$ and R$^{42}$ and R$^{43}$ and R$^{44}$ together with the atoms to which they are bonded form a cycloheteroalkyl or substituted cycloheteroalkyl ring. In other embodiments, R$^{12}$ is —OH, —SH, —CN, —CH$_2$OH or —CO$_2$H.

In some embodiments, a compound of structural Formula (XIII) is provided:

(XIII)

wherein:
D is =O or =S;
A is NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$;
R$^{17}$ is alkyl or aryl;
R$^{35}$ is hydrogen, —OH, —OCH$_3$, —OC$_2$H$_5$, —OC$_3$H$_7$, —CH$_3$, —C$_2$H$_5$, —CH(CH$_3$)$_2$, chloro, fluoro, —CH$_2$OH, —CH$_2$OCH$_3$, —CN, —NR$^{39}$R$^{40}$, —C(O)NR$^{39}$R$^{40}$, —CO$_2$R$^{40}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$);
R$^{36}$ is hydrogen, —OCH$_3$, —OC$_2$H$_5$, —OC$_3$H$_7$, —OH, —CH$_3$, —C$_2$H$_5$, —CH(CH$_3$)$_2$, chloro, fluoro, —CH$_2$OH, —CH$_2$OCH$_3$, —CN, —NR$^{41}$R$^{41}$, —C(O)NR$^{41}$R$^{42}$, —CO$_2$R$^{41}$, —SO$_2$NR$^{41}$R$^{42}$, —NR$^{41}$SO$_2$R$^{42}$, —B(OR$^{41}$)(OR$^{42}$), —P(O)(OR$^{41}$)(OR$^{42}$) or —P(O)(R$^{41}$)(OR$^{42}$);
R$^{37}$ is hydrogen, —OCH$_3$, —OC$_2$H$_5$, —OC$_3$H$_7$, —OH, —CH$_3$, —C$_2$H$_5$, —CH(CH$_3$)$_2$, chloro, fluoro, —CH$_2$OH, —CH$_2$OCH$_3$, —CN, —NR$^{43}$R$^{44}$, —C(O)NR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$);
R$^{38}$ is hydrogen, —OCH$_3$, —OC$_2$H$_5$, —OC$_3$H$_7$, —OH, —CH$_3$, —C$_2$H$_5$, —CH(CH$_3$)$_2$, chloro, fluoro, —CH$_2$OH, —CH$_2$OCH$_3$, —CN, —NR$^{45}$R$^{46}$, —C(O)NR$^{45}$R$^{46}$, —CO$_2$R$^{45}$, —SO$_2$NR$^{45}$R$^{46}$, —NR$^{45}$SO$_2$R$^{46}$, —B(OR$^{45}$)(OR$^{46}$), —P(O)(OR$^{45}$)(OR$^{46}$) or —P(O)(R$^{45}$)(OR$^{46}$); and
R$^{39}$-R$^{46}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl or alternatively R$^{39}$ and R$^{40}$, R$^{41}$ and R$^{42}$, R$^{43}$ and R$^{44}$ and R$^{45}$ and R$^{46}$ together with the atoms to which they are bonded form a cycloheteroalkyl or substituted cycloheteroalkyl ring.

In other embodiments, when A is =O, A is —NH$_2$ and R$^{35}$, R$^{36}$, R$^{37}$ and R$^{38}$ are hydrogen then R$^{17}$ is not methyl, ethyl or phenyl.

In some embodiments, R$^{35}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —NR$^{39}$R$^{40}$, —C(O)NR$^{39}$R$^{40}$, —CO$_2$R$^{40}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$), R$^{36}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —NR$^{41}$R$^{41}$, —C(O)NR$^{41}$R$^{42}$, —CO$_2$R$^{41}$, —SO$_2$NR$^{41}$R$^{42}$, —NR$^{41}$SO$_2$R$^{42}$, —B(OR$^{41}$)(OR$^{42}$), —P(O)(OR$^{41}$)(OR$^{42}$) or —P(O)(R$^{41}$)(OR$^{42}$), R$^{37}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —NR$^{43}$R$^{44}$, —C(O)NR$^{43}$R$^{44}$, —CO$_2$R$^{43}$, —SO$_2$NR$^{43}$R$^{44}$, —NR$^{43}$SO$_2$R$^{44}$, —B(OR$^{43}$)(OR$^{44}$), —P(O)(OR$^{43}$)(OR$^{44}$) or —P(O)(R$^{43}$)(OR$^{44}$) and R$^{38}$ is hydrogen, —OCH$_3$, —OC$_2$H$_5$, —OC$_3$H$_7$, —CH$_3$, —C$_2$H$_5$, —CH(CH$_3$)$_2$, —CH$_2$OH, —CH$_2$OCH$_3$, —CN, —NR$^{45}$R$^{46}$, —C(O)NR$^{45}$R$^{46}$, —CO$_2$R$^{45}$, —SO$_2$NR$^{45}$R$^{46}$, —NR$^{45}$SO$_2$R$^{46}$, —B(OR$^{45}$)(OR$^{46}$), —P(O)(OR$^{45}$)(OR$^{46}$) or —P(O)(R$^{45}$)(OR$^{46}$).

In some embodiments, a compound of structural Formula (XIV) is provided:

(XIV)

wherein:
A is NH$_2$, —NHCH$_3$, —N(CH$_3$)$_2$, —NHOCH$_3$, —NOCH$_3$, —NHC(O)CH$_3$, —NHC(O)OCH$_3$, —NHC (O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$;

R$^{17}$ is alkyl or aryl;

R$^{36}$ is hydrogen, —OCH$_3$, —OC$_2$H$_5$, —OC$_3$H$_7$, —C$_2$H$_5$, —CH(CH$_3$)$_2$, —CH$_2$OH, —CH$_2$OCH$_3$, —CN, —NR$^{41}$R$^{41}$, —C(O)NR$^{41}$R$^{42}$, —CO$_2$R$^{41}$, —SO$_2$NR$^{39}$R$^{40}$, —NR$^{39}$SO$_2$R$^{40}$, —B(OR$^{39}$)(OR$^{40}$), —P(O)(OR$^{39}$)(OR$^{40}$) or —P(O)(R$^{39}$)(OR$^{40}$);

R$^{37}$ is hydrogen, —OCH$_3$, —OC$_2$H$_5$, —OC$_3$H$_7$, —C$_2$H$_5$, —CH(CH$_3$)$_2$, —CH$_2$OH, —CH$_2$OCH$_3$, —CN, —NR$^{43}$R$^{44}$, —C(O)NR$^{43}$R$^{44}$, —CO$_2$R$^{43}$, —SO$_2$NR$^{41}$R$^{42}$, —NR$^{41}$SO$_2$R$^{42}$, —B(OR$^{41}$)(OR$^{42}$), —P(O)(OR$^{41}$)(OR$^{42}$) or —P(O)(R$^{41}$)(OR$^{42}$); and R$^{41}$-R$^{43}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively R$^{41}$ and R$^{42}$ and R$^{43}$ and R$^{44}$ together with the atoms to which they are bonded form a cycloheteroalkyl or substituted cycloheteroalkyl ring. In some embodiments, when R$^{36}$ and R$^{37}$ are methyl, D is =O and A is —NH$_2$, then R$^{17}$ is not methyl.

In some embodiments, compounds having the structures below are provided:

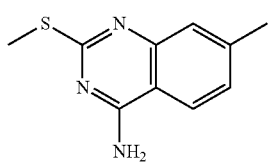
171

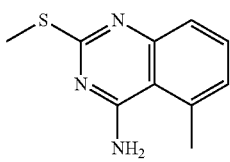
173

In other embodiments, compounds having the structures below are provided:

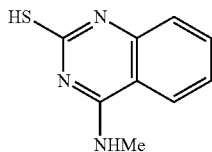
175

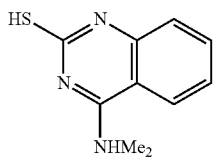
177

In still other embodiments, compounds having the structures below are provided:

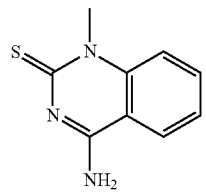
137

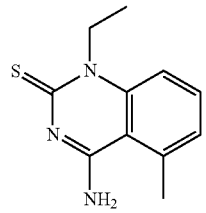
139

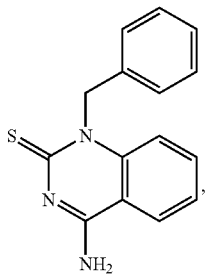
141

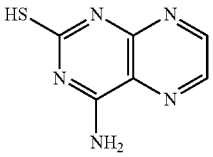
151

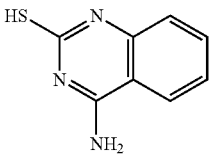
153

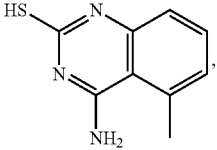
155

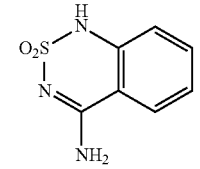
159

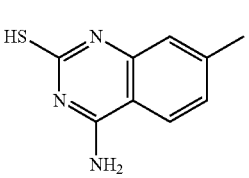
167

-continued
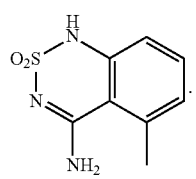
169
In still other embodiments, a compound having the structure below is provided:
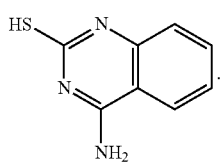
179
In still other embodiments, compounds having the structures below are provided:
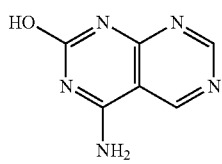
181
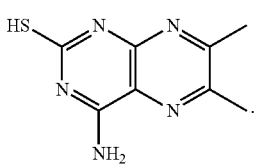
182
In some embodiments, compounds having the structure below are provided:
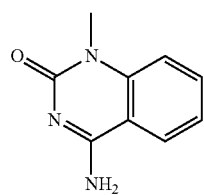
143
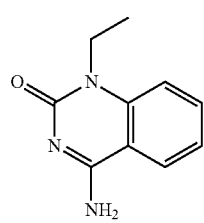
145
-continued
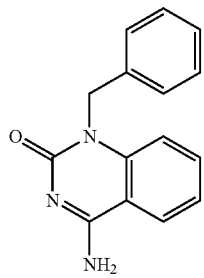
147
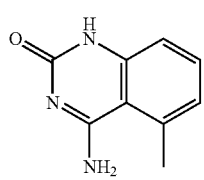
157
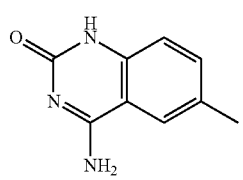
161
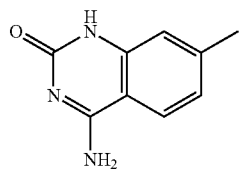
163
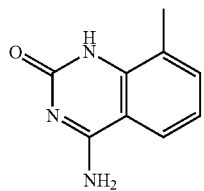
165
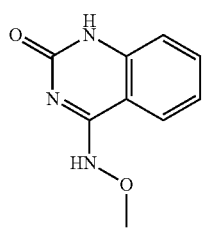
166
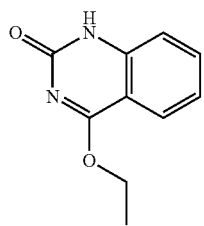
168

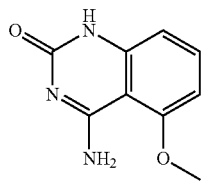
170
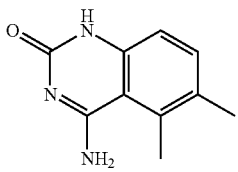
172
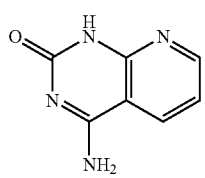
174
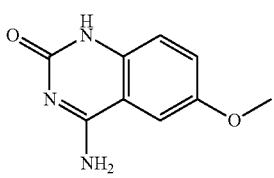
176
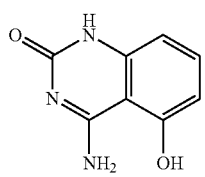
178
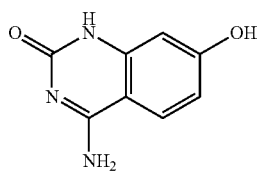
180
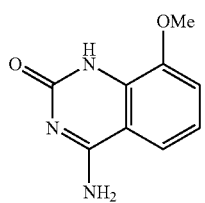
182
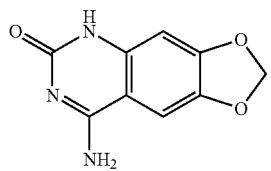
184
In still other embodiments, a compound having the structure below is provided:
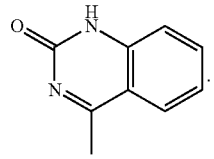
183
In still other embodiments, a compound having the structure below is provided:
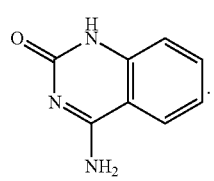
149
In some embodiments, a compound having the structure below is provided:
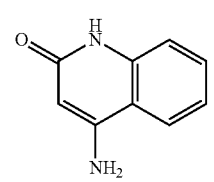
186
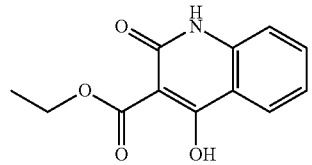
188
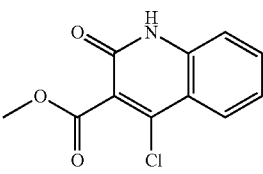
190
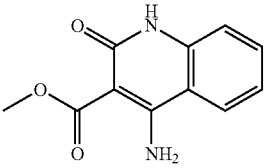
204
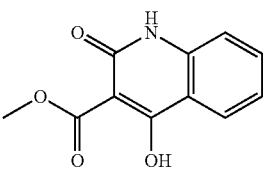
192

In still other embodiments, compounds having the structures below are provided:

In some embodiments, compounds of structural formula (XV) below are provided:

$$\text{XV}$$

wherein:

D is —SH or —OH; and

A is —OH, —NH$_2$, —NHCH$_3$, —N(CH$_3$)$_2$, —NHOCH$_3$, —NOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$, or —CH$_2$NHC(O)CH$_3$;

provided that at least one of L, M, T or R is a heteroatom.

In some embodiments, when p is 0, L is —NH—, M is —CH(CH$_2$OEt),

R is

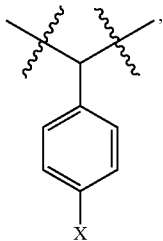,

X is hydrogen, chloro or methoxy, A is —NH$_2$ then D is not —SH;

when p is 0, L is —CH$_2$—, M is —NCH$_3$—, R is —C(CH$_3$)$_2$—, A is —NH$_2$, then D is not —SH or —OH;

when p is 0, L is —NH—, M is —CH(CH$_2$OH)—, R is

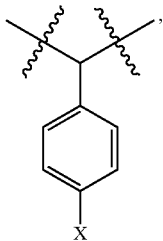,

X is hydrogen or methoxy, A is —NH$_2$ then D is not —SH;

when p is 0, L is —NH—, M is —CH(CH$_3$)—, R is

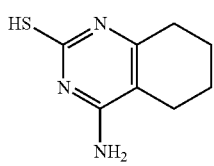,

A is —NH$_2$ then D is not —SH;

L is —S—, M, R and T are —CH$_2$—, A is —NH$_2$ then D is not —OH;

L is —NH—, M and T are —CH$_2$—, R is —CH(CH$_3$)—, A is —NH$_2$ then D is not —OH;

and M is —N(COPh)—, L, R and T are —CH$_2$—, A is —NH$_2$ then D is not —OH.

In some embodiments, compounds having the structures below are provided:

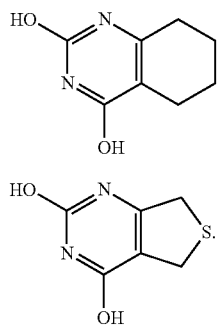

201

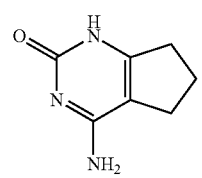

203

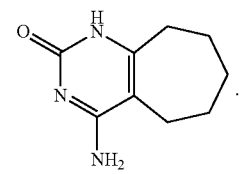

205

In other embodiments, compounds having the structure below are provided:

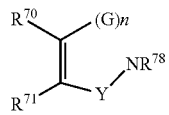

206

208

In some aspects, a compound of structural Formula (XVI) is provided:

$$\text{(XVI)}$$

or a salt, solvate, hydrate or N-oxide thereof wherein:

each G is independently —C(R$^{77}$)(R$^{78}$)—, —C(O)—, —NR$^{77}$— or —S(O)$_2$—;

n is 1, 2 or 3;

provided that when n is greater than one then only one G is —C(O)—, —C(S), —S(O)$_2$— or —NR$^{77}$—;

Y is —C(O)—, —C(S) or —S(O)$_2$—;

R$^{70}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{72}$, —S(O)$_a$R$^{72}$, —NR$^{72}$R$^{73}$, —CONR$^{72}$R$^{73}$, —CO$_2$R$^{72}$, —NR$^{72}$CO$_2$R$^{73}$, —NR$^{72}$CONR$^{73}$R$^{74}$, —NR$^{72}$CSNR$^{73}$R$^{74}$ or —NR$^{72}$C(=NH)NR$^{73}$R$^{74}$, —SO$_2$NR$^{72}$R$^{73}$, —NR$^{72}$SO$_2$R$^{73}$, —NR$^{72}$SO$_2$NR$^{73}$R$^{74}$, —B(OR$^{72}$)(OR$^{73}$), —P(O)(OR$^{72}$)(OR$^{73}$) or —P(O)(R$^{72}$)(OR$^{73}$);

a and b are independently 0, 1 or 2;

R$^{71}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{74}$, —S(O)$_b$R$^{74}$, —NR$^{74}$R$^{75}$, —CONR$^{74}$R$^{75}$, —CO$_2$R$^{74}$, —NR$^{74}$CO$_2$R$^{75}$, —NR$^{74}$CONR$^{75}$R$^{76}$, —NR$^{74}$CSNR$^{75}$R$^{76}$ or —NR$^{74}$C(=NH)NR$^{75}$R$^{76}$, —SO$_2$NR$^{74}$R$^{75}$, —NR$^{74}$SO$_2$R$^{75}$, —NR$^{74}$SO$_2$NR$^{75}$R$^{76}$, —B(OR$^{74}$)(OR$^{75}$), —P(O)(OR$^{74}$)(OR$^{75}$), —P(O)(R$^{74}$)(OR$^{75}$) or alternatively, R$^{71}$ and R$^{72}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

R$^{72}$-R$^{76}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, R$^{72}$ and R$^{73}$, R$^{73}$ and R$^{74}$, R$^{74}$ and R$^{75}$ and R$^{75}$ and R$^{76}$ together with the atoms to which they are bonded form a cycloheteroalkyl or substituted cycloheteroalkyl ring; and R$^{77}$-R$^{78}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, R$^{77}$ and R$^{78}$, together with the atoms to which they are bonded form a cycloalkyl, substituted cycloalkyl, cycloheteroalkyl or substituted cycloheteroalkyl ring.

In some embodiments, when G is —C(O)— and R$^{78}$ is hydrogen, R$^{71}$ and R$^{72}$ do not form a phenyl ring. In other embodiments, R$^{70}$ and R$^{71}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring.

In still other embodiments, a compound of structural formula (XVII), (XVIII), (XIX) or (XX) is provided:

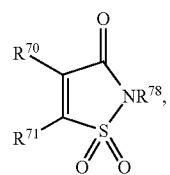

(XVII)

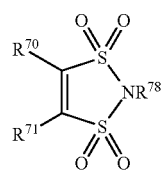

(XVIII)

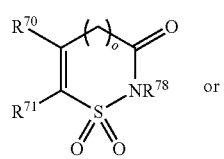

(XIX)

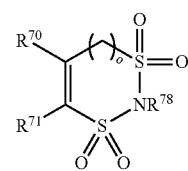

(XX)

where o is 1 or 2.

In some embodiments, R$^{70}$ and R$^{71}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring.

In still other embodiments, a compound of structural formula (XXI) is provided:

(XXI)

wherein:
X is O or S;
H is —N— or —CR$^{81}$—;
I is —N— or —CR$^{82}$—;
J is —N— or —CR$^{83}$—;
K is —N— or —CR$^{84}$—;
with the proviso that no more than 2 of H, I, J or K are —N—;
R$^{81}$ is hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NR$^{85}$R$^{86}$, —CO$_2$R$^{85}$, —SO$_2$NR$^{85}$R$^{86}$, —NR$^{85}$SO$_2$R$^{86}$, —B(OR$^{85}$)(OR$^{86}$), —P(O)(OR$^{85}$)(OR$^{86}$) or —P(O)(R$^{85}$)(OR$^{86}$);
R$^{82}$ is hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NR$^{86}$R$^{87}$, —CO$_2$R$^{86}$, —SO$_2$NR$^{86}$R$^{87}$, —NR$^{86}$SO$_2$R$^{87}$, —B(OR$^{86}$)(OR$^{87}$), —P(O)(OR$^{86}$)(OR$^{87}$) or —P(O)(R$^{86}$)(OR$^{87}$);
R$^{83}$ is hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NR$^{88}$R$^{89}$, —CO$_2$R$^{88}$, —SO$_2$NR$^{88}$R$^{89}$, —NR$^{88}$SO$_2$R$^{89}$, —B(OR$^{88}$)(OR$^{89}$), —P(O)(OR$^{88}$)(OR$^{89}$) or —P(O)(R$^{88}$)(OR$^{89}$);
R$^{84}$ is hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NR$^{90}$R$^{91}$, —CO$_2$R$^{90}$, —SO$_2$NR$^{90}$R$^{91}$, —NR$^{90}$SO$_2$R$^{91}$, —B(OR$^{90}$)(OR$^{91}$), —P(O)(OR$^{90}$)(OR$^{91}$) or —P(O)(R$^{90}$)(OR$^{91}$); and $R^{85}$-$R^{91}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively $R^{85}$ and $R^{86}$, $R^{87}$ and $R^{88}$, $R^{89}$ and $R^{90}$ and $R^{91}$ and $R^{92}$ together with the atoms to which they are bonded form a cycloalkyl, substituted cycloalkyl, cycloheteroalkyl or substituted cycloheteroalkyl ring;

provided that $R^{81}$, $R^{82}$, $R^{83}$ and $R^{84}$ are not all hydrogen.

In some embodiments, $R^{81}$, $R^{82}$, $R^{83}$ and $R^{84}$ are independently hydrogen, alkoxy, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —C(O)NHMe, —CO$_2$H, —CO$_2$CH$_3$, —SO$_2$N(CH$_3$)$_2$, —NHSO$_2$CH$_3$, —B(OH)$_2$ or —P(O)(OH)$_2$.

In still other embodiments, compounds having the structures below are provided:

207

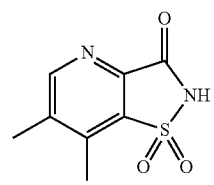
209

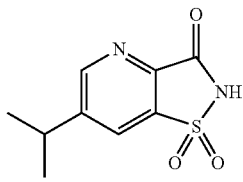
211

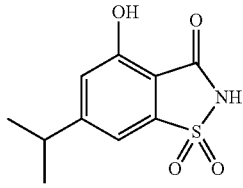
213

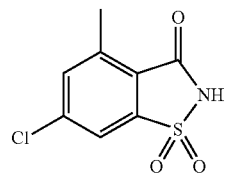
215

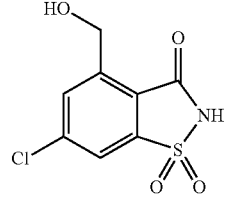
217

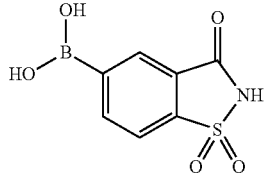
219

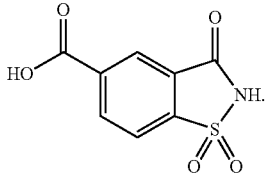
221

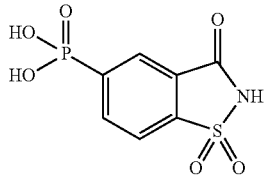
223

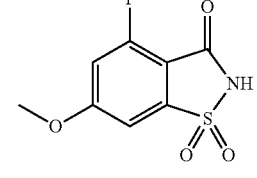
225

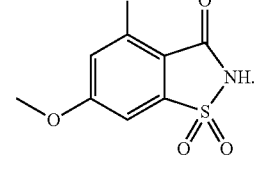
227

In still another aspect, a compound of structural Formula (XXII) is provided:

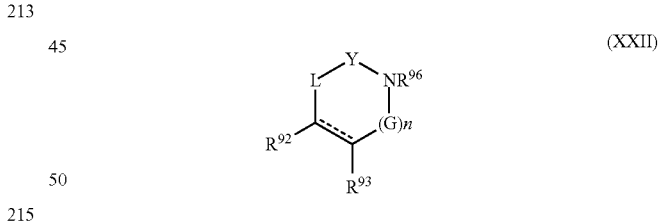
(XXII)

or a salt, solvate, hydrate or N-oxide thereof wherein:
each G is independently —C(R$^{94}$)(R$^{95}$)—, —C(O)—, —NR$^{94}$— or —S(O)$_2$—;
n is 1, 2 or 3;
provided that when n is greater than one then only one G is —C(O)—, —S(O)$_2$— or —NR$^{94}$—;
Y is —C(O)—, —C(S)— or —S(O)$_2$—;
L is —C(R$^{104}$)(R$^{105}$)—, —O—, or —NR$^{104}$—;
$R^{92}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{98}$, —S(O)$_y$R$^{98}$, —NR$^{98}$R$^{99}$, —CONR$^{98}$R$^{99}$, —CO$_2$R$^{98}$, —NR$^{98}$CO$_2$R$^{99}$, —NR$^{98}$CONR$^{99}$R$^{100}$, —NR$^{98}$CSNR$^{99}$R$^{100}$ or —NR$^{98}$C(=NH)NR$^{99}$R$^{100}$, —SO$_2$NR$^{98}$R$^{99}$, —NR$^{98}$SO$_2$R$^{99}$, —NR$^{98}$SO$_2$NR$^{99}$R$^{100}$, —B(OR$^{98}$)(OR$^{99}$), —P(O)(OR$^{98}$)(OR$^{99}$) or —P(O)(R$^{98}$)(OR$^{99}$);

R$^{93}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —CN, —NO$_2$, —OR$^{100}$, —S(O)$_z$R$^{101}$, —NR$^{101}$R$^{102}$, —CONR$^{101}$R$^{102}$, —CO$_2$R$^{101}$, —NR$^{101}$CO$_2$R$^{102}$, —NR$^{101}$CONR$^{102}$R$^{103}$, —NR$^{101}$CSNR$^{102}$R$^{103}$ or —NR$^{101}$C(=NH)NR$^{102}$R$^{103}$, —SO$_2$NR$^{101}$R$^{102}$, —NR$^{101}$SO$_2$NR$^{102}$, —NR$^{101}$SO$_2$R$^{102}$R$^{103}$, —B(OR$^{101}$)(OR$^{102}$), —P(O)(OR$^{101}$)(OR$^{102}$), —P(O)(R$^{101}$)(OR$^{102}$) or alternatively, R$^{92}$ and R$^{93}$ together with the atoms to which they are bonded form an aryl, substituted aryl, heteroaryl, substituted heteroaryl, cycloalkyl, substituted cycloalkyl, cycloheteroalkyl or substituted cycloheteroalkyl ring where the ring is optionally fused to another aryl, substituted aryl, heteroaryl, substituted heteroaryl, cycloalkyl, substituted cycloalkyl, cycloheteroalkyl or substituted cycloheteroalkyl ring;

y and z are independently 0, 1 or 2;

R$^{98}$-R$^{103}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, R$^{98}$ and R$^{99}$, R$^{99}$ and R$^{100}$, R$^{101}$ and R$^{102}$ and R$^{101}$ and R$^{102}$ together with the atoms to which they are bonded form a cycloalkyl, substituted cycloalkyl, cycloheteroalkyl or substituted cycloheteroalkyl ring;

R$^{94}$-R$^{95}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, R$^{94}$ and R$^{95}$, together with the atoms to which they are bonded form a cycloalkyl, substituted cycloalkyl, cycloheteroalkyl or substituted cycloheteroalkyl ring;

R$^{96}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl; and R$^{104}$-R$^{105}$ are independently hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl or substituted heteroarylalkyl or alternatively, R$^{104}$ and R$^{105}$, together with the atoms to which they are bonded form a cycloalkyl, substituted cycloalkyl, cycloheteroalkyl or substituted cycloheteroalkyl ring.

In some embodiments, when L is O, R$^{95}$ is hydrogen, R$^{92}$ is methyl and the bond connecting the carbon atoms bonded to R$^{92}$ and R$^{93}$ is a double bond then R$^{93}$ is not hydrogen.

In some embodiments, a compound of structural formula (XXIII) is provided:

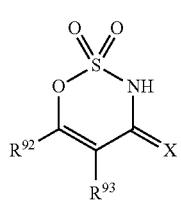

(XXIII)

where when R$^{92}$ is —CH$_3$ then R$^{93}$ is not hydrogen and that both R$^{92}$ and R$^{93}$ are not hydrogen.

In some embodiments, R$^{92}$ and R$^{93}$ are independently are independently hydrogen, —OCH$_3$, —OC$_2$H$_5$, —OC$_3$H$_7$, alkyl, —CH$_3$, —C$_2$H$_5$, —CH(CH$_3$)$_2$, —CH$_2$OH, halo, chloro, fluoro, —CH$_2$OCH$_3$, —CN, —SCH$_3$, —C(O)NHMe, —CO$_2$H, —CO$_2$CH$_3$, —SO$_2$N(CH$_3$)$_2$, —NHSO$_2$CH$_3$, —B(OH)$_2$ or —P(O)(OH)$_2$. In other embodiments, R$^{92}$ and R$^{93}$ together with the atoms to which they are attached form a cycloalkyl, cycloheteroalkyl, aryl or heteroaryl ring.

In other embodiments, compounds having the structures below are provided:

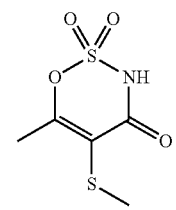

229

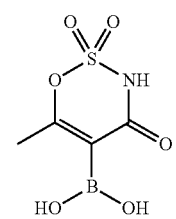

231

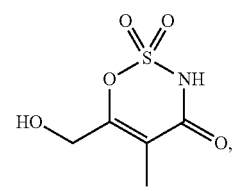

233

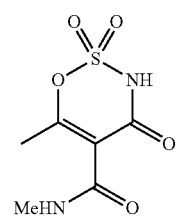

235

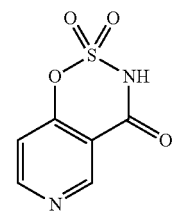

237

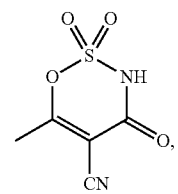

239

-continued

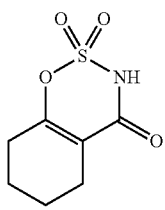

241

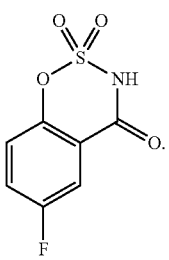

243

In general, the compounds of the present invention, e.g., compounds with the formulae described herein can be synthesized according to the following exemplary procedures and/or schemes.

Pyrimidines B including fused pyrimidine derivatives such as quinazolines and pyrido[2,3-d]pyrimidines are synthesized from 2-amino nitriles, 2-amino ketones, or 2-amino carboxyl derivatives A by reaction with the corresponding carboxyl derivatives as illustrated in Scheme 1 (Rad-Moghadam et al., *J. of Heterocyclic Chem.* 2006, 43, 913; Roy et al., *J. Org. Chem.* 2006, 71, 382; Jung et al., *J. Med. Chem.* 2006, 49, 955; Khabnadideh et al., *Bioorg. Med. Chem.* 2005, 13, 2637). The amino group in the starting material A can be further functionalized by alkylation (Brown et al., *J. Med. Chem.* 1990, 33, 1771) or reductive amination (Uehling et al., *J. Med. Chem.* 2006, 49, 2758, etc.) to provide the corresponding N-monosubstituted 2-amino nitriles, 2-amino ketones or 2-amino carboxyl derivatives C. The coupling reaction of A or C with iso(thio)cyanates such as, for example, benzoyliso(thio)cyanates and subsequent cyclization by treatment with NaOH provides the pyrimidin-2(1H)-(thi)one derivatives E including, but not limited to, fused pyrimidin-2(1H)-(thi)ones such as quinazolin-2(1H)-(thi) one and pyrido[2,3-d]pyrimidin-2(1H)-(thi)one derivatives (El-Sherbeny et al., *Med. Chem. Rev.* 2000, 10, 122 and references cited therein; Reddy et al., *Synthetic Commun.* 1988, 18, 525; Wilson, *Org. Lett.* 2001, 3, 585, and references cited therein). Direct cyclization of A or C with (thio)ureas in the presence of NaOH also results in the formation of pyrimidin-2(1H)-(thi)one derivatives E (Scheme 1) (Naganawa et al., *Bioorg. Med. Chem.* 2006, 14, 7121 and references cited therein).

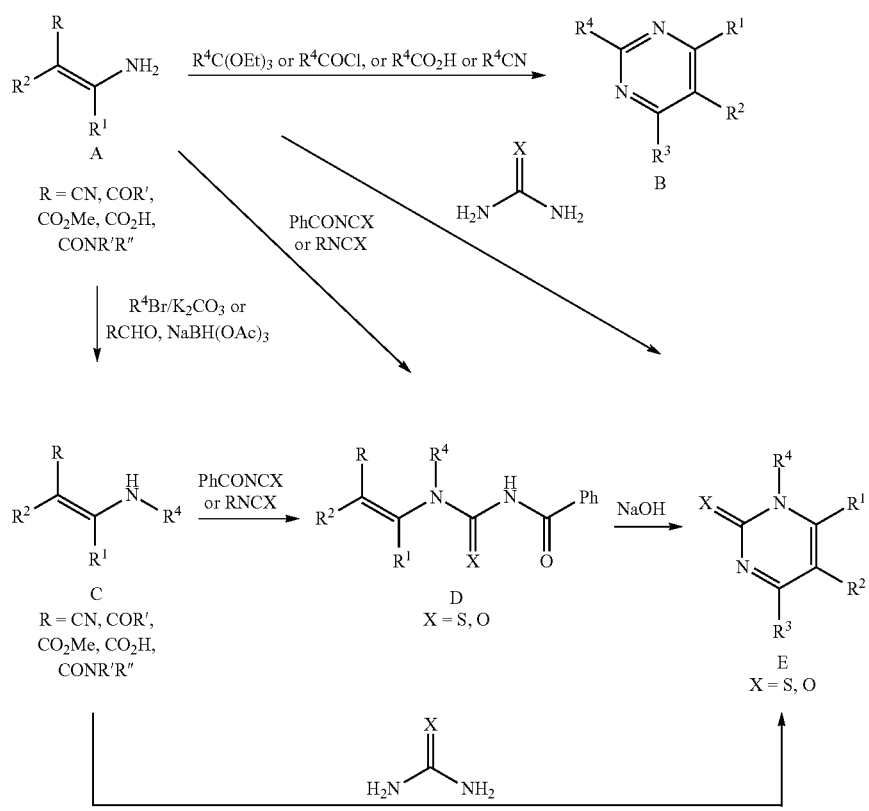

Scheme 1

Pyrimidines B and pyrimidin-2(1H)-(thi)ones E can also be prepared from corresponding 1,3-dicarbonyl derivatives and α,β-unsaturated carbonyl derivatives by condensation with guanidines, amidines, or (thio)urea derivatives as shown in Scheme 2 (Sharma et al., *Eur. J. Med. Chem.* 2006, 41, 83, and references cited therein; Bellur et al., *Tetrahedron* 2006, 62, 5426 and references cited therein; Hauser et al., *J. Org. Chem.* 1953, 18, 588).

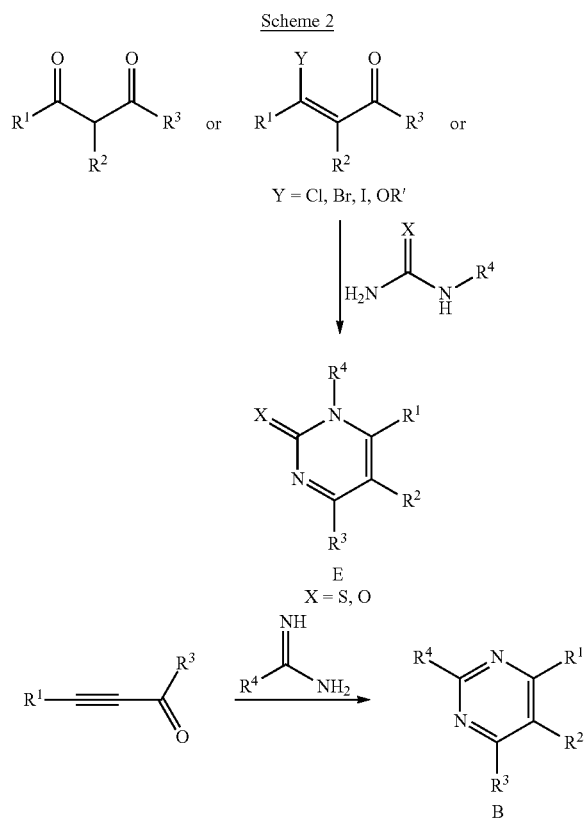

Various pyrimidines and pyrimidin-2(1H)-(thi)ones as well as their fused pyrimidine and pyrimidin-2(1H)-(thi)one derivatives such as quinazolines and quinazolin-2(1H)-ones can be synthesized from pyrimidine-2,4(1H,3H)-dione derivatives as well as the fused pyrimidine-2,4(1H,3H)-diones such as quinazoline-2,4(1H,3H)-dione and pyrido[2,3-d]pyrimidine-2,4(1H,3H)-dione derivatives (Scheme 3). Reaction of pyrimidine-2,4(1H,3H)-dione derivatives with phosgene or POCl$_3$ provides the corresponding 2,4-dichloropyrimidines (Lee et al., *Synlett.* 2006, 65 and references cited therein). Subsequent displacements of the two chlorides with various nucleophiles resulted in the formation of pyrimidines and pyrimidin-2(1H)-(thi)ones as well as fused pyrimidine and pyrimidin-2(1H)-(thi)one derivatives (Kanuma et al., *Bioorg. & Med. Chem. Lett.* 2005, 15, 3853 and references cited therein; Liu et al., *Bioorg. & Med. Chem. Lett.* 2007, 17, 668; Wilson et al., *Bioorg. & Med. Chem.* 2007, 15, 77; Boarland et al., *J. Chem. Soc.* 1951, 1218).

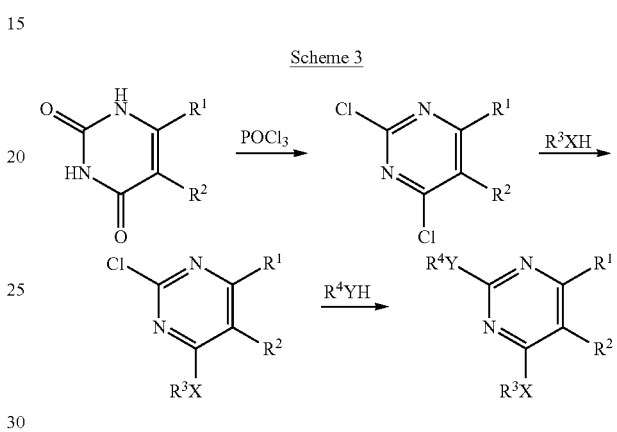

Similarly, [1,2,6]thiadiazine-2,2-dioxides and fused[1,2,6]thiadiazine-2,2-dioxide derivatives such as, for example, 1H-benzo[c][1,2,6]thiadiazine-2,2-dioxides are also synthesized from 2-amino nitriles, 2-amino ketones, or 2-amino carboxyl derivatives A or C (Scheme 4), by reaction with NH$_2$SO$_2$Cl (Hirayama et al., *Bioorg. & Med. Chem.* 2002, 10, 1509; Kanbe et al., *Bioorg. & Med. Chem. Lett.* 2006, 16, 4090 and references cited therein) or NH$_2$SO$_2$NH$_2$ (Maryanoff et al., *J. Med. Chem.* 2006, 49, 3496, and references cited therein) and followed by cyclization in the presence of NaOH (Goya et al., *Heterocycles,* 1986, 24, 3451; Albrecht et al., *J. Org. Chem.* 1979, 44, 4191; Goya et al., *Arch. Pharm.* (Weinheim) 1984, 317, 777). The condensation of the corresponding 1,3-dicarbonyl derivatives, α,β-unsaturated carbonyl derivatives with sulfamide derivatives (Scheme 4) also results in the formation of [1,2,6]thiadiazine-2,2-dioxide derivatives (Wright, *J. Org. Chem.* 1964, 29, 1905).

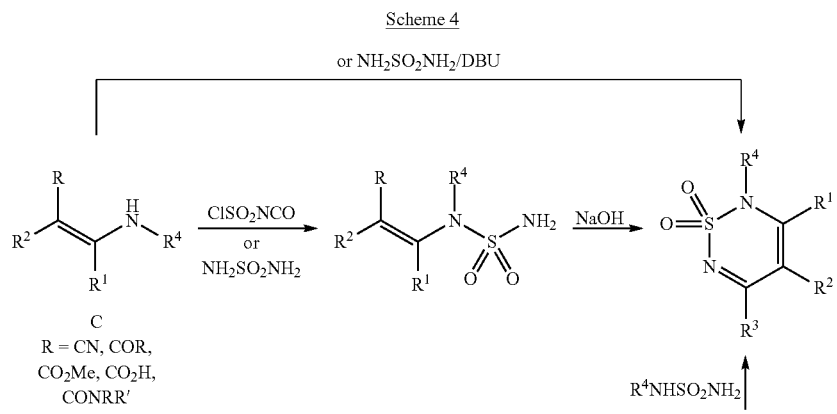

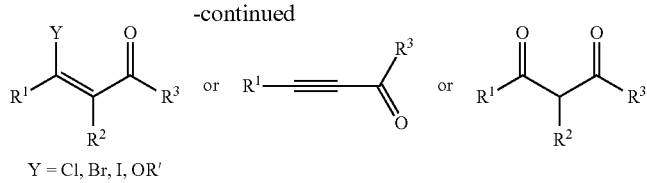

Y = Cl, Br, I, OR'

Methods for the synthesis of thieno[2,3-d]pyrimidine derivatives are described in Scheme 5. 2-Amino thiophene derivatives 303 are synthesized via the Gewald reaction (Chen et al., *Synthetic Communication* 2004, 34, 3801 and references cited therein; Elmegeed et al., *Eur. J. Med. Chem.* 2005, 40, 1283 and references cited therein). Compound 303 can be cyclized with the corresponding carboxyl derivatives to give the thieno[2,3-d]pyrimidine derivatives 304 (Rad-Moghadam, *J. Heterocyclic Chem.* 2006, 43, 913; Seijas et al., *Tetrahedron Lett.* 2000, 41, 2215, and references cited therein; Jung et al., *J. Med. Chem.* 2006, 49, 955.).

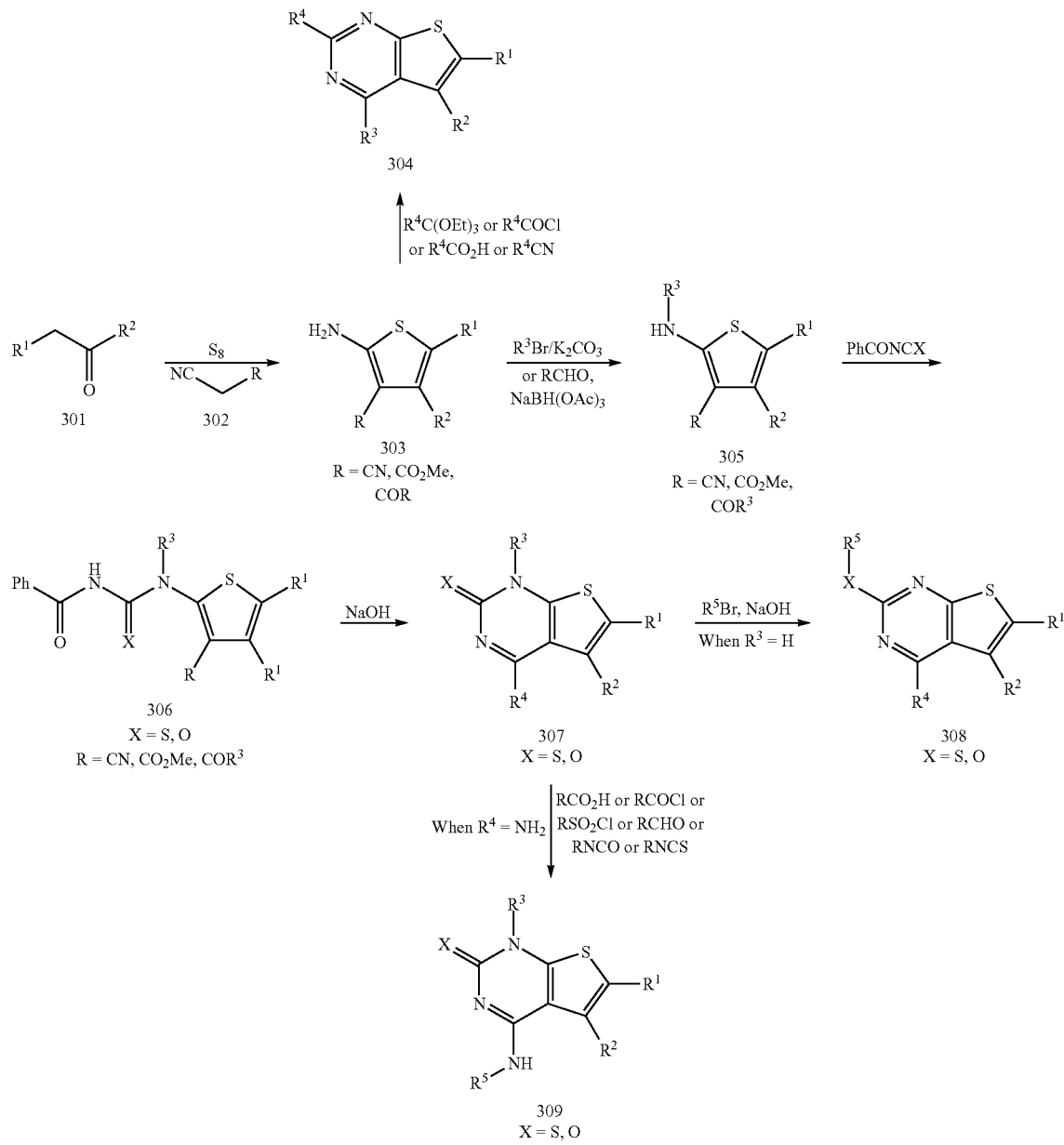

Scheme 5

2-Amino thiophene derivatives 303 can be further alkylated by either treatment with R₃Br/K₂CO₃ or with RCHO/NaBH(OAc)₃ to give the N-alkylated 2-amino thiophene derivatives 305 (Brown et al., *J. Med. Chem.* 1990, 33, 1771; Uehling et al., *J. Med. Chem.* 2006, 49, 2758 and references cited therein), which are then reacted, for example, with benzoyliso(thio)cyanate to give the corresponding benzoyl(thio)urea derivatives 306. Compounds 306 may be cyclized by treatment with NaOH to provide thieno[2,3-d]pyrimidine derivatives 7 (El-Sherbeny et al., *Med. Chem. Rev.* 2000, 10, 122, and references cited therein; Reddy et al., *Synthetic Commun.* 1988, 18, 525; Wilson, *Org. Lett.* 2001, 3, 585 and references cited therein). When $R^3$=H, compounds 307 may be reacted with R₅Br/NaOH to give the alkylated products 8 (Hirota et al., *Bioorg. Med. Chem.* 2003, 11, 2715.). When $R^4$=NH₂, the amino group can be further functionalized to give the products 309.

Similarly, quinazolin-2(1H)-one and quinazolin-2(1H)-thione derivatives 402 were synthesized from various 2-aminobenzoic acid derivatives, 2-aminobenzonitrile derivatives, 2-aminoacetophenone derivatives and 2-aminobenzamide derivatives 400 as shown in Scheme 6. Coupling reaction of compounds 400 with benzoyl iso(thio)cyanates lead to the formation of corresponding benzoyl(thio)urea derivatives 401. Their cyclization in the presence of NaOH provides the quinazolin-2(1H)-(thi)one derivatives 402 (El-Sherbeny, *Med. Chem. Rev.* 2000, 10, 122 and references cited therein; Reddy et al., *Synthetic Commun.* 1988, 18, 525; Wilson, *Org. Lett.* 2001, 3, 585 and references cited therein).

Scheme 6

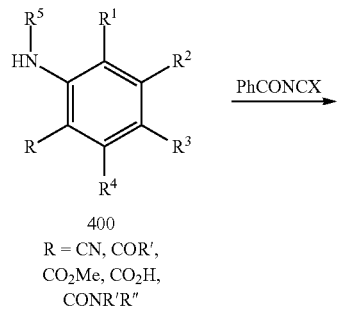

400
R = CN, COR',
CO₂Me, CO₂H,
CONR'R"

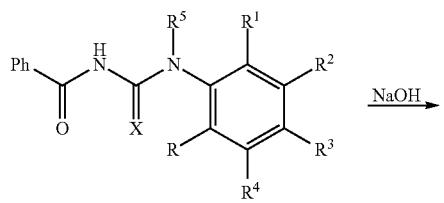

401
X = S, O
R = CN, COR',
CO₂Me, CO₂H,
CONR'R"

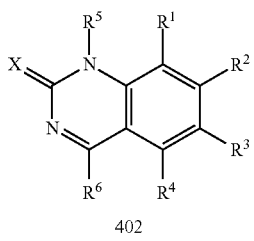

402
X = S, O 1H-benzo[c][1,2,6]thiadiazine-2,2-dioxide derivatives 404 are synthesized from the same starting materials 400 (Scheme 7) via their reactions with sulfamide or sulfamoyl chloride, followed by cyclization with NaOH. Direct reaction of compounds 400 with sulfamide in the presence of DBU at the elevated temperature also resulted in the formation of 1H-benzo[c][1,2,6]thiadiazine-2,2-dioxide derivatives 404 (Maryanoff et al., *J. Med. Chem.* 2006, 49, 3496, and references cited therein).

Scheme 7

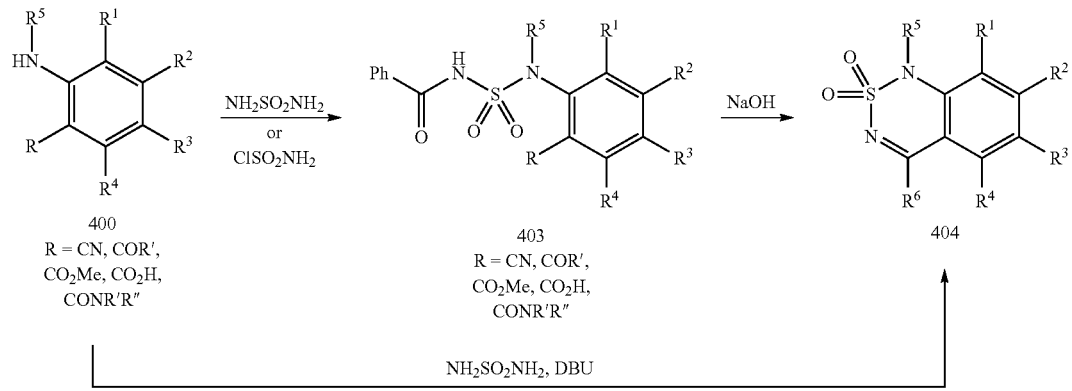

Quinazoline derivatives are also synthesized from quinazoline-2,4(1H,3H)-diones (Scheme 8). Reaction of quinazoline-2,4(1H,3H)-diones with POCl₃ provided the corresponding dichloroquinazolines (Zunszain et al., *Bioorg. & Med. Chem.* 2005, 13, 3681 and references cited therein). Subsequent displacements of the two chlorides with various nucleophiles resulted in formation of quinazoline derivatives (Scheme 8) (Kanuma et al., *Bioorg. & Med. Chem. Lett.* 2005, 15, 3853 and references cited therein; Blackburn, *Bioorg. & Med. Chem. Lett.* 2006, 16, 2621).

Scheme 8

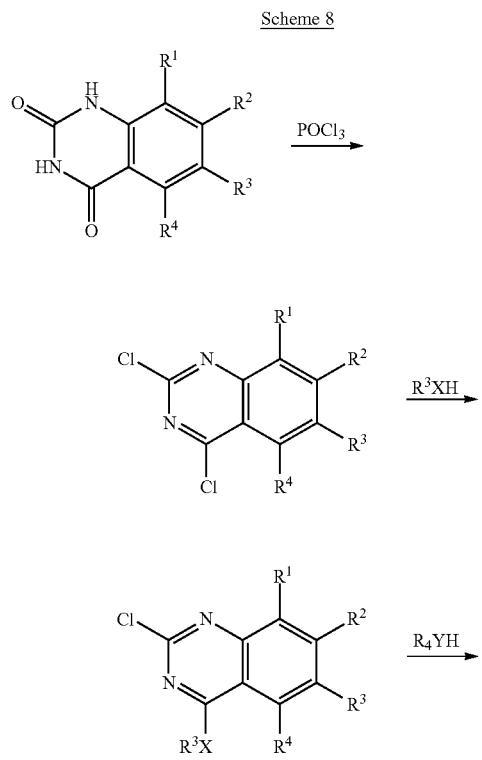

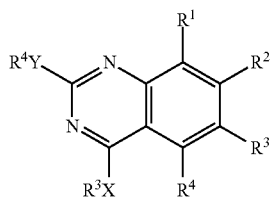

4-Amino-5,6,7,8-tetrahydroquinazolin-2(1H)-(thi)one derivatives and 4-amino-5,6,7,8-tetrahydro-1H-benzo[c][1,2,6]thiadiazine-2,2-dioxide derivatives, as well as structural analogs with different ring sizes, as shown in Scheme 9, are generally synthesized according to the methods described therein. Thorpe-Ziegler cyclization of dinitriles in the presence of base provides β-amino-α,β-unsaturated nitrile derivatives (Winkler et al., *Tetrahedron* 2005, 61, 4249; Yoshizawa et al., *Green Chem.* 2002, 4, 68, and references cited therein; Rodriguez-Hahn et al., *Synthetic Commun.* 1984, 14, 967, and references cited therein; Francis et al., *J. Med. Chem.* 1991, 34, 2899). The β-amino-α,β-unsaturated nitriles may be reacted, for example, with benzoyliso(thio)cyanate and subsequently cyclized by treatment with NaOH to provide 4-amino-5,6,7,8-tetrahydroquinazolin-2(1H)-(thi)one derivatives (El-Sherbeny et al., *Med. Chem. Rev.* 2000, 10, 122, and references cited therein; Reddy et al., *Synthetic Commun.* 1988, 18, 525) as well as their structural analogs with different ring sizes (Scheme 9). Similarly reaction of β-amino-α,β-unsaturated nitrile derivatives with sulfamoyl chloride, followed by treatment with NaOH provides 4-amino-5,6,7,8-tetrahydro-1H-benzo[c][1,2,6]thiadiazine-2,2-dioxide derivatives, as well as structural analogs with different ring size (Scheme 9) (Hirayama et al., *Bioorg. & Med. Chem.* 2002, 10, 1509; Kanbe et al., *Bioorg. & Med. Chem. Lett.* 2006, 16, 4090 and references cited therein).

Scheme 9

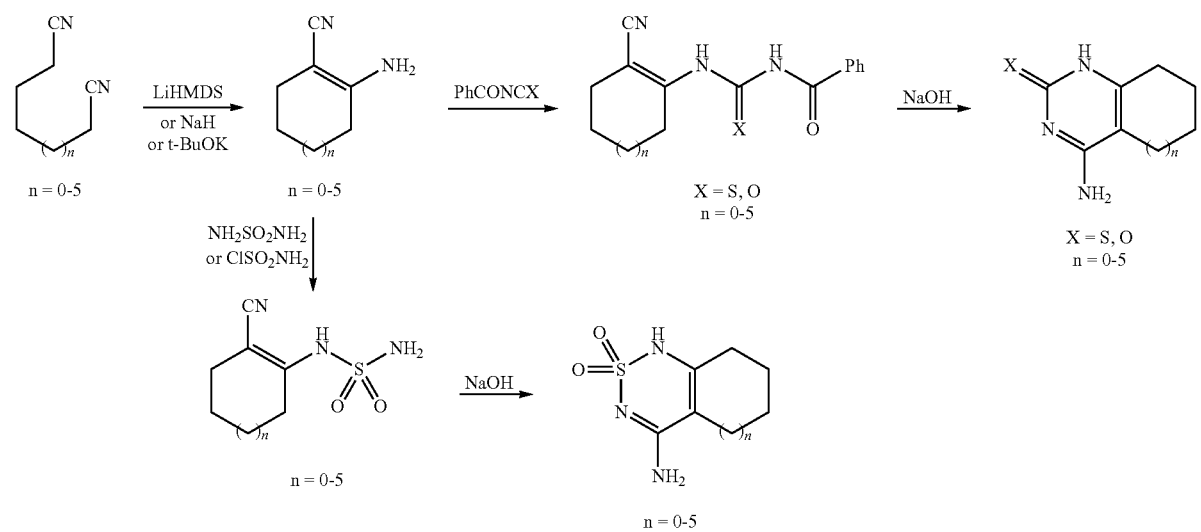

Acesulfame and fused acesulfame derivatives C such as benzo[e][1,2,3]oxathiazin-4(3H)-one-2,2-dioxides can be synthesized via the reaction of 1,3-dicarbonyl derivatives A or 2-hydroxy carboxyl derivatives B and D with $SO_3$ or $ClSO_2NH_2$, as described in Scheme 10 (Linkies et al, *Synthesis* 1990, 405 and references cited therein; Ahmed et al., *J. Org. Chem.* 1988, 53, 4112; Ahmed et al., *Heterocycles* 1989, 29, 1391).

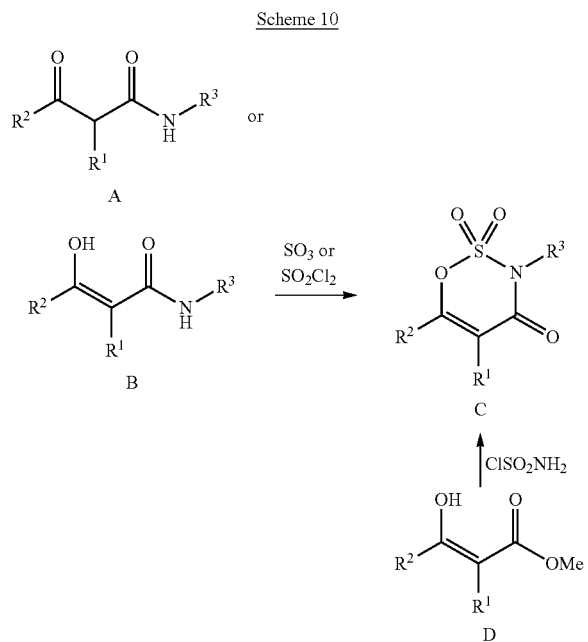

Acesulfame derivatives C can also be synthesized via cyclization of alkynes or enols with $FSO_2NCO$ (Clauss et al., *Tetrahedron Lett.* 1970, 2, 119) or $ClSO_2NCO$ (Rasmussen et al., *J. Org. Chem.* 1973, 38, 2114; Etter et al., *J. Org. Chem.* 1986, 51, 5405; Tripathi et al., *Indian J. Chem. Sect. B* 1987, 26B, 1082.) as shown in Scheme 11.

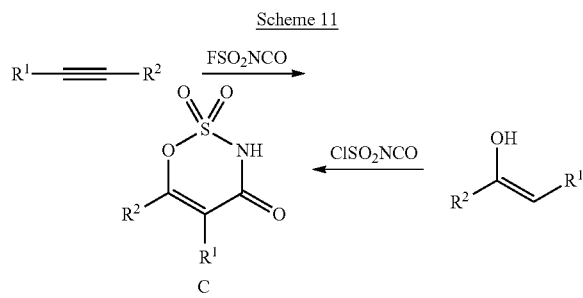

Saccharin derivatives may be synthesized by direct oxidative cyclization of N-alkyl-o-methyl-arenesulfonamides as shown in Scheme 12 (Xu et al., *Tetrahedron* 2006, 62, 7902 and references cited therein; Pal et al., *Letters in Drug Design & Discovery* 2005, 2, 329). Cyclization of o-carboxyl-arenesulfonyl chloride derivatives with primary amines can also provide saccharin derivatives (Robinson et al., *Eur. J. Org. Chem.* 2006, 19, 4483 and references cited therein; Yamada et al., *J. Med. Chem.* 2005, 48, 7457 and references cited therein; Da Settimo et al., *J. Med. Chem.* 2005, 48, 6897).

Other heteroaromatic fused isothiazol-3(2H)-one-1,1-dioxide derivatives may be synthesized similarly.

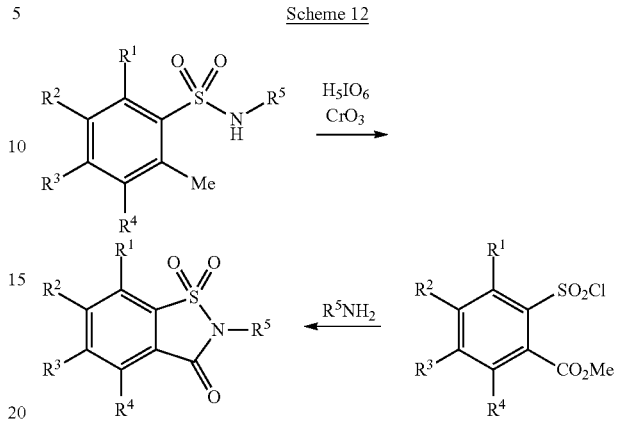

According to the present invention, chemosensory receptor modifiers or chemosensory receptor ligand modifiers of the present invention can be used for one or more methods of the present invention, e.g., modulating a chemosensory receptor and/or its ligands. In general, chemosensory receptor modifiers and chemosensory receptor ligand modifiers of the present invention are provided in a composition, e.g., pharmaceutical, medicinal or comestible composition, or alternatively in a formulation, e.g., a pharmaceutical or medicinal formulation or a food or beverage product or formulation.

In one embodiment, the chemosensory receptor modifiers or chemosensory receptor ligand modifiers provided by the present invention can be used at very low concentrations on the order of a few parts per million, in combination with one or more known sweeteners, natural or artificial, so as to reduce the concentration of the known sweetener required to prepare a comestible composition having the desired degree of sweetness.

Commonly used known or artificial sweeteners for use in such combinations of sweeteners include but are not limited to the common saccharide sweeteners, e.g., sucrose, fructose, glucose, and sweetener compositions comprising those natural sugars, such as corn syrup or other syrups or sweetener concentrates derived from natural fruit and vegetable sources, or semi-synthetic "sugar alcohol" sweeteners such as erythritol, isomalt, lactitol, mannitol, sorbitol, xylitol, maltodextrin, and the like, or well known artificial sweeteners such as aspartame, saccharin, acesulfame-K, cyclamate, sucralose, and alitame; or any mixture thereof.

Chemosensory receptor modifiers and chemosensory receptor ligand modifiers of the present invention can also be provided, individually or in combination, with any comestible composition known or later discovered. A variety of classes, subclasses and species of comestible compositions are known. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads.

Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof.

Exemplary comestible compositions also include ice creams, breakfast cereals, sweet beverages or solid or liquid concentrate compositions for preparing beverages, ideally so as to enable the reduction in concentration of previously known saccharide sweeteners, or artificial sweeteners.

In another embodiment, the chemosensory receptor modifiers and chemosensory receptor ligand modifiers are added to food or beverage products or formulations. Examples of food and beverage products or formulations include any entity described in the Wet Soup Category, the Dehydrated and Culinary Food Category, the Beverage Category, the Frozen Food Category, the Snack Food Category, and seasonings or seasoning blends.

In general, "Wet Soup Category" usually means wet/liquid soups regardless of concentration or container, including frozen Soups. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consomme) to sauces (cream or cheese-based soups).

"Dehydrated and Culinary Food Category" usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

"Beverage Category" usually means beverages, beverage mixes and concentrates, including but not limited to, alcoholic and non-alcoholic, ready to drink beverages, liquid concentrate formulations for preparing beverages such as sodas, and dry powdered beverage precursor mixes.

Other examples of food and beverage products or formulations include carbonated and non-carbonated beverages, e.g., sodas, fruit or vegetable juices, alcoholic and non-alcoholic beverages, confectionery products, e.g., cakes, cookies, pies, candies, chewing gums, gelatins, ice creams, sorbets, puddings, jams, jellies, salad dressings, and other condiments, cereal, and other breakfast foods, canned fruits and fruit sauces and the like. Exemplary food and beverage products or formulations also include sweet coatings, frostings, or glazes for comestible products.

In yet another embodiment, the chemosensory receptor modifier and chemosensory receptor ligand modifier can be formulated, individually or in combination, in flavor preparations to be added to food and beverage formulations or products.

Typically at least a chemosensory receptor modulating amount, a chemosensory receptor ligand modulating amount, a sweet flavor modulating amount, a sweet flavoring agent amount, or a sweet flavor enhancing amount of one or more of the chemosensory receptor modifiers or chemosensory receptor ligand modifiers of the present invention will be added to the comestible or medicinal product, optionally in the presence of known sweeteners, e.g., so that the sweet flavor modified comestible or medicinal product has an increased sweet taste as compared to the comestible or medicinal product prepared without the modifiers of the present invention, as judged by human beings or animals in general, or in the case of formulations testing, as judged by a majority of a panel of at least eight human taste testers, via procedures commonly known in the field.

The concentration of sweet flavoring agent needed to modulate or improve the flavor of the comestible or medicinal product or composition will of course depend on many variables, including the specific type of comestible composition and its various other ingredients, especially the presence of other known sweet flavoring agents and the concentrations thereof, the natural genetic variability and individual preferences and health conditions of various human beings tasting the compositions, and the subjective effect of the particular compound on the taste of such chemosensory compounds.

One application of the chemosensory receptor modifiers and/or chemosensory receptor ligand modifiers is for modulating (inducing, enhancing or inhibiting) the sweet taste or other taste properties of other natural or synthetic sweet tastants, and comestible compositions made therefrom. A broad but also low range of concentrations of the compounds or entities of the present invention would typically be required, i.e., from about 0.001 ppm to 100 ppm, or narrower alternative ranges from about 0.1 ppm to about 10 ppm, from about 0.01 ppm to about 30 ppm, from about 0.05 ppm to about 10 ppm, from about 0.01 ppm to about 5 ppm, or from about 0.02 ppm to about 2 ppm, or from about 0.01 ppm to about 1 ppm.

In yet another embodiment, the chemosensory receptor modifier and chemosensory receptor ligand modifier of the present invention can be provided in pharmaceutical compositions containing a therapeutically effective amount of one or more compounds of the present invention, preferably in purified form, together with a suitable amount of a pharmaceutically acceptable vehicle, so as to provide the form for proper administration to a patient.

When administered to a patient, the compounds of the present invention and pharmaceutically acceptable vehicles are preferably sterile. Water is a preferred vehicle when a compound of the present invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of the present invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the present invention into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, $20^{th}$ Edition, 2000).

For topical administration a compound of the present invention may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In some embodiments, the compounds of the present invention are formulated in accordance with routine procedures as a pharmaceutical composition adapted for intravenous administration to human beings. Typically, compounds of the present invention for intravenous administration are solutions in sterile isotonic aqueous buffer. For injection, a compound of the present invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent.

Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound of the present invention is administered by infusion, it can be dispensed, for example, with an infusion bottle containing sterile pharmaceutical grade water or saline. When the compound of the present invention is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation.

Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of the present invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the present invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

A compound of the present invention may also be formulated in rectal or vaginal pharmaceutical compositions such as suppositories or retention enemas, e.g., containing conventional suppository bases such as cocoa butter or other glycerides.

In addition to the formulations described previously, a compound of the present invention may also be formulated as a depot preparation. Such long acting formulations may be administered by implantation (for example, subcutaneously or intramuscularly) or by intramuscular injection. Thus, for example, a compound of the present invention may be formulated with suitable polymeric or hydrophobic materials (for example, as an emulsion in an acceptable oil) or ion exchange resins, or as sparingly soluble derivatives, for example, as a sparingly soluble salt.

When a compound of the present invention is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

A compound of the present invention, and/or pharmaceutical composition thereof, will generally be used in an amount effective to achieve the intended purpose. For use to treat or prevent diseases or disorders the compounds of the present invention and/or pharmaceutical compositions thereof, are administered or applied in a therapeutically effective amount.

The amount of a compound of the present invention that will be effective in the treatment of a particular disorder or condition disclosed herein will depend on the nature of the disorder or condition and can be determined by standard clinical techniques known in the art. In addition, in vitro or in vivo assays may optionally be employed to help identify optimal dosage ranges. The amount of a compound of the present invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In some embodiment, the compounds of the present invention are delivered by oral sustained release administration. Dosing may be repeated intermittently, may be provided alone or in combination with other drugs and may continue as long as required for effective treatment of the disease state or disorder.

Suitable dosage ranges for oral administration depend on potency, but are generally between about 0.001 mg to about 200 mg of a compound of the present invention per kilogram body weight. Dosage ranges may be readily determined by methods known to the artisan of ordinary skill the art.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the present invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

Preferably, a therapeutically effective dose of a compound of the present invention described herein will provide therapeutic benefit without causing substantial toxicity. Toxicity of compounds of the present invention may be determined using standard pharmaceutical procedures and may be readily ascertained by the skilled artisan. The dose ratio between toxic and therapeutic effect is the therapeutic index. A compound of the present invention will preferably exhibit particularly high therapeutic indices in treating disease and disorders. The dosage of a compound of the present invention described herein will preferably be within a range of circulating concentrations that include an effective dose with little or no toxicity.

In certain embodiments of the present invention, the compounds of the present invention and/or pharmaceutical compositions thereof can be used in combination therapy with at least one other agent. The compound of the present invention and/or pharmaceutical composition thereof and the other agent can act additively or, more preferably, synergistically. In some embodiments, a compound of the present invention and/or pharmaceutical composition thereof is administered concurrently with the administration of another agent, which may be part of the same pharmaceutical composition as the compound of the present invention or a different pharmaceutical composition. In other embodiments, a pharmaceutical composition of the present invention is administered prior or subsequent to administration of another agent.

In still another embodiment, the chemosensory receptor modifiers and chemosensory receptor ligand modifiers of the present invention and/or pharmaceutical compositions thereof may be advantageously used in human medicine.

When used to treat and/or prevent diseases or disorders, the compounds described herein and/or pharmaceutical compositions may be administered or applied singly, or in combination with other agents. The compounds and/or pharmaceutical compositions thereof may also be administered or applied singly, in combination with other active agents.

Methods of treatment and prophylaxis by administration to a patient of a therapeutically effective amount of a compound described herein and/or pharmaceutical composition thereof are provided herein. The patient may be an animal, more preferably, a mammal and most preferably, a human.

In one example, the compounds described herein and/or pharmaceutical compositions thereof, are administered orally. The compounds of the present invention and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound described herein and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner and will depend in-part upon the site of the medical condition. In most instances, administration will result in the release of the compounds and/or pharmaceutical compositions thereof into the bloodstream.

In another example, it may be desirable to administer one or more compounds of the present invention and/or pharmaceutical composition thereof locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the condition.

In yet another example, it may be desirable to introduce one or more compounds of the present invention and/or pharmaceutical compositions thereof into the central nervous system by any suitable route, including intraventricular, intrathecal and epidural injection. Intraventricular injection may be facilitated by an intraventricular catheter, for example, attached to a reservoir, such as an Ommaya reservoir.

A compound of the present invention and/or pharmaceutical composition thereof may also be administered directly to the lung by inhalation. For administration by inhalation, a compound of the present invention and/or pharmaceutical composition thereof may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver compounds of the present invention and/or pharmaceutical compositions thereof directly to the lung.

Alternatively, a Dry Powder Inhaler ("DPI") device may be used to administer a compound of the invention and/or pharmaceutical composition thereof to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound of the present invention and a suitable powder base such as lactose or starch for these systems.

Another type of device that may be used to deliver a compound of the present invention and/or pharmaceutical composition thereof to the lung is a liquid spray device supplied, for example, by Aradigm Corporation, Hayward, Calif. Liquid spray systems use extremely small nozzle holes to aerosolize liquid drug formulations that may then be directly inhaled into the lung.

In yet another example, a nebulizer is used to deliver a compound of the present invention and/or pharmaceutical composition thereof to the lung. Nebulizers create aerosols from liquid drug formulations by using, for example, ultrasonic energy to form fine particles that may be readily inhaled (see e.g., Verschoyle et al., *British J. Cancer*, 1999, 80, Suppl. 2, 96). Examples of nebulizers include devices supplied by Sheffield Pharmaceuticals, Inc (See, Armer et al., U.S. Pat. No. 5,954,047; van der Linden et al., U.S. Pat. No. 5,950,619; van der Linden et al., U.S. Pat. No. 5,970,974), and Batelle Pulmonary Therapeutics, Columbus, Ohio.

In yet another example, an electrohydrodynamic ("EHD") aerosol device is used to deliver a compound of the present invention and/or pharmaceutical composition thereof to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering a compound of the present invention and/or pharmaceutical composition thereof to the lung with an EHD aerosol device and such optimization is routinely performed by one of skill in the art. EHD aerosol devices may more efficiently deliver compounds to the lung than other pulmonary delivery technologies.

In yet another example, the compounds of the present invention and/or pharmaceutical compositions thereof can be delivered in a vesicle, in particular a liposome (Langer, 1990, *Science* 249:1527-1533; Treat et al., in "Liposomes in the Therapy of Infectious Disease and Cancer," Lopez-Berestein and Fidler (eds.), Liss, New York, pp. 353-365 (1989); see generally "Liposomes in the Therapy of Infectious Disease and Cancer," Lopez-Berestein and Fidler (eds.), Liss, New York, pp. 353-365 (1989)).

In yet another example, the compounds of the present invention and/or pharmaceutical compositions thereof can be delivered via sustained release systems, preferably oral sustained release systems. In one embodiment, a pump may be used (See, Langer, supra, Sefton, 1987, *CRC Crit. Ref Biomed Eng.* 14:201; Saudek et al., 1989, *N. Engl. J. Med.* 321:574).

In yet another example, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105).

In still other embodiments, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, *Int. J. Pharm. Tech. & Prod. Mfr.*, 1984, 5(3) 1-9). Factors affecting drug release are well known to the skilled artisan and have been described in the art (Bamba et al., *Int. J. Pharm.*, 1979, 2, 307).

In yet another example, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another example, osmotic delivery systems are used for oral sustained release administration (Verma et al., *Drug Dev. Ind. Pharm.*, 2000, 26:695-708). In yet other embodiments, OROS™ osmotic devices are used for oral sustained release delivery devices (Theeuwes et al., U.S. Pat. No. 3,845,770; Theeuwes et al., U.S. Pat. No. 3,916,899).

In still another example, a controlled-release system can be placed in proximity of the target of the compounds and/or pharmaceutical composition of the invention, thus requiring only a fraction of the systemic dose (See, e.g., Goodson, in "Medical Applications of Controlled Release," supra, vol. 2, pp. 115-138 (1984). Other controlled-release systems discussed in Langer, 1990, *Science* 249:1527-1533 may also be used.

Having now generally described the invention, the same will be more readily understood by reference to the following examples, which are provided by way of illustration and are not intended as limiting. It is understood that various modifications and changes can be made to the herein disclosed exemplary embodiments without departing from the spirit and scope of the invention.

EXAMPLES

Experiment 1

Modeling and Identification of Potential Chemosensory Receptor Ligand Enhancer

General Procedure

The general procedures for identifying a potential chemosensory receptor ligand enhancer is summarized as the following.

1. Constructing a model of the structure of the Venus flytrap T1R2 domain
2. Docking a chemosensory receptor ligand, e.g., a sweetener into the active site of the structure of the Venus flytrap domain of T1R2, with or without T1R3 present
3. Docking a chemosensory receptor ligand enhancer, e.g., a sweet enhancer into the active site in the presence of the chemosensory receptor ligand, e.g., the sweetener
4. Selecting a chemosensory receptor ligand enhancer, e.g., sweet enhancer candidate based on two criteria: a) it fits the active site in the model, and b) it forms productive interactions with the Venus flytrap domain of T1R2 and with the chemosensory receptor ligand, e.g., the sweetener. Interactions can be van der Waals, burial of hydrophobic atoms or atomic groups, hydrogen bonds, ring stacking interactions, or salt-bridging electrostatic interactions. Key residues for such interactions include the hinge residues, the near active site, the pincer residues, e.g., interacting residues described in the present invention. Candidates are not restricted to fitting completely within the active site, as it is open and chemosensory receptor ligand enhancer candidates may extend beyond the active site as long as they partially extend into it.

Model of the Structure

A model of the structure of the Venus Flytrap T1R2 domain may come from crystal structures of T1R2 or of T1R2 complexed with T1R3. The domains may be in open or in closed form, and may or may not be APO or contain a ligand. Alternatively a model of the structure of the Venus Flytrap T1R2 domain may be built using standard homology modeling methods using crystal structures of available Venus flytrap domains such as the mGluR receptor Venus flytrap domains as templates to construct the model.

An example of a procedure for building such a model is to use the commercial software Homology or Modeller from the Accelrys Corporation that is well documented in the literature and available commercially. Alternative conformations of the model may further be explored using additional molecular mechanical techniques that may include but are not limited to normal mode analysis to explore relative movement of the lobes of the model, loop generation techniques to generate alternative conformations of loops in the model, or Monte Carlo and/or molecular dynamics simulations.

Docking

A chemosensory receptor ligand, e.g., sweetener was first docked into the active site of T1R2. Its modeled pose in the active site was selected by its ability to form productive van der Waals, ring stacking, hydrogen bonding, and/or salt bridging interactions with interacting residues within the active site of the Venus flytrap domain of T1R2.

A candidate for a chemosensory receptor ligand modifier, e.g., sweet enhancer was then docked into the active site in the presence of the ligand, e.g., the sweetener described in the previous paragraph. Its active pose and its candidacy as a potential chemosensory receptor ligand modifier, e.g., sweet enhancer was based on its ability to form productive interactions in the form of van der Waals, ring stacking, hydrogen bonding, and/or salt bridging interactions with interacting residues described in the present invention, with additional residues of the T1R2 domain, and optionally with the chemosensory receptor ligand, e.g., the sweetener placed in the active site as described above.

Candidate for Chemosensory Receptor Ligand Modifiers

A molecule was considered a candidate if it can be docked into the active site in the presence of a chemosensory receptor ligand, e.g., sweetener, forming productive interactions with interacting residues described in the present invention. We defined two spaces within the active site: a first space occupied by a chemosensory receptor ligand, e.g., sweetener, and a second space occupied by a chemosensory receptor ligand modifier, e.g., enhancer. Modeling and mutagenesis results established key residues that were considered to be likely to line these spaces for the chemosensory receptor ligand, e.g., sweeteners and chemosensory receptor ligand modifier, e.g., sweet enhancers. In the context of our study, "residue lining the space" meant that the residue had backbone and/or side-chain atoms that were positioned so that they can potentially interact with atoms of the chemosensory receptor ligand, e.g., sweetener (space #1) and/or chemosensory receptor ligand modifier, e.g., sweet enhancer (space #2). While the chemosensory receptor ligand, e.g., sweetener and chemosensory receptor ligand modifier, e.g., sweet enhancer themselves cannot occupy the same space, their corresponding spaces may overlap due to the ability of residues to contact both the chemosensory receptor ligand, e.g., sweetener and the chemosensory receptor ligand modifier, e.g., sweet enhancer, due to protein flexibility, due to ligand flexibility, and due to the potential for multiple binding modes for a chemosensory receptor ligand, e.g., sweetener or chemosensory receptor ligand modifier, e.g., sweet enhancer. Information on important residues lining space #1 and space #2 came from modeling and docking and from site directed mutagenesis.

The hinge residues are considered to be associated with the first space (space #1). We have discovered that one of the spaces occupied by a chemosensory receptor ligand, e.g., sweetener is partially lined by residues herein called hinge residues. Many Venus flytrap domains have been crystallized with agonists including mGluR1, mGluR2, and mGluR3 that show agonists forming interactions with homologous residues to those identified herein for T1R2. Many chemosensory receptor ligands, e.g., sweeteners docked to the model of T1R2 can be docked to this region. Our site directed mutagenesis also provides strong evidence to support the finding that hinge residues or residues spatially adjacent to it are key residues to the activation of a chemosensory receptor, e.g., T1R2 related receptor. Since chemosensory receptor ligands, e.g., sweeteners vary in size, there are additional residues lining this first space for larger residues where the list of these additional residues is dependent, partially on the size of the chemosensory receptor ligand, e.g., sweetener.

Pincer residues are considered to be associated with the second space (space #2). Venus flytrap domains are known to transition from an "open" state to a "closed" state on agonist binding. The flytrap domain is comprised of two lobes commonly referred to in the literature as the upper lobe and lower lobe. In the "open" state the lobes are further apart, while in the closed state the lobes undergo a relative motion that brings the upper and lower lobe closer together. In addition to direct stabilization of the closed state of T1R2 by the agonist, our modeling study has demonstrated that there is additional stabilization of the closed state through interactions of residues on the upper lobe with corresponding residues on the lower lobe that are herein called the "pincer residues". We have discovered that an interacting site, e.g., interacting space for a chemosensory receptor ligand modifier, e.g., sweet enhancer is the space that is partially lined by these pincer residues, since additional interactions in this region can further stabilize the closed, agonized form of the Venus flytrap domain. Our site directed mutagenesis study also provides evidence to support the finding that pincer residues and residues spatially adjacent to them are key residues associated with modulation of chemosensory receptor ligand, e.g., enhancement activity of the ligand.

The first space and second space can be swapped. In the above discussion the chemosensory receptor modifier, e.g., sweetener binds to the hinge while the chemosensory receptor ligand modifier, e.g., sweet enhancer binds to the pincer region. This is just one example and should not be construed restrictively. For example, our modeling and docking study has also demonstrated that a likely binding mode for saccharine as an agonist (sweetener) involves binding to the pincer region. Such result was further supported by our site-directed mutagenesis. With a chemosensory receptor modifier, e.g., sweetener bound to the pincer region there is opportunity for further stabilization of the closed form of the Venus flytrap domain through binding of a chemosensory receptor ligand modifier, e.g., sweet enhancer to the hinge region.

Procedural Definitions.

1. Docking

Docking is generally considered as the process of translating and rotating the candidate molecule relative to a chemosensory receptor, e.g., T1R2 structural model while simultaneously adjusting internal torsional angles of the candidate molecule to fit the candidate molecule into the active site of the chemosensory receptor, e.g., T1R2 structural model. Poses of the candidate molecule (positions, relative orientations, and internal torsions) are selected based on whether the molecule fits the active site, and whether the molecule can form productive van der Waals interactions, hydrogen bonds, ring stacking interactions, and salt bridge interactions with residues of the active site and with the chemosensory receptor ligand, e.g., sweetener. Key residues can be identified. A candidate is considered more likely if it interacts with sets of residues in the active site as the hinge region, the near active site, the pincer residues, and the totality of the active site. It is also considered more likely if it forms direct interactions with a chemosensory receptor ligand, e.g., a sweetener.

2. Homology Modeling

Homology modeling is generally considered as the process of constructing a model of the Venus flytrap domain of a chemosensory receptor, e.g., T1R2 from its amino acid sequence and from the three dimensional coordinates of one or more homologous Venus flytrap domain proteins. Homology modeling may be performed using standard methods well-described in the literature and available in commercial software such as the Homology program or Modeler from the Accelrys Corporation. Models based on experimentally determined structures of open and closed forms, as well as animation of models using normal mode analysis, were used to define the pincer residues discussed above.

Exemplary Illustrations of Modeling Studies

FIGS. 5 to 10 illustrate interacting spaces and residues associated with one of our molecular modeling studies.

Experiment 2

Mutagenesis Study for Identification of Chemosensory Receptor Ligand Modifier Enhancer In our previous patent applications (International Publication No. WO07047988 and International Publication No. WO070104709), we described a method using human-rat chimeric sweet-umami chimeric receptors to map the binding sites of sweet and umami tastants. Our data demonstrated that a number of sweeteners, including sucrose, fructose, aspartame, neotame, D-tryptophan (D-Trp), Acesulfame K, saccharin and dulcin, all interact with the T1R2 Venus flytrap domain (VFT), while the umami tastants, including L-glutamate, inosine-5'-monophosphate (IMP), and guanosine-5'-monophosphate (GMP), all interact with the T1R1 Venus flytrap domain.

Under the guidance of molecular modeling, we performed site-directed mutagenesis on human T1R2 VFT. The mutagenesis was done using the routine PCR-based method. Human T1R2 mutants were transiently transfected into HEK293 cell together with the human T1R3 wild type cDNA, and the transfected cells were characterized using an automated FLIPR machine or a calcium imaging system as described in our previous patent applications. In order to control for plasma membrane expression, protein folding and other factors that might contribute to changes in receptor activity, we used 2 sweeteners which interact with other domains of the human sweet receptor as positive controls. The 2 control sweeteners were cyclamate and compound X (Senomyx). It is known from our previous data that cyclamate interacts with the human T1R3 transmembrane domain, while compound X interacts with the human T1R2 transmembrane domain.

The mutagenesis data for a number of sweeteners are summarized in the following tables. Based on the data, we concluded that 6 residues (S40, S144, S165, Y103, D142, P277) are critical for interaction with those sweeteners.

Mutagenesis Data on FLIPR

|       | Aspartame (15 Mm) | D-Trp (20 mM) | Fructose (200 mM) | Sucrose (200 mM) | Sucralose (3.2 mM) | Cyclamate (80 mM) | S3819 (25 μM) |
|-------|---|---|---|---|---|---|---|
| WT    | +++ | +++ | +++ | +++ | +++ | +++ | +++ |
| V384F | ++ | ++ | ++ | ++ | ++ | +++ | +++ |
| V384A | ++ | ++ | ++ | ++ | ++ | +++ | +++ |
| E382A | + | ++ | + | + | ++ | ++ | ++ |
| S165I | − | − | + | + | ++ | ++ | ++ |
| D278A | ++ | ++ | ++ | + | − | +++ | +++ |
| K65A  | ++ | ++ | + | + | + | ++ | ++ |
| S165A | +++ | ++ | ++ | ++ | ++ | ++ | +++ |
| I67A  | +++ | +++ | +++ | +++ | +++ | +++ | +++ |
| N143A | +++ | ++ | ++ | ++ | +++ | +++ | +++ |
| S303A | +++ | +++ | ++ | ++ | ++ | +++ | +++ |
| Q328A | +++ | +++ | +++ | +++ | +++ | +++ | +++ |
| T184A | +++ | ++ | +++ | +++ | +++ | +++ | +++ |
| T242A | +++ | ++ | ++ | ++ | ++ | +++ | +++ |
| L279A | +++ | +++ | ++ | ++ | ++ | ++ | +++ |
| T326A | ++ | ++ | ++ | ++ | ++ | ++ | ++ |

Mutagenesis Data on Calcium Imaging

|       | Aspartame (15 mM) | D-Trp (20 mM) | Fructose (200 mM) | Sucrose (200 mM) | Sucralose (3.2 mM) | Cyclamate (80 mM) | S3819 (25 μM) |
|-------|---|---|---|---|---|---|---|
| WT    | ++ | ++ | ++ | ++ | ++ | ++ | ++ |
| I167A | + | + | + | + | + | + | + |
| Y103A | − | + | + | + | − | + | + |
| D278A | + | + | + | + | − | ++ | ++ |
| D307A | + | + | − | − | + | + | + |
| E302A | − | + | + | + | + | + | + |
| S165I | − | − | + | + | + | + | + |
| S40A  | − | − | − | − | − | + | + |
| D142A | − | − | − | − | − | + | + |
| R383A | − | − | − | − | − | − | + |
| A305F | − | − | − | − | − | − | + |
| Y215A | − | − | − | − | − | − | − |
| D142I | − | − | − | − | − | − | − |

Additional Mutations on R383

|       | Aspartame (15 mM) | Neotame (80 μM) | Sucrose (200 mM) | Sucralose (3.2 mM) | D-Trp (20 mM) | Cyclamate (80 mM) | S3819 (25 μM) |
|-------|---|---|---|---|---|---|---|
| WT    | ++ | +++ | ++ | +++ | +++ | +++ | +++ |
| R383H | + | ++ | + | ++ | ++ | ++ | ++ |
| R383Q | − | + | − | + | + | + | + |
| R383I | − | − | − | − | − | − | − |
| R383F | − | ++ | − | − | + | + | + |
| R383K | − | + | − | + | + | + | + |
| R383N | − | + | − | + | + | + | + |
| R383S | − | + | − | + | + | + | + |
| R383A | − | − | − | − | − | − | + |

Figure 11:
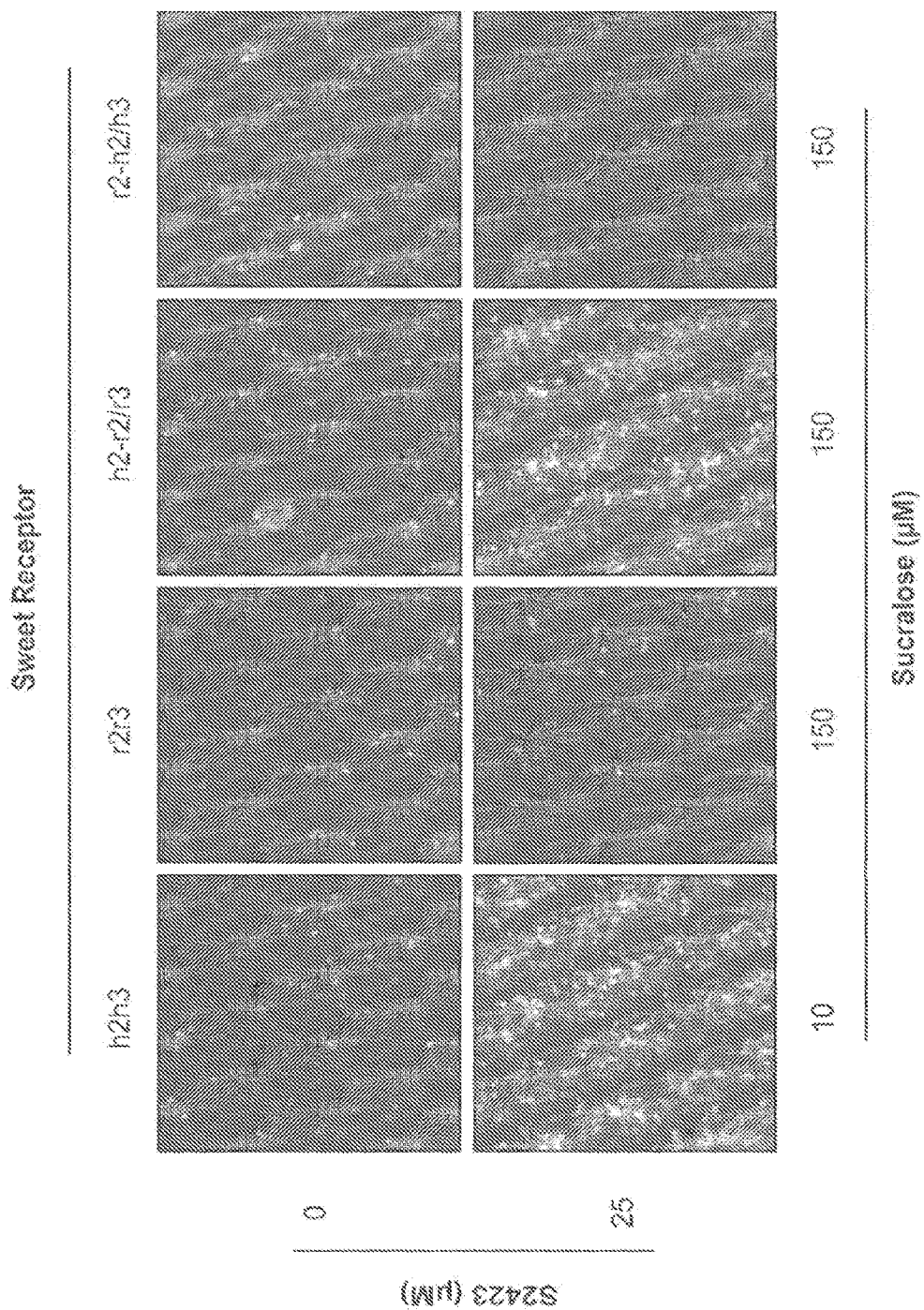
FIG. 11 shows exemplary results for mapping studies using human-rat chimeric receptors.

The sweet enhancer, compound A, is selective for the human sweet receptor, and inactive on the rat sweet receptor. Using the previously described human-rat chimeric receptors, we mapped the binding site of compound A to hT1R2 VFT. As shown in FIG. 11, compound A enhanced the sucralose activity on human sweet receptor (h2/h3) but not rat sweet receptor (r2/r3). When we replaced the rat receptor T1R2 VFT with its human counterpart (h2-r2/r3), the receptor can be enhanced by compound A. On the other hand, when we replaced the human receptor T1R2 VFT with its rat counterpart (r2-h2/h3), the receptor can no longer be enhanced by compound A. We conclude that compound A interacts with human T1R2 VFT. Due to the different sensitivity of human and rat receptors to sucralose, different sucralose concentrations were used to achieve ~EC20 of the different receptors.

Following compound A, 8 more analogues have been identified to enhance the sucralose activity of human sweet receptor. The same mapping experiments were carried out on these 8 analogues, and we observed the same activity pattern as compound A as summarized in the following table. We conclude that all 8 compound A analogues interact with human T1R2 VFT.

|  | h2/h3 | r2/r3 | h2-r2/r3 | r2-h2/h3 |
|---|---|---|---|---|
| Compound A (25 μM) | + | − | + | − |
| Compound A1 (25 μM) | + | − | + | − |
| Compound A2 (25 μM) | + | − | + | − |
| Compound A3 (25 μM) | + | − | + | − |
| Compound A4 (25 μM) | + | − | + | − |
| Compound A5 (25 μM) | + | − | + | − |
| Compound A6 (25 μM) | + | − | + | − |
| Compound A7 (25 μM) | + | − | + | − |
| Compound A8 (100 μM) | + | − | + | − |

Figure 12:
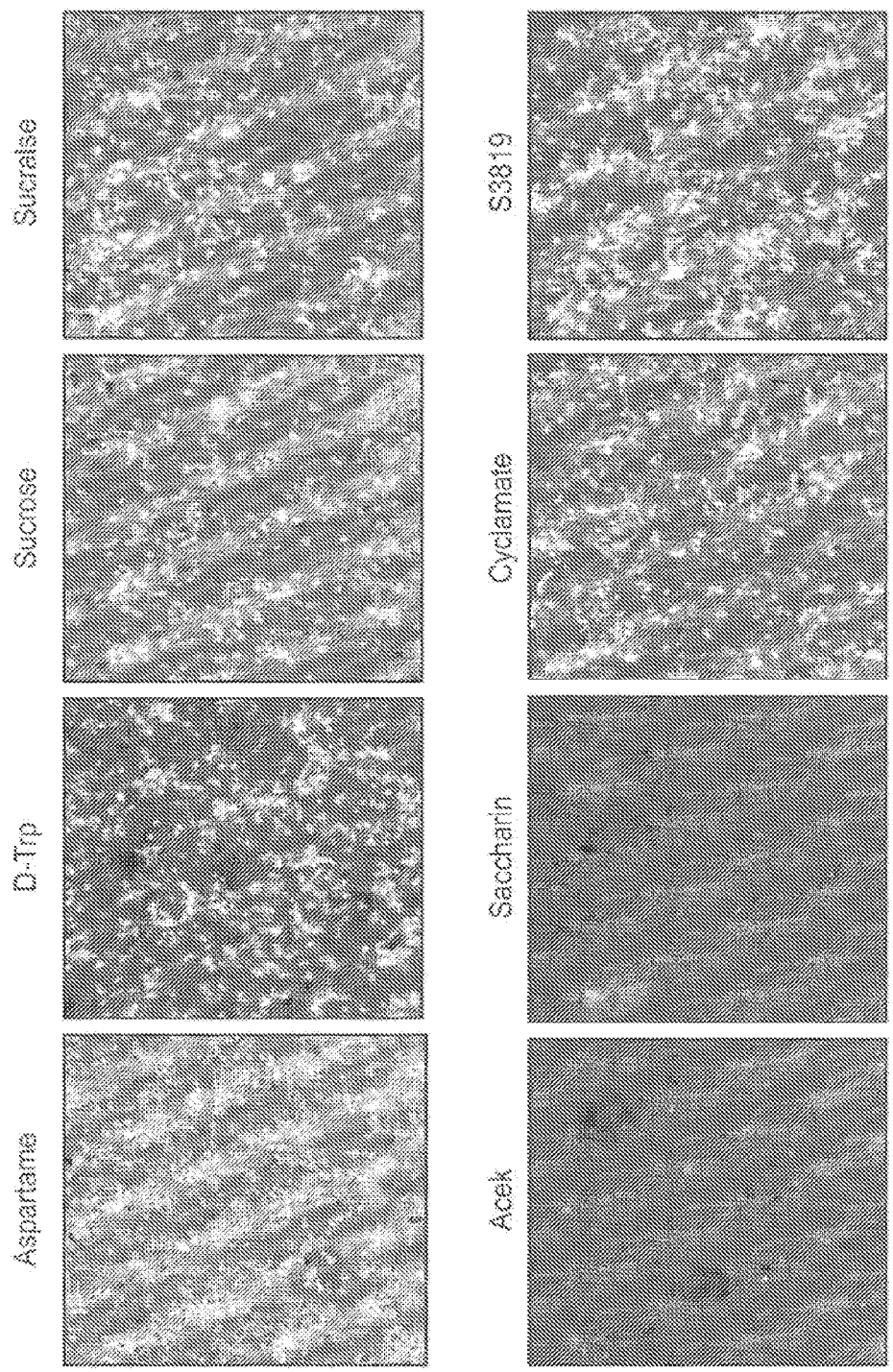
FIG. 12 shows results for exemplary mutagenesis results.

After mapping the enhancers to human T1R2 VFT, we performed mutagenesis analysis to further define the interaction site. As summarized in the following table, six residues (K65, D278, L279, D307, R383, V384) were identified as critical for the activities of compound A and analogous. Interestingly, V384 is also important for the activities of 2 structurally related sweeteners (as shown in FIG. 12), saccharin and acesulfame K (AceK), indicating that these sweeteners might occupy similar space in the human T1R2 VFT. The concentrations for the sweeteners are Aspartame (15 mM), D-Trp (20 mM), Sucrose (200 mM), Sucralose (3.2 mM), AceK (8 mM), Saccharin (3.2 mM), Cyclamate (80 mM), S3819 (25 μM).

| hT1R2 | Sucralose | A | A4 | A1 | A5 | A2 | A6 | A3 | A8 | A7 |
|---|---|---|---|---|---|---|---|---|---|---|
|  |  | Enhancement Activity (at 25 μM) for Compound A and its analogs | | | | | | | | |
| WT | ++ | ++ | ++ | +++ | ++ | +++ | ++ | + | ++ | +++ |
| V384A | ++ | ++ | ++ | +++ | ++ | +++ | ++ | + | ++ | +++ |
| E382A | ++ | ++ | ++ | +++ | ++ | +++ | ++ | + | ++ | +++ |
| Y103A | − | + | + | ++ | + | ++ | + | + | ++ | ++ |
| P277A | + | ++ | + | +++ | + | +++ | + | + | ++ | +++ |
| D278A* | − | ++ | + | +++ | + | +++ | + | + | + | ++ |
| K65A | + | − | − | − | − | − | − | − | − | − |
| L279A | ++ | − | − | − | − | − | − | − | − | − |
| V384F | ++ | + | + | + | + | + | + | − | + | + |
| S165I | ++ | ++ | ++ | +++ | ++ | +++ | ++ | + | ++ | +++ |
| I67A | ++ | ++ | ++ | +++ | ++ | +++ | ++ | + | ++ | +++ |
| S165A | ++ | + | ++ | +++ | ++ | +++ | ++ | + | ++ | +++ |
| N143A | ++ | ++ | ++ | +++ | ++ | +++ | ++ | + | ++ | +++ |
| T326A | ++ | ++ | ++ | +++ | ++ | +++ | ++ | + | ++ | +++ |
| T242A | ++ | ++ | ++ | +++ | ++ | +++ | ++ | + | ++ | +++ |
| S303A | ++ | ++ | ++ | +++ | ++ | +++ | ++ | + | ++ | +++ |
| Q328A | ++ | ++ | ++ | +++ | ++ | +++ | ++ | + | ++ | +++ |
| T184V | ++ | ++ | ++ | +++ | ++ | +++ | ++ | + | ++ | +++ |
| T184A | ++ | ++ | ++ | +++ | ++ | +++ | ++ | + | ++ | +++ |
| V64M | ++ | ++ | ++ | +++ | ++ | +++ | ++ | + | ++ | +++ |
| S168T | ++ | ++ | ++ | +++ | ++ | +++ | ++ | + | ++ | +++ |
| R383H | ++ | ++ | ++ | +++ | ++ | +++ | ++ | + | ++ | +++ |
| S40T | + | ++ | ++ | +++ | ++ | +++ | ++ | + | ++ | +++ |
| I167A | + | + | + | ++ | + | ++ | + | + | + | ++ |
| E302A | + | + | + | ++ | + | ++ | + | + | + | ++ |
| R383F | + | − | − | − | − | − | − | − | − | − |
| D307A | + | − | − | − | − | − | − | − | − | − |
| D142A | − | + | + | ++ | + | ++ | + | + | + | ++ |
| S40A | − | + | + | ++ | + | ++ | + | + | + | ++ |
| R383A | − | + | + | ++ | + | ++ | + | + | + | ++ |
| A305F | − | − | − | − | − | − | − | − | − | − |

*D278 is a critical residue for the enhancers, because all enhancers in the above table show agonist activity on D278A mutant, i.e., they activate the mutant receptor in the absence of sucralose.

Experiment 3

Chemical Synthesis of the Compounds of the Present Invention

Example 1

4-Amino-5,6-dimethylthieno[2,3-d]pyrimidine-2(1H)-thione

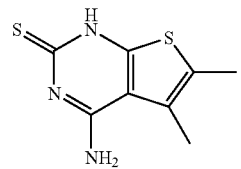

A solution of N-(3-cyano-4,5-dimethylthiophen-2-ylcarbamothioyl)benzamide (example 1a) (1.90 g, 6.03 mmol) and NaOH (2 N, 8.3 mL) in EtOH (25 mL) was stirred at 100° C. under nitrogen for half an hour. After cooling to room temperature, the clear reaction solution was filtered and the filtrate was carefully neutralized with 10% AcOH with vigorous stirring at 0° C. The resultant precipitate was collected by filtration, washed with warm water and then 20% EtOH in water to give the final product 4-amino-5,6-dimethylthieno[2,3-d]pyrimidine-2(1H)-thione (1.11 g, 87%) as an off-white solid. M.p.: >260° C. $^1$H NMR (400 MHz, DMSO-$d_6$) δ2.25 (s, 3H), 2.26 (s, 3H). MS 212 (MH$^+$).

Example 1a

N-(3-Cyano-4,5-dimethylthiophen-2-ylcarbamothioyl)benzamide

To a solution of 2-amino-4,5-dimethylthiophene-3-carbonitrile (1.52 g, 10.0 mmol) in 1.4-dioxane (20 mL) was added benzoylisothiocyanate (1.63 g, 10.0 mmol). The reaction mixture was then stirred at room temperature under nitrogen overnight. The precipitation was collected by filtration, washed with EtOAc/Hexanes (1:4), and dried under vacuum overnight to give N-(3-Cyano-4,5-dimethylthiophen-2-ylcarbamothioyl)benzamide as a white solid. $^1$H NMR (400 MHz, CDCl$_3$) δ2.23 (s, 3H), 2.31 (s, 3H), 7.58-7.54 (m, 2H), 7.68-7.66 (m, 1H), 7.94 (d, J=7.2 Hz, 2H), 9.13 (bs, 1H). MS 316 (MH$^+$).

Example 2

4-Aminoquinazoline-2(1H)-thione

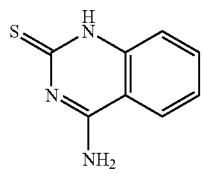

Prepared as in example 1 from N-(2-cyanophenylcarbamothioyl)benzamide (Example 2a). $^1$H NMR (400 MHz, DMSO-d$_6$) δ7.25 (dt, J=1.0, 8.2 Hz, 1H), 7.35 (d, J=8.2 Hz, 1H), 7.65 (dt, J=1.0, 8.2 Hz, 1H), 8.05 (dd, J=1.0, 8.1 Hz, 1H), 8.30 (s, 1H), 8.35 (s, 1H), 12.34 (s, 1H). MS 178 (MH$^+$).

Example 2a

N-(2-Cyanophenylcarbamothioyl)benzamide

Prepared as in Example 1a from 2-aminobenzonitrile and benzoyl isothiocyanate as a pale-yellow solid. $^1$H NMR (400 MHz, DMSO-d$_6$) δ7.35-7.56 (m, 3H), 7.67 (t, 1H), 7.75-7.76 (d, J=5.2 Hz, 2H), 7.89-7.91 (d, J=7.2 Hz, 2H), 7.98-8.01 (dd, J1=1.6 Hz, J2=8.2 Hz, 2H), 11.90 (s, 1H), 12.54 (s, 1H). MS 282 (MH$^+$).

Example 3

4-Amino-5-methylquinazoline-2(1H)-thione

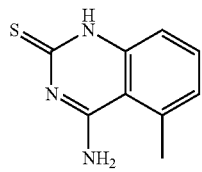

Prepared as in example 1 from N-(2-cyano-3-methylphenylcarbamothioyl)benzamide (Example 3a) as an off-white solid. M.p.: >250° C. $^1$H NMR (400 MHz, DMSO-d$_6$) δ2.68 (s, 3H), 7.03 (d, J=6.8 Hz, 1H), 7.13 (b, 1H), 7.22 (d, J=6.8 Hz, 1H), 7.48 (t, J=6.8 Hz, 1H), 8.50 (b, 1H), 12.26 (s, 1H). $^{13}$C NMR (DMSO-d$_6$) δ23.26, 109.86, 114.37, 127.16, 134.31, 136.97, 143.57, 160.58, 179.67. MS 192 (MH$^+$).

Example 3a

N-(2-Cyanophenylcarbamothioyl)benzamide

Prepared as in example 1a from 2-amino-6-methylbenzonitrile and benzoyl isothiocyanate as a pale-yellow solid. $^1$H NMR (400 MHz, DMSO-d$_6$) δ7.40 (m, 1H), 7.52-7.69 (m, 5H), 7.98-8.01 (m, 2H), 11.99 (s, 1H), 12.54 (s, 1H). MS 296 (MH$^+$).

Example 4

4-amino-5,6-dimethylthieno[2,3-d]pyrimidin-2(1H)-one

A solution of N-(3-cyano-4,5-dimethylthiophen-2-ylcarbamoyl)benzamide (example 4a) (44.35 g, 148.1 mmol) and NaOH (2 N, 204 mL) in EtOH (400 mL) was stirred at 100° C. under nitrogen for four hours. The clear reaction solution was filtered and the filtrate was cooling to room temperature, and then was carefully neutralized with 10% AcOH (~120 mL) with vigorous stirring at 0° C. After stirring overnight from 0° C. to room temperature, the resultant precipitate was collected by filtration, washed with warm water (60-70° C., 150 mL×4) and 20% EtOH in water (200 mL×2), and then dried at 50° C. under vacuum overnight to give the final product 4-amino-5,6-dimethylthieno[2,3-d]pyrimidin-2(1H)-one (27.7 g, 96%) as a white solid. $^1$H NMR (400 MHz, DMSO-d$_6$) δ7.98 (brs, 1H), 2.24 (s, 3H), 2.19 (s, 3H). MS 196 (MH$^+$).

Example 4a

N-(3-cyano-4,5-dimethylthiophen-2-ylcarbamoyl)benzamide

To a solution of 2-amino-4,5-dimethylthiophene-3-carbonitrile (example 4b) (25 g, 164.5 mmol) in 1.4-dioxane (600 mL) was added benzoyl isocyanate (24.2 g, 164.5 mmol). The reaction mixture was then stirred at room temperature under nitrogen overnight. The precipitate was collected by filtration, washed with 1.4-dioxane (20 mL×3), and dried under vacuum at 40° C. for 3 hours to give N-(3-cyano-4,5-dimethylthiophen-2-ylcarbamoyl)benzamide (44.35 g, 90%) as a white solid. $^1$H NMR (400 MHz, DMSO-d$_6$) δ2.10 (s, 3H), 2.24 (s, 3H), 7.52-7.56 (m, 2H), 7.64-7.69 (m, 1H), 8.01-8.03 (m, 2H), 11.57 (brs, 1H), 12.05 (brs, 1H). MS 300 (MH$^+$).

Example 4b 2-amino-4,5-dimethylthiophene-3-carbonitrile

To a solution of butanone (162.0 mL, 1.8 mol), sulfur (57.99 g, 1.8 mol), and malononitrile (119.49 g, 1.8 mol) in anhydrous Ethanol (1.2 L) was added at 0° C. triethylamine (251.4 mL, 1.8 mol). The reaction was stirred at 0° C. for 15 minutes then heated at 80° C. for 70 minutes. After cooling to room temperature, ethanol (920 mL) was removed reduced pressure and aqueous NaCl (30%, 750 mL) was added. The resulting mixture was stirred for 10 minutes and extracted with diethyl ether (1 L). The aqueous layer was further extracted with diethyl ether (500 mL) and the insoluble solids were removed by filtration after which the organic layer was separated and combined with the first diethyl ether extract. The combined organic extract was dried over MgSO$_4$, filtered and concentrated under reduced pressure. The residue was stirred for 2 hours in dichloromethane (300 mL) and a solid was collected. More solid was isolated from the dichloromethane solution cooled to −78° C. The combined solid product was refluxed in dichloromethane (600 mL) for 10 minutes then stirred at room temperature for 30 minutes and cooled to −78° C. The resultant precipitate was collected by filtration to give the crude product (115 g). The filtrate was concentrated and the residue was chromatographed on silica gel (eluent: dichloromethane) to provide a solid that was combined with the previous crude product. The resulting residue was purified by flash chromatography on silica gel (dichloromethane) to yield 2-amino-4,5-dimethylthiophene-3-carbonitrile (105 g, 38%) as an off white solid. $^1$H NMR (400 MHz, DMSO-d$_6$) δ1.93 (d, J=1.2 Hz, 3H), 2.07 (d, J=1.2 Hz, 3H), 3.33 (s, 2H). MS 153 (MH$^+$).

Example 5

4-Amino-5,6-butylenethieno[2,3-d]pyrimidine-2 (1H)-thione

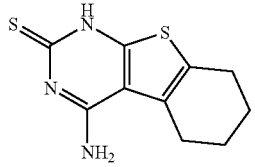

39

Prepared as in Example 1 from N-(3-cyano-4,5,6,7-tetrahydrobenzo[b]thiophen-2-ylcarbamothioyl)benzamide (Example 5a). $^1$H NMR (400 MHz, DMSO-d$_6$) δ1.75 (m, 4H), 2.62 (m, 2H), 2.74 (m, 2H). MS 238 (MH$^+$).

Example 5a

N-(3-Cyano-4,5,6,7-tetrahydrobenzo[b]thiophen-2-ylcarbamothioyl)-benzamide

Prepared as in example 1a from 2-amino-4,5,6,7-tetrahydrobenzo[b]thiophene-3-carbonitrile (example 5b) and benzoylisothiocyanate as a pale-yellow solid. MS 342 (MH$^+$).

Example 5b

2-Amino-4,5,6,7-tetrahydrobenzo[b]thiophene-3-carbonitrile

A solution of cyclohexanone (1.96 g, 20.0 mmol), malononitrile (1.32 g, 20.0 mmol), sulfur (640 mg, 20.0 mmol), and triethylamine (2.03 g, 20 mmol) in EtOH (50 mL) was refluxed for 6 h under nitrogen. The solvent was removed under reduced pressure and the residue partitioned between EtOAc and water. The organic layer was separated, washed with brine, and dried over Na$_2$SO$_4$. After evaporation of the solvent, the residue was purified by chromatography on silica gel eluting with EtOAc/Hexanes (2:3) to give the title product as a yellow solid. $^1$H NMR (400 MHz, CDCl$_3$) δ1.79 (m, 4H), 2.50 (m, 4H), 4.59 (s, 2H). MS 179 (MH$^+$).

Example 6

4-Amino-5-methylquinazolin-2(1H)-one

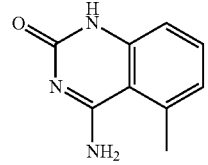

157

Prepared as in example 1 from N-(2-cyano-3-methylphenylcarbamoyl)benzamide (example 6a). $^1$H NMR (400 MHz, DMSO-d$_6$) δ3.04 (s, 3H), 7.43 (d, J=7.2 Hz, 1H), 7.51 (d, J=7.2 Hz, 1H), 7.97 (t, J=7.2 Hz, 1H). MS 176 (MH$^+$).

Example 6a

N-(2-Cyano-3-methylphenylcarbamoyl)benzamide

Prepared as in example 1a from 2-amino-6-methylbenzonitrile and benzoyl isocyanate as an off-white solid. $^1$H NMR (400 MHz, DMSO-d$_6$) δ7.19 (d, J=7.6 Hz, 1H), 7.52-7.68 (m, 5H), 8.02-8.08 (m, 2H), 11.32 (s, 1H), 11.46 (s, 1H). MS 280 (MH$^+$).

Example 7

4-Amino-6-ethyl-5-methylthieno[2,3-d]pyrimidin-2 (1H)-one

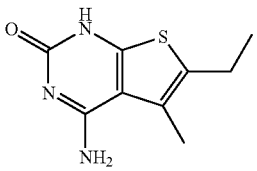

75

Prepared as in Example 1 from N-(3-cyano-5-ethyl-4-methylthiophen-2-ylcarbamoyl)benzamide (Example 7a). $^1$H NMR (400 MHz, DMSO-d$_6$) δ1.11 (t, J=7.6 Hz, 3H), 2.26 (s, 3H), 2.60-2.67 (q, J=7.6 Hz, 2H). MS 210 (MH$^+$).

Example 7a

N-(3-Cyano-5-ethyl-4-methylthiophen-2-ylcarbamoyl)benzamide

Prepared as in example 1a from 2-amino-5-ethyl-4-methylthiophene-3-carbonitrile (example 7b) and benzoyl isocyanate as a pale-yellow solid. MS 314 (MH$^+$).

Example 7b

2-Amino-5-ethyl-4-methylthiophene-3-carbonitrile

Prepared as in example 5b from 2-pentanone, malononitrile, and sulfur as a yellow solid. MS 167 (MH$^+$).

Example 8

4-Amino-6-methylthieno[2,3-d]pyrimidin-2(1H)-one

77

Prepared as in Example 1 from N-(3-cyano-5-methylthiophen-2-ylcarbamoyl)benzamide (Example 8a). $^1$H NMR (400 MHz, DMSO-$d_6$) δ2.34 (s, 3H), 6.97 (s, 1H), 7.50 (s, 1H). MS 182 (MH$^+$).

Example 8a

N-(3-Cyano-5-methylthiophen-2-ylcarbamoyl)benzamide

Prepared as in Example 1a from 2-amino-5-methylthiophene-3-carbonitrile and benzoyl isocyanate as a white solid. $^1$H NMR (400 MHz, DMSO-$d_6$) δ2.36 (d, J=1.2 Hz, 3H), 6.89 (d, J=1.2 Hz, 1H), 7.55 (t, J=8.0 Hz, 2H), 7.66 (d, J=7.2 Hz, 1H), 8.03-8.01 (m, 2H), 11.60 (brs, 1H), 12.08 (bs, 1H). MS 286 (MH$^+$).

Example 9

4-Amino-6-(hydroxymethyl)-5-methylthieno[2,3-d]pyrimidine-2(1H)-thione

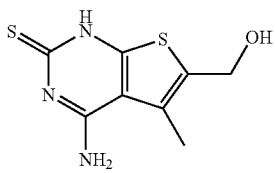

37

Prepared as in Example 1 from N-(3-cyano-5-(hydroxymethyl)-4-methylthiophen-2-ylcarbamothioyl)benzamide (Example 9a). $^1$H NMR (400 MHz, DMSO-$d_6$) δ2.30 (s, 3H), 4.54-4.55 (d, J=5.2 Hz, 2H), 5.54 (t, 1H). MS 228 (MH$^+$).

Example 9a

N-(3-Cyano-5-(hydroxymethyl)-4-methylthiophen-2-ylcarbamothioyl)-benzamide

Prepared as in example 1a from 2-amino-5-(hydroxymethyl)-4-methylthiophene-3-carbonitrile (Example 9b) and benzoyl isothiocyanate as a yellow solid. MS 332 (MH$^+$).

Example 9b

2-Amino-5-(hydroxymethyl)-4-methylthiophene-3-carbonitrile

Prepared as in example 5b from 4-hydroxybutan-2-one, malononitrile, and sulfur as a yellow solid. $^1$H NMR (400 MHz, DMSO-$d_6$) δ1.97 (s, 3H), 4.30-4.31 (d, J=5.6 Hz, 2H), 5.10 (t, 1H), 7.00 (s, 2H).

Example 10

4-Amino-5,6,7,8-tetrahydroquinazoline-2(1H)-thione

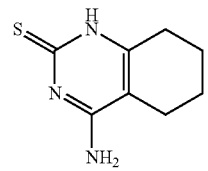

201

Prepared as in Example 1 from N-(2-cyanocyclohex-1-enylcarbamothioyl)benzamide (Example 10a) as a white solid. $^1$H NMR (400 MHz, DMSO-$d_6$) δ 1.60-1.65 (m, 4H), 2.13 (m, 2H), 2.38 (m, 2H), 6.93 (s, 1H), 7.56 (s, 1H), 11.84 (s, 1H). MS 182 (MH$^+$).

Example 10a

N-(2-Cyanocyclohex-1-enylcarbamothioyl)benzamide

Prepared as in Example 1a from 2-aminocyclohex-1-enecarbonitrile (Example 10b) and benzoyl isothiocyanate as a white solid. MS 286 (MH$^+$).

Example 10b

2-Aminocyclohex-1-enecarbonitrile

A stirred mixture of 1,7-heptanedinitrile (24.44 g, 0.2 mol) and t-BuOK (22.44 g, 0.2 mol) was heated at 80° C. for 3 h under nitrogen. The mixture was then cooled down to room temperature and stored at that temperature overnight. The residue was treated with water, and extracted with ether (2×). The combined organic layers were washed with brine, dried over Na$_2$SO$_4$, filtered and concentrated. The residue was purified by recrystallization from MeOH to give the title compound as a white solid (18.2 g, 75%). $^1$H NMR (400 MHz, CDCl$_3$) δ1.58-1.71 (m, 4H), 2.12-2.20 (m, 4H), 4.23 (bs, 2H). MS 123 (MH$^+$).

Example 11

4-Amino-6-methylthieno[2,3-d]pyrimidin-2(1H)-one

69

Prepared as in Example 1 from N-(3-cyanothiophen-2-ylcarbamoyl)benzamide (Example 11a). $^1$H NMR (400 MHz, DMSO-$d_6$) δ6.97 (s, J=5.2 Hz, 1H), 7.31 (d, J=6.0 Hz, 1H), 7.60 (s, 2H), 11.38 (bs, 1H). MS 168 (MH$^+$).

Example 11a

N-(3-Cyanothiophen-2-ylcarbamoyl)benzamide

Prepared as in Example 1a from 2-aminothiophene-3-carbonitrile and benzoyl isocyanate as a white solid. ¹H NMR (400 MHz, DMSO-d₆) δ7.23-7.19 (m, 2H), 7.55 (t, J=8.0 Hz, 2H), 7.70-7.66 (m, 1H), 8.04-8.02 (m, 2H), 11.62 (bs, 1H), 12.18 (bs, 1H). MS 272 (MH⁺).

Example 12

4-Aminoquinazolin-2(1H)-one

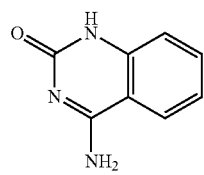

149

Prepared as in Example 1 from N-(2-cyanophenylcarbamoyl)benzamide (Example 12a) as a white solid (156 mg, 41%). ¹H NMR (400 MHz, DMSO-d₆) δ7.12-7.20 (m, 2H), 7.59-7.63 (m, 1H), 8.08-8.10 (d, 1H), 8.60 (b, 2H), 11.2 (b, 1H). ¹³C NMR (DMSO-d₆) δ108.72, 115.98, 122.32, 125.51, 135.38, 142.96, 154.96, 163.51. MS 162 (MH⁺).

Example 12a

N-(2-Cyanophenylcarbamoyl)benzamide

Prepared as in Example 1a from 2-aminobenzonitrile and benzoyl isocyanate as a white powder (661 mg, 59%). ¹H NMR (400 MHz, DMSO-d₆) δ7.27-7.29 (t, 1H), 7.52-7.56 (t, 1H), 7.64-7.74 (m, 2H), 7.82-7.85 (dd, 1H), 8.02-8.04 (m, 2H), 8.22-8.24 (d, 1H). MS 266 (MH⁺).

Example 13

4-Amino-6-methoxy-5-methylthieno[2,3-d]pyrimidin-2(1H)-one

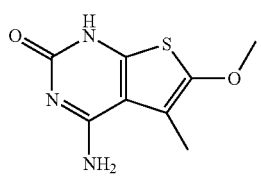

79

Prepared as in Example 1 from N-(3-cyano-5-methoxy-4-methylthiophen-2-ylcarbamoyl)benzamide (Example 13a). ¹H NMR (400 MHz, DMSO-d₆) δ2.19 (s, 3H), 3.78 (s, 3H), 2.74 (s, 2H). MS 212 (MH⁺).

Example 13a

N-(3-Cyano-5-methoxy-4-methylthiophen-2-ylcarbamoyl)benzamide

Prepared as in Example 1a from 2-amino-5-methoxy-4-methylthiophene-3-carbonitrile (example 13b) and benzoyl isocyanate as an off-white solid. ¹H NMR (400 MHz, DMSO-d₆) δ2.03 (s, 3H), 3.86 (s, 3H), 7.54 (t, J=7.2 Hz, 2H), 7.67 (t, J=7.6 Hz, 1H), 8.01-8.03 (d, J=8.4 Hz, 2H), 11.60 (s, 1H), 12.03 (s, 1H). MS 316 (MH⁺).

Example 13b

2-Amino-5-methoxy-4-methylthiophene-3-carbonitrile

Prepared as in Example 5b from 1-methoxypropan-2-one, malononitrile, and sulfur as a brown solid. MS 169 (MH⁺).

Example 14

4-Amino-6-methylquinazolin-2(1H)-one

161

Prepared as in Example 1 from N-(2-cyano-4-methylphenylcarbamoyl)benzamide (Example 14a) as a white solid (259 mg, 57%). ¹H NMR (400 MHz, DMSO-d₆) δ2.29 (s, 3H), 6.99-7.05 (m, 1H), 7.35-7.37 (d, 1H), 7.72 (b, 2H), 7.79 (s, 1H) 10.55 (bs, 1H). MS 176 (MH⁺).

Example 14a

N-(2-Cyano-4-methylphenylcarbamoyl)benzamide

Prepared as in Example 1a from 2-amino-5-methylbenzonitrile (Example 14b) as a white powder (724 mg, 46%). MS 280 (MH⁺).

Example 14b

2-Amino-5-methylbenzonitrile

5-Methyl-2-nitrobenzonitrile (1.92 g, 11.84 mmol) was added in portions to a stirred solution of SnCl₂ (11.22 g, 59.2 mmol) in conc. HCl (12 mL) and EtOH (12 mL). The reaction temperature was maintained at 20-30° C. using an ice bath. The reaction mixture was then stirred at room temperature for 1 h and poured into an ice cold aqueous solution of NaOH (6N, app. 30 mL) to neutralize to pH7. The product was extracted into EtOAc, washed with brine, dried over MgSO₄ and concentrated to provide the title product (1.56 g, 99%) as a yellow-brown solid. ¹H NMR (400 MHz, DMSO-d₆) δ2.21 (s, 3H), 5.79 (bs, 2H), 6.68-6.71 (d, 1H), 7.10-7.13 (dd, 1H), 7.15 (s, 1H). ¹³C NMR (DMSO-d₆) δ20.13, 93.99, 116.12, 118.94, 125.38, 132.32, 135.76, 150.21. MS 133 (MH⁺).

Example 15

4-Amino-8-methylquinazolin-2(1H)-one

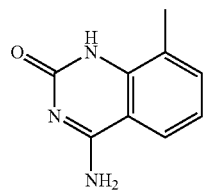

165

Prepared as in Example 1 from N-(2-cyano-6-methylphenylcarbamoyl)benzamide (Example 15a) as a white solid (60 mg, 56%). $^1$H NMR (400 MHz, DMSO-$d_6$) δ2.29 (s, 3H), 6.96-7.00 (t, 1H), 7.37-7.38 (d, 1H), 7.70-7.72 (b, 2H), 7.80-7.82 (d, 1H), 9.87 (bs, 1H). MS 176 (MH$^+$).

Example 15a

N-(2-Cyano-6-methylphenylcarbamoyl)benzamide

Prepared as in Example 1a from 2-amino-3-methylbenzonitrile (Example 15b) and benzoyl isocyanate as a white powder (186 mg, 67%). MS 280 (MH$^+$).

Example 15b

2-Amino-3-methylbenzonitrile

To a solution of 2-bromo-6-methylaniline (126 μL, 1 mmol) in dry NMP (3 mL) was added CuCN (197 mg, 2.2 mmol). The mixture was irradiated in a microwave at 220° C. for 40 minutes, cooled to room temperature and poured into a mixture of ammonia (50% w/v, 10 mL) and ice. The mixture was stirred for 30 min and the product was extracted with dichloromethane (3×20 mL). The organic layers were combined, washed with water and brine, dried over MgSO$_4$ and concentrated. The crude material was purified on silica gel (50% EtOAc/hexanes) to yield a brown oil that crystallized on standing (128 mg, 96%). $^1$H NMR (400 MHz, DMSO-$d_6$) δ2.08 (s, 3H), 5.68 (bs, 2H), 6.51-6.55 (t, 1H), 7.17-7.19 (d, 1H), 7.22-7.24 (dd, 1H). MS 133 (MH$^+$).

Example 16

4-Aminopyrimido[4,5-d]pyrimidin-2(1H)-one

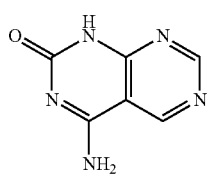

181

Prepared as in Example 1 from N-(2-cyano-4,5-dimethylfuran-3-ylcarbamoyl)benzamide (Example 16a). $^1$H NMR (400 MHz, DMSO-$d_6$) δ8.91 (s, 1H), 8.92 (s, 1H), 9.24 (s, 2H), 11.50 (b, 1H). MS 164 (MH$^+$).

Example 16a

N-(2-Cyano-4,5-dimethylfuran-3-ylcarbamoyl)benzamide

Prepared as in Example 1a from 4-aminopyrimidine-5-carbonitrile and benzoyl isocyanate as an off-white powder. MS 268 (MH$^+$).

Example 17

4-Amino-7-methylquinazoline-2(1H)-thione

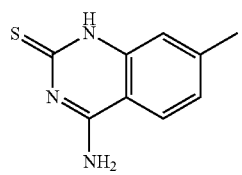

167

Prepared as in Example 1 from N-(2-cyano-5-methylphenylcarbamothioyl)benzamide (Example 17a). $^1$H NMR (400 MHz, DMSO-$d_6$) δ2.35 (s, 3H), 7.08 (d, J=8.0 Hz, 1H), 7.13 (s, 1H), 7.93 (d, J=8.0 Hz, 1H), 8.21 (s, 1H), 8.24 (s, 1H), 12.26 (s, 1H). MS 192 (MH$^+$).

Example 17a

N-(2-Cyano-5-methylphenylcarbamothioyl)benzamide

Prepared as in Example 1a from 2-amino-4-methylbenzonitrile and benzoyl isothiocyanate as a pale-yellow powder. $^1$H NMR (400 MHz, DMSO-$d_6$) δ7.32 (d, J=8.0 Hz, 1H), 7.51-7.58 (m, 3H), 7.67 (t, J=7.8 Hz, 1H), 7.78 (d, J=8.0 Hz, 1H), 7.98-8.01 (m, 2H), 11.88 (s, 1H), 12.49 (s, 1H). MS 296 (MH$^+$).

Example 18

4-Amino-5,6-dimethylfuro[2,3-d]pyrimidin-2(1H)-one

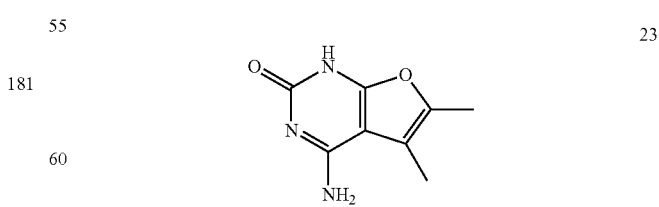

23

Prepared as in Example 1 from N-(2-cyano-4,5-dimethylfuran-3-ylcarbamoyl)benzamide (Example 18a). $^1$H NMR (400 MHz, DMSO-$d_6$) δ2.11 (s, 3H), 2.20 (s, 3H). MS 180 (MH$^+$).

Example 18a

N-(2-Cyano-4,5-dimethylfuran-3-ylcarbamoyl)benzamide

Prepared in a similar manner to Example 1a from 2-amino-4,5-dimethylfuran-3-carbonitrile and benzoyl isocyanate as an off-white solid. MS 284 (MH$^+$).

Example 19

4-Amino-7-methylquinazolin-2(1H)-one

163

Prepared as in Example 1 from N-(2-cyano-5-methylphenylcarbamoyl)benzamide (Example 19a). $^1$H NMR (400 MHz, DMSO-d$_6$) δ2.59 (s, 3H), 7.37 (s, 1H), 7.49 (d, J=7.2 Hz, 1H), 8.21 (d, J=7.2 Hz, 1H). MS 176 (MH$^+$).

Example 19a

N-(2-Cyano-5-methylphenylcarbamoyl)benzamide

Prepared as in Example 1a from 2-amino-4-methylbenzonitrile and benzoyl isocyanate as a white solid. $^1$H NMR (400 MHz, DMSO-d$_6$) δ7.10-7.13 (m, 1H), 7.54 (t, J=7.8 Hz, 2H), 7.66 (t, J=7.8 Hz, 1H), 7.71 (d, J=8.0 Hz, 1H), 8.02-8.04 (m, 2H), 8.07 (s, 1H), 11.32 (s, 1H), 11.44 (s, 1H). MS 280 (MH$^+$).

Example 20

4-Amino-1-benzyl-5,6-dimethylthieno[2,3-d]pyrimidine-2(1H)-thione

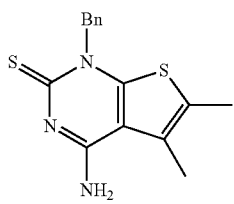

127

Prepared as in Example 1 from N-(benzyl(3-cyano-4,5-dimethylthiophen-2-yl)carbamothioyl)benzamide (Example 20a). MS 302 (MH$^+$).

Example 20a

N-(Benzyl(3-cyano-4,5-dimethylthiophen-2-yl)carbamothioyl)-benzamide

Prepared as in Example 1a from 2-(benzylamino)-4,5-dimethylthiophene-3-carbonitrile (Example 20b) and benzoyl isothiocyanate. MS 406 (MH$^+$).

Example 20b

2-(Benzylamino)-4,5-dimethylthiophene-3-carbonitrile

To a solution of 2-amino-4,5-dimethylthiophene-3-carbonitrile (151 mg, 1.0 mmol) and benzaldehyde (106 mg, 1 mmol) in 15 mL of 4% acetic acid in dichloroethane was added silica supported cyanoborohydride (2.0 g. 2.0 mmol). The reaction was placed in a microwave reactor for 5 minutes at 135° C. Silica supported cyanoborohydride was removed by filtration, and the product was purified by prep HPLC using acetonitrile/water as solvent. MS 243 (MH$^+$).

Example 21

4-Amino-1-ethyl-5,6-dimethylthieno[2,3-d]pyrimidin-2(1H)-one

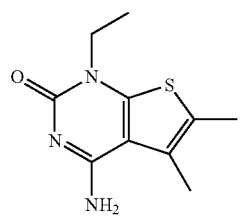

129

Prepared as in Example 1 from N-((3-cyano-4,5-dimethylthiophen-2-yl)(ethyl)carbamoyl)benzamide (Example 21a). MS 224 (MH$^+$).

Example 21a

N-((3-Cyano-4,5-dimethylthiophen-2-yl)(ethyl)carbamoyl)benzamide

Prepared in a similar manner to Example 1a from 2-(ethylamino)-4,5-dimethylthiophene-3-carbonitrile (Example 21b) and benzoyl isocyanate. MS 328 (MH$^+$).

Example 21b

2-(Ethylamino)-4,5-dimethylthiophene-3-carbonitrile

To a mixture of 2-(benzylamino)-4,5-dimethylthiophene-3-carbonitrile (302 mg, 2.0 mmol), potassium carbonate (276 mg, 2.0 mmol), and a catalytic amount of potassium iodide in acetonitrile (1 mL) in a 20 mL microwave vial was added ethyl iodide (310 mg, 2.0 mmol). The reaction vial was placed in a microwave reactor for 15 minutes at 165° C. The reaction mixture was dissolved in ethyl acetate and washed with water and brine. The ethyl acetate portion was dried over sodium sulfate and solvent was evaporated under reduced pressure, and the product was purified by prep HPLC using acetonitrile/water as solvent. MS 181 (MH$^+$).

Example 22

4-Amino-1,5,6-trimethylthieno[2,3-d]pyrimidin-2(1H)-one

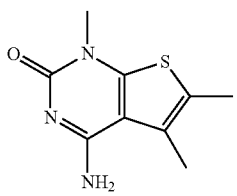

Prepared as in Example 1 from N-((3-cyano-4,5-dimethylthiophen-2-yl)(methyl)carbamoyl)benzamide (Example 22a). MS 210 (MH$^+$).

Example 22a

N-((3-Cyano-4,5-dimethylthiophen-2-yl)(methyl)carbamoyl)-benzamide

Prepared as in Example 1a from 4,5-dimethyl-2-(methylamino)thiophene-3-carbonitrile (Example 22b) and benzoyl isocyanate. MS 314 (MH$^+$).

Example 22b 4,5-Dimethyl-2-(methylamino)thiophene-3-carbonitrile

Prepared as in Example 21b from 2-amino-4,5-dimethylthiophene-3-carbonitrile and methyl iodide.

Example 23

1H-Benzo[c][1,2,6]thiadiazin-4-amine-2,2-dioxide

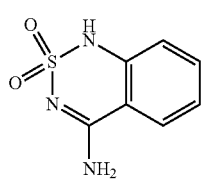

A stirred mixture of 2-cyanoaniline (236 mg, 2.0 mmol), sulfamide (192 mg, 2.0 mmol) and DBU (304 mg, 2.0 mmol) was heated at 160° C. under nitrogen for 3 days. After cooling to room temperature, the reaction mixture was diluted with water and extracted three times with EtOAc. The aqueous layer was removed under vacuum and the residue was purified by chromatography on silica gel eluting with 10% MeOH in dichloromethane to give the title compound as a pale yellow solid. $^1$H NMR (400 MHz, DMSO-d$_6$) δ7.03 (dd, J=0.8, 8.0 Hz, 1H), 7.12 (dt, J=0.8, 8.0 Hz, 1H), 7.56 (dt, J=0.8, 8.0 Hz, 1H), 7.85 (dd, J=0.8, 8.0 Hz, 1H). MS 198 (MH$^+$).

Example 24

5-Methyl-1H-benzo[c][1,2,6]thiadiazin-4-amine-2,2-dioxide

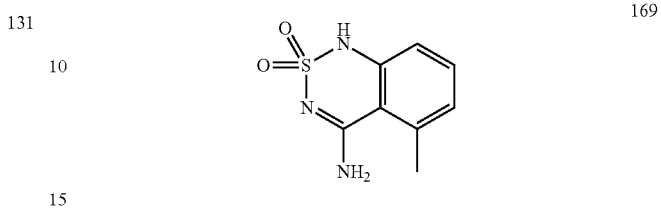

A solution of N-(2-cyano-3-methylphenyl)sulfamide (Example 24a) (211 mg, 1.0 mmol) in EtOH was treated with NaOH (2.0 N, 1.0 mL, 2.0 mmol) and the resultant solution was heated to 100° C. and stirred at that temperature for 0.5 h. After cooling to room temperature, the clear reaction solution was filtered and the filtration was carefully neutralized with 10% AcOH while with vigorous stirring at 0° C. The resultant precipitate was collected by filtration, washed with warm water and 20% EtOH in water to give the title product 5-Methyl-1H-benzo[c][1,2,6]thiadiazin-4-amine-2,2-dioxide as an off-white solid. $^1$H NMR (400 MHz, DMSO-d$_6$) δ2.59 (s, 3H), 6.85-6.87 (d, J=8.4 Hz, 1H), 6.92-6.94 (d, J=7.2 Hz, 1H), 7.24 (s, 1H), 7.37 (t, J=7.6 Hz, 1H), 8.24 (s, 1H), 10.76 (s, 1H). MS 212 (MH$^+$).

Example 24a

N-(2-Cyano-3-methylphenyl)sulfamide

A solution of 2-amino-6-methylbenzonitrile (1.32 g, 10 mmol) and sulfamide (4.81 g, 50 mmol) in dry 1,4-dioxane (50 mL) was refluxed under nitrogen for 3 days. After the reaction mixture was cooled down to room temperature, the precipitate was filtered and washed with dioxane. The filtrate was concentrated under reduced pressure, and the residue was purified by chromatography on silica gel eluting with EtOAc/hexanes (3:7) to give the title compound as a pale-white solid. $^1$H NMR (400 MHz, DMSO-d$_6$) δ2.44 (s, 3H), 7.19-7.21 (m, 3H), 7.39-7.41 (d, J=8.4 Hz, 1H), 7.53 (t, J=8.0 Hz, 1H), 9.41 (s, 1H).

Example 25

5,6-Dimethyl-2-(methylthio)thieno[2,3-d]pyrimidin-4-amine

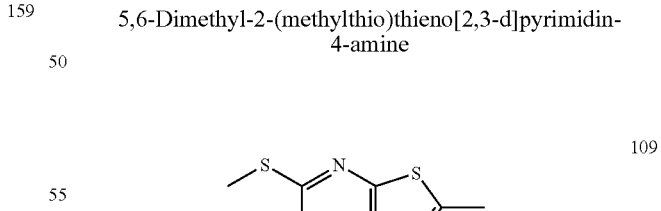

To a suspension of N-(3-cyano-4,5-dimethylthiophen-2-ylcarbamothioyl)-benzamide (Example 1a) (1.33 g, 4.22 mmol) in ethanol (25 mL) was added NaOH (2.0 N, 5.8 mL) at room temperature under nitrogen. After stirring at 100° C. under nitrogen for 0.5 h, the reaction mixture was cooled in an ice bath and MeI (0.8 mL) was added dropwise. After stirring for another 0.5 h, the resulting precipitate was collected by filtration, rinsed with water, 20% EtOH/H₂O, and dried under vacuum to give the title compound (840 mg, 89%). ¹H NMR (400 MHz, DMSO-d₆) δ2.32 (s, 3H), 2.34 (s, 3H), 2.42 (s, 3H), 6.93 (bs, 2H). MS 226 (MH⁺).

Example 26

2-Methoxy-5,6-dimethylthieno[2,3-d]pyrimidin-4-amine

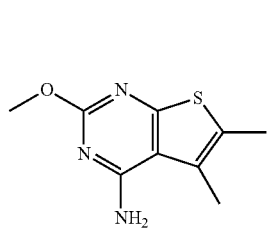

Prepared in a similar manner to Example 25 from N-(3-cyano-4,5-dimethylthiophen-2-ylcarbamoyl)benzamide (Example 4a) and methyl iodide in 86% yield. ¹H NMR (400 MHz, CDCl₃) δ2.35 (s, 3H), 2.36 (s, 3H), 3.53 (s, 3H), 6.0 (bs, 2H). MS 210 (MH⁺).

Example 27

5,6-Dimethyl-2-(methylthio)furo[2,3-d]pyrimidin-4-amine

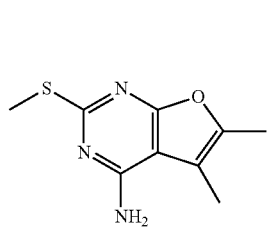

Prepared as in Example 25 from N-(2-cyano-4,5-dimethylfuran-3-ylcarbamothioyl)benzamide (Example 27a). ¹H NMR (400 MHz, DMSO-d₆) δ2.16 (s, 3H), 2.23 (s, 3H), 2.41 (s, 3H), 6.92 (s, 2H). MS 210 (MH⁺).

Example 27a

N-(2-Cyano-4,5-dimethylfuran-3-ylcarbamothioyl) benzamide

Prepared as in Example 1a from 2-amino-4,5-dimethylfuran-3-carbonitrile and benzoyl isothiocyanate. MS 300 (MH⁺).

Example 28

7-Methyl-2-(methylthio)quinazolin-4-amine

Prepared as in Example 25 from N-(2-cyano-5-methylphenylcarbamothioyl)benzamide (Example 17a). ¹H NMR (400 MHz, DMSO-d₆) δ2.40 (s, 3H), 2.45 (s, 3H), 7.17 (dd, J=2.0, 8.8 Hz, 1H), 7.32 (s, 1H), 7.71 (b, 2H), 8.01 (d, J=8.4 Hz, 1H). MS 206 (MH⁺).

Example 29

5-Methyl-2-(methylthio)quinazolin-4-amine

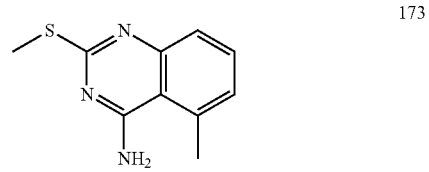

Prepared as in Example 25 from N-(2-cyano-3-methylphenylcarbamothioyl)benzamide (Example 3a). ¹H NMR (400 MHz, DMSO-d₆) δ2.46 (s, 3H), 2.75 (s, 3H), 7.11 (d, J=7.2 Hz, 1H), 7.33 (d, J=7.2 Hz, 1H), 7.51 (dd, J=0.8, 7.2 Hz, 1H). MS 206 (MH⁺).

Example 30

5,6-Dimethylthieno[2,3-d]pyrimidine-2,4-diamine

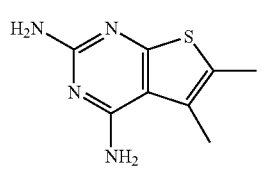

A mixture of 2-amino-4,5-dimethylthiophene-3-carbonitrile (500 mg, 3.29 mmol), cyanoguanidine (276.6 mg, 3.29 mmol) and HCl (2 N, 1.5 mL) in water (10 mL) was refluxed under nitrogen for 2 h. The reaction mixture was cooled to room temperature, and basified with diluted NaOH aqueous solution to PH 7~8. After evaporation of water, the residue was purified by preparative HPLC eluting with acetonitrile and water to give the title compound (33 mg, 5%). ¹H NMR (400 MHz, DMSO-d₆) δ2.22 (s, 3H), 2.27 (s, 3H), 5.85 (bs, 2H), 6.29 (bs, 2H). MS 195 (MH⁺).

Example 31

2,5,6-Trimethylthieno[2,3-d]pyrimidin-4-amine

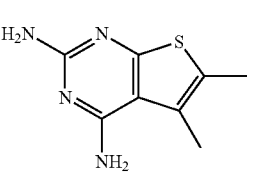

A mixture of 2-amino-4,5-dimethylthiophene-3-carbonitrile (200 mg, 1.32 mmol), ammonia acetate (204 mg, 2.64 mmol), and triethyl orthoacetate (2.0 mL) was stirred in a sealed tube at 120° C. overnight. After the reaction mixture was cooling down to room temperature, the precipitate was collected by filtration, rinsed with EtOAc and dried in the air to give title compound (52 mg, 60%) as a yellow solid. ¹H NMR (400 MHz, CDCl₃) δ2.41 (s, 3H), 2.45 (s, 3H), 2.56 (s, 3H), 5.28 (bs, 2H). MS 194 (MH⁺).

Example 32

5,6-Dimethylthieno[2,3-d]pyrimidin-4-amine

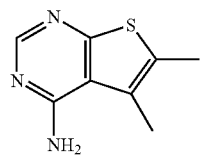
117

Prepared as in Example 31 from 2-amino-4,5-dimethylthiophene-3-carbonitrile and triethyl orthoformate. ¹H NMR (400 MHz, DMSO-d₆) δ2.36 (s, 3H), 2.39 (s, 3H), 6.85 (bs, 2H), 8.14 (s, 1H). MS 180 (MH⁺).

Example 33

2-Ethyl-5,6-dimethylthieno[2,3-d]pyrimidin-4-amine

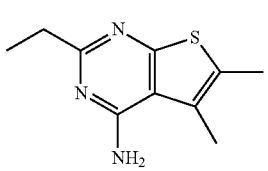
119

Prepared as in Example 31 from 2-amino-4,5-dimethylthiophene-3-carbonitrile and triethyl orthopropanate. ¹H NMR (400 MHz, DMSO-d₆) δ1.19 (t, J=7.6 Hz, 3H), 2.33 (s, 3H), 2.36 (s, 3H), 2.61 (q, J=7.6 Hz, 2H), 6.74 (bs, 2H). MS 208 (MH⁺).

Example 34

5,6-Dimethyl-2-phenylthieno[2,3-d]pyrimidin-4-amine

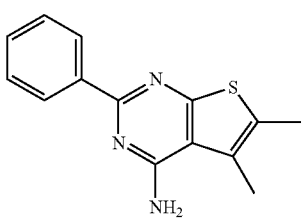
121

A mixture of 2-amino-4,5-dimethylthiophene-3-carbonitrile (152 mg, 1.0 mmol), ammonia acetate (308.3 mg, 4.0 mmol) and triethyl orthobenzoate (2.0 mL) in a sealed tube was put in a microwave at 200° C. for 20 min. After the reaction mixture was cooled to room temperature, it was diluted with EtOAc, washed with saturated NaHCO₃ and H₂O. The solvent was removed by vacuum and the residue was purified by preparative HPLC eluting with acetonitrile and water to give the title compound (80 mg, 31%). ¹H NMR (400 MHz, CDCl₃) δ2.45 (s, 3H), 2.48 (s, 3H), 5.34 (bs, 2H), 7.46-7.43 (m, 3H), 8.4-8.38 (m, 2H). MS 256 (MH⁺).

Example 35

5,6-Dimethyl-2-propylthieno[2,3-d]pyrimidin-4-amine

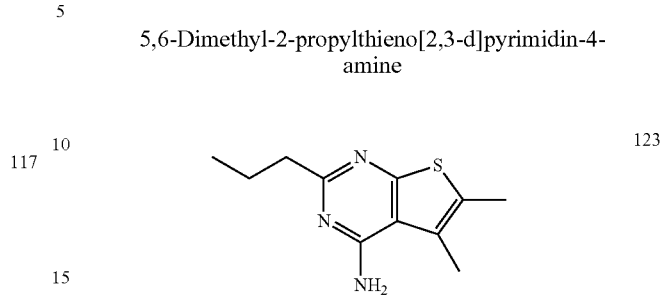
123

Prepared as in Example 34 from 2-amino-4,5-dimethylthiophene-3-carbonitrile and triethyl orthobutanate. ¹H NMR (400 MHz, DMSO-d₆) δ0.87 (t, J=7.6 Hz, 3H), 1.72-1.67 (m, 2H), 2.33 (s, 3H), 2.36 (s, 3H), 2.57 (t, J=7.2 Hz, 2H), 6.73 (bs, 2H). MS 222 (MH⁺).

Example 36

5,6-Dimethyl-2-(methylsulfonyl)thieno[2,3-d]pyrimidin-4-amine

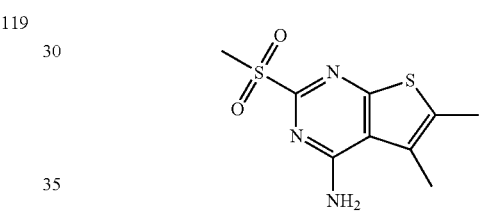
125

To a suspension of 5,6-dimethyl-2-(methylthio)thieno[2,3-d]pyrimidin-4-amine (Example 1) (200 mg, 0.89 mmol) in DCM (25 mL) was added m-chloroperoxybenzoic acid (767 mg, 4.44 mmol). After stirring at room temperature overnight, the reaction mixture was diluted with EtOAc, washed with water and brine, dried over Na₂SO₄, filtered and evaporated. The residue was purified by preparative HPLC eluting with acetonitrile and water to give the title compound (45 mg, 20%). ¹H NMR (400 MHz, DMSO-d₆) δ2.42 (s, 6H), 3.27 (s, 3H). MS 258 (MH⁺).

Example 37

Ethyl 5,6-dimethyl-2-thioxo-1,2-dihydrothieno[2,3-d]pyrimidin-4-ylcarbamate

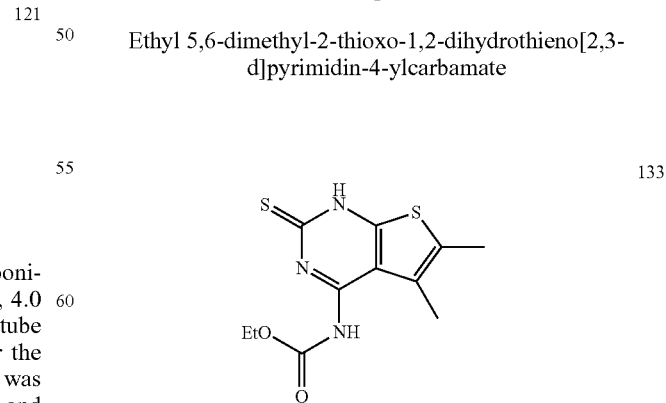
133

To a suspension of 4-amino-5,6-dimethylthieno[2,3-d]pyrimidine-2(1H)-thione (211 mg, 1 mmol) in DMF (5 mL) was added Et$_3$N (0.21 mL, 1.5 mmol) and ethyl chloroformate (0.143 mL, 1.5 mmol). The reaction mixture was stirred at room temperature overnight, then diluted with EtOAc, washed with water and brine, dried over Na$_2$SO$_4$, filtered and evaporated. The residue was purified on Biotage SP-1 eluting with EtOAc/hexane to give the title compound (154 mg, 54%). $^1$H NMR (400 MHz, DMSO-d$_6$) δ1.22 (t, J=7.2 Hz, 3H), 2.38 (s, 3H), 2.39 (s, 3H), 4.25 (q, J=7.2 Hz, 2H), 7.25-7.21 (m, 2H). MS 284 (MH$^+$)

Example 38

2-Chloroquinazolin-4-amine

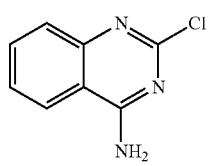

185

To a solution of 2,4-dichloroquinazoline (2.0 g, 10 mmol) in THF (10 mL), was added ammonia (28-30% in water, 18 mL). The reaction mixture was stirred at room temperature overnight. The reaction mixture was diluted with EtOAc, washed with saturated NaHCO$_3$, water and brine, dried over Na$_2$SO$_4$, filtered and evaporated. The resulting solid was washed with EtOAc to give the title compound (1.3 g, 72%). $^1$H NMR (400 MHz, DMSO-d$_6$) δ7.52-7.48 (m, 1H), 7.6-7.58 (m, 1H), 7.8-7.76 (m, 1H), 8.22-8.20 (m, 1H), 8.32 (bs, 2H).

Example 39

2-Chloro-N-methylquinazolin-4-amine

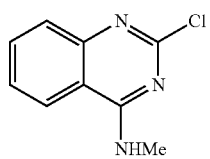

187

Prepared as in Example 38 from 2,4-dichloroquinazoline and methylamine. $^1$H NMR (400 MHz, DMSO-d$_6$) δ2.98 (d, J=4.4 Hz, 3H), 7.53-7.49 (m, 1H), 7.61-7.58 (m, 1H), 7.79-7.75 (m, 1H), 88.19-8.17 (m, 1H), 78 (bs, 1H).

Example 40

2-Chloro-N,N-dimethylquinazolin-4-amine

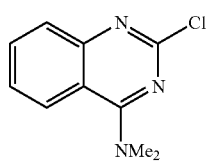

189

Prepared as in Example 38 from 2,4-dichloroquinazoline and dimethylamine. $^1$H NMR (400 MHz, CDCl$_3$) δ3.42 (s, 6H), 7.42-7.39 (m, 1H), 7.72-7.70 (m, 1H), 7.79-7.77 (m, 1H), 8.03-8.01 (m, 1H). MS 208 (MH$^+$).

Example 41

N2,N2,N4,N4-Tetramethylquinazoline-2,4-diamine

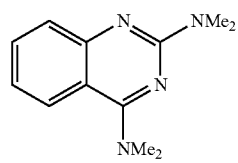

191

Prepared as in Example 38 from 2,4-dichloroquinazoline and dimethylamine. $^1$H NMR (400 MHz, CDCl$_3$) δ3.27-3.23 (m, 12H), 7.01-6.97 (m, 1H), 7.51-7.47 (m, 2H), 7.80-7.78 (m, 1H). MS 217 (MH$^+$).

Example 42

2-Hydrazinylquinazolin-4-amine

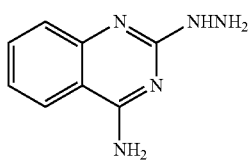

193

A mixture of 2-chloroquinazolin-4-amine (Example 38) (100 mg, 0.56 mmol) and hydrazine (0.09 mL, 2.79 mmol) in ethanol (5 mL) was heated in a sealed tube at 80° C. overnight. After the reaction mixture was cooled down, the resulting precipitate was collected by filtration, rinsed with ethanol and dried in the air to give the title compound (84 mg, 86%). $^1$H NMR (400 MHz, DMSO-d$_6$) δ4.2 (bs, 2H), 4.6 (bs, 2H), 7.0 (t, J=7.2 Hz, 1H), 7.27 (d, J=8.0 Hz, 1H), 7.43 (s, 1H), 7.61 (s, 1H), 7.87 (d, J=7.6 Hz, 1H).

Example 43

2-(Hydroxyamino)quinazolin-4-amine

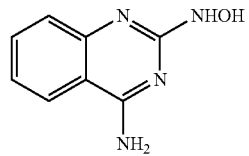

195

Prepared as in Example 42 from 2-chloroquinazolin-4-amine (Example 38) and hydroxylamine. $^1$H NMR (400

MHz, DMSO-d$_6$) δ7.44-7.35 (m, 2H), 7.78-7.74 (m, 2H), 8.24-8.22 (m, 1H), 8.95-8.76 (m, 2H). MS 177 (MH$^+$).

Example 44

2-(Methoxyamino)quinazolin-4-amine

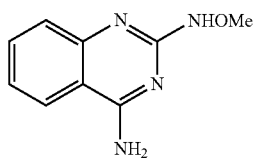

Prepared as in Example 42 from 2-chloroquinazolin-4-amine (Example 38) and methoxylamine. $^1$H NMR (400 MHz, DMSO-d$_6$) δ3.79 (s, 3H), 7.48-7.44 (m, 1H), 7.86-7.80 (m, 2H), 8.27 (d, J=8.0 Hz, 1H), 8.99 (s, 1H), 9.16 (s, 1H), 12.39-12.08 (m, 1H). MS 191 (MH$^+$).

Example 45

N'-(4-Aminoquinazolin-2-yl)acetohydrazide

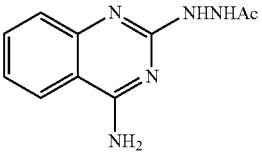

Prepared as in Example 42 from 2-chloroquinazolin-4-amine (Example 38) and methoxylamine. $^1$H NMR (400 MHz, DMSO-d$_6$) δ1.86 (s, 3H), 7.09 (t, J=7.2 Hz, 1H), 7.27 (d, J=8.4 Hz, 1H), 7.54-7.44 (m, 3H), 8.04-7.99 (m, 2H), 9.63 (s, 1H). MS 218 (MH$^+$).

Example 46

4-(Methylamino)quinazoline-2(1H)-thione

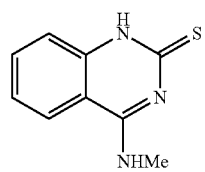

A mixture of 2-chloro-N-methylquinazolin-4-amine (Example 39) (100 mg, 0.52 mmol), thiourea (47.5 mg, 0.62 mmol) and formic acid (0.02 mL, 0.52 mmol) in ethanol (5 mL) was refluxed for 1.5 h. After cooling to room temperature, the reaction mixture was neutralized with diluted NaOH aqueous solution. The solvent was removed under vacuum and the residue was purified by preparative HPLC eluting with acetonitrile and water to give the title compound (18 mg, 18%). $^1$H NMR (400 MHz, DMSO-d$_6$) δ2.99 (d, J=4.8 Hz, 3H), 7.25 (t, J=7.6 Hz, 1H), 7.35 (d, J=8.0 Hz, 1H), 7.65-7.61 (m, 1H), 8.0 (d, J=8.0 Hz, 1H), 8.70 (d, J=4.4 Hz, 1H), 12.32 (s, 1H). MS 192 (MH$^+$).

Example 47

4-(Dimethylamino)quinazoline-2(1H)-thione

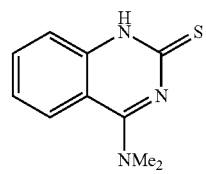

Prepared as in Example 46 from 2-chloro-N,N-dimethylquinazolin-4-amine (Example 40) and thiourea. $^1$H NMR (400 MHz, DMSO-d$_6$) δ3.31 (s, 6H), 7.24-7.19 (m, 1H), 7.40-7.38 (m, 1H), 7.65-7.61 (m, 1H), 8.00 (d, J=8.0 Hz, 1H), 12.35 (s, 1H). MS 206 (MH$^+$).

Example 48

5,6,7,8-Tetrahydroquinazoline-2,4(1H,3H)-dione

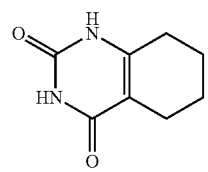

A solution of 2-oxocyclohexanecarbonitrile (615 mg, 5.0 mmol) and urea (600 mg, 10.0 mmol) in 1.25 N HCl in EtOH (20 mL) was refluxed over night. After it was cooled down to 0° C., the precipitation was collected by filtration, washed with EtOH/H$_2$O, and dried under vacuum overnight to give the product as a white solid. $^1$H NMR (400 MHz, CD$_3$OD) δ1.67-1.80 (m, 4H), 2.25-2.29 (m, 2H), 2.38-2.42 (m, 2H). MS 167 (MH$^+$).

Example 49

5,7-Dihydrothieno[3,4-d]pyrimidine-2,4(1H,3H)-dione

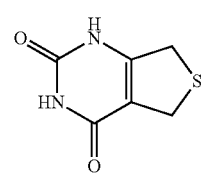

Prepared as in Example 48 from 4-oxotetrahydrothiophene-3-carbonitrile as a white solid. $^1$H NMR (400

MHz, DMSO-$d_6$) δ3.74 (t, J=3.6 Hz, 2H), 3.96 (t, J=3.6 Hz, 2H), 11.06 (s, 1H), 11.21 (s, 1H). MS 171 (MH$^+$).

Example 50

5,6-Dimethyl-2-thioxo-2,3-dihydrothieno[2,3-d]pyrimidin-4(1H)-one

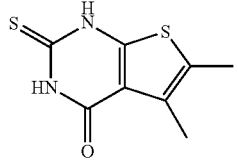

To a suspension of ethyl 4,5-dimethyl-2-thioureidothiophene-3-carboxylate (Example 50a) (37 mg, 0.17 mmol) in dry EtOH (10 mL) was added sodium hydroxide (21 mg, 0.52 mmol). The reaction mixture was then stirred at room temperature for 5 minutes and refluxed for 10 minutes. The reaction mixture was cooled to room temperature, neutralized with 10% AcOH and then concentrated to dryness. The residue was purified by chromatography on silica gel (Gradient 0-50% EtOAc in Hexanes) to give the title compound (8 mg) in 24% yield. $^1$H NMR (400 MHz, DMSO-$d_6$) δ2.25 (s, 6H), 12.24 (s, 1H), 13.27 (s, 1H). MS 202 (MH$^+$).

Example 50a

Ethyl 4,5-dimethyl-2-thioureidothiophene-3-carboxylate

To a solution of ethyl 2-isothiocyanato-4,5-dimethylthiophene-3-carboxylate (Example 50b) (1.21 g, 5.27 mmol) in dichloromethane (10 mL) was added ammonia (7 M in MeOH, 1.12 mL, 7.91 mmol) at 0° C. The reaction mixture was then stirred at room temperature for 3 h, quenched with water and extracted with dichloromethane (3×). The combined organic layers were washed with brine, dried over MgSO$_4$, filtered and concentrated. The dark orange residue was purified by chromatography on silica gel (Gradient 0-50% EtOAc in Hexanes) to give the title compound (37.1 mg, 3%). $^1$H NMR (400 MHz, DMSO-$d_6$) δ1.32 (t, 3H, J=7.1 Hz), 2.18 (s, 3H), 2.19 (s, 3H), 4.30 (q, 2H, J=7.1 Hz), 8.43 (s, 2H), 11.38 (s, 1H). MS 259 (MH$^+$).

Example 50b

Ethyl 2-isothiocyanato-4,5-dimethylthiophene-3-carboxylate

To a mixture of thiophosgene (5.10 mL, 7.64 mmol) and calcium carbonate (1.05 g, 10.54 mmol) in CHCl$_3$/H$_2$O (½ by volume, 6 mL) was added dropwise a solution of ethyl 2-amino-4,5-dimethylthiophene-3-carboxylate (1.05 g, 5.27 mmol) in CHCl$_3$ (7 mL) at 0° C. over a period of 1 h. The reaction mixture was the stirred for 2.5 h at 0° C., washed with water (3×). The organic layer was dried over MgSO$_4$, filtered and concentrated to give the title compound (1.21 g, 100%).

$^1$H NMR (400 MHz, DMSO-$d_6$) δ1.32 (t, 3H, J=7.1 Hz), 2.19 (s, 3H), 2.30 (s, 3H), 4.28 (q, 2H, J=7.1 Hz).

Example 51

4-Ethyl-5,6-dimethylthieno[2,3-d]pyrimidin-2(1H)-one

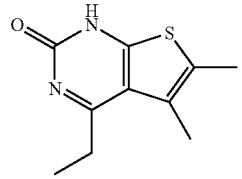

To a solution of 1-(4,5-dimethyl-3-propionylthiophen-2-yl)urea (Example 51a) (15.4 mg, 0.068 mmol) in dry EtOH (10 mL) was added sodium hydroxide (8.4 mg, 0.20 mmol). The reaction mixture was then stirred at RT for 30 minutes under nitrogen. The reaction mixture was neutralized with 10% AcOH and then concentrated to dryness. The residue was purified by chromatography on silica gel (Gradient 0-10% MeOH in dichloromethane) to give the title compound (2.7 mg, 19%). $^1$H NMR (400 MHz, CDCl$_3$) δ1.42 (t, J=7.6 Hz, 3H), 2.31 (s, 3H), 2.33 (s, 3H), 3.06 (q, J=7.6 Hz, 2H). MS 209 (MH$^+$).

Example 51a 1-(4,5-Dimethyl-3-propionylthiophen-2-yl)urea

To a solution of triphosgene (68 mg, 0.224 mmol) in dry dichloromethane (2 mL) was added dropwise a mixture of 1-(2-amino-4,5-dimethylthiophen-3-yl)propan-1-one (Example 51b) (111 mg, 0.605 mmol) and DIEA (0.24 mL, 1.344 mmol) in dry dichloromethane (3.5 mL) over a period of 20 minutes. After the reaction mixture was stirred for 5 minutes, a mixture of ammonia (7 M in MeOH, 0.086 mL, 0.605 mmol) and DIEA (0.24 mL, 1.344 mmol) in dry dichloromethane (2 mL) was added in one portion. The reaction mixture was then stirred at room temperature for 1 h under nitrogen. The reaction mixture was concentrated to dryness. The residue was dissolved in EtOAc (50 mL) and then washed with 10% NaHSO$_4$, 5% NaHCO$_3$, and brine. The organic layer was dried over MgSO$_4$, filtered and concentrated. The yellow residue was purified by chromatography on silica gel (Gradient 0-50% EtOAc in Hexanes) to give the title compound (15.4 mg, 30%). $^1$H NMR (400 MHz, CDCl$_3$) δ1.18 (t, 3H, J=7.2 Hz), 2.25 (s, 3H), 2.30 (s, 3H), 2.87 (q, 2H, J=7.2 Hz), 4.77 (s, 2H), 11.99 (s, 1H). MS 227 (MH$^+$).

Example 51b 1-(2-Amino-4,5-dimethylthiophen-3-yl)propan-1-one

To a solution of 3-oxopentanenitrile (971 mg, 10 mmol) in dry EtOH (100 mL) was added sulfur (2.57 g, 10 mmol), butanone (0.91 mL, 10 mmol) and morpholine (0.88 mL, 10 mmol) at room temperature under nitrogen. The reaction mixture was then refluxed at 90° C. for 6 h, and then stirred overnight at room temperature under nitrogen. The orange brown reaction mixture was concentrated. The residue was diluted with water, and extracted with EtOAc (2×). The combined organic layers were washed with brine, dried over MgSO$_4$, filtered and concentrated. The residue was purified twice: first by chromatography on silica gel (Gradient 0-25% EtOAc in hexanes), and then by Prep HPLC (0-90% acetonitrile in water) to give the title compound (123 mg, 7%). $^1$H NMR (400 MHz, CDCl$_3$) δ1.17 (t, 3H, J=7.2 Hz), 2.17 (s, 3H), 2.24 (s, 3H), 2.78 (q, 2H, J=7.2 Hz), 6.81 (s, 2H). MS 184 (MH$^+$).

Example 52

4-Ethyl-5,6-dimethylthieno[2,3-d]pyrimidin-2(1H)-one

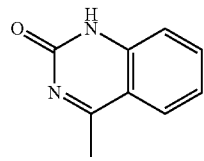

183

To a solution of methylmagnesium bromide (3.0 M in ether, 4.0 mL, 12.0 mmol) in dry ether (5 mL) was added dropwise a solution of 2-aminobenzonitrile (723 mg, 6.0 mmol) in dry ether (5 mL) at RT under nitrogen. After it was refluxed for 2 h under nitrogen, the reaction mixture was cooled down to 0° C. and methyl chloroformate (0.7 mL, 9.0 mmol) was added dropwise. Dry THF (5 mL) was added to dissolve the resultant precipitate. The reaction mixture was then refluxed overnight under nitrogen. The reaction mixture was acidified with 1N HCl and then neutralized with 5% NaHCO$_3$ aqueous solution. The water mixture was washed with EtOAc and the water layer was concentrated. The residue was purified by Prep HPLC ((0-90% acetonitrile in water) to give the title compound (15.2 mg). $^1$H NMR (400 MHz, CD$_3$OD) δ2.79 (s, 3H), 7.33 (d, J=7.1 Hz, 1H), 7.34 (t, J=7.1 Hz, 1H), 7.75 (td, J=1.2, 7.8 Hz, 1H), 8.03 (dd, J=1.2 8.4 Hz, 1H). MS 161 (MH$^+$).

Example 53

4-aminopyrido[2,3-d]pyrimidin-2(1H)-one

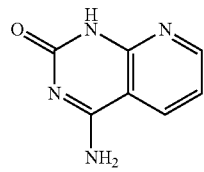

174

A solution of N-(3-cyanopyridin-2-ylcarbamoyl)benzamide (example 53a) (360 mg, 1.35 mmol) and NaOH (2 N, 1.85 mL) in EtOH (5 mL) was stirred at 100° C. under nitrogen for half an hour. After cooling to room temperature, the clear reaction solution was filtered and the filtrate was carefully neutralized with 10% AcOH with vigorous stirring at 0° C. The resultant precipitate was collected by filtration, and washed with warm 20% EtOH in water to give the final product 4-aminopyrido[2,3-d]pyrimidin-2(1H)-one (120 mg, 55%) as a white solid. $^1$H NMR (400 MHz, DMSO-d$_6$) δ7.22 (dd, J=4.4 Hz, 4.8 Hz, 1H), 7.29 (dd, J=4.8 Hz, 1H), 8.24 (dd, J=2 Hz, 1.6 Hz, 1H), 8.59 (dd, J=2 Hz, 1.6 Hz, 1H), 8.66-8.71 (m, 2H), 8.70 (d, J=1.2 Hz, 1H). MS 162 (MH$^+$).

Example 53a

N-(3-cyanopyridin-2-ylcarbamoyl)benzamide

To a solution of 2-amino-3-cyanopyridine (300 mg, 2.5 mmol) in 1,4-dioxane (5 mL) was added benzoyl isocyanate (370 mg, 2.5 mmol). The reaction mixture was then stirred at room temperature under nitrogen overnight. The precipitation was collected by filtration, washed with EtOAc/Hexanes (1:4), and dried under vacuum to give N-(3-cyanopyridin-2-ylcarbamoyl)benzamide as a white solid (360 mg, 54%). MS 266 (MH$^+$).

Example 54

5,6-dimethylquinazoline-2,4(1H,3H)-dione

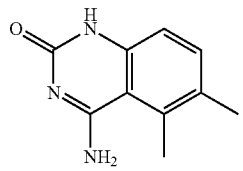

172

Prepared as in Example 53 from N-(2-cyano-3,4-dimethylphenylcarbamoyl)benzamide (Example 54a) as a white solid (90 mg, 66%). $^1$H NMR (400 MHz, DMSO-d$_6$) δ2.24 (s, 3H), 2.54 (s, 3H), 6.87 (d, J=8.4 Hz, 1H), 7.32 (d, J=8.4 Hz, 1H), 10.51 (s, 1H). MS 189 (MH$^+$).

Example 54a

N-(2-cyano-3,4-dimethylphenylcarbamoyl)benzamide

Prepared as in Example 53a from 6-amino-2,3-dimethylbenzonitrile and benzoyl isocyanate as a off-white solid (210 mg, 72%). $^1$H NMR (400 MHz, DMSO-d$_6$) δ2.27 (s, 3H), 2.43 (s, 3H), 7.48 (d, J=6.4 Hz, 2H), 7.53 (t, J=8 Hz, 7.6 Hz, 2H), 7.65 (t, J=7.2 Hz, 1H), 7.94 (d, J=8 Hz, 1H), 8.03 (d, J=7.6 Hz, 2H), 11.29 (s, 1H), 11.37 (s, 1H). MS 293 (MH$^+$).

Example 55

4-amino-7-methoxyquinazolin-2(1H)-one

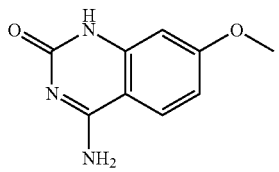

204

Prepared as in example 53 from N-(2-cyano-5-methoxyphenylcarbamoyl)benzamide (Example 55a) as a white solid (24 mg, 37%). $^1$H NMR (400 MHz, DMSO-d$_6$) δ3.79 (s, 3H), 6.63 (d, J=4 Hz, 1H), 6.67 (dd, J=2.4 Hz, 2.8 Hz, 1H), 7.67 (br, 2H), 7.89 (d, J=8.8 Hz, 1H), 10.61 (s, 1H). MS 191 (MH$^+$).

Example 55a

N-(2-cyano-5-methoxyphenylcarbamoyl)benzamide

Prepared as in Example 53a from 2-amino-4-methoxybenzonitrile and benzoyl isocyanate as white solid (99 mg, 45%). $^1$H NMR (400 MHz, DMSO-d$_6$) δ3.86 (s, 3H), 6.87 (dd, J=2.5 Hz, 2.4 Hz, 1H), 7.54 (t, J=8 Hz, 2H), 7.66 (t, J=1.2 Hz, 1H), 7.77 (d, J=7.2 Hz, 1H), 7.89 (d, J=8.4 Hz, 1H), 8.03 (d, J=2.8 Hz, 2H), 11.35 (s, 1H), 11.52 (s, 1H). MS 295 (MH$^+$).

Example 56

4-amino-5-methoxyquinazolin-2(1H)-one

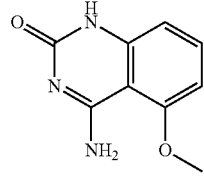

170

Prepared as in example 53 from N-(2-cyano-3-methoxyphenylcarbamoyl)benzamide (Example 56a) as a light yellow solid (35 mg, 51%). $^1$H NMR (400 MHz, DMSO-d$_6$) δ3.93 (s, 3H), 6.67 (dd, J=7.6 Hz, 8.4 Hz, 2H), 7.45 (t, J=8 Hz, 1H), 7.75 (s, 1H), 7.93-7.97 (br, 1H), 10.69 (s, 1H). MS 191 (MH$^+$).

Example 56a

N-(2-cyano-3-methoxyphenylcarbamoyl)benzamide

Prepared as in Example 53a from 2-amino-6-methoxybenzonitrile and benzoyl isocyanate as light orange solid (118 mg, 41%). $^1$H NMR (400 MHz, DMSO-d$_6$) δ3.94 (s, 3H), 6.98 (d, J=8 Hz, 1H), 7.54 (t, J=8 hz, 2H), 7.64 (t, J=8.4 Hz, 2H), 7.88 (d, J=8.4 Hz, 1H), 8.04 (d, J=5.6 Hz, 2H), 11.35 (s, 1H), 11.51 (s, 1H). MS 295 (MH$^+$).

Example 57

4-amino-5-hydroxyquinazolin-2(1H)-one

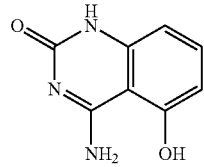

178

Prepared as in example 53 from N-(2-cyano-3-hydroxyphenylcarbamoyl)benzamide (Example 57a) as a green solid (50 mg, 53%). $^1$H NMR (400 MHz, DMSO-d$_6$) δ6.66 (d, J=8.4 Hz, 1H), 6.73 (d, J=7.6 Hz, 1H), 7.57 (t, J=8.8 Hz, 1H), 9.47 (s, 1H), 9.68 (s, 1H), 11.84 (s, 1H). MS 177 (MH$^+$).

Example 57a

N-(2-cyano-3-hydroxyphenylcarbamoyl)benzamide

Prepared as in Example 53a from 2-amino-6-hydroxybenzonitrile and benzoyl isocyanate as an off-white solid (166 mg, 46%). $^1$H NMR (400 MHz, DMSO-d$_6$) δ6.76 (d, J=8.4 Hz, 1H), 7.46 (t, J=8 Hz, 1H), 7.54 (t, J=8 Hz, 2H), 7.66-7.73 (m, 2H), 8.04-8.06 (d, J=8 Hz, 2H), 11.24 (s, 1H), 11.30 (s, 1H), 11.42 (s, 1H). MS 281 (MH$^+$).

Example 58

4-amino-7-hydroxyquinazolin-2(1H)-one

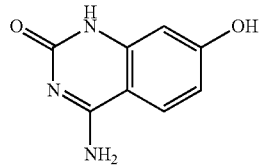

180

Prepared as in example 53 from N-(2-cyano-5-hydroxyphenylcarbamoyl)benzamide (Example 58a) as a light grey solid (104 mg, 41%). $^1$H NMR (400 MHz, DMSO-d$_6$) δ6.51 (s, 2H), 6.52 (d, J=2.4 Hz, 1H), 7.69-7.72 (br, 1H), 7.82 (d, J=9.2 Hz, 2H), 10.57 (br, 1H). MS 177 (MH$^+$).

Example 58a

N-(2-cyano-5-hydroxyphenylcarbamoyl)benzamide

Prepared as in Example 53a, but refluxed in acetone instead of 1,4-dioxane, from 2-amino-4-hydroxybenzonitrile and benzoyl isocyanate as a yellow solid (399 mg, 94%). MS 281 (MH$^+$).

Example 59

4-amino-8-methoxyquinazolin-2(1H)-one

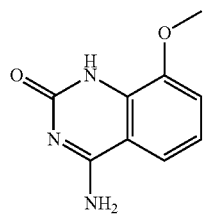

182

Prepared as in example 53 from N-(2-cyano-6-methoxyphenylcarbamoyl)benzamide (Example 59a) as a dark white solid (75 mg, 39%). $^1$H NMR (400 MHz, DMSO-d$_6$) δ3.86 (s, 3H), 7.02 (t, J=8.4 Hz, 1H), 7.17 (d, J=7.2 Hz, 1H), 7.56 (d, J=7.6 Hz, 1H), 7.85 (br, 2H), 9.73 (s, 1H). MS 191 (MH$^+$).

Example 59a

N-(2-cyano-6-methoxyphenylcarbamoyl)benzamide

Prepared as in Example 53a from 2-amino-3-methoxybenzonitrile and benzoyl isocyanate as a light orange solid (280 mg, 95%). $^1$H NMR (400 MHz, DMSO-d$_6$) δ3.89 (s, 3H), 7.42 (t, J=3.2 Hz, 2H), 7.46 (d, J=3.6 Hz, 1H), 7.54 (t, J=8 Hz, 2H), 7.66 (t, J=7.6 Hz, 1H), 8.05 (d, J=8.6 Hz, 2H), 10.55 (s, 1H), 11.32 (s, 1H). MS 295 (MH$^+$).

Example 60

8-amino-[1,3]dioxolo[4,5-g]quinazolin-6(5H)-one

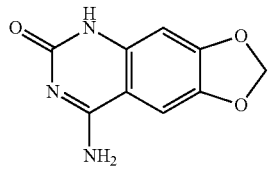

184

Prepared as in example 53 from N-(6-cyanobenzo[d][1,3]dioxol-5-ylcarbamoyl)benzamide (Example 60a) as a light yellow solid (80 mg, 77%). $^1$H NMR (400 MHz, DMSO-d$_6$) δ6.24 (s, 2H), 6.74 (s, 1H), 7.75 (s, 1H), 9.36 (d, J=10.4 Hz, 1H), 9.80 (d, J=7.2 Hz, 1H), 12.01 (s, 1H). MS 205 (MH$^+$).

Example 60a

N-(6-cyanobenzo[d][1,3]dioxol-5-ylcarbamoyl)benzamide

Prepared as in Example 53a from 6-aminobenzo[d][1,3]dioxole-5-carbonitrile and benzoyl isocyanate as a yellow solid (157 mg, 82%). $^1$H NMR (400 MHz, DMSO-d$_6$) δ6.19 (s, 2H), 7.42 (s, 1H), 7.54 (t, J=8 Hz, 2H), 7.66 (t, J=7.6 Hz, 1H), 7.74 (s, 1H), 8.03 (d, J=9.2 Hz, 2H), 11.32 (d, J=12.8 Hz, 2H). MS 309 (MH$^+$).

Example 61

4-(Methoxyamino)quinazolin-2(1H)-one

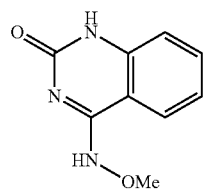

166

To a suspension of 2,4-dichloroquinazoline (995 mg, 5.0 mmol) in dry EtOH (100 mL), were added methoxyamine hydrochloride (569 mg, 5.5 mmol) and NaOH (227 mg, 5.5 mmol) in one portion at 0° C. The reaction mixture was stirred at 0° C. for 1 hour, then placed in a refrigerator at 4° C. for 72 h. Upon completion, the reaction was concentrated, and the residue was dissolved in EtOAc and washed with saturated NaHCO$_3$ (1×) and brine (1×). The organic phase was dried over MgSO$_4$, filtered and concentrated. The crude product was purified by preparative HPLC (10-90% CH$_3$CN in H$_2$O) to provide 4-(methoxyamino)quinazolin-2(1H)-one (556 mg, 36%) as an off-white solid. $^1$H NMR (400 MHz, DMSO-d$_6$) δ3.68 (s, 3H), 7.02 (t, J=7.4 Hz, 1H), 7.35 (d, J=7.9 Hz, 1H), 7.52 (ddd, J=8.1, 7.0, 1.5 Hz, 1H), 7.77 (dd, J=7.8, 1.4 Hz, 1H), 10.13 (br s, 1H), 10.89 (br s, 1H). MS 192.2 (MH$^+$).

Example 62

4-Ethoxyquinazolin-2(1H)-one

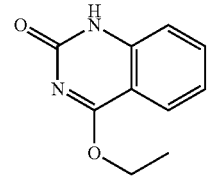

168

Purification by preparative HPLC (10-90% CH$_3$CN in H$_2$O) of the crude reaction of example 61 also provided 4-ethoxyquinazolin-2(1H)-one (90 mg, 9%) as an off-white solid. $^1$H NMR (400 MHz, DMSO-d$_6$) δ1.35 (t, J=7.0 Hz, 3H), 4.44 (q, J=7.0 Hz, 2H), 7.34 (ddd, J=8.1, 7.0, 1.2 Hz, 1H), 7.46 (dd, J=8.2, 1.0 Hz, 1H), 7.71 (ddd, J=8.5, 7.0, 1.2 Hz, 1H), 8.01 (dd, J=8.2, 1.5 Hz, 1H), 12.25 (br s, 1H). MS 191.1 (MH$^+$).

Example 63

4-Amino-5-methyl-2-oxo-1,2-dihydrothieno[2,3-d]pyrimidine-6-carboxylic acid

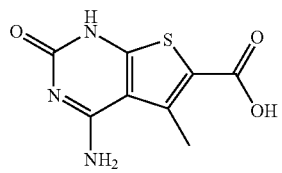

84

To a solution of tert-butyl 4-amino-5-methyl-2-oxo-1,2-dihydrothieno[2,3-d]pyrimidine-6-carboxylate (example 64a) (10.7 g, 38.03 mmol) in CH$_2$Cl$_2$ (25 mL), was added trifluoroacetic acid (25 mL, 324.5 mmol). The reaction mixture was stirred at rt overnight. The precipitated solid was collected by filtration, and washed with CH$_2$Cl$_2$ to yield 4-Amino-5-methyl-2-oxo-1,2-dihydrothieno[2,3-d]pyrimidine-6-carboxylic acid (6.98 g, 82%) as a light brown solid. $^1$H NMR (400 MHz, DMSO-d$_6$) δ2.78 (s, 3H). MS 226.0 (MH$^+$).

Example 64 tert-Butyl 4-amino-5-methyl-2-oxo-1,2-dihydrothieno[2,3-d]pyrimidine-6-carboxylate

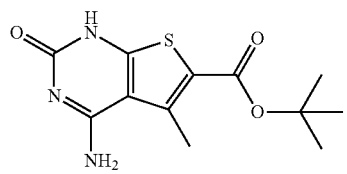

82

To a suspension of tert-butyl 5-(3-benzoylureido)-4-cyano-3-methylthiophene-2-carboxylate (example 64a) (18 g, 60.52 mmol) in EtOH (200 mL) was added NaOH (75 mL, 2N). The suspension became clear, and the mixture was heated to reflux for 30 min. After cooling to rt, the reaction was filtered, and the filtrate was cooled to 0° C. in an ice/water bath. The solution was neutralized with 10% acetic acid. The precipitated solid was collected by filtration, and heated in EtOH at 80° C. under $N_2$ for 20 min. After cooling to rt, the product was collected by filtration and washed with 10% EtOH in $H_2O$ to yield tert-Butyl 4-amino-5-methyl-2-oxo-1, 2-dihydrothieno[2,3-d]pyrimidine-6-carboxylate (10.73 g, 63%) as a brown solid. $^1H$ NMR (400 MHz, DMSO-$d_6$) δ1.51 (s, 9H), 2.73 (s, 3H), 3.18 (s, 2H). MS 282.2 ($MH^+$).

Example 64a tert-butyl 5-(3-benzoylureido)-4-cyano-3-methylthiophene-2-carboxylate To a solution of tert-butyl 5-amino-4-cyano-3-methylthiophene-2-carboxylate (example 64b) (16 g, 67.14 mmol) in dioxane (200 mL), was added benzoyl isocyanate (10 g, 67.14 mmol). The reaction mixture was stirred at rt overnight, and upon completion was diluted with EtOAc, washed with $NaHCO_3$, water, brine, dried over $MgSO_4$, filtered and concentrated to yield tert-butyl 5-(3-benzoylureido)-4-cyano-3-methylthiophene-2-carboxylate (21.78 g, 84%) as a brown solid. $^1H$ NMR (400 MHz, DMSO-$d_6$) δ1.54 (s, 9H), 3.58 (s, 3H), 7.58 (t, J=7.5 Hz, 2H), 7.71 (t, J=7.5 Hz, 1H), 7.88 (d, J=7.5 Hz, 1H), 8.05 (d, J=7.5 Hz, 2H), 12.25 (br s, 1H).

Example 64b tert-butyl 5-amino-4-cyano-3-methylthiophene-2-carboxylate

To a solution of tert-butyl 3-oxobutanoate (30 mL, 183.94 mmol) in dry EtOH (360 mL), were added elemental sulfur (5.90 g, 183.94 mmol), malononitrile (12.16 g, 183.94 mmol) and triethylamine (25.6 mL, 183.94 mmol). The reaction mixture was heated to 80° C., and stirred for 2 h. After cooling to rt, the mixture was concentrated under reduced pressure. The resulting residue was dissolved in EtOAc, washed with $NaHCO_3$, water, brine, dried over $MgSO_4$, filtered and concentrated. The crude residue was purified by flash chromatography on silica gel (20% EtOAc in hexane) to yield tert-butyl 5-amino-4-cyano-3-methylthiophene-2-carboxylate (31.2 g, 73%) as a brown solid.

Example 65

4-Aminoquinolin-2(1H)-one

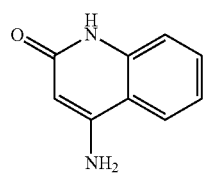

186

4-Amino-2-oxo-1,2-dihydroquinoline-3-carboxylic acid (Example 64) (0.030 g, 0.15 mmol) was heated neat at 295° C. for 10 minutes, then cooled to room temperature to give 4-aminoquinolin-2(1H)-one (0.023 g, 99%) as a light yellow solid. M.p.: >250° C. $^1H$ NMR (400 MHz, DMSO-$d_6$) δ5.42 (s, 1H), 6.55 (s, 2H), 7.07 (t, J=7.6 Hz, 1H), 7.19 (d, J=8.0 Hz, 1H), 7.42 (t, J=7.2 Hz, 1H), 7.86 (d, J=7.6 Hz, 1H), 10.71 (s, 1H). MS 161 ($MH^+$).

Example 66

4-Amino-2-oxo-1,2-dihydroquinoline-3-carboxylic acid

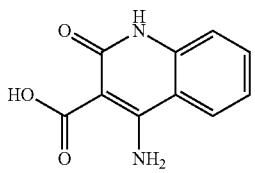

196

Benzyl 4-amino-2-oxo-1,2-dihydroquinoline-3-carboxylate (Example 66a) (0.6 g, 2.04 mmol) was dissolved in DMF (8 mL) and heated at 70° C. under a hydrogen balloon in the presence of 10% Pd/C (0.15 g) for 1 hour. The Pd/C was filtered out and washed with dichloromethane and the solvents were removed under vacuum. The residue was dissolved/suspended in NaOH (2M, 40 mL), stirred at room temperature for 30 minutes and the solution washed with dichloromethane. The aqueous layer was cooled to 0° C. and acidified to pH 1 with 2M HCl. The resultant precipitate was collected and washed with dichloromethane to give 4-amino-2-oxo-1,2-dihydroquinoline-3-carboxylic acid (0.050 g, 12%) as a light yellow solid. M.p.: >250° C. $^1H$ NMR (400 MHz, DMSO-$d_6$) δ7.32 (m, 1H), 7.39 (d, J=7.6 Hz, 1H), 7.69 (m, 1H), 8.27 (d, J=8.4 Hz, 1H), 8.86 (s, 1H), 9.87 (s, 1H), 11.95 (s, 1H). MS 205 ($MH^+$).

Example 66a

Benzyl 4-amino-2-oxo-1,2-dihydroquinoline-3-carboxylate

Benzyl 4-chloro-2-oxo-1,2-dihydroquinoline-3-carboxylate (Example 66b) (0.55 g, 1.75 mmol) was dissolved in DMF (8 mL) and 4-methoxybenzylamine (0.56 mL, 4.31 mmol) was added. The reaction was heated at 115° C. for 30 minutes, then cooled to room temperature and poured into ice water. The resultant precipitate was dissolved in 10 mL TFA and stirred at room temperature for 15 minutes, then the mixture was poured into ice water. The resultant precipitate was collected, dissolved in dichloromethane, dried over $MgSO_4$, filtered and evaporated to give the crude benzyl 4-amino-2-oxo-1,2-dihydroquinoline-3-carboxylate (600 mg) which was used as this without further purification. MS 295 ($MH^+$).

Example 66b

Benzyl 4-chloro-2-oxo-1,2-dihydroquinoline-3-carboxylate

Dibenzylmalonate (7.75 mL, 31.6 mmol) was added slowly to a suspension of 60% sodium hydride in mineral oil (1.41 g, 35.3 mmol) in anhydrous DMF (100 mL) at −20° C. under nitrogen. After stirring at room temperature for 30 minutes, isatoic anhydride (5.0 g, 30.7 mmol) was added, and the reaction was heated at 120° C. for 1 hour. The reaction was then cooled to −50° C. and oxalyl chloride (10.7 mL, 123 mmol) was slowly added. The reaction mixture was stirred at room temperature for 2 hours then poured into aqueous NaCl (10%, 750 mL) at 0° C., and the resultant precipitate was filtered out. The precipitate was dissolved in dichloromethane, dried over MgSO$_4$, filtered and evaporated under reduced pressure. Diethyl ether was added to the residue, and the resultant solid was collected to give benzyl 4-chloro-2-oxo-1,2-dihydroquinoline-3-carboxylate (3.56 g, 37% yield) which was used without further purification. MS 314 (MH$^+$).

Example 67

Ethyl 4-hydroxy-2-oxo-1,2-dihydroquinoline-3-carboxylate

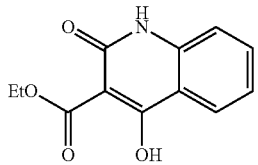

188

Diethylmalonate (11.4 mL, 75.1 mmol) was added slowly to a suspension of 60% sodium hydride in mineral oil (3.09 g, 77.3 mmol) in anhydrous DMF (100 mL) at −10° C. under nitrogen. After stirring at room temperature for 30 minutes, isatoic anhydride (12.0 g, 73.6 mmol) was added, and the reaction was heated at 115° C. for 2.5 hours. The reaction was cooled to room temperature, then poured into ice water (1.4 L) and acidified to pH 4 with 2M HCl. The resultant precipitate was collected, then dissolved/suspended in dichloromethane (450 mL). The dichloromethane solution was filtered out then evaporated to provide a residue that was vigorously triturated with diethyl ether (150 mL) for 1 hour. The solid was collected to give ethyl 4-hydroxy-2-oxo-1,2-dihydroquinoline-3-carboxylate (3.63 g, 21%) as a white solid. M.p.: 190° C. $^1$H NMR (400 MHz, DMSO-d$_6$) δ1.31 (t, J=7.2 Hz, 3H), 4.35 (q, J=7.2 Hz, 2H), 7.21 (m, 1H), 7.27 (d, J=8.0 Hz, 1H), 7.63 (m, 1H), 7.93 (dd, J=0.8, 8.4 Hz, 1H), 11.51 (s, 1H), 13.40 (s, 1H). MS 234 (MH$^+$).

Example 68

Methyl 4-amino-2-oxo-1,2-dihydroquinoline-3-carboxylate

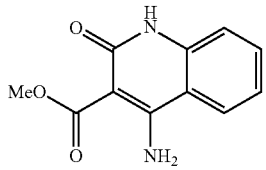

210

Methyl 4-(4-methoxybenzylamino)-2-oxo-1,2-dihydroquinoline-3-carboxylate (Example 68a) (0.841 g, 2.49 mmol) was dissolved in TFA (5 mL) and stirred at room temperature for 30 minutes. The TFA was removed under reduced pressure, and the residue was dissolved in dichloromethane, then precipitated out by adding excess diethyl ether. The resultant solid was collected by filtration, suspended in dichloromethane, and washed with concentrated sodium bicarbonate. The solid was collected to give methyl 4-amino-2-oxo-1,2-dihydroquinoline-3-carboxylate (0.230 g, 42%) as a white solid. M.p.: 236° C. $^1$H NMR (400 MHz, DMSO-d$_6$) δ3.73 (s, 3H), 7.12 (t, J=8.0 Hz, 1H), 7.17 (d, J=8.0 Hz, 1H), 7.52 (t, J=8.0 Hz, 1H), 8.08 (d, J=8.0 Hz, 1H), 8.38 (bs, 2H), 10.88 (bs, 1H). MS 219 (MH$^+$).

Example 68a

Methyl 4-(4-methoxybenzylamino)-2-oxo-1,2-dihydroquinoline-3-carboxylate

Methyl 4-chloro-2-oxo-1,2-dihydroquinoline-3-carboxylate (Example 69) (0.928 g, 3.91 mmol) was dissolved in DMF (6 mL), and 4-methoxybenzylamine (1.14 mL, 8.78 mmol) was added. The reaction was heated at 90° C. for 30 minutes, then cooled to room temperature and poured into a stirred mixture of 50 mL hexanes and 100 mL ice water. The resultant precipitate was collected by filtration and further chromatographed on silica gel (0% to 20% MeOH in dichloromethane) to give methyl 4-(4-methoxybenzylamino)-2-oxo-1,2-dihydroquinoline-3-carboxylate as an off white solid (0.841 g, 64%). MS 339 (MH$^+$).

Example 69

Methyl 4-chloro-2-oxo-1,2-dihydroquinoline-3-carboxylate

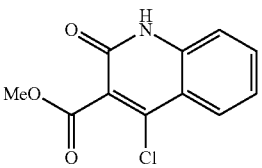

190

Dimethylmalonate (2.2 mL, 19.2 mmol) was added slowly to a suspension of 60% sodium hydride in mineral oil (0.81 g, 20.3 mmol) in anhydrous DMF (100 mL) at −10° C. under nitrogen. After stirring at room temperature for 30 minutes, isatoic anhydride (3.0 g, 18.4 mmol) was added, and the reaction mixture was heated at 115° C. for 2.5 hours. The reaction was then cooled to −40° C. and oxalyl chloride (6 mL, 68.8 mmol) was slowly added. The reaction was stirred at room temperature for 20 minutes, and was then poured into 1200 mL of 10% NaCl at 0° C. The resultant precipitate was collected by filtration to give crude methyl 4-chloro-2-oxo-1,2-dihydroquinoline-3-carboxylate (1.40 g, 32%), which was used without further purification. $^1$H NMR (400 MHz, DMSO-d$_6$) δ3.87 (s, 3H), 7.39 (m, 2H), 7.70 (m, 1H), 7.92 (d, J=8.4 Hz, 1H), 12.49 (s, 1H). MS 238 (MH$^+$).

Example 70

Methyl 4-hydroxy-2-oxo-1,2-dihydroquinoline-3-carboxylate

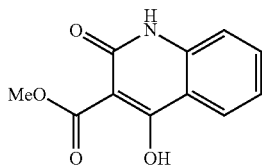

192

Dimethylmalonate (2.2 mL, 19.2 mmol) was added slowly to a suspension of 60% sodium hydride in mineral oil (0.81 g, 20.3 mmol) in anhydrous DMF (50 mL) at −10° C. under nitrogen. After stirring at room temperature for 30 minutes, isatoic anhydride (3.0 g, 18.4 mmol) was added, and the reaction was heated at 115° C. for 2.5 hours. The reaction was cooled to room temperature, then poured into ice water (500 mL) and acidified to pH 2 with 2M HCl. The resultant precipitate was collected by filtration to give crude methyl 4-hydroxy-2-oxo-1,2-dihydroquinoline-3-carboxylate (2.89 g, 72%), which was used without further purification. $^1$H NMR (400 MHz, DMSO-$d_6$) δ3.86 (s, 3H), 7.23 (m, 2H), 7.63 (m, 1H), 7.94 (dd, J=0.8, 8.0 Hz, 1H), 11.55 (s, 1H), 13.33 (s, 1H). MS 220 (MH$^+$).

Example 71

4-Amino-2-oxo-1,2-dihydroquinoline-3-carbonitrile

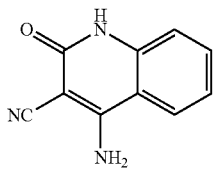

200

4-chloro-2-oxo-1,2-dihydroquinoline-3-carbonitrile (example 72) (0.66 g, 3.23 mmol) was suspended in DMF (7 mL), and 4-methoxybenzylamine (0.94 mL, 7.26 mmol) was added. The reaction was heated at 100° C. for 1 hour and the DMF was removed under vacuum. The residue was dissolved in TFA (6 mL) and stirred at room temperature for 30 minutes and dichloromethane (10 mL) was added. The solid product that formed was collected, suspended in water and the solution stirred overnight. The solid was collected by filtration to give 4-amino-2-oxo-1,2-dihydroquinoline-3-carbonitrile (0.150 g, 25%) as a white solid. M.p.: >250° C. $^1$H NMR (400 MHz, DMSO-$d_6$) δ7.19 (m, 2H), 7.57 (m, 1H), 7.88 (bs, 2H), 8.12 (d, J=7.6 Hz, 1H), 11.23 (s, 1H). MS 186 (MH$^+$).

Example 72

4-chloro-2-oxo-1,2-dihydroquinoline-3-carbonitrile

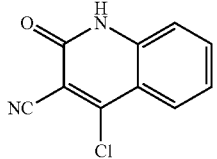

198

2,4-dichloroquinoline-3-carbonitrile (Example 72a) (0.95 g, 4.26 mmol) and ammonium acetate (0.36 g, 4.67 mmol) were heated in acetic acid (20 mL) at 140° C. for 4 hours, then cooled to room temperature. The reaction was poured into ice water (400 mL), and the resultant precipitate was collected by filtration to give 4-chloro-2-oxo-1,2-dihydroquinoline-3-carbonitrile (0.668 g, 77%) as a light yellow solid. M.p.: >250° C. $^1$H NMR (400 MHz, DMSO-$d_6$) δ7.42 (m, 2H), 7.79 (m, 1H), 7.96 (d, J=8.4 Hz, 1H), 12.72 (s, 1H). MS 205 (MH$^+$)

Example 72a 2,4-dichloroquinoline-3-carbonitrile

N-cyclohexyl-4-hydroxy-2-oxo-1,2-dihydroquinoline-3-carboxamide (Example 73) (1.18 g, 4.12 mmol) was dissolved in phosphorus oxychloride (15 mL) and triethylamine (1.72 mL, 12.4 mmol) was slowly added. The reaction was heated at 120° C. for 7 hours, then cooled to room temperature and poured carefully into ice water (300 mL). The resultant precipitate was collected by filtration to give 2,4-dichloroquinoline-3-carbonitrile (0.848 g, 92%), which was used without further purification. MS 223 (MH$^+$).

Example 73

N-cyclohexyl-4-hydroxy-2-oxo-1,2-dihydroquinoline-3-carboxamide

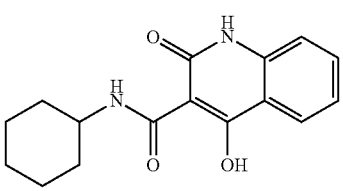

194

Methyl 4-hydroxy-2-oxo-1,2-dihydroquinoline-3-carboxylate (Example 70) (2.70 g, 12.3 mmol) was suspended in toluene (27 mL), and cyclohexylamine (1.40 g, 14.1 mmol) was added. The reaction was heated at 115° C. for 5 hours, then cooled to room temperature. Diethyl ether (50 mL) was added, and the resultant precipitate was collected by filtration to give N-cyclohexyl-4-hydroxy-2-oxo-1,2-dihydroquinoline-3-carboxamide (1.22 g, 35%) as an off white solid. M.p.: 221° C. $^1$H NMR (400 MHz, DMSO-$d_6$) δ1.37 (m, 4H), 1.55 (m, 1H), 1.68 (m, 2H), 1.88 (m, 2H), 3.86 (m, 1H), 7.28 (t, J=8.0 Hz, 1H), 7.36 (d, J=8.0 Hz, 1H), 7.68 (t, J=7.6 Hz, 1H), 7.95 (d, J=8.0 Hz, 1H), 10.35 (d, J=7.6 Hz, 1H), 11.83 (bs, 1H). MS 287 (MH⁺).

Example 74

4-amino-2-oxo-1,2-dihydroquinoline-3-carboxamide

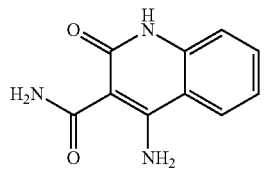

202

N,N-bis(4-methoxybenzyl)-4-(4-methoxybenzylamino)-2-oxo-1,2-dihydroquinoline-3-carboxamide (Example 74a) (2.0 g, 3.55 mmol) was dissolved in TFA (15 mL) and the solution was stirred at room temperature for 6 hours. The TFA was removed under vacuum, and the resultant solid was stirred in water overnight, then collected by filtration to give 1.8 grams of crude final product. $^1$H NMR (400 MHz, DMSO-d$_6$) δ7.18 (m, 2H), 7.25 (d, J=7.2 Hz, 1H), 7.56 (t, J=8.0 Hz, 1H), 8.09 (d, J=7.6 Hz, 2H), 9.83 (d, J=4.8 Hz, 1H), 10.85 (bs, 1H), 11.12 (s, 1H). MS 204 (MH⁺).

Example 74a

N,N-bis(4-methoxybenzyl)-4-(4-methoxybenzylamino)-2-oxo-1,2-dihydroquinoline-3-carboxamide 4-chloro-N,N-bis(4-methoxybenzyl)-2-oxo-1,2-dihydroquinoline-3-carboxamide (Example 74b) (4.25 g, 9.18 mmol) was dissolved in DMF (20 mL), and 4-methoxybenzylamine (2.68 mL, 20.6 mmol) was added. The reaction was heated at 100° C. for 1.5 hours, then cooled to room temperature and poured into ice water (300 mL). The resultant precipitate was collected by filtration and further chromatographed on silica gel (0% to 20% MeOH in dichloromethane) to give crude N,N-bis(4-methoxybenzyl)-4-(4-methoxybenzylamino)-2-oxo-1,2-dihydroquinoline-3-carboxamide (3.65 g, 71%), which was used without further purification. MS 564 (MH⁺).

Example 74b 4-chloro-N,N-bis(4-methoxybenzyl)-2-oxo-1,2-dihydroquinoline-3-carboxamide Triethylamine (5.73 mL, 41.2 mmol) was added to phosphorus oxychloride (60 mL), followed by 4-hydroxy-N,N-bis(4-methoxybenzyl)-2-oxo-1,2-dihydroquinoline-3-carboxamide (Example 74c) (6.11 g, 13.7 mmol). The reaction was heated at 65° C. for 4 hours, then cooled to room temperature and carefully poured into ice water (1200 mL). The solution was extracted dichloromethane (2×200 mL. The organic layers were combined and washed with water, dried over MgSO$_4$, filtered and evaporated. The residue was dissolved in dichloromethane (18 mL) and poured into 200 mL of 30% hexanes in diethyl ether. The resultant precipitate was collected by filtration to give crude 4-chloro-N,N-bis(4-methoxybenzyl)-2-oxo-1,2-dihydroquinoline-3-carboxamide (4.25 g, 67%) which was used without further purification. MS 463 (MH⁺).

Example 74c

4-Hydroxy-N,N-bis(4-methoxybenzyl)-2-oxo-1,2-dihydroquinoline-3-carboxamide

Ethyl 4-hydroxy-2-oxo-1,2-dihydroquinoline-3-carboxylate (Example 67) (3.58 g, 15.4 mmol) and bis(4-methoxybenzyl)amine (4.54 g, 17.6 mmol) were suspended in toluene (36 mL) and heated at 115° C. for 5 hours, then cooled to room temperature. Diethyl ether was added (50 mL), and the resultant precipitate was collected by filtration to give crude 4-hydroxy-N,N-bis(4-methoxybenzyl)-2-oxo-1,2-dihydroquinoline-3-carboxamide (6.45 g, 95%) which was used without further purification.

Example 75

4-Amino-6,7-dihydro-1H-cyclopenta[d]pyrimidin-2(5H)-one

206

A solution of N-(2-cyanocyclopent-1-enylcarbamoyl)benzamide (example 75a) (500 mg, 1.96 mmol) and NaOH (2 N, 2.7 mL) in EtOH (20 mL) was stirred at 100° C. under nitrogen for 2 hours. After cooling to room temperature, the clear reaction solution was filtered and the filtrate was carefully neutralized with 10% AcOH with vigorous stirring at 0° C. The resultant precipitate was collected by filtration, washed with warm water and then 20% EtOH in water to give the final product 4-amino-6,7-dihydro-1H-cyclopenta[d]pyrimidin-2(5H)-one (200 mg, 68%) as a white solid. $^1$H NMR (400 MHz, DMSO-d$_6$) δ10.57 (brs, 1H), 6.93 (brs, 1H), 6.65 (brs, 1H), 2.56 (t, J=7.2 Hz, 2H), 2.43 (t, J=7.6 Hz, 2H) 1.96-1.89 (m, 2H). MS 152 (MH⁺).

Example 75a

N-(2-cyanocyclopent-1-enylcarbamoyl)benzamide

To a solution of 2-aminocyclopent-1-enecarbonitrile (400 mg, 3.7 mmol) in 1.4-dioxane (20 mL) was added benzoyl isocyanate (545 g, 3.7 mmol). The reaction mixture was then stirred at room temperature under nitrogen overnight. The precipitate was collected by filtration, washed with 1.4-dioxane, and dried to give N-(2-cyanocyclopent-1-enylcarbamoyl)benzamide (720 mg, 76%) as a white solid. $^1$H NMR (400 MHz, CDCl$_3$) δ11.33 (s, 1H), 11.22 (brs, 1H), 7.99-7.97 (m, 2H), 7.67-7.63 (m, 1H), 7.54-7.51 (m, 2H), 3.04-3.0 (m, 2H), 2.51-2.47 (m, 2H) 1.95-1.90 (m, 2H). MS 256 (MH⁺).

Example 76

4-amino-6,7,8,9-tetrahydro-1H-cyclohepta[d]pyrimidin-2(5H)-one

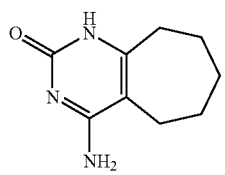

208

Prepared as in example 75 from (Z)—N-(2-cyanocyclohept-1-enylcarbamoyl)benzamide (Example 76a). $^1$H NMR (400 MHz, DMSO-d$_6$) δ 10.29 (brs, 1H), 6.72 (brs, 2H), 2.49-2.46 (m, 2H), 2.38-2.36 (m, 2H) 1.72-1.66 (m, 2H), 1.52-1.48 (m, 2H) 1.41-1.36 (m, 2H). MS 180 (MH$^+$).

Example 76a

(Z)—N-(2-cyanocyclohept-1-enylcarbamoyl)benzamide

Prepared as in Example 75a from (Z)-2-aminocyclohept-1-enecarbonitrile and benzoyl isocyanate as a white solid. MS 284 (MH$^+$).

Experiment 4

Biological Assay

An HEK293 cell line derivative (Chandrashekar et al., *Cell* 100, 703-711, 2000) which stably expresses Gα15 and hT1R2/hT1R3 (Li et al., *Proc Natl Acad Sci USA* 99, 4692-4696, 2002) (see also, International Publication No. WO 03/001876) was used in biological assays in association with identifying compounds with sweet taste enhancing properties.

Compounds were initially selected based on their activity on the hT1R2/hT1R3-HEK293-Gα15 cell line Li et al., supra. Activity was determined using an automated fluorometric imaging assay on a FLIPR instrument (Fluorometric Intensity Plate Reader, Molecular Devices, Sunnyvale, Calif.) (designated FLIPR assay). Cells from one clone (designated clone S-9) were seeded into 384-well plates (at approximately 50,000 cells per well) in a medium containing DMEM Low Glucose (Invitrogen, Carlsbad, Calif.), 10% dialyzed fetal bovine serum (Invitrogen, Carlsbad, Calif.), 100 Units/ml Penicillin G, and 100 µg/ml Streptomycin (Invitrogen, Carlsbad, Calif.) (Li et al., 2002) (see also, International Publication No. WO 03/001876).

S-9 cells were grown for 24 hours at 37° C. S-9 cells were then loaded with the calcium dye Fluo-3 AM (Molecular Probes, Eugene, Oreg.), 4 µM in a phosphate buffered saline (D-PBS) (Invitrogen, Carlsbad, Calif.), for 1 hour at room temperature. After replacement with 25 µl D-PBS, stimulation was performed in the FLIPR instrument and at room temperature by the addition of 25 µl D-PBS supplemented with compounds at concentrations corresponding to three times the desired final level (Stimulation 1).

Cells were incubated with the compounds for 7.5 minutes and then another stimulation was performed in the FLIPR instrument by the addition of 25 µl of D-PBS supplemented with a sub-optimal concentration of sweeteners (producing about 5% to 20% receptor activity) (Stimulation 2).

Alternatively after replacement with 25 µl D-PBS per well, stimulation was performed in the FLIPR instrument at room temperature by addition of 25 µl D-PBS supplemented with different stimuli.

Typical sweeteners used include, but are not limited to D-Glucose, D-Fructose, Sucralose, Aspartame and Sucrose. Receptor activity was then quantified by determining the maximal fluorescence increases (using a 480 nm excitation and 535 nm emission) after normalization to basal fluorescence intensity measured before stimulation. Compounds producing an increase in sweetener-mediated receptor activity were chosen for further characterization and quantification of potential enhancement properties.

In this follow assay, a fixed concentration of compounds was added in duplicates to 10 consecutive columns (20 wells total) during stimulation 1. Typical compound concentrations tested were 300 µM, 100 µM, 50 µM, 30 µM, 10 µM, 3 µM and 1 µM, 0.3 µM, 0.1 µM, or 0.03 µM. After the 7.5 minute incubation period, increasing concentrations of sweetener (to generate a dose-response curve) was presented in the same wells, in duplicates, during stimulation 2. The relative efficacy of compounds at enhancing the receptor was determined by the calculating the magnitude of a shift in the EC$_{50}$ for the sweetener. Enhancement was defined as a ratio (EC$_{50}$R) corresponding to the EC$_{50}$ of sweeteners, determined in the absence of the test compound, divided by the EC$_{50}$ of the sweetener, determined in the presence of the test compound. In some embodiments, compounds have an EC$_{50}$R between about 1 (e.g., >1) and about 1000. In other embodiments, compounds have an EC$_{50}$R between about 1.25 and about 500. In still other embodiments, compounds have an EC$_{50}$R between about 1.50 and about 100. In yet other embodiments, compounds have an EC$_{50}$R between about 1 (e.g., >1) and about 50.

In still other embodiment, compounds at about 50 µM have an EC$_{50}$R between about 1 (e.g., >1) and about 1000, between about 1.25 and about 500, between about 1.50 and about 100, or between about 1 (e.g., >1) and about 50. Assay results for compounds are illustrated in the table below.

| Compound Number | Pre-incubated Sucralose EC$_{50}$R (50 µM) | Co-stimulation Sucralose EC$_{50}$R (50 µM) |
|---|---|---|
| 300 | 5.20 | 4.46 |
| 301 | 2.41 | 1.93 |
| 302 | 2.19 | 2.44 |
| 303 | 2.19 | 3.77 |
| 304 | 1.73 | 4.14 |
| 305 | 1.58 | 2.98 |
| 306 | 1.00 | 1.32 |
| 307 | 1.02 | 1.38 |
| 308 | 1.12 | 1.12 |
| 309 | 1.11 | 1.07 |
| 310 | 0.86 | 1.01 |
| 311 | 1.08 | 1.11 |
| 312 | 0.73 | 0.78 |
| 313 | 0.95 | 0.97 |
| 314 | 1.11 | 1.06 |
| 315 | 0.84 | 1.05 |
| 316 | 0.99 | 1.11 |
| 317 | 0.90 | 1.04 |
| 318 | 0.86 | |
| 319 | 1.03 | 1.09 |
| 320 | 1.06 | |
| 322 | 0.92 | 0.98 |
| 323 | 1.10 | 1.89 |
| 324 | 0.87 | 1.12 |

-continued

| Compound Number | Pre-incubated Sucralose EC$_{50}$R (50 μM) | Co-stimulation Sucralose EC$_{50}$R (50 μM) |
|---|---|---|
| 325 | | 1.10 |
| 326 | | 0.99 |
| 327 | | 0.86 |
| 328 | | 0.96 |
| 329 | | 0.72 |
| 330 | | 1.16 |
| 331 | | 1.25 |
| 332 | 1.03 | 1.35 |
| 333 | 0.87 | 1.36 |
| 334 | 1.23 | 0.74 |
| 335 | 0.99 | |
| 336 | 0.99 | |
| 337 | 0.90 | 0.96 |
| 338 | | 0.93 |
| 339 | | 1.07 |
| 340 | 0.89 | |
| 341 | | 0.82 |
| 342 | 1.15 | 1.02 |
| 343 | 0.98 | 1.35 |

Experiment 5

Sweet Flavor and Sweet Flavor Enhancement Measurement Using Human Panelists

Test samples containing experimental compounds were compared to a dose-response curve for perceived sweetness intensity of sucralose concentrations to determine equivalent sweetness intensity.

A group of eight or more panelists tasted solutions including sucralose at various concentrations, as well as the experimental compound both with and without added sucralose. Panelists then rated sweetness intensity of all samples on a structured horizontal line scale, anchored from 0 to 15, where 0 equals no sweetness and 15 equals equivalent sweetness to a 15% sucrose sample. Scores for sweetness intensity were averaged across panelists. Then using the average scores and/or equation of the line for the sucralose dose-response curve, equivalent sweetness sucralose concentrations were determined for the samples containing experimental compounds.

Subjects had been previously familiarized with the key attribute taste and were trained to use the 0 to 15 point line scale. Subjects refrained from eating or drinking (except water) for at least 1 hour prior to the test. Subjects ate a cracker and rinsed with water several times to clean the mouth.

Sucralose solutions were provided at a wide range of concentrations, such as 100 ppm, 200 ppm, 300 ppm, 400 ppm, and 500 ppm in order to create a dose-response curve. Samples containing experimental compound were prepared both alone and in a 100 ppm sucralose solution. All samples were made up in low sodium buffer pH 7.1. In order to aid dispersion, solutions can be made up in 0.1% ethanol.

The solutions were dispensed in 20 ml volumes into 1 oz. sample cups and served to the subjects at room temperature. All samples were presented in randomized counterbalanced order to reduce response bias. Further, two sessions of testing may be used to check panel precision.

Subjects tasted each sample individually and rate sweetness intensity on the line scale prior to tasting the next sample. All samples were expectorated. Subjects may retaste the samples but can only use the volume of sample given. Subjects must rinse with water between samples. Eating an unsalted cracker between samples may be required depending on the samples tasted.

The scores for each sample were averaged across subjects and standard error was calculated. The dose-response curve was plotted graphically, and this may be used to ensure the panel is rating accurately; i.e., increasing the concentration of sucralose should correspond to increased average scores for sweetness. A 2-way ANOVA (factors being samples and panelists) and multiple comparison tests (such as Tukey's Honestly Significant Difference test) can be used to determine differences among samples and/or panelists. A 3-way ANOVA, with sessions as the third factor, can be used to determine if there is any difference in the ratings between sessions.

The results of human taste tests with a compound 7 are found below. Table 1 indicates that 100 μM compound 7 in 100 ppm sucralose has sweetness equivalent to 200 ppm sucralose. Table 2 indicates that 100 μM compound 7 alone has no sweetness, and therefore can be defined as a true sweet enhancer.

7

TABLE 1

Average sweetness scores for various sucralose samples, including 100 ppm sucralose with 100 μM compound 7, n = 32 (16 Panelists × 2 replicates). Tukey's Value = 1.409 (α = 0.05).

| Sample | Average | Standard Error | Tukey's HSD Significance (5%) |
|---|---|---|---|
| 100 ppm Sucralose | 6.3 | 0.3 | A |
| 100 ppm Sucralose + 100 μM 7 | 10.2 | 0.5 | B |
| 200 ppm Sucralose | 10.4 | 0.5 | B |
| 300 ppm Sucralose | 11.5 | 0.4 | Bc |
| 400 ppm Sucralose | 12.3 | 0.4 | C |

TABLE 2

Average sweetness scores for 100 μM compound 7 and low sodium buffer, n = 15 (15 Panelists × 1 rep). Tukey's Value = 0.186 (α = 0.05).

| Sample | Average | Standard Error | Tukey's HSD Significance (5%) |
|---|---|---|---|
| Low Sodium Buffer (contains no sweeteners) | 0.1 | 0.1 | A |
| 100 μM 7 | 0.1 | 0.1 | A |

The results of human taste tests with compound 1 are found below. Table 3 indicates that 100 μM compound in 100 ppm sucralose has sweetness equivalent to about 600 ppm sucralose. Table 4 shows a dose response curve of compound 1 with 100 ppm sucralose which shows that the sweetness of sucralose is significantly enhanced by addition of increasing amounts of compound 1. Table 5 indicates that 100 μM compound 1 alone has little or no sweetness, and therefore can be defined as a true sweet enhancer.

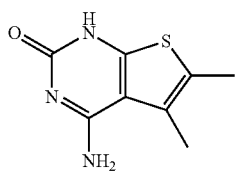

1

TABLE 3

Average sweetness scores, n = 12 (12 Panelists × 1 rep). Tukey's Value = 2.449 (α = 0.05), 2.209 (α = 0.10).

| Treatment | Average | SD | St Er | Tukey (5%) | Tukey (10%) |
|---|---|---|---|---|---|
| 100 ppm Sucralose | 7.4 | 1.7 | 0.5 | a | a |
| 200 ppm Sucralose | 10.4 | 1.9 | 0.6 | b | b |
| 300 ppm Sucralose | 10.5 | 2.8 | 0.8 | b | b |
| 400 ppm Sucralose | 11.2 | 2.4 | 0.7 | bc | bc |
| 600 ppm Sucralose | 13.0 | 1.4 | 0.4 | c | c |
| 100 μM 1 + 100 ppm Sucralose | 13.3 | 1.6 | 0.5 | c | c |

TABLE 4

Average sweetness scores, n = 26 (14 Panelists × 1 rep; 12 panelists × 1 rep). Tukey's Value = 1.584 (α = 0.05), 1.452 (α = 0.10).

| Treatment | Average | SD | St Er | Tukey (5%) | Tukey (10%) |
|---|---|---|---|---|---|
| 100 ppm sucralose | 6.3 | 1.5 | 0.3 | a | a |
| 100 ppm sucralose + 3.12 μM 1 | 7.4 | 1.7 | 0.3 | ab | ab |
| 100 ppm sucralose + 6.25 μM 1 | 8.4 | 1.8 | 0.4 | bc | bc |
| 100 ppm sucralose + 12.5 μM 1 | 9.1 | 1.9 | 0.4 | cd | cd |
| 200 ppm sucralose | 9.5 | 2.0 | 0.4 | cd | cd |
| 300 ppm sucralose | 10.3 | 2.7 | 0.5 | d | d |
| 100 ppm sucralose + 25 μM 1 | 10.3 | 1.6 | 0.3 | d | d |
| 400 ppm sucralose | 12.1 | 1.9 | 0.4 | e | e |
| 100 ppm sucralose + 50 μM 1 | 12.3 | 1.5 | 0.3 | e | e |

TABLE 5

Average sweetness scores, n = 12 (12 Panelists × 1 rep). Tukey's Value = 0.809 (α = 0.05), 0.723 (α = 0.10).

| Treatment | Average | SD | St Er | Tukey (5%) | Tukey (10%) |
|---|---|---|---|---|---|
| 0% Sucrose | 0.0 | 0.0 | 0.0 | a | a |
| 100 uM 1 in LSB | 0.2 | 0.3 | 0.1 | a | a |
| 2% Sucrose | 2.4 | 1.0 | 0.3 | b | b |

The results of human taste tests with compound 149 are found below. Table 6 indicates that 100 μM compound in 100 ppm sucralose has sweetness equivalent to about between 200 and 300 ppm sucralose. Table 7 indicates that 100 μM compound 149 alone has no sweetness, and therefore can be defined as a true sweet enhancer.

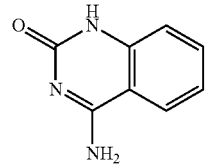

149

TABLE 6

Average sweetness scores, n = 13 (13 Panelists × 1 rep). Tukey's Value = 2.333 (α = 0.05), 2.087 (α = 0.10).

| Treatment | Average | SD | St Er | Tukey (5%) | Tukey (10%) |
|---|---|---|---|---|---|
| 100 ppm Sucralose | 6.5 | 1.3 | 0.4 | a | a |
| 200 ppm Sucralose | 9.1 | 2.0 | 0.6 | b | b |
| 100 ppm Sucralose + 100 μM 149 | 9.8 | 1.8 | 0.5 | b | bc |
| 300 ppm Sucralose | 10.8 | 2.8 | 0.8 | b | bc |
| 400 ppm Sucralose | 11.2 | 2.3 | 0.6 | b | c |

TABLE 7

Average sweetness scores, n = 13 (13 Panelists × 1 rep). Tukey's Value = 0.906 (α = 0.05), 0.811 (α = 0.10).

| Treatment | Average | SD | St Er | Tukey (5%) | Tukey (10%) |
|---|---|---|---|---|---|
| 100 uM 149 in LSB | 0.0 | 0.0 | 0.0 | a | a |
| 0% Sucrose | 0.0 | 0.1 | 0.0 | a | a |
| 2% Sucrose | 1.8 | 1.0 | 0.3 | b | b |

The invention claimed is:
1. A method of enhancing the sweet taste of a comestible composition comprising contacting the comestible composition with a compound of Formula (IIa):

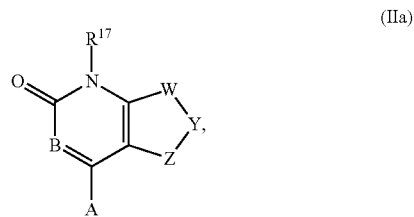

(IIa)

or a pharmaceutically acceptable salt thereof; wherein:
A is hydrogen, alkyl, substituted alkyl, aryl, substituted aryl, arylalkyl, substituted arylalkyl, heteroaryl, substituted heteroaryl, heteroarylalkyl, substituted heteroarylalkyl, —CN, —OR$^9$, —S(O)$_c$R$^9$, —NR$^9$COR$^{10}$, —NHOR$^9$, —NR$^9$R$^{10}$, —CONR$^9$R$^{10}$, —CO$_2$R$^9$, —NR$^9$CO$_2$R$^{10}$, —NR$^9$CONR$^{10}$R$^{11}$, —NR$^9$CSNR$^{10}$R$^{11}$, or —NR$^9$C(═NH)NR$^{10}$R$^{11}$;
R$^{17}$ is hydrogen, alkyl, or substituted alkyl;
B is —N—;
Y forms a single bond with W and a double bond with Z;
W is —S—;
Y is —C(R$^{26}$)—;
Z is —C(R$^{27}$)—;
R$^{26}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —OR$^{31}$, —OCOR$^{31}$, —NR$^{31}$R$^{32}$, —CONR$^{31}$R$^{32}$, or —CO$_2$R$^{31}$;

R$^{27}$ is hydrogen, alkyl, substituted alkyl, aryl, substituted aryl, arylalkyl, substituted arylalkyl, acyl, substituted acyl, heteroalkyl, substituted heteroalkyl, heteroaryl, substituted heteroaryl, heteroarylalkyl, substituted heteroarylalkyl, —OR$^{33}$, —OCOR$^{33}$, —NR$^{33}$R$^{34}$, —CONR$^{33}$R$^{34}$, or —CO$_2$R$^{33}$;

R$^9$, R$^{10}$, R$^{11}$, R$^{19}$, R$^{31}$, R$^{32}$, R$^{33}$, and R$^{34}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; alternatively R$^9$ and R$^{10}$, R$^{10}$ and R$^{11}$, R$^{31}$ and R$^{32}$, or R$^{33}$ and R$^{34}$, together with the atoms to which they are bonded, form a cycloheteroalkyl or substituted cycloheteroalkyl ring;

wherein the substituted acyl, substituted alkyl, substituted cycloheteroalkyl, substituted aryl, substituted arylalkyl, substituted heteroalkyl, substituted heteroaryl, and substituted heteroarylalkyl, and substituted cycloheteroalkyl each independently comprises one or more substituent groups selected from the group consisting of —R$^a$, halo, =O, —OR$^b$, —SR$^b$, =S, —NR$^c$R$^c$, =NR$^b$, =N—OR$^b$, trihalomethyl, —CN, —NO$_2$, —S(O)$_2$R$^b$, —S(O)$_2$NR$^b$, —S(O)$_2$OR$^b$, —OS(O)$_2$R$^b$, —OS(O)$_2$OR$^b$, —P(O)(OR$^b$)(OR$^b$), —C(O)R$^b$, —C(NR$^b$)R$^b$, —C(O)OR$^b$, —C(O)NR$^c$R$^c$, —C(NR$^b$)NR$^c$R$^c$, —OC(O)R$^b$, —OC(O)OR$^b$, —NR$^b$C(O)R$^b$, —NR$^b$C(O)OR$^b$, —NR$^b$C(O)NR$^c$R$^c$, —NR$^b$C(NR$^b$)R$^b$ and —NR$^b$C(NR$^b$)NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s are taken together with the nitrogen atom to which they are bonded form a 4-, 5-, 6- or 7-membered cycloheteroalkyl; and the comestible composition comprises at least one sweetener selected from the group consisting of sucrose and sucralose.

2. The method of claim 1, wherein A is hydrogen, alkyl, substituted alkyl, aryl, substituted aryl, arylalkyl, substituted arylalkyl, heteroaryl, substituted heteroaryl, heteroarylalkyl, substituted heteroarylalkyl, —CN, —S(O)$_c$R$^9$, —NR$^9$R$^{10}$, —CONR$^9$R$^{10}$, —CO$_2$R$^9$, or —NR$^9$CO$_2$R$^{10}$.

3. The method of claim 1, wherein A is hydrogen, alkyl, substituted alkyl, aryl, substituted aryl, —CN, —S(O)$_c$R$^9$, —NR$^9$R$^{10}$, —CONR$^9$R$^{10}$, —CO$_2$R$^9$, or —NR$^9$CO$_2$R$^{10}$.

4. The method of claim 1, wherein R$^{17}$ is hydrogen, alkyl, or substituted alkyl.

5. The method of claim 1, wherein
A is hydrogen, alkyl, substituted alkyl, aryl, substituted aryl, —CN, —S(O)$_c$R$^9$, —NR$^9$COR$^{10}$, —NR$^9$R$^{10}$, —CONR$^9$R$^{10}$, —CO$_2$R$^9$, or —NR$^9$CO$_2$R$^{10}$; and
R$^{17}$ is hydrogen, alkyl, or substituted alkyl.

6. The method of claim 1, wherein
R$^{26}$ is hydrogen, alkyl, substituted alkyl, acyl, substituted acyl, heteroalkyl, substituted heteroalkyl, —OR$^{31}$, —OCOR$^{31}$, —NR$^{31}$R$^{32}$, —CONR$^{31}$R$^{32}$ or —CO$_2$R$^{31}$; and
R$^{27}$ is hydrogen, alkyl, substituted alkyl, acyl, substituted acyl, heteroalkyl, substituted heteroalkyl, —OR$^{33}$, —OCOR$^{33}$, —NR$^{33}$R$^{34}$, —CONR$^{33}$R$^{34}$ or —CO$_2$R$^{33}$.

7. The method of claim 1, wherein
R$^{26}$ is hydrogen, alkyl, or substituted alkyl; and
R$^{27}$ is hydrogen, alkyl, or substituted alkyl.

8. The method of claim 1, wherein
A is hydrogen, alkyl, substituted alkyl, aryl, substituted aryl, —CN, —NO$_2$, —S(O)$_c$R$^9$, —NR$^9$R$^{10}$, —CONR$^9$R$^{10}$, —CO$_2$R$^9$ or —NR$^9$CO$_2$R$^{10}$;
R$^{17}$ is hydrogen, alkyl, or substituted alkyl;
R$^{26}$ is hydrogen, alkyl, substituted alkyl, acyl, substituted acyl, heteroalkyl, substituted heteroalkyl, —OR$^{31}$, —OCOR$^{31}$, —NR$^{31}$R$^{32}$, —CONR$^{31}$R$^{32}$ or —CO$_2$R$^{31}$; and
R$^{27}$ is hydrogen, alkyl, substituted alkyl, acyl, substituted acyl, heteroalkyl, substituted heteroalkyl, —OR$^{33}$, —OCOR$^{33}$, —NR$^{33}$R$^{34}$, —CONR$^{33}$R$^{34}$ or —CO$_2$R$^{33}$.

9. The method of claim 1, wherein
A is —OH, —NH$_2$, —NHCH$_3$, —N(CH$_3$)$_2$, —NHOCH$_3$, —NHC(O)CH$_3$, —NHC(O)OCH$_3$, —NHC(O)NH$_2$, —NHC(S)NH$_2$, —NHC(NH)NH$_2$, —CN, —CH$_2$OH, —CH$_2$NH$_2$, —CH$_2$NHCH$_3$, —CH$_2$N(CH$_3$)$_2$, —CO$_2$H, —CONH$_2$, —CONHCH$_3$ or —CH$_2$NHC(O)CH$_3$;
R$^{17}$ is hydrogen, methyl, ethyl, propyl, iso-propyl, n-butyl, iso-butyl, sec-butyl, t-butyl, or benzyl;
R$^{26}$ is hydrogen, —CF$_3$, methyl, ethyl, propyl, iso-propyl, n-butyl, iso-butyl, sec-butyl or t-butyl; and
R$^{27}$ is hydrogen, —CF$_3$, methyl, ethyl, propyl, iso-propyl, n-butyl, iso-butyl, sec-butyl or t-butyl.

10. The method of claim 1, wherein the compound is selected from the group consisting of

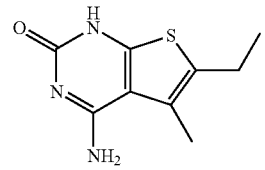

75

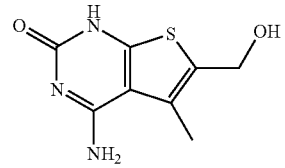

71

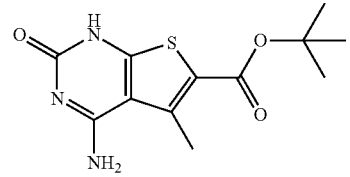

82

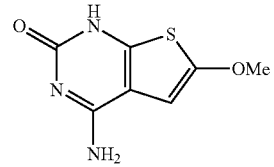

79

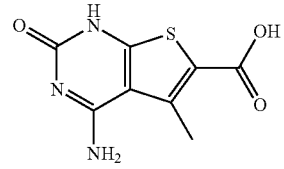

84

-continued

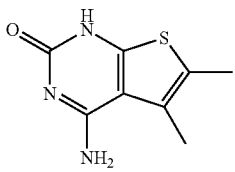

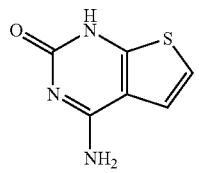

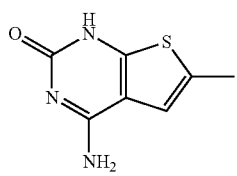

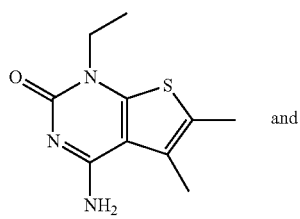

and

-continued

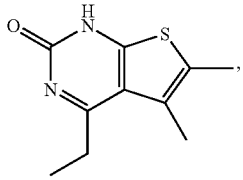

or a pharmaceutically acceptable salt thereof.

11. The method of claim 1, wherein the compound has a concentration from 0.0001 ppm to 10 ppm.

12. The method of claim 1, wherein the compound has a concentration from 0.0001 ppm to 100 ppm.

13. The method of claim 1, wherein the compound has a concentration from 0.01 ppm to 100 ppm.

14. The method of claim 1, wherein the comesible composition is a food or beverage product.

15. The method of claim 14, wherein the food or beverage product is selected from the group consisting of confectioneries, bakery products, dairy products, sweet and savory snacks, meal replacement products, ready meals, soups, pastas, noodles, canned foods, frozen foods, dried foods, chilled foods, oils and fats, baby foods, spreads, a cooking aid product, a meal solution product, a meal enhancement product, a seasoning, a seasoning blend, cake, cookie, pie, candy, chewing gum, gelatin, ice creams, sorbet, pudding, jam, jelly, salad dressing, condiments, cereals, canned fruits, fruit sauces, a carbonated or non-carbonated beverage, a beverage mix, a beverage concentrate, soda, juice, an alcoholic beverage, and combinations thereof.

* * * * *